United States Patent
Curran et al.

(10) Patent No.: US 8,835,429 B2
(45) Date of Patent: Sep. 16, 2014

(54) PYRIMIDINE COMPOUNDS, THEIR USE AS MTOR KINASE AND PL3 KINASE INHIBITORS, AND THEIR SYNTHESES

(75) Inventors: Kevin Joseph Curran, Somerville, MA (US); Joshua Aaron Kaplan, Seattle, WA (US); David James Richard, Littleton, MA (US); Jeroen Cunera Verheijen, Westborough, MA (US); Arie Zask, New York, NY (US)

(73) Assignee: Wyeth LLC, New York, NY (US)

( * ) Notice: Subject to any disclaimer, the term of this patent is extended or adjusted under 35 U.S.C. 154(b) by 356 days.

(21) Appl. No.: 13/264,776

(22) PCT Filed: Apr. 15, 2010

(86) PCT No.: PCT/US2010/031191
§ 371 (c)(1),
(2), (4) Date: Feb. 8, 2012

(87) PCT Pub. No.: WO2010/120998
PCT Pub. Date: Oct. 21, 2010

(65) Prior Publication Data
US 2012/0134959 A1 May 31, 2012

Related U.S. Application Data

(60) Provisional application No. 60/170,138, filed on Apr. 17, 2009.

(51) Int. Cl.
*C07D 498/08* (2006.01)
*A61K 31/5386* (2006.01)

(52) U.S. Cl.
CPC .................................... *C07D 498/08* (2013.01)
USPC ........................................ 514/230.5; 544/105

(58) Field of Classification Search
USPC ........................................ 544/105; 514/230.5
See application file for complete search history.

(56) References Cited

PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Fry, Review: Phosphoinositide 3-kinase signaling in breast cancer: how big a role might it play?, Breast Cancer Res 2001, 3:304-312.*
Kawashima et al., CAPLUS Abstract 133:89550 (2000).*
Simone, Oncology: Introduction, Cecil Textbook of Medicine, 20$^{th}$ Edition, vol. 1, pp. 1004-1010, 1996.*
Berridge, M., et al., "Inositol trisphosphate, a novel second messenger in cellular signal transduction," *Nature*, 1984, vol. 312, 315.
Brumbaugh, K., et al., "The mRNA Surveillance Protein hSMG-1 Functions in Genotoxic Stress Response Pathways in Mammalian Cells," *Molecular Cell*, 2004, vol. 14, issue 5, 585-598.
Geoerger, B., et al., "Antitumor Activity of the Rapamycin Analog CCI-779 in Human Primitive Neuroectodermal Tumor/Medulloblastoma Models as Single Agent and in Combination Chemotherapy," *Cancer Research*, 2001, vol. 61, 1527-1532.
Y. Nishizuka, "Turnover of INositol Phospholipids and Signal Transduction," *Science*, 1984, vol. 225, 1365.
Raynaud, F., et al., "Pharmacologic Characterization of a Potent Inhibitor of Class I Phosphatidylinositide 3-Kinases," *Cancer Research*, 2007, vol. 67, 5840-5850.
Teachey, D., et al, "The MTOR inhibitor CCI-779 induces apoptosis and hinibits growth in preclinical models of primary adult human ALL," *Blood*, 2006, vol. 107(3), 1149-1155.
Vanhaesebroeck, B., et al., "Phosphoinositide 3-kinases: a conserved family of signal transducers," *Trend in Biochemical Sciences*, 1997, vol. 22, 267.
Verheijen, J.C. and Zask, A., "Phosphatidylinositol 3-kinase (PI3K) inhibitors as anticancer drugs," *Drugs of the Future*, 2007, vol. 32(6), 537-547.
Whitman, M., et al., "Type I phosphatidylinositol kinase makes a novel inositol phospholipid, phosphatidylinositol-3-phosphate," *Letters to Nature*, 1988, vol. 332, 664.
Yaguchi, S., et al., "Antitumor Acitivty of ZSTK474, A New Phosphatidylinositol 3-Kinase Inhibitor," *Journal of the National Cancer Institute*, 2006, vol. 98:545-556.
Yamashita, A., et al. "Human SMG-1, a novel phosphatidylinositol 3-kinase-related protein kinase, associates with components of the mRNA surveillance complex and is involved in the regulation of nonsense-mediated mRNA decay," *Genes Devolopment*, 2001, vol. 15, 2215-2228.

* cited by examiner

*Primary Examiner* — Deepak Rao
(74) *Attorney, Agent, or Firm* — David Rubin

(57) ABSTRACT

The invention relates to pyrimidine compounds of the Formula I: or a pharmaceutically acceptable salt thereof, wherein the constituent variables are as defined herein, compositions comprising the compounds, and methods for making and using the compounds.

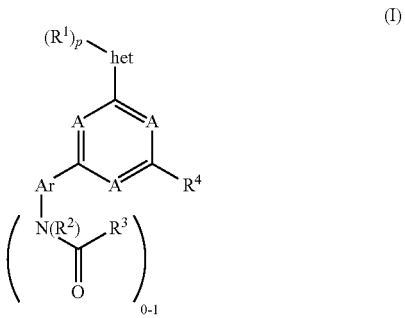

18 Claims, No Drawings

PYRIMIDINE COMPOUNDS, THEIR USE AS MTOR KINASE AND PL3 KINASE INHIBITORS, AND THEIR SYNTHESES

CROSS-REFERENCE TO RELATED APPLICATIONS

This application is a 371 application of PCT/US2010/31191, filed on Apr. 15, 2010, which claims the benefit of U.S. Provisional Application No. 61/170,138 filed on Apr. 17, 2009, the contents of which is hereby incorporated by reference in its entirety.

FIELD OF THE INVENTION

The invention relates to pyrimidine compounds, compositions comprising such a compound, methods of synthesizing such compounds, and methods for treating mTOR-related diseases comprising the administration of an effective amount of such a compound. The invention relates to methods for treating PI3K-related diseases comprising the administration of an effective amount of such a compound. The invention also relates to methods for treating hSMG-1-related diseases comprising the administration of an effective amount of such a compound.

BACKGROUND OF THE INVENTION

Phosphatidylinositol (hereinafter abbreviated as "PI") is one of the phospholipids in cell membranes. In recent years it has become clear that PI plays an important role also in intracellular signal transduction. It is well recognized in the art that PI (4,5) bisphosphate (PI(4,5)P2 or PIP2) is degraded into diacylglycerol and inositol (1,4,5) triphosphate by phospholipase C to induce activation of protein kinase C and intracellular calcium mobilization, respectively [M. J. Berridge et al., Nature, 312, 315 (1984); Y. Nishizuka, Science, 225, 1365 (1984)].

In the late 1980s, phosphatidylinositol-3 kinase ("PI3K") was found to be an enzyme that phosphorylates the 3-position of the inositol ring of phosphatidylinositol [D. Whitman et al., Nature, 332, 664 (1988)]. When PI3K was discovered, it was originally considered to be a single enzyme. Recently however, it was clarified that a plurality of PI3K subtypes exists. Three major subtypes of PI3Ks have now been identified on the basis of their in vitro substrate specificity, and these three are designated class I (a & b), class II, and class III [B. Vanhaesebroeck, Trend in Biol. Sci., 22, 267 (1997)].

The class Ia PI3K subtype has been most extensively investigated to date. Within the class Ia subtype there are three isoforms (α, β, & δ) that exist as hetero dimers of a catalytic 110-kDa subunit and regulatory subunits of 50-85 kDa. The regulatory subunits contain SH2 domains that bind to phosphorylated tyrosine residues within growth factor receptors or adaptor molecules and thereby localize PI3K to the inner cell membrane. At the inner cell membrane PI3K converts PIP2 to PIP3 (phosphatidylinositol-3,4,5-trisphosphate) that serves to localize the downstream effectors PDK1 and Akt to the inner cell membrane where Akt activation occurs. Activated Akt mediates a diverse array of effects including inhibition of apoptosis, cell cycle progression, response to insulin signaling, and cell proliferation. Class Ia PI3K subtypes also contain Ras binding domains (RBD) that allow association with activated Ras providing another mechanism for PI3K membrane localization. Activated, oncogenic forms of growth factor receptors, Ras, and even PI3K kinase have been shown to aberrantly elevate signaling in the PI3K/Akt/mTOR pathway resulting in cell transformation. As a central component of the PI3K/Akt/mTOR signaling pathway PI3K (particularly the class Ia isoform) has become a major therapeutic target in cancer drug discovery.

Substrates for class I PI3Ks are PI, PI(4)P and PI(4,5)P2, with PI(4,5)P2 being the most favored. Class I PI3Ks are further divided into two groups, class Ia and class Ib, because of their activation mechanism and associated regulatory subunits. The class Ib PI3K is p110γ that is activated by interaction with G protein-coupled receptors. Interaction between p110γ and G protein-coupled receptors is mediated by regulatory subunits of 110, 87, and 84 kDa.

PI and PI(4)P are the known substrates for class II PI3Ks; PI(4,5)P2 is not a substrate for the enzymes of this class. Class II PI3Ks include PI3K C2α, C2β and C2γ isoforms, which contain C2 domains at the C terminus, implying that their activity is regulated by calcium ions.

The substrate for class III PI3Ks is PI only. A mechanism for activation of the class III PI3Ks has not been clarified. Because each subtype has its own mechanism for regulating activity, it is likely that activation mechanism(s) depend on stimuli specific to each respective class of PI3K.

The compound PI103 (3-(4-(4-morpholinyl)pyrido[3',':4,5]furo[3,2-d]pyrimidin-2-yl)phenol) inhibits PI3K$_\alpha$ and PI3K$_\gamma$ as well as the mTOR complexes with IC$_{50}$ values of 2, 3, and 50-80 nM respectively. I.P. dosing in mice of this compound in human tumor xenograft models of cancer demonstrated activity against a number of human tumor models, including the glioblastoma (PTEN null U87MG), prostate (PC3), breast (MDA-MB-468 and MDA-MB-435) colon carcinoma (HCT 116); and ovarian carcinoma (SKOV3 and IGROV-1); (Raynaud et al, Pharmacologic Characterization of a Potent Inhibitor of Class I Phosphatidylinositide 3-Kinases, Cancer Res. 2007 67: 5840-5850).

The compound ZSTK474 (2-(2-difluoromethylbenzoimidazol-1-yl)-4,6-dimorpholino-1,3,5-triazine) inhibits PI3K$_\alpha$ and PI3K$_\gamma$ but not the mTOR enzyme with IC$_{50}$ values of 16, 4.6 and >10,000 nM respectively (Dexin Kong and Takao Yamori, ZSTK474 is an ATP-competitive inhibitor of class I phosphatidylinositol 3 kinase isoforms, Cancer Science, 2007, 98:10 1638-1642). Chronic oral administration of ZSTK474 in mouse human xenograft cancer models completely inhibited growth that originated from a non-small-cell lung cancer (A549), a prostate cancer (PC-3), and a colon cancer (WiDr) at a dose of 400 mg/kg. (Yaguchi et al, Antitumor Activity of ZSTK474, a New Phosphatidylinositol 3-Kinase Inhibitor, J. Natl. Cancer Inst. 98: 545-556).

The compound NVP-BEZ-235 (2-methyl-2-(4-(3-methyl-2-oxo-8-(quinolin-3-yl)-2,3-dihydro-1H-imidazo[4,5-c]quinolin-1-yl)phenyl)propanenitrile) inhibits both PI3K$_\alpha$ and PI3K$_\gamma$ as well as the mTOR enzyme with IC$_{50}$ values 4, 5, and "nanomolar". Testing in human tumor xenograft models of cancer demonstrated activity against human tumor models of prostate (PC-3) and glioblastoma (U-87) cancer. It entered clinical trials in December of 2006 (Verheijen, J. C. and Zask, A., Phosphatidylinositol 3-kinase (PI3K) inhibitors as anticancer drugs, Drugs Fut. 2007, 32(6): 537-547).

The compound SF-1126 (a prodrug form of LY-294002, which is 2-(4-morpholinyl)-8-phenyl-4H-1-benzopyran-4-one) is "a pan-PI3K inhibitor". It is active in preclinical mouse cancer models of prostate, breast, ovarian, lung, multiple myeloma, and brain cancers. It began clinical trials in April 2007 for the solid tumors endometrial, renal cell, breast, hormone refractory prostate and ovarian cancers. (Verheijen, J. C. and Zask, A., Phosphatidylinositol 3-kinase (PI3K) inhibitors as anticancer drugs, Drugs Fut. 2007, 32(6): 537-547).

Exelixis Inc. (So. San Francisco, Calif.) recently filed INDs for XL-147 (a selective pan-PI3K inhibitor of unknown structure) and XL-765 (a mixed inhibitor of mTOR and PI3K of unknown structure) as anticancer agents. TargeGen's short-acting mixed inhibitor of PI3Kγ and δ, TG-100115, is in phase I/II trials for treatment of infarct following myocardial ischemia-reperfusion injury. Cerylid's antithrombotic PI3Kβ inhibitor CBL-1309 (structure unknown) has completed preclinical toxicology studies.

According to Verheijen, J. C. and Zask, A., Phosphatidylinositol 3-kinase (PI3K) inhibitors as anticancer drugs, *Drugs Fut.* 2007, 32(6): 537-547, Although it seems clear that inhibition of the α isoform is essential for the antitumor activity of PI3K inhibitors, it is not clear whether a more selective inhibitor of a particular PI3K isoform may lead to fewer unwanted biological effects. It has recently been reported that non-PI3Kα class I isoforms (PI3Kβ, δ and γ) have the ability to induce oncogenic transformation of cells, suggesting that nonisoform-specific inhibitors may offer enhanced therapeutic potential over specific inhibitors.

Selectivity versus other related kinases is also an important consideration for the development of PI3K inhibitors. While selective inhibitors may be preferred in order to avoid unwanted side effects, there have been reports that inhibition of multiple targets in the PI3K/Akt pathway (e.g., PI3Kα and mTOR [mammalian target of rapamycin]) may lead to greater efficacy. It is possible that lipid kinase inhibitors may parallel protein kinase inhibitors in that nonselective inhibitors may also be brought forward to the clinic.

Mammalian Target of Rapamycin, mTOR, is a cell-signaling protein that regulates the response of tumor cells to nutrients and growth factors, as well as controlling tumor blood supply through effects on Vascular Endothelial Growth Factor, VEGF. Inhibitors of mTOR starve cancer cells and shrink tumors by inhibiting the effect of mTOR. All mTOR inhibitors bind to the mTOR kinase. This has at least two important effects. First, mTOR is a downstream mediator of the PI3K/Akt pathway. The PI3K/Akt pathway is thought to be over-activated in numerous cancers and may account for the widespread response from various cancers to mTOR inhibitors. The over-activation of the upstream pathway would normally cause mTOR kinase to be over-activated as well. However, in the presence of mTOR inhibitors, this process is blocked. The blocking effect prevents mTOR from signaling to downstream pathways that control cell growth. Over-activation of the PI3K/Akt kinase pathway is frequently associated with mutations in the PTEN gene, which is common in many cancers and may help predict what tumors will respond to mTOR inhibitors. The second major effect of mTOR inhibition is anti-angiogenesis, via the lowering of VEGF levels.

In lab tests, certain chemotherapy agents were found to be more effective in the presence of mTOR inhibitors. George, J. N., et al., Cancer Research, 61, 1527-1532, 2001. Additional lab results have shown that some rhabdomyosarcoma cells die in the presence of mTOR inhibitors. The complete functions of the mTOR kinase and the effects of mTOR inhibition are not completely understood.

There are three mTOR inhibitors, which have progressed into clinical trials. These compounds are Wyeth's Torisel, also known as 42-(3-hydroxy-2-(hydroxymethyl)-rapamycin 2-methylpropanoate, CCI-779 or Temsirolimus; Novartis' Everolimus, also known as 42-O-(2-hydroxyethyl)-rapamycin, or RAD 001; and Ariad's AP23573 also known as 42-(dimethylphopsinoyl)-rapamycin. The FDA has approved Torisel for the treatment of advanced renal cell carcinoma. In addition, Torisel is active in a NOS/SCID xenograft mouse model of acute lymphoblastic leukemia [Teachey et al, *Blood*, 107(3), 1149-1155, 2006]. On Mar. 30, 2009, the U.S. Food and Drug Administration (FDA) approved Everolimus (AFINITOR™) for the treatment of patients with advanced renal cell carcinoma. AP23573 has been given orphan drug and fast-track status by the FDA for treatment of soft-tissue and bone sarcomas.

The three mTOR inhibitors have non-linear, although reproducible pharmacokinetic profiles. Mean area under the curve (AUC) values for these drugs increase at a less than dose related way. The three compounds are all semi-synthetic derivatives of the natural macrolide antibiotic rapamycin. It would be desirable to find fully synthetic compounds, which inhibit mTOR that are more potent and exhibit improved pharmacokinetic behaviors.

The most recently described PI3K family member was identified in human cells and named human SMG-1 or hSMG-1. Yamashita (Genes Dev. 2001 15: 2215-2228) characterized two isoforms of hSMG-1 proteins, p430 and p400, which are expressed in various cell lines of human, monkey, rat, and mouse. Yamashita's p400 hSMG-1 isoform is a 3529-amino-acid protein of 396,040 Daltons. Brumbaugh (Molecular Cell, Volume 14, Issue 5, 4 Jun. 2004, Pages 585-598) isolated a 3521 amino acid polypeptide with a deduced molecular mass of 395 kDa. Brumbaugh's hSMG-1 is eight amino acids shorter at the amino terminus than the protein isolated by Yamashita.

Both hUpf1 and p53 are physiological targets for hSMG-1 in intact cells. Rapamycin in the presence of purified recombinant FKBP12 does not inhibit the kinase activity of hSMG-1. Wortmannin, the modified steroidal anti-infective agent, and the purine caffeine inhibit the kinase activity of hSMG-1 with $IC_{50}$ values of ~60 nM and 0.3 mM, respectively. However, these are non-specific protein kinase inhibitors.

Specific inhibition of hSMG-1 is a potential therapeutic strategy because inhibitors of hSMG-1 cause the accumulation of truncated p53 proteins from a premature translation termination codon (PTC) allele, as well as the increase in the level of mRNA with PTC, opening the possibility of the above strategy by specifically suppressing nonsense-mediated mRNA decay (NMD) through the inhibition of hSMG-1.

One-fourth of all mutations in human genetic diseases and cancers are of the type that can target the corresponding mRNA for NMD. Although NMD protects cells against deleterious gain-of-function mutations caused by the dominant negative effects of aberrant truncated proteins, there are some cases in which the truncated protein does not show such an effect, rather, it retains residual activity and can compensate for the normal gene function. Thus, the specific inhibition of NMD may provide a novel therapeutic strategy based on the type of mutation rather than on the gene in which the mutation resides.

The inhibitors of SMG-1 can rescue the synthesis of mature proteins through two independent mechanisms (i.e., the inhibition of NMD to increase the mRNA level and the suppression of translational termination that leads to the synthesis of a read-through mature protein product). In this sense, the specific inhibitors of hSMG-1 will be of potential therapeutic importance for all the genetic diseases associated with PTC mutations.

As explained above, PI3K inhibitors, mTOR inhibitors, and hSMG-1 inhibitors are expected to be novel types of medicaments useful against cell proliferation disorders, especially as carcinostatic agents. Thus, it would be advantageous to have new PI3K inhibitors, mTOR inhibitors, and hSMG-1 inhibitors as potential treatment regimens for mTOR-, PI3K-, and hSMG-1-related diseases. The instant invention is directed to these and other important ends.

SUMMARY OF THE INVENTION

In one aspect, the invention provides compounds of the Formula I:

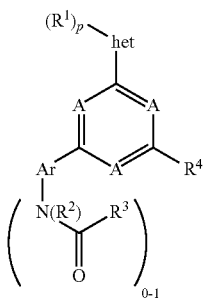

or a pharmaceutically acceptable salt thereof, wherein the constituent variables are as defined below. In other aspects, the invention provides compositions comprising a compound of the invention, and methods for making compounds of the invention. In further aspects, the invention provides methods for inhibiting PI3K, mTOR and hSMG-1 in a subject, and methods for treating PI3K-related, mTOR-related and hSMG-1-related disorders in a mammal in need thereof.

DETAILED DESCRIPTION OF THE INVENTION

In one aspect, the invention provides compounds of the Formula:

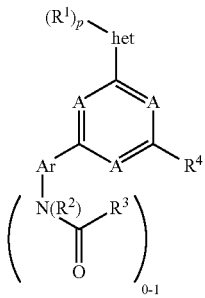

or a pharmaceutically acceptable salt thereof wherein;
$R^1$ is independently $C_1$-$C_6$alkyl-, $C_6$-$C_{14}$aryl-, $C_1$-$C_9$heteroaryl-, halogen, or hydroxyl;
p is 0, 1, 2, 3, or 4;
het is a bridged $C_5$-$C_9$heterobicyclyl- group containing at least one oxygen atom, at least one nitrogen atom, and optionally additional heteroatoms selected from oxygen, sulfur and nitrogen, and is connected to the pyrimidinyl group through one of the nitrogen atoms;
one of A is C—$R^5$ and the other two are N;
Ar is $C_6$-$C_{14}$aryl- or $C_1$-$C_9$heteroaryl- wherein the $C_6$-$C_{14}$aryl- or $C_1$-$C_9$heteroaryl- is optionally substituted with from 1 to 4 substituents independently selected from $C_1$-$C_6$alkyl-, halogen, haloalkyl-, hydroxyl, hydroxyl($C_1$-$C_6$alkyl)-, $H_2N$—, aminoalkyl-, di($C_1$-$C_6$alkyl)amino-, $HO_2C$—, ($C_1$-$C_6$alkoxy)carbonyl-, ($C_1$-$C_6$alkyl)carboxyl-, di($C_1$-$C_6$alkyl)amido-, $H_2NC(O)$—, ($C_1$-$C_6$alkyl)amido-, and $O_2N$—;
and wherein the $C_6$-$C_{14}$aryl- or $C_1$-$C_9$heteroaryl- is bonded to the pyrimidine core through a carbon atom of the $C_6$-$C_{14}$aryl- or $C_1$-$C_9$heteroaryl-;
$R^2$ is H or $C_1$-$C_6$alkyl-;
$R^3$ is $R^6$—, $R^7R^8N$—, $R^9S$—, or $R^9O$—;
$R^6$— is:
a) H;
b) $C_1$-$C_6$alkyl- optionally substituted with from 1 to 3 substituents independently selected from:
  i) $C_1$-$C_6$alkoxy-,
  ii) $H_2N$—,
  iii) ($C_1$-$C_6$alkyl)amino-,
  iv) di($C_1$-$C_6$alkyl)amino-,
  v) $C_6$-$C_{14}$aryl-,
  vi) $C_1$-$C_9$heterocyclyl- optionally substituted by $C_1$-$C_6$alkyl-,
  vii) and $C_1$-$C_9$heteroaryl-;
c) $C_1$-$C_6$alkoxy-;
d) $C_1$-$C_9$heteroaryl- optionally substituted with from 1 to 3 substituents independently selected from:
  i) $C_1$-$C_6$alkyl- optionally substituted with $H_2N$—,
  ii) heterocyclyl($C_1$-$C_6$alkyl)-,
  iii) halogen,
  iv) hydroxyl,
  v) $H_2N$—,
  vi) $O_2N$—,
  vii) $H_2NSO_2$—,
  viii) $HO_2C$—,
  ix) ($C_1$-$C_6$alkoxy)carbonyl-,
  x) ($C_1$-$C_6$alkoxy)C(O)NH—,
  xi) ($C_1$-$C_6$alkyl)amino-,
  xii) di($C_1$-$C_6$alkyl)amino-,
  xiii) $R^{10}R^{11}NC(O)$—,
  xiv) $R^{10}O$—,
  xv) $R^{10}R^{11}N$—,
  xvi) $R^{10}R^{11}NS(O)_2$—,
  xvii) $R^{10}S(O)_2NR^{11}$—,
  xviii) $R^{10}R^{11}NC(O)NH$—,
  xix) $R^{10}S$—,
  xx) $R^{10}S(O)$—,
  xxi) $R^{10}S(O)_2$—,
  xxii) $R^{10}C(O)$—,
  xxiii) $C_1$-$C_9$heterocyclyl- optionally substituted by $C_1$-$C_6$alkyl- or $C_1$-$C_6$hydroxylalkyl-,
  xxiv) $C_1$-$C_6$hydroxylalkyl-,
  xxv) and perfluoro($C_1$-$C_6$)alkyl-;
e) $C_1$-$C_6$hydroxylalkyl-;
f) $C_1$-$C_9$heterocyclyl-;
g) $C_6$-$C_{14}$aryl- optionally substituted with from 1 to 3 substituents independently selected from:
  i) $C_1$-$C_6$alkyl- optionally substituted with $H_2N$—,
  ii) heterocyclyl($C_1$-$C_6$alkyl)-,
  iii) halogen,
  iv) hydroxyl,
  v) $H_2N$—,
  vi) $O_2N$—,
  vii) $H_2NSO_2$—,
  viii) $HO_2C$—,
  ix) ($C_1$-$C_6$alkoxy)carbonyl-,
  x) ($C_1$-$C_6$alkoxy)C(O)NH—,
  xi) ($C_1$-$C_6$alkyl)amino-,
  xii) di($C_1$-$C_6$alkyl)amino-,
  xiii) $R^{10}R^{11}NC(O)$—,
  xiv) $R^{10}O$—, xv) $R^{10}R^{11}N-$,
xvi) $R^{10}R^{11}NS(O)_2-$,
xvii) $R^{10}S(O)_2NR^{11}-$,
xviii) $R^{10}R^{11}NC(O)NH-$,
xix) $R^{10}S-$,
xx) $R^{10}S(O)-$,
xxi) $R^{10}S(O)_2-$,
xxii) $R^{10}C(O)-$,
xxiii) $C_1$-$C_9$heterocyclyl- optionally substituted by $C_1$-$C_6$alkyl- or $C_1$-$C_6$hydroxylalkyl-,
xxiv) $C_1$-$C_6$hydroxylalkyl-,
xxv) and perfluoro($C_1$-$C_6$)alkyl-;
h) or $C_3$-$C_8$cycloalkyl-;
$R^{10}$ and $R^{11}$ are each independently H, $C_1$-$C_6$alkoxy-, $C_1$-$C_6$alkyl-, $C_1$-$C_6$alkoxy($C_2$-$C_6$alkylene)-, ($C_1$-$C_6$alkyl)amino-$C_2$-$C_6$alkylene-, di($C_1$-$C_6$alkyl)amino-$C_2$-$C_6$alkylene-, $C_2$-$C_6$alkenyl, $C_2$-$C_6$alkynyl, ($C_6$-$C_{14}$aryl)alkyl-, $C_3$-$C_8$cycloalkyl-, $C_1$-$C_9$heteroaryl-, ($C_1$-$C_9$heteroaryl)alkyl-, $C_1$-$C_9$heterocyclyl- optionally substituted by $C_1$-$C_6$alkyl-, or heterocyclyl($C_1$-$C_6$alkyl-);
or $R^{10}$ and $R^{11}$, when taken together with the nitrogen to which they are attached, form a 3- to 7-membered heterocycle wherein up to two of the carbon atoms of the heterocycle are optionally replaced with —N(H)—, —N($C_1$-$C_6$alkyl)-, —N($C_3$-$C_8$cycloalkyl)-, —N($C_6$-$C_{14}$aryl)-, —N($C_1$-$C_9$heteroaryl)-, —S—, —SO—, —S(O)$_2$—, or —O— and wherein any carbon atom of the heterocycle is optionally substituted with from 1 or 2 substituents independently selected from $C_1$-$C_6$alkyl-, $H_2N-$, ($C_1$-$C_6$alkyl)amino-, di($C_1$-$C_6$alkyl)amino-, and $C_1$-$C_9$heterocyclyl-;
$R^7$ and $R^8$ are each independently selected from:
  (a) H;
  (b) $C_1$-$C_6$alkyl- optionally substituted with from 1 to 3 substituents independently selected from:
    (i) $C_1$-$C_8$acyl-
    (ii) $C_1$-$C_6$alkoxy- optionally substituted with —NH$_2$,
    (iii) ($C_1$-$C_6$alkoxy)carbonyl-,
    (iv) $H_2N-$,
    (v) ($C_1$-$C_6$alkyl)amino-,
    (vi) di($C_1$-$C_6$alkyl)amino-,
    (vii) ($C_1$-$C_6$alkyl)carboxyamido-, optionally substituted with
      A) $H_2N-$,
      B) ($C_1$-$C_6$alkyl)amino-,
      C) or di($C_1$-$C_6$alkyl)amino-,
    (viii) $C_6$-$C_{14}$aryl-,
    (ix) $C_3$-$C_8$cycloalkyl-
    (x) halogen,
    (xi) $C_1$-$C_9$heterocyclyl- optionally substituted by $C_1$-$C_6$alkyl-,
    (xii) $HO_2C-$,
    (xiii) NC—,
    (xiv) $R^{10}C(O)NR^{11}-$,
    (xv) $R^{10}R^{11}NC(O)-$,
    (xvi) and $C_1$-$C_9$heteroaryl-;
  (c) $C_1$-$C_6$alkoxy-;
  (d) $C_1$-$C_9$heteroaryl- optionally substituted with from 1 to 3 substituents independently selected from:
    (i) $C_1$-$C_6$alkoxy- optionally substituted with
      A) $H_2N-$,
      B) ($C_1$-$C_6$alkyl)amino-,
      C) di($C_1$-$C_6$alkyl)amino-,
      D) $C_1$-$C_9$heterocyclyl- optionally substituted by $C_1$-$C_6$alkyl-,
      E) or hydroxyl,
    (ii) ($C_1$-$C_6$alkoxy)carbonyl-,
    (iii) ($C_1$-$C_6$alkoxy)C(O)NH—,
    (iv) $C_1$-$C_6$alkyl- optionally substituted with
      A) $H_2N-$,
      B) ($C_1$-$C_6$alkyl)amino-,
      C) or di($C_1$-$C_6$alkyl)amino-,
    (v) ($C_1$-$C_6$alkyl)amino-,
    (vi) di($C_1$-$C_6$alkyl)amino-,
    (vii) ($C_1$-$C_6$alkyl)amido- optionally substituted with
      A) $H_2N-$,
      B) ($C_1$-$C_6$alkyl)amino-,
      C) or di($C_1$-$C_6$alkyl)amino-,
    (viii) ($C_1$-$C_6$alkyl)carboxyamido-,
    (ix) $C_1$-$C_9$heterocyclyl- optionally substituted by $C_1$-$C_6$alkyl- or $C_1$-$C_6$hydroxylalkyl-,
    (x) heterocyclyl($C_1$-$C_6$alkyl)- optionally substituted by $C_1$-$C_6$alkyl-,
    (xi) halogen,
    (xii) hydroxyl,
    (xiii) $C_1$-$C_6$hydroxylalkyl-,
    (xiv) perfluoro($C_1$-$C_6$)alkyl-,
    (xv) $H_2N-$,
    (xvi) $O_2N-$,
    (xvii) $H_2NSO_2-$,
    (xviii) $HO_2C-$,
    (xix) NC—,
    (xx) $R^{10}R^{11}NC(O)-$,
    (xxi) $R^{10}R^{11}NNHC(O)-$,
    (xxii) $R^{10}O-$,
    (xxiii) $R^{10}R^{11}N-$,
    (xxiv) $R^{10}R^{11}NS(O)_2-$,
    (xxv) $R^{10}S(O)_2NR^{11}-$,
    (xxvi) $R^{10}R^{11}NC(O)NH-$,
    (xxvii) $R^{10}S-$,
    (xxviii) $R^{10}S(O)-$,
    (xxix) $R^{10}S(O)_2-$,
    (xxx) and $R^{10}C(O)-$;
  (e) $C_1$-$C_6$hydroxylalkyl-;
  (f) $C_1$-$C_9$heterocyclyl- optionally substituted with from 1 to 3 substituents independently selected from:
    (i) $C_1$-$C_6$alkyl-,
    (ii) heterocyclyl($C_1$-$C_6$alkyl)-,
    (iii) ($C_6$-$C_{14}$aryl)alkyl-,
    (iv) $C_1$-$C_8$acyl-,
    (v) ($C_1$-$C_6$alkoxy)carbonyl-,
    (vi) ($C_1$-$C_6$alkyl)carboxyl-,
    (vii) halogen,
    (viii) $C_1$-$C_6$haloalkyl-,
    (ix) hydroxyl,
    (x) $C_1$-$C_6$hydroxylalkyl-,
    (xi) $H_2N-$,
    (xii) ($C_1$-$C_6$alkyl)amino-,
    (xiii) di($C_1$-$C_6$alkyl)amino-,
    (xiv) $HO_2C-$,
    (xv) ($C_1$-$C_6$alkoxy)carbonyl-,
    (xvi) ($C_1$-$C_6$alkyl)carboxyl-,
    (xvii) ($C_1$-$C_6$alkyl)amido-,
    (xviii) $H_2NC(O)-$,
    (xix) ($C_1$-$C_6$alkyl)carboxyamido-,
    (xx) and —$NO_2$;
  (g) $C_6$-$C_{14}$aryl- optionally substituted with from 1 to 3 substituents independently selected from:
    (i) $C_1$-$C_6$alkoxy- optionally substituted with
      A) $H_2N-$,
      B) ($C_1$-$C_6$alkyl)amino-,
      C) di($C_1$-$C_6$alkyl)amino-, D) $C_1$-$C_9$heterocyclyl- optionally substituted by $C_1$-$C_6$alkyl-,
E) and hydroxyl,
(ii) ($C_1$-$C_6$alkoxy)carbonyl-,
(iii) ($C_1$-$C_6$alkoxy)C(O)NH—,
(iv) $C_1$-$C_6$alkyl- optionally substituted with
 A) $H_2N$—,
 B) ($C_1$-$C_6$alkyl)amino-,
 C) or di($C_1$-$C_6$alkyl)amino-,
(v) ($C_1$-$C_6$alkyl)amino-,
(vi) di($C_1$-$C_6$alkyl)amino-,
(vii) ($C_1$-$C_6$alkyl)amido- optionally substituted with
 A) $H_2N$—,
 B) ($C_1$-$C_6$alkyl)amino-,
 C) or di($C_1$-$C_6$alkyl)amino-,
(viii) ($C_1$-$C_6$alkyl)carboxyamido-,
(ix) $C_1$-$C_9$heterocyclyl- optionally substituted by $C_1$-$C_6$alkyl- or $C_1$-$C_6$hydroxylalkyl-,
(x) heterocyclyl($C_1$-$C_6$alkyl)- optionally substituted by $C_1$-$C_6$alkyl-,
(xi) halogen,
(xii) hydroxyl,
(xiii) $C_1$-$C_6$hydroxylalkyl-,
(xiv) perfluoro($C_1$-$C_6$)alkyl-,
(xv) $H_2N$—,
(xvi) $O_2N$—,
(xvii) $H_2NSO_2$—,
(xviii) $HO_2C$—,
(xix) NC—,
(xx) $R^{10}R^{11}NC(O)$—,
(xxi) $R^{10}R^{11}NNHC(O)$—,
(xxii) $R^{10}O$—,
(xxiii) $R^{10}R^{11}N$—,
(xxiv) $R^{10}R^{11}NS(O)_2$—,
(xxv) $R^{10}S(O)_2NR^{11}$—,
(xxvi) $R^{10}R^{11}NC(O)NH$—,
(xxvii) $R^{10}S$—,
(xxviii) $R^{10}S(O)$—,
(xxix) $R^{10}S(O)_2$—,
(xxx) and $R^{10}C(O)$—;
(h) and $C_3$-$C_8$cycloalkyl- optionally substituted with from 1 to 3 substituents independently selected from:
(i) $C_1$-$C_6$alkyl- optionally substituted with halogen,
(ii) ($C_1$-$C_6$alkoxy)carbonyl-,
(iii) ($C_1$-$C_6$alkyl)amido-,
(iv) ($C_1$-$C_6$alkyl)carboxyamido-,
(v) ($C_1$-$C_6$alkyl)carboxyl-,
(vi) $C_1$-$C_6$alkoxy-,
(vii) $H_2N$—,
(viii) ($C_1$-$C_6$alkyl)amino-,
(ix) di($C_1$-$C_6$alkyl)amino-,
(x) hydroxyl,
(xi) $H_2NC(O)$—,
(xii) $HO_2C$—,
(xiii) and —$NO_2$;
wherein any two hydrogen atoms on the same carbon atom of the $C_3$-$C_8$cycloalkyl-ring can be replaced by an oxygen atom to form an oxo (=O) substituent,
and wherein any two hydrogen atoms on the same carbon atom of the $C_3$-$C_8$cycloalkyl-ring can be replaced by an alkylenedioxy group so that the alkylenedioxy group, when taken together with the carbon atom to which it is attached, forms a 5- to 7-membered heterocycle containing two oxygen atoms;
or $R^7$ and $R^8$, when taken together with the nitrogen to which they are attached, form a 3- to 7-membered heterocycle wherein up to two of the carbon atoms of the heterocycle are optionally replaced with —N(H)—, —N($C_1$-$C_6$alkyl)-, —N($C_6$-$C_{14}$aryl)-, —S—, —SO—, —S(O)$_2$—, or —O—;
$R^9$ is $C_1$-$C_6$alkyl-, ($C_6$-$C_{14}$aryl)alkyl- optionally substituted by $H_2N$—, $C_1$-$C_9$heterocyclyl-optionally substituted by $C_1$-$C_6$alkyl-, $C_3$-$C_8$cycloalkyl-, $C_1$-$C_6$hydroxylalkyl-, or $C_1$-$C_6$perfluoroalkyl-;
$R^4$ is:
(a) hydrogen;
(b) $C_1$-$C_8$acyl-;
(c) $C_1$-$C_6$alkyl-;
(d) $H_2N$— optionally substituted with $C_1$-$C_9$heterocycle,
(e) ($C_1$-$C_6$alkyl)amino- optionally substituted with ($C_1$-$C_6$alkyl)SO$_2$—,
(f) di($C_1$-$C_6$alkyl)amino- optionally substituted with ($C_1$-$C_6$alkyl)SO$_2$—,
(g) ($C_1$-$C_6$alkyl)amino-$C_1$-$C_6$alkylene-,
(h) di($C_1$-$C_6$alkyl)amino-$C_1$-$C_6$alkylene-,
(i) amino($C_1$-$C_6$alkyl)-;
(j) $C_3$-$C_8$cycloalkyl-;
(k) $C_6$-$C_{14}$aryl- optionally substituted with a substituent selected from:
 (i) $HO_2C$—,
 (ii) $C_1$-$C_6$hydroxylalkyl-,
 (iii) $R^{12}R^{13}NC(O)$—,
 (iv) and ($C_1$-$C_6$alkoxy)carbonyl-;
(l) $C_1$-$C_9$heterocycle optionally substituted with $C_1$-$C_6$alkyl-;
(m) ($C_1$-$C_9$heteroaryl)alkyl-;
(n) heterocyclyl($C_1$-$C_6$alkyl)-;
(o) ($C_6$-$C_{14}$aryl)alkyl-;
(p) heterocyclyl($C_1$-$C_6$alkyl);
(q) ($C_1$-$C_9$heteroaryl)alkyl-;
(r) ($C_6$-$C_{14}$aryl)alkyl-;
(s) $C_1$-$C_6$hydroxylalkyl-;
(t) $C_1$-$C_6$perfluoroalkyl-;
(u) $C_1$-$C_9$heteroaryl- optionally substituted with a substituent selected from:
 (i) $HO_2C$—,
 (ii) $C_1$-$C_6$hydroxylalkyl-,
 (iii) $R^{12}R^{13}NC(O)$—,
 (iv) and ($C_1$-$C_6$alkoxy)carbonyl-;
(v) $R^3C(O)$—N($R^2$)—Ar—;
(w) $R^{12}R^{13}NC(O)$—;
(x) $R^{14}OC(O)$—;
(y) or $R^{14}S(O)_2$—;
$R^5$ is:
(a) hydrogen;
(b) $C_1$-$C_8$acyl-;
(c) $C_1$-$C_6$alkyl-;
(d) amino($C_1$-$C_6$alkyl)-;
(e) $C_3$-$C_8$cycloalkyl-;
(f) $C_6$-$C_{14}$aryl- optionally substituted with a substituent selected from:
 (i) $HO_2C$—,
 (ii) $C_1$-$C_6$hydroxylalkyl-,
 (iii) $R^{12}R^{13}NC(O)$—,
 (iv) and ($C_1$-$C_6$alkoxy)carbonyl-;
(g) halogen;
(h) $C_1$-$C_9$heterocycle optionally substituted with $C_1$-$C_6$alkyl-;
(i) ($C_1$-$C_9$heteroaryl)alkyl-;
(j) heterocyclyl($C_1$-$C_6$alkyl)-;
(k) ($C_6$-$C_{14}$aryl)alkyl-;
(l) heterocyclyl($C_1$-$C_6$alkyl);
(m) ($C_1$-$C_9$heteroaryl)alkyl-;
(n) ($C_6$-$C_{14}$aryl)alkyl-;
(o) $C_1$-$C_6$hydroxylalkyl-;

(p) $C_1$-$C_6$perfluoroalkyl-;
(q) $C_1$-$C_9$heteroaryl- optionally substituted with a substituent selected from:
 (i) $HO_2C—$,
 (ii) $C_1$-$C_6$hydroxylalkyl-,
 (iii) $R^{12}R^{13}NC(O)—$,
 (iv) and ($C_1$-$C_6$alkoxy)carbonyl-;
(r) $R^{12}R^{13}NC(O)—$;
(s) $R^{14}OC(O)—$;
(t) or $R^{14}S(O)_2—$;

$R^{12}$ and $R^{13}$ are each independently H, $C_1$-$C_6$alkyl-, $C_3$-$C_8$cycloalkyl-, $C_6$-$C_{14}$aryl-, $C_1$-$C_9$heteroaryl-, ($C_1$-$C_9$heteroaryl)alkyl-, heterocyclyl($C_1$-$C_6$alkyl)-, ($C_6$-$C_{14}$aryl)alkyl-, or $C_1$-$C_9$heterocyclyl- optionally substituted by $C_1$-$C_6$alkyl-;

or $R^{12}$ and $R^{13}$, when taken together with the nitrogen to which they are attached, form a 3- to 7-membered heterocycle wherein up to two of the carbon atoms of the heterocycle are optionally replaced with —N(H)—, —N($C_1$-$C_6$alkyl)-, —N($C_6$-$C_{14}$aryl)-, —S—, —SO—, —S(O)$_2$—, or —O—;

$R^{14}$ is $C_1$-$C_6$alkyl-, $C_6$-$C_{14}$aryl-, ($C_6$-$C_{14}$aryl)alkyl-, $C_1$-$C_9$heterocyclyl- optionally substituted by $C_1$-$C_6$alkyl-, $C_3$-$C_8$cycloalkyl-, $C_1$-$C_6$hydroxylalkyl-, or $C_1$-$C_6$perfluoroalkyl-.

In one aspect, the invention provides compounds of the Formula II:

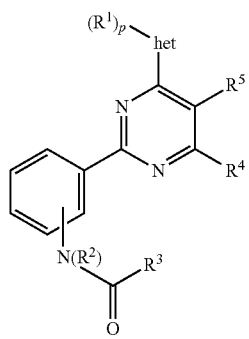

II or a pharmaceutically acceptable salt thereof, wherein the constituent variables are as defined for Formula I.

In one aspect, the invention provides compounds of the Formula III:

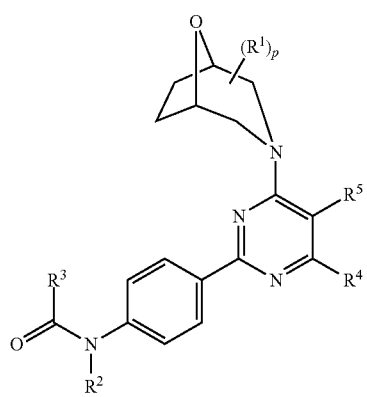

III or a pharmaceutically acceptable salt thereof, wherein the constituent variables are as defined above for Formula I.

In one aspect, the invention provides compounds of the Formula IV:

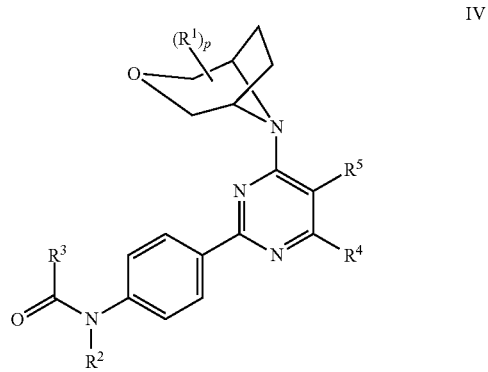

IV or a pharmaceutically acceptable salt thereof, wherein the constituent variables are as defined above for Formula I.

In one aspect, the invention provides compounds of the Formula V:

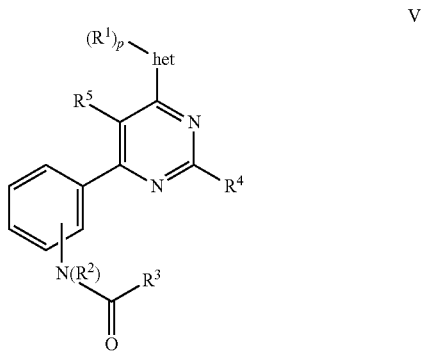

V or a pharmaceutically acceptable salt thereof, wherein the constituent variables are as defined above for Formula I.

In one aspect, the invention provides compounds of the Formula VI:

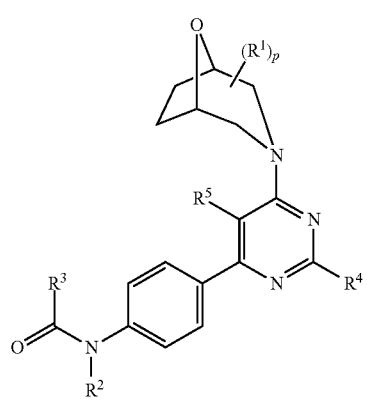

VI or a pharmaceutically acceptable salt thereof, wherein the constituent variables are as defined above for Formula I.

In one embodiment, p is 0.
In one embodiment, Ar is phenyl.
In one embodiment, $R^2$ is H.
In one embodiment, $R^3$ is $R^7R^8N$—.
In one embodiment, $R^7$ is selected from $C_1$-$C_9$heteroaryl- optionally substituted with from 1 to 3 substituents independently selected from $C_1$-$C_9$heterocyclyl- optionally substituted by $C_1$-$C_6$alkyl-, heterocyclyl($C_1$-$C_6$alkyl)- optionally substituted by $C_1$-$C_6$alkyl-, $R^{10}R^{11}NC(O)$—, and $R^{10}O$—; and $C_6$-$C_{14}$aryl- optionally substituted with from 1 to 3 substituents independently selected from $C_1$-$C_9$heterocyclyl- optionally substituted by $C_1$-$C_6$alkyl-, heterocyclyl($C_1$-$C_6$alkyl)- optionally substituted by $C_1$-$C_6$alkyl-, $R^{10}R^{11}NC(O)$—, and $R^{10}O$—.

In one embodiment, $R^7$ is $C_1$-$C_9$heteroaryl-.
In one embodiment, $R^7$ is pyridyl-.
In one embodiment, $R^7$ is 4-pyridyl-.
In one embodiment, $R^7$ is $C_6$-$C_{14}$aryl- substituted with $C_1$-$C_9$heterocyclyl- optionally substituted by $C_1$-$C_6$alkyl-.
In one embodiment, $R^7$ is $C_6$-$C_{14}$aryl- substituted with heterocyclyl($C_1$-$C_6$alkyl)- optionally substituted by $C_1$-$C_6$alkyl-.
In one embodiment, $R^7$ is $C_6$-$C_{14}$aryl- substituted with $R^{10}R^{11}NC(O)$—.
In one embodiment, $R^8$ is H.
In one embodiment, $R^4$ is $C_1$-$C_9$heterocyclyl-.
In one embodiment, $R^5$ is H.

Illustrative compounds of the present Formula II are set forth below:
1-{4-[4-(3,7-dioxa-9-azabicyclo[3.3.1]non-9-yl)-6-(isopropylamino)pyrimidin-2-yl]phenyl}-3-pyridin-4-ylurea;
1-{4-[4-(3,7-dioxa-9-azabicyclo[3.3.1]non-9-yl)-6-(isopropylamino)pyrimidin-2-yl]phenyl}-3-{4-[(4-methylpiperazin-1-yl)methyl]phenyl}urea;
1-{4-[4-(3,7-dioxa-9-azabicyclo[3.3.1]non-9-yl)-6-(isopropylamino)pyrimidin-2-yl]phenyl}-3-[4-(4-methylpiperazin-1-yl)phenyl]urea; and
1-{4-[2-(dimethylamino)ethoxy]phenyl}-3-{4-[4-(3,7-dioxa-9-azabicyclo[3.3.1]non-9-yl)-6-(isopropylamino)pyrimidin-2-yl]phenyl}urea.

Illustrative compounds of the present Formula III are set forth below:
1-methyl-3-{4-[4-(8-oxa-3-azabicyclo[3.2.1]oct-3-yl)-6-phenylpyrimidin-2-yl]phenyl}urea;
2-hydroxyethyl {4-[4-(8-oxa-3-azabicyclo[3.2.1]oct-3-yl)-6-phenylpyrimidin-2-yl]phenyl}carbamate;
1-[4-(4-methylpiperazin-1-yl)phenyl]-3-{4-[4-(8-oxa-3-azabicyclo[3.2.1]oct-3-yl)-6-phenylpyrimidin-2-yl]phenyl}urea;
1-ethyl-3-{4-[4-(8-oxa-3-azabicyclo[3.2.1]oct-3-yl)-6-phenylpyrimidin-2-yl]phenyl}urea;
1-cyclopropyl-3-{4-[4-(8-oxa-3-azabicyclo[3.2.1]oct-3-yl)-6-phenylpyrimidin-2-yl]phenyl}urea;
1-{4-[4-(8-oxa-3-azabicyclo[3.2.1]oct-3-yl)-6-phenylpyrimidin-2-yl]phenyl}-3-pyridin-4-ylurea;
1-[4-(hydroxymethyl)phenyl]-3-{4-[4-(8-oxa-3-azabicyclo[3.2.1]oct-3-yl)-6-phenylpyrimidin-2-yl]phenyl}urea;
1-{4-[2-(dimethylamino)ethoxy]phenyl}-3-{4-[4-(8-oxa-3-azabicyclo[3.2.1]oct-3-yl)-6-phenylpyrimidin-2-yl]phenyl}urea;
2-hydroxyethyl {4-[4-(8-oxa-3-azabicyclo[3.2.1]oct-3-yl)pyrimidin-2-yl]phenyl}carbamate;
1-methyl-3-{4-[4-(8-oxa-3-azabicyclo[3.2.1]oct-3-yl)pyrimidin-2-yl]phenyl}urea;
1-{4-[4-(8-oxa-3-azabicyclo[3.2.1]oct-3-yl)pyrimidin-2-yl]phenyl}-3-pyridin-4-ylurea;
1-[4-(4,6-di-8-oxa-3-azabicyclo[3.2.1]oct-3-ylpyrimidin-2-yl)phenyl]-3-methylurea;
1-[4-(4,6-di-8-oxa-3-azabicyclo[3.2.1]oct-3-ylpyrimidin-2-yl)phenyl]-3-pyridin-4-ylurea;
1-[4-(4,6-di-8-oxa-3-azabicyclo[3.2.1]oct-3-ylpyrimidin-2-yl)phenyl]-3-[4-(4-methylpiperazin-1-yl)phenyl]urea;
1-[4-(4,6-di-8-oxa-3-azabicyclo[3.2.1]oct-3-ylpyrimidin-2-yl)phenyl]-1-ethyl-3-pyridin-4-ylurea;
1-[4-(4,6-di-8-oxa-3-azabicyclo[3.2.1]oct-3-ylpyrimidin-2-yl)phenyl]-1-ethyl-3-[4-(4-methylpiperazin-1-yl)phenyl]urea;
bis(2-hydroxyethyl){[6-(8-oxa-3-azabicyclo[3.2.1]oct-3-yl)pyrimidine-2,4-diyl]di-4,1-phenylene}biscarbamate;
N',N'''-{[6-(8-oxa-3-azabicyclo[3.2.1]oct-3-yl)pyrimidine-2,4-diyl]di-4,1-phenylene}bis(1-methylurea);
N',N'''-{[6-(8-oxa-3-azabicyclo[3.2.1]oct-3-yl)pyrimidine-2,4-diyl]di-4,1-phenylene}bis(1-ethylurea);
N',N'''-{[6-(8-oxa-3-azabicyclo[3.2.1]oct-3-yl)pyrimidine-2,4-diyl]di-4,1-phenylene}bis(1-cyclopropylurea);
N,N''-{[6-(8-oxa-3-azabicyclo[3.2.1]oct-3-yl)pyrimidine-2,4-diyl]di-4,1-phenylene}bis(3-pyridin-3-ylurea);
N,N''-{[6-(8-oxa-3-azabicyclo[3.2.1]oct-3-yl)pyrimidine-2,4-diyl]di-4,1-phenylene}bis(3-pyridin-4-ylurea);
N',N'''-{[6-(8-oxa-3-azabicyclo[3.2.1]oct-3-yl)pyrimidine-2,4-diyl]di-4,1-phenylene}bis{1-[4-(4-methylpiperazin-1-yl)phenyl]urea};
4,4'-{[6-(8-oxa-3-azabicyclo[3.2.1]oct-3-yl)pyrimidine-2,4-diyl]bis(4,1-phenylenecarbamoylimino)}dibenzamide;
1-methyl-3-{4-[4-(1-methylethoxy)-6-(8-oxa-3-azabicyclo[3.2.1]oct-3-yl)pyrimidin-2-yl]phenyl}urea;
1-cyclopropyl-3-{4-[4-(1-methylethoxy)-6-(8-oxa-3-azabicyclo[3.2.1]oct-3-yl)pyrimidin-2-yl]phenyl}urea;
1-{4-[4-(1-methylethoxy)-6-(8-oxa-3-azabicyclo[3.2.1]oct-3-yl)pyrimidin-2-yl]phenyl}-3-pyridin-4-ylurea;
1-{4-[4-(1-methylethoxy)-6-(8-oxa-3-azabicyclo[3.2.1]oct-3-yl)pyrimidin-2-yl]phenyl}-3-[4-(4-methylpiperazin-1-yl)phenyl]urea;
1-methyl-3-(4-{4-[(1-methylethyl)amino]-6-(8-oxa-3-azabicyclo[3.2.1]oct-3-yl)pyrimidin-2-yl}phenyl)urea;
1-cyclopropyl-3-(4-{4-[(1-methylethyl)amino]-6-(8-oxa-3-azabicyclo[3.2.1]oct-3-yl)pyrimidin-2-yl}phenyl)urea;
1-(4-{4-[(1-methylethyl)amino]-6-(8-oxa-3-azabicyclo[3.2.1]oct-3-yl)pyrimidin-2-yl}phenyl)-3-pyridin-4-ylurea;
1-(4-{4-[(1-methylethyl)amino]-6-(8-oxa-3-azabicyclo[3.2.1]oct-3-yl)pyrimidin-2-yl}phenyl)-3-[4-(4-methylpiperazin-1-yl)phenyl]urea;
N~3~,N~3~-dimethyl-N-(4-[(1-methylethyl)amino]-6-(8-oxa-3-azabicyclo[3.2.1]oct-3-yl)-2-{4-[(pyridin-3-ylcarbamoyl)amino]phenyl}pyrimidin-5-yl)-beta-alaninamide;
1-methyl-3-{4-[4-(8-oxa-3-azabicyclo[3.2.1]oct-3-yl)-6-(trifluoromethyl)pyrimidin-2-yl]phenyl}urea;
1-cyclopropyl-3-{4-[4-(8-oxa-3-azabicyclo[3.2.1]oct-3-yl)-6-(trifluoromethyl)pyrimidin-2-yl]phenyl}urea;
2-hydroxyethyl {4-[4-(8-oxa-3-azabicyclo[3.2.1]oct-3-yl)-6-(trifluoromethyl)pyrimidin-2-yl]phenyl}carbamate;
1-{4-[4-(8-oxa-3-azabicyclo[3.2.1]oct-3-yl)-6-(trifluoromethyl)pyrimidin-2-yl]phenyl}-3-pyridin-4-ylurea;
1-[4-(4-methylpiperazin-1-yl)phenyl]-3-{4-[4-(8-oxa-3-azabicyclo[3.2.1]oct-3-yl)-6-(trifluoromethyl)pyrimidin-2-yl]phenyl}urea;
tert-butyl methyl(4-{[(4-{4-[(methylsulfonyl)methyl]-6-(8-oxa-3-azabicyclo[3.2.1]oct-3-yl)pyrimidin-2-yl}phenyl)carbamoyl]amino}benzyl)carbamate;
1-methyl-3-(4-{4-[(methylsulfonyl)methyl]-6-(8-oxa-3-azabicyclo[3.2.1]oct-3-yl)pyrimidin-2-yl}phenyl)urea;

1-ethyl-3-(4-{4-[(methylsulfonyl)methyl]-6-(8-oxa-3-azabicyclo[3.2.1]oct-3-yl)pyrimidin-2-yl}phenyl)urea;
1-cyclopropyl-3-(4-{4-[(methylsulfonyl)methyl]-6-(8-oxa-3-azabicyclo[3.2.1]oct-3-yl)pyrimidin-2-yl}phenyl)urea;
1-(4-{4-[(methylsulfonyl)methyl]-6-(8-oxa-3-azabicyclo[3.2.1]oct-3-yl)pyrimidin-2-yl}phenyl)-3-phenylurea;
1-(4-{4-[(methylsulfonyl)methyl]-6-(8-oxa-3-azabicyclo[3.2.1]oct-3-yl)pyrimidin-2-yl}phenyl)-3-pyridin-3-ylurea;
1-(4-{4-[(methylsulfonyl)methyl]-6-(8-oxa-3-azabicyclo[3.2.1]oct-3-yl)pyrimidin-2-yl}phenyl)-3-pyridin-4-ylurea;
1-[4-(4-methylpiperazin-1-yl)phenyl]-3-(4-{4-[(methylsulfonyl)methyl]-6-(8-oxa-3-azabicyclo[3.2.1]oct-3-yl)pyrimidin-2-yl}phenyl)urea;
1-(4-{4-[(methylsulfonyl)methyl]-6-(8-oxa-3-azabicyclo[3.2.1]oct-3-yl)pyrimidin-2-yl}phenyl)-3-(4-piperazin-1-ylphenyl)urea;
1-{4-[2-(dimethylamino)ethoxy]phenyl}-3-(4-{4-[(methylsulfonyl)methyl]-6-(8-oxa-3-azabicyclo[3.2.1]oct-3-yl)pyrimidin-2-yl}phenyl)urea;
1-{4-[(4-methylpiperazin-1-yl)methyl]phenyl}-3-(4-{4-[(methylsulfonyl)methyl]-6-(8-oxa-3-azabicyclo[3.2.1]oct-3-yl)pyrimidin-2-yl}phenyl)urea; and
1-{4-[(methylamino)methyl]phenyl}-3-(4-{4-[(methylsulfonyl)methyl]-6-(8-oxa-3-azabicyclo[3.2.1]oct-3-yl)pyrimidin-2-yl}phenyl)urea.

Illustrative compounds of the present Formula IV are set forth below:
1-[4-(4,6-di-3-oxa-8-azabicyclo[3.2.1]oct-8-ylpyrimidin-2-yl)phenyl]-3-pyridin-4-ylurea;
1-{4-[2-(dimethylamino)ethoxy]phenyl}-3-[4-(4,6-di-3-oxa-8-azabicyclo[3.2.1]oct-8-ylpyrimidin-2-yl)phenyl]urea;
1-[4-(4,6-di-3-oxa-8-azabicyclo[3.2.1]oct-8-ylpyrimidin-2-yl)phenyl]-3-[4-(4-methylpiperazin-1-yl)phenyl]urea;
1-[4-(4,6-di-3-oxa-8-azabicyclo[3.2.1]oct-8-ylpyrimidin-2-yl)phenyl]-3-{4-[(4-methylpiperazin-1-yl)methyl]phenyl}urea;
1-[4-(4,6-di-3-oxa-8-azabicyclo[3.2.1]oct-8-ylpyrimidin-2-yl)phenyl]-3-{4-[(4-methylpiperazin-1-yl)carbonyl]phenyl}urea;
1-{4-[4-(isopropylamino)-6-(3-oxa-8-azabicyclo[3.2.1]oct-8-yl)pyrimidin-2-yl]phenyl}-3-pyridin-4-ylurea;
1-{4-[2-(dimethylamino)ethoxy]phenyl}-3-{4-[4-(isopropylamino)-6-(3-oxa-8-azabicyclo[3.2.1]oct-8-yl)pyrimidin-2-yl]phenyl}urea;
1-{4-[4-(isopropylamino)-6-(3-oxa-8-azabicyclo[3.2.1]oct-8-yl)pyrimidin-2-yl]phenyl}-3-[4-(4-methylpiperazin-1-yl)phenyl]urea;
1-{4-[4-(isopropylamino)-6-(3-oxa-8-azabicyclo[3.2.1]oct-8-yl)pyrimidin-2-yl]phenyl}-3-{4-[(4-methylpiperazin-1-yl)methyl]phenyl}urea;
1-{4-[4-(isopropylamino)-6-(3-oxa-8-azabicyclo[3.2.1]oct-8-yl)pyrimidin-2-yl]phenyl}-3-[6-(4-methylpiperazin-1-yl)pyridin-3-yl]urea;
1-[4-(4,6-di-3-oxa-8-azabicyclo[3.2.1]oct-8-ylpyrimidin-2-yl)phenyl]-3-pyridin-3-ylurea;
1-[4-(5-chloro-4,6-di-3-oxa-8-azabicyclo[3.2.1]oct-8-ylpyrimidin-2-yl)phenyl]-3-pyridin-3-ylurea;
1-[4-(5-chloro-4,6-di-3-oxa-8-azabicyclo[3.2.1]oct-8-ylpyrimidin-2-yl)phenyl]-3-[4-(4-methylpiperazin-1-yl)phenyl]urea;
1-{4-[4-(3-oxa-8-azabicyclo[3.2.1]oct-8-yl)-6-(tetrahydro-2H-pyran-4-ylamino)pyrimidin-2-yl]phenyl}-3-pyridin-4-ylurea;
1-[4-(4-methylpiperazin-1-yl)phenyl]-3-{4-[4-(3-oxa-8-azabicyclo[3.2.1]oct-8-yl)-6-(tetrahydro-2H-pyran-4-ylamino)pyrimidin-2-yl]phenyl}urea;
1-{4-[4-{[2-(methylsulfonyl)ethyl]amino}-6-(3-oxa-8-azabicyclo[3.2.1]oct-8-yl)pyrimidin-2-yl]phenyl}-3-pyridin-3-ylurea;
1-{4-[(4-methylpiperazin-1-yl)methyl]phenyl}-3-{4-[4-{[2-(methylsulfonyl)ethyl]amino}-6-(3-oxa-8-azabicyclo[3.2.1]oct-8-yl)pyrimidin-2-yl]phenyl}urea;
1-{4-[4-(3-oxa-8-azabicyclo[3.2.1]oct-8-yl)-6-(tetrahydro-2H-pyran-4-ylamino)pyrimidin-2-yl]phenyl}-3-pyridin-3-ylurea;
1-{4-[2-(dimethylamino)ethoxy]phenyl}-3-{4-[4-(3-oxa-8-azabicyclo[3.2.1]oct-8-yl)-6-(tetrahydro-2H-pyran-4-ylamino)pyrimidin-2-yl]phenyl}urea;
1-{4-[4-{[2-(methylsulfonyl)ethyl]amino}-6-(3-oxa-8-azabicyclo[3.2.1]oct-8-yl)pyrimidin-2-yl]phenyl}-3-pyridin-4-ylurea;
1-{4-[2-(dimethylamino)ethoxy]phenyl}-3-{4-[4-{[2-(methylsulfonyl)ethyl]amino}-6-(3-oxa-8-azabicyclo[3.2.1]oct-8-yl)pyrimidin-2-yl]phenyl}urea;
1-[4-(4-methylpiperazin-1-yl)phenyl]-3-{4-[4-{[2-(methylsulfonyl)ethyl]amino}-6-(3-oxa-8-azabicyclo[3.2.1]oct-8-yl)pyrimidin-2-yl]phenyl}urea;
1-{4-[(4-methylpiperazin-1-yl)methyl]phenyl}-3-{4-[4-(3-oxa-8-azabicyclo[3.2.1]oct-8-yl)-6-(tetrahydro-2H-pyran-4-ylamino)pyrimidin-2-yl]phenyl}urea;
1-{4-[4-(diethylamino)-6-(3-oxa-8-azabicyclo[3.2.1]oct-8-yl)pyrimidin-2-yl]phenyl}-3-pyridin-4-ylurea;
1-{4-[4-(diethylamino)-6-(3-oxa-8-azabicyclo[3.2.1]oct-8-yl)pyrimidin-2-yl]phenyl}-3-[4-(4-methylpiperazin-1-yl)phenyl]urea;
1-(4-{4-[(1-methylethyl)amino]-6-(3-oxa-8-azabicyclo[3.2.1]oct-8-yl)pyrimidin-2-yl}phenyl)-3-[4-(pyrrolidin-1-ylmethyl)phenyl]urea;
1-(4-{4-[(1-methylethyl)amino]-6-(3-oxa-8-azabicyclo[3.2.1]oct-8-yl)pyrimidin-2-yl}phenyl)-3-pyridin-3-ylurea;
1-{4-[(dimethylamino)methyl]phenyl}-3-(4-{4-[(1-methylethyl)amino]-6-(3-oxa-8-azabicyclo[3.2.1]oct-8-yl)pyrimidin-2-yl}phenyl)urea;
1-(4-{4-[(1-methylethyl)amino]-6-(3-oxa-8-azabicyclo[3.2.1]oct-8-yl)pyrimidin-2-yl}phenyl)-3-[4-(2-pyrrolidin-1-ylethoxy)phenyl]urea;
1-(4-{4-[(dimethylamino)methyl]-6-(3-oxa-8-azabicyclo[3.2.1]oct-8-yl)pyrimidin-2-yl}phenyl)-3-pyridin-3-ylurea;
1-(4-{4-[(dimethylamino)methyl]-6-(3-oxa-8-azabicyclo[3.2.1]oct-8-yl)pyrimidin-2-yl}phenyl)-3-methylurea;
1-(4-{4-[(dimethylamino)methyl]-6-(3-oxa-8-azabicyclo[3.2.1]oct-8-yl)pyrimidin-2-yl}phenyl)-3-ethylurea;
1-(4-(4-(3-oxa-8-azabicyclo[3.2.1]octan-8-yl)-6-((dimethylamino)methyl)pyrimidin-2-yl)phenyl)-3-cyclopropylurea;
1-(4-(4-(3-oxa-8-azabicyclo[3.2.1]octan-8-yl)-6-((dimethylamino)methyl)pyrimidin-2-yl)phenyl)-3-(4-(4-methylpiperazin-1-yl)phenyl)urea;
1-(4-(4-(3-oxa-8-azabicyclo[3.2.1]octan-8-yl)-6-((dimethylamino)methyl)pyrimidin-2-yl)phenyl)-3-(4-(2-(dimethylamino)ethoxy)phenyl)urea;
1-(4-(4-(3-oxa-8-azabicyclo[3.2.1]octan-8-yl)-6-((dimethylamino)methyl)pyrimidin-2-yl)phenyl)-3-(4-((dimethylamino)methyl)phenyl)urea;
1-(4-(4-(3-oxa-8-azabicyclo[3.2.1]octan-8-yl)-6-((dimethylamino)methyl)pyrimidin-2-yl)phenyl)-3-phenylurea;

1-{4-[4-(3-oxa-8-azabicyclo[3.2.1]oct-8-yl)-6-(tetrahydro-2H-pyran-4-yl)pyrimidin-2-yl]phenyl}-3-pyridin-3-ylurea;
1-{4-[4-(3-oxa-8-azabicyclo[3.2.1]oct-8-yl)-6-(tetrahydro-2H-pyran-4-yl)pyrimidin-2-yl]phenyl}-3-pyridin-4-ylurea;
1-[4-(4-methylpiperazin-1-yl)phenyl]-3-{4-[4-(3-oxa-8-azabicyclo[3.2.1]oct-8-yl)-6-(tetrahydro-2H-pyran-4-yl)pyrimidin-2-yl]phenyl}urea;
1-[6-(4-methylpiperazin-1-yl)pyridin-3-yl]-3-{4-[4-(3-oxa-8-azabicyclo[3.2.1]oct-8-yl)-6-(tetrahydro-2H-pyran-4-yl)pyrimidin-2-yl]phenyl}urea;
1-{4-[(4-methylpiperazin-1-yl)carbonyl]phenyl}-3-{4-[4-(3-oxa-8-azabicyclo[3.2.1]oct-8-yl)-6-(tetrahydro-2H-pyran-4-yl)pyrimidin-2-yl]phenyl}urea;
1-(4-{[4-(1-methylethyl)piperazin-1-yl]carbonyl}phenyl)-3-{4-[4-(3-oxa-8-azabicyclo[3.2.1]oct-8-yl)-6-(tetrahydro-2H-pyran-4-yl)pyrimidin-2-yl]phenyl}urea;
1-{4-[2-(dimethylamino)ethoxy]phenyl}-3-{4-[4-(3-oxa-8-azabicyclo[3.2.1]oct-8-yl)-6-(tetrahydro-2H-pyran-4-yl)pyrimidin-2-yl]phenyl}urea;
1-(4-{4-[(3R)-3-methylmorpholin-4-yl]-6-(3-oxa-8-azabicyclo[3.2.1]oct-8-yl)pyrimidin-2-yl}phenyl)-3-pyridin-4-ylurea;
1-(4-{4-[(3R)-3-methylmorpholin-4-yl]-6-(3-oxa-8-azabicyclo[3.2.1]oct-8-yl)pyrimidin-2-yl}phenyl)-3-[4-(4-methylpiperazin-1-yl)phenyl]urea;
1-(4-{4-[(3R)-3-methylmorpholin-4-yl]-6-(3-oxa-8-azabicyclo[3.2.1]oct-8-yl)pyrimidin-2-yl}phenyl)-3-[6-(4-methylpiperazin-1-yl)pyridin-3-yl]urea;
1-(4-{4-[(2R,6S)-2,6-dimethylmorpholin-4-yl]-6-(3-oxa-8-azabicyclo[3.2.1]oct-8-yl)pyrimidin-2-yl}phenyl)-3-pyridin-4-ylurea;
1-(4-{4-[(2R,6S)-2,6-dimethylmorpholin-4-yl]-6-(3-oxa-8-azabicyclo[3.2.1]oct-8-yl)pyrimidin-2-yl}phenyl)-3-[4-(4-methylpiperazin-1-yl)phenyl]urea;
1-(4-{4-[(2R,6S)-2,6-dimethylmorpholin-4-yl]-6-(3-oxa-8-azabicyclo[3.2.1]oct-8-yl)pyrimidin-2-yl}phenyl)-3-[6-(4-methylpiperazin-1-yl)pyridin-3-yl]urea;
1-(4-{4-[(2R,6S)-2,6-dimethylmorpholin-4-yl]-6-(3-oxa-8-azabicyclo[3.2.1]oct-8-yl)pyrimidin-2-yl}phenyl)-3-{4-[(4-methylpiperazin-1-yl)carbonyl]phenyl}urea;
1-(4-{4-[(2R,6S)-2,6-dimethylmorpholin-4-yl]-6-(3-oxa-8-azabicyclo[3.2.1]oct-8-yl)pyrimidin-2-yl}phenyl)-3-(4-{[4-(1-methylethyl)piperazin-1-yl]carbonyl}phenyl)urea;
1-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)-3-pyridin-4-ylurea;
1-[4-(4-methylpiperazin-1-yl)phenyl]-3-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)urea;
1-{4-[(dimethylamino)methyl]phenyl}-3-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)urea;
1-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)-3-pyridin-4-ylurea;
1-[4-(4-methylpiperazin-1-yl)phenyl]-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea;
1-{4-[(4-methylpiperazin-1-yl)methyl]phenyl}-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea;
1-{4-[2-(dimethylamino)ethoxy]phenyl}-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea;
1-(4-{4-[(3R)-3-methylmorpholin-4-yl]-6-(3-oxa-8-azabicyclo[3.2.1]oct-8-yl)pyrimidin-2-yl}phenyl)-3-pyridin-3-ylurea;
1-(4-{4-[(3R)-3-methylmorpholin-4-yl]-6-(3-oxa-8-azabicyclo[3.2.1]oct-8-yl)pyrimidin-2-yl}phenyl)-3-{4-[(4-methylpiperazin-1-yl)methyl]phenyl}urea;
1-{4-[2-(dimethylamino)ethoxy]phenyl}-3-(4-{4-[(3R)-3-methylmorpholin-4-yl]-6-(3-oxa-8-azabicyclo[3.2.1]oct-8-yl)pyrimidin-2-yl}phenyl)urea;
N,N-dimethyl-4-{[(4-{4-[(3R)-3-methylmorpholin-4-yl]-6-(3-oxa-8-azabicyclo[3.2.1]oct-8-yl)pyrimidin-2-yl}phenyl)carbamoyl]amino}benzamide;
1-(4-{4-[(3R)-3-methylmorpholin-4-yl]-6-(3-oxa-8-azabicyclo[3.2.1]oct-8-yl)pyrimidin-2-yl}phenyl)-3-{4-[(4-methylpiperazin-1-yl)carbonyl]phenyl}urea;
1-(4-{[4-(1-methylethyl)piperazin-1-yl]carbonyl}phenyl)-3-(4-{4-[(3R)-3-methylmorpholin-4-yl]-6-(3-oxa-8-azabicyclo[3.2.1]oct-8-yl)pyrimidin-2-yl}phenyl)urea; and
1-(4-{4-[(dimethylamino)methyl]-6-(3-oxa-8-azabicyclo[3.2.1]oct-8-yl)pyrimidin-2-yl}phenyl)-3-methylurea.

Illustrative compounds of the present Formula VI are set forth below:
1-[4-(2,6-di-8-oxa-3-azabicyclo[3.2.1]oct-3-ylpyrimidin-4-yl)phenyl]-3-methylurea;
1-[4-(2,6-di-8-oxa-3-azabicyclo[3.2.1]oct-3-ylpyrimidin-4-yl)phenyl]-3-pyridin-4-ylurea;
1-[4-(2,6-di-8-oxa-3-azabicyclo[3.2.1]oct-3-ylpyrimidin-4-yl)phenyl]-3-[4-(4-methylpiperazin-1-yl)phenyl]urea; and
1-cyclopropyl-3-[4-(2,6-di-8-oxa-3-azabicyclo[3.2.1]oct-3-ylpyrimidin-4-yl)phenyl]urea.

Intermediates useful for making compounds of the present Formula I are set forth below:
4-[4-(8-oxa-3-azabicyclo[3.2.1]oct-3-yl)pyrimidin-2-yl]aniline;
4-[4-chloro-6-(8-oxa-3-azabicyclo[3.2.1]oct-3-yl)pyrimidin-2-yl]aniline;
4-[2-chloro-6-(8-oxa-3-azabicyclo[3.2.1]oct-3-yl)pyrimidin-4-yl]aniline;
8,8'-[2-(4-nitrophenyl)pyrimidine-4,6-diyl]bis(3-oxa-8-azabicyclo[3.2.1]octane);
4-(4,6-di-3-oxa-8-azabicyclo[3.2.1]oct-8-ylpyrimidin-2-yl)aniline;
4-{4-[(methylsulfonyl)methyl]-6-(8-oxa-3-azabicyclo[3.2.1]oct-3-yl)pyrimidin-2-yl}aniline;
4-(5-chloro-4,6-di-3-oxa-8-azabicyclo[3.2.1]oct-8-ylpyrimidin-2-yl)aniline;
9-(6-chloro-2-(4-nitrophenyl)pyrimidin-4-yl)-3,7-dioxa-9-azabicyclo[3.3.1]nonane;
6-(3,7-dioxa-9-azabicyclo[3.3.1]nonan-9-yl)-N-isopropyl-2-(4-nitrophenyl)pyrimidin-4-amine;
2-(4-aminophenyl)-6-(3,7-dioxa-9-azabicyclo[3.3.1]nonan-9-yl)-N-isopropylpyrimidin-4-amine;
6-(3-oxa-8-azabicyclo[3.2.1]octan-8-yl)-2-(4-nitrophenyl)-N-(tetrahydro-2H-pyran-4-yl)pyrimidin-4-amine;
2-(4-aminophenyl)-6-(3-oxa-8-azabicyclo[3.2.1]octan-8-yl)-N-(tetrahydro-2H-pyran-4-yl)pyrimidin-4-amine;
6-(3-oxa-8-azabicyclo[3.2.1]octan-8-yl)-N-(2-(methylsulfonyl)ethyl)-2-(4-nitrophenyl)pyrimidin-4-amine;
2-(4-aminophenyl)-6-(3-oxa-8-azabicyclo[3.2.1]octan-8-yl)-N-(2-(methylsulfonyl)ethyl)pyrimidin-4-amine;
6-(3-oxa-8-azabicyclo[3.2.1]octan-8-yl)-N,N-diethyl-2-(4-nitrophenyl)pyrimidin-4-amine;
2-(4-aminophenyl)-6-(3-oxa-8-azabicyclo[3.2.1]octan-8-yl)-N,N-diethylpyrimidin-4-amine;

4-(4-(3-oxa-8-azabicyclo[3.2.1]octan-8-yl)-6-((dimethylamino)methyl)pyrimidin-2-yl)aniline;

8-[6-(3,6-dihydro-2H-pyran-4-yl)-2-(4-nitrophenyl)pyrimidin-4-yl]-3-oxa-8-azabicyclo[3.2.1]octane; and 4-[4-(3-oxa-8-azabicyclo[3.2.1]oct-8-yl)-6-(tetrahydro-2H-pyran-4-yl)pyrimidin-2-yl]aniline.

In other aspects, the invention provides pharmaceutical compositions comprising compounds or pharmaceutically acceptable salts of the compounds of the present Formula I and a pharmaceutically acceptable carrier.

In other aspects, the invention provides that the pharmaceutically acceptable carrier suitable for oral administration and the composition comprises an oral dosage form.

In other aspects, the invention provides a composition comprising a compound of Formula I; a second compound selected from the group consisting of a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, docetaxel, paclitaxel, leucovorin, levamisole, irinotecan, estramustine, etoposide, nitrogen mustards, BCNU, carmustine, lomustine, vinblastine, vincristine, vinorelbine, cisplatin, carboplatin, oxaliplatin, imatinib mesylate, Avastin (bevacizumab), hexamethylmelamine, topotecan, tyrosine kinase inhibitors, tyrphostins, herbimycin A, genistein, erbstatin, lavendustin A, hydroxyzine, glatiramer acetate, interferon beta-1a, interferon beta-1b, and natalizumab and lavendustin A; and a pharmaceutically acceptable carrier.

In other aspects, the second compound is Avastin.

In other aspects, the invention provides a method of treating a PI3K-related disorder, comprising administering to a mammal in need thereof a compound of Formula I in an amount effective to treat a PI3K-related disorder.

In other aspects, the PI3K-related disorder is selected from restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, and cancer.

In other aspects, the PI3K-related disorder is cancer.

In other aspects, the cancer is selected from the group consisting of leukemia, skin cancer, bladder cancer, breast cancer, uterus cancer, ovary cancer, prostate cancer, lung cancer, colon cancer, pancreas cancer, renal cancer, gastric cancer, and brain cancer.

In other aspects, the invention provides a method of treating an mTOR-related disorder, comprising administering to a mammal in need thereof a compound of Formula I in an amount effective to treat an mTOR-related disorder.

In other aspects, the mTOR-related disorder is selected from restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, and cancer.

In other aspects, the mTOR-related disorder is cancer.

In other aspects, the cancer is selected from the group consisting of leukemia, skin cancer, bladder cancer, breast cancer, uterus cancer, ovary cancer, prostate cancer, lung cancer, colon cancer, pancreas cancer, renal cancer, gastric cancer, and brain cancer.

In other aspects, the invention provides a method of treating an hSMG-1-related disorder, comprising administering to a mammal in need thereof a compound of Formula I in an amount effective to treat an hSMG-1-related disorder.

In other aspects, the hSMG-1-related disorder is selected from restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, and cancer.

In other aspects, the hSMG-1-related disorder is cancer.

In other aspects, the cancer is selected from the group consisting of leukemia, skin cancer, bladder cancer, breast cancer, uterus cancer, ovary cancer, prostate cancer, lung cancer, colon cancer, pancreas cancer, renal cancer, gastric cancer, and brain cancer.

In other aspects, the invention provides a method of treating advanced renal cell carcinoma, comprising administering to a mammal in need thereof a compound of Formula I in an amount effective to treat advanced renal cell carcinoma.

In other aspects, the invention provides a method of treating acute lymphoblastic leukemia, comprising administering to a mammal in need thereof a compound of Formula I in an amount effective to treat acute lymphoblastic leukemia.

In other aspects, the invention provides a method of treating acute malignant melanoma, comprising administering to a mammal in need thereof a compound of Formula I in an amount effective to treat malignant melanoma.

In other aspects, the invention provides a method of treating soft-tissue or bone sarcoma, comprising administering to a mammal in need thereof a compound of Formula I in an amount effective to treat soft-tissue or bone sarcoma.

In other aspects, the invention provides a method of treating a cancer selected from the group consisting of leukemia, skin cancer, bladder cancer, breast cancer, uterus cancer, ovary cancer, prostate cancer, lung cancer, colon cancer, pancreas cancer, renal cancer, gastric cancer, and brain cancer comprising administering to a mammal in need thereof a composition comprising a compound of Formula I; a second compound selected from the group consisting of a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, docetaxel, paclitaxel, leucovorin, levamisole, irinotecan, estramustine, etoposide, nitrogen mustards, BCNU, carmustine, lomustine, vinblastine, vincristine, vinorelbine, cisplatin, carboplatin, oxaliplatin, imatinib mesylate, Avastin (bevacizumab), hexamethylmelamine, topotecan, tyrosine kinase inhibitors, tyrphostins, herbimycin A, genistein, erbstatin, and lavendustin A; and a pharmaceutically acceptable carrier. in an amount effective to treat the cancer.

In other aspects, the invention provides a method of inhibiting mTOR in a subject, comprising administering to a subject in need thereof a compound of Formula I in an amount effective to inhibit mTOR.

In other aspects, the invention provides a method of inhibiting PI3K in a subject, comprising administering to a subject in need thereof a compound of Formula I in an amount effective to inhibit PI3K.

In other aspects, the invention provides a method of inhibiting hSMG-1 in a subject, comprising administering to a subject in need thereof a compound of Formula I in an amount effective to inhibit hSMG-1.

In other aspects, the invention provides a method of inhibiting mTOR, PI3K, and hSMG-1 together in a subject, comprising administering to a subject in need thereof a compound of Formula I in an amount effective to inhibit mTOR, PI3K, and hSMG-1.

In other aspects, the invention provides a method of synthesizing a compound of Formula 68:

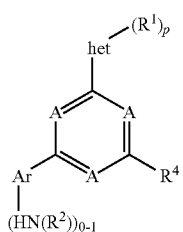

comprising reacting a pyrimidine compound of the formula 66:

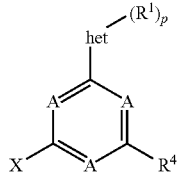

with a dioxaborolan-2-yl compound 67:

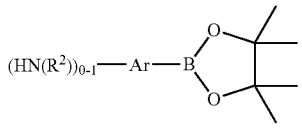

to give 68 wherein the variables are as defined for Formula I.

In other aspects, the invention provides a method of synthesizing a compound of Formula I further comprising, when $N(R^2)H$ is present, reacting compound 68 with an acylating agent $R^3C(O)X$, wherein X is a leaving group, and wherein $R^3$ is as defined in Formula I to give I:

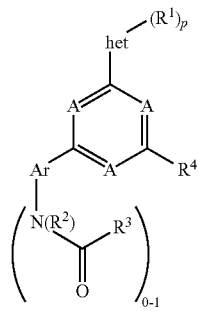

or a pharmaceutically acceptable salt thereof.

Representative "pharmaceutically acceptable salts" include but are not limited to, e.g., water-soluble and water-insoluble salts, such as the acetate, aluminum, amsonate (4,4-diaminostilbene-2,2-disulfonate), benzathine (N,N'-dibenzylethylenediamine), benzenesulfonate, benzoate, bicarbonate, bismuth, bisulfate, bitartrate, borate, bromide, butyrate, calcium, calcium edetate, camsylate (camphorsulfonate), carbonate, chloride, choline, citrate, clavulariate, diethanolamine, dihydrochloride, diphosphate, edetate, edisylate (camphorsulfonate), esylate (ethanesulfonate), ethylenediamine, fumarate, gluceptate (glucoheptonate), gluconate, glucuronate, glutamate, hexafluorophosphate, hexylresorcinate, hydrabamine (N,N'-bis(dehydroabietyl) ethylenediamine), hydrobromide, hydrochloride, hydroxynaphthoate, 1-hydroxy-2-naphthoate, 3-hydroxy-2-naphthoate, iodide, isothionate (2-hydroxyethanesulfonate), lactate, lactobionate, laurate, lauryl sulfate, lithium, magnesium, malate, maleate, mandelate, meglumine (1-deoxy-1-(methylamino)-D-glucitol), mesylate, methyl bromide, methylnitrate, methylsulfate, mucate, napsylate, nitrate, N-methylglucamine ammonium salt, oleate, oxalate, palmitate, pamoate (4,4'-methylenebis-3-hydroxy-2-naphthoate, or embonate), pantothenate, phosphate, picrate, polygalacturonate, potassium, propionate, p-toluenesulfonate, salicylate, sodium, stearate, subacetate, succinate, sulfate, sulfosalicylate, suramate, tannate, tartrate, teoclate (8-chloro-3,7-dihydro-1,3-dimethyl-1H-purine-2,6-dione), triethiodide, tromethamine (2-amino-2-(hydroxymethyl)-1,3-propanediol), valerate, and zinc salts.

Some compounds within the present invention possess one or more chiral centers, and the present invention includes each separate enantiomer of such compounds as well as mixtures of the enantiomers. Where multiple chiral centers exist in compounds of the present invention, the invention includes each combination as well as mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

An "effective amount" when used in connection a compound of the present invention of this invention is an amount effective for inhibiting mTOR or PI3K in a subject.

DEFINITIONS

The following definitions are used in connection with the compounds of the present invention unless the context indicates otherwise. In general, the number of carbon atoms present in a given group is designated "$C_x$-$C_y$," where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like.

"Acyl-" refers to a group having a straight, branched, or cyclic configuration or a combination thereof, attached to the parent structure through a carbonyl functionality. Such groups may be saturated or unsaturated, aliphatic or aromatic, and carbocyclic or heterocyclic. Examples of a $C_1$-$C_8$acyl-group include acetyl-, benzoyl-, nicotinoyl-, propionyl-, isobutyryl-, oxalyl-, and the like. Lower-acyl refers to acyl groups containing one to four carbons. An acyl group can be unsubstituted or substituted with one or more of the following groups: halogen, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2NC(O)$—, ($C_1$-$C_6$alkyl)NHC(O)—, di($C_1$-$C_6$alkyl)NC(O)—, —CN, hydroxyl, $C_1$-$C_6$alkoxy-, $HO_2C-$, $(C_1$-$C_6$alkoxy)carbonyl-, $(C_1$-$C_6$alkyl)C(O)-, $C_6$-$C_{14}$aryl-, $C_1$-$C_9$heteroaryl-, or $C_3$-$C_8$cycloalkyl-.

"Alkenyl-" refer to a straight or branched chain unsaturated hydrocarbon containing at least one double bond. Examples of a $C_2$-$C_{10}$alkenyl- group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene and 5-decene. An alkenyl- group can be unsubstituted or substituted with one or more of the following groups: halogen, $H_2N-$, $(C_1$-$C_6$alkyl)amino-, di($C_1$-$C_6$alkyl)amino-, $(C_1$-$C_6$alkyl)C(O)N($C_1$-$C_3$alkyl)-, $(C_1$-$C_6$alkyl)carboxyamido-, $HC(O)NH-$, $H_2NC(O)-$, $(C_1$-$C_6$alkyl)NHC(O)-, di($C_1$-$C_6$alkyl)NC(O)-, $NC-$, hydroxyl, $C_1$-$C_6$alkoxy-, $C_1$-$C_6$alkyl-, $HO_2C-$, $(C_1$-$C_6$alkoxy)carbonyl-, $(C_1$-$C_6$alkyl)C(O)-, $C_6$-$C_{14}$aryl-, $C_1$-$C_9$heteroaryl-, and $C_3$-$C_8$cycloalkyl-.

"Alkoxy-" refers to the group $R-O-$ where R is an alkyl group, as defined below. Exemplary $C_1$-$C_6$alkoxy- groups include but are not limited to methoxy, ethoxy, n-propoxy, 1-propoxy, n-butoxy and t-butoxy. An alkoxy group can be unsubstituted or substituted with one or more of the following groups: halogen, hydroxyl, $C_1$-$C_6$alkoxy-, $H_2N-$, $(C_1$-$C_6$alkyl)amino-, di($C_1$-$C_6$alkyl)amino-, $(C_1$-$C_6$alkyl)C(O)N($C_1$-$C_3$alkyl)-, $(C_1$-$C_6$alkyl)carboxyamido-, $HC(O)NH-$, $H_2NC(O)-$, $(C_1$-$C_6$alkyl)NHC(O)-, di($C_1$-$C_6$alkyl)NC(O)-, $NC-$, $C_1$-$C_6$alkoxy-, $HO_2C-$, $(C_1$-$C_6$alkoxy)carbonyl-, $(C_1$-$C_6$alkyl)C(O)-, $C_1$-$C_9$heteroaryl-, $C_3$-$C_8$cycloalkyl-, $C_1$-$C_6$haloalkyl-, amino($C_1$-$C_6$alkyl)-, $(C_1$-$C_6$alkyl)carboxyl-, $C_1$-$C_6$-carboxyamidoalkyl-, or $O_2N-$.

"(Alkoxy)carbonyl-" refers to the group alkyl-O—C(O)—. Exemplary $(C_1$-$C_6$alkoxy)carbonyl- groups include but are not limited to methoxy, ethoxy, n-propoxy, 1-propoxy, n-butoxy and t-butoxy. An (alkoxy)carbonyl group can be unsubstituted or substituted with one or more of the following groups: halogen, hydroxyl, $H_2N-$, $(C_1$-$C_6$alkyl)amino-, di($C_1$-$C_6$alkyl)amino-, $(C_1$-$C_6$alkyl)C(O)N($C_1$-$C_3$alkyl)-, $(C_1$-$C_6$alkyl)carboxyamido-, $HC(O)NH-$, $H_2NC(O)-$, $(C_1$-$C_6$alkyl)NHC(O)-, di($C_1$-$C_6$alkyl)NC(O)-, $NC-$, $C_1$-$C_6$alkoxy-, $HO_2C-$, $(C_1$-$C_6$alkoxy)carbonyl-, $(C_1$-$C_6$alkyl)C(O)-, $C_1$-$C_9$heteroaryl-, $C_3$-$C_8$cycloalkyl-, $C_1$-$C_6$haloalkyl-, amino($C_1$-$C_6$alkyl)-, $(C_1$-$C_6$alkyl)carboxyl-, $C_1$-$C_6$-carboxyamidoalkyl-, or $O_2N-$.

"Alkyl-" refers to a hydrocarbon chain that may be a straight chain or branched chain, containing the indicated number of carbon atoms, for example, a $C_1$-$C_{10}$alkyl- group may have from 1 to 10 (inclusive) carbon atoms in it. In the absence of any numerical designation, "alkyl" is a chain (straight or branched) having 1 to 6 (inclusive) carbon atoms in it. Examples of $C_1$-$C_6$alkyl- groups include, but are not limited to, methyl, ethyl, propyl, butyl, pentyl, hexyl, isopropyl, isobutyl, sec-butyl, tert-butyl, isopentyl, neopentyl, and isohexyl. An alkyl- group can be unsubstituted or substituted with one or more of the following groups: halogen, $H_2N-$, $(C_1$-$C_6$alkyl)amino-, di($C_1$-$C_6$alkyl)amino-, $(C_1$-$C_6$alkyl)C(O)N($C_1$-$C_3$alkyl)-, $(C_1$-$C_6$alkyl)carboxyamido-, $HC(O)NH-$, $H_2NC(O)-$, $(C_1$-$C_6$alkyl)NHC(O)-, di($C_1$-$C_6$alkyl)NC(O)-, $NC-$, hydroxyl, $C_1$-$C_6$alkoxy-, $C_1$-$C_6$alkyl-, $HO_2C-$, $(C_1$-$C_6$alkoxy)carbonyl-, $(C_1$-$C_6$alkyl)C(O)-, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, $(C_1$-$C_6$alkyl)carboxyl-, $C_1$-$C_6$-carboxyamidoalkyl-, or $O_2N-$.

"(Alkyl)amido-" refers to a $-C(O)NH-$ group in which the nitrogen atom of said group is attached to a $C_1$-$C_6$alkyl group, as defined above. Representative examples of a $(C_1$-$C_6$alkyl)amido- group include, but are not limited to, $-C(O)NHCH_3$, $-C(O)NHCH_2CH_3$, $-C(O)NHCH_2CH_2CH_3$, $-C(O)NHCH_2CH_2CH_2CH_3$, $-C(O)NHCH_2CH_2CH_2CH_2CH_3$, $-C(O)NHCH(CH_3)_2$, $-C(O)NHCH_2CH(CH_3)_2$, $-C(O)NHCH(CH_3)CH_2CH_3$, $-C(O)NH-C(CH_3)_3$ and $-C(O)NHCH_2C(CH_3)_3$.

"(Alkyl)amino-" refers to an $-NH$ group, the nitrogen atom of said group being attached to an alkyl group, as defined above. Representative examples of an $(C_1$-$C_6$alkyl)amino- group include, but are not limited to $CH_3NH-$, $CH_3CH_2NH-$, $CH_3CH_2CH_2NH-$, $CH_3CH_2CH_2CH_2NH-$, $(CH_3)_2CHNH-$, $(CH_3)_2CHCH_2NH-$, $CH_3CH_2CH(CH_3)NH-$ and $(CH_3)_3CNH-$. An (alkyl)amino group can be unsubstituted or substituted with one or more of the following groups: halogen, $H_2N-$, $(C_1$-$C_6$alkyl)amino-, di($C_1$-$C_6$alkyl)amino-, $(C_1$-$C_6$alkyl)C(O)N($C_1$-$C_3$alkyl)-, $(C_1$-$C_6$alkyl)carboxyamido-, $HC(O)NH-$, $H_2NC(O)-$, $(C_1$-$C_6$alkyl)NHC(O)-, di($C_1$-$C_6$alkyl)NC(O)-, $NC-$, hydroxyl, $C_1$-$C_6$alkoxy-, $HO_2C-$, $(C_1$-$C_6$alkoxy)carbonyl-, $(C_1$-$C_6$alkyl)C(O)-, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, $(C_1$-$C_6$alkyl)carboxyl-, $C_1$-$C_6$-carboxyamidoalkyl-, or $O_2N-$.

"(Alkyl)carboxyamido-" refers to a $-NHC(O)-$ group in which the carbonyl carbon atom of said group is attached to a $C_1$-$C_6$alkyl group, as defined above. Representative examples of a $(C_1$-$C_6$alkyl)carboxyamido- group include, but are not limited to, $-NHC(O)CH_3$, $-NHC(O)CH_2CH_3$, $-NHC(O)CH_2CH_2CH_3$, $-NHC(O)CH_2CH_2CH_2CH_3$, $-NHC(O)CH_2CH_2CH_2CH_2CH_3$, $-NHC(O)CH(CH_3)_2$, $-NHC(O)CH_2CH(CH_3)_2$, $-NHC(O)CH(CH_3)CH_2CH_3$, $-NHC(O)-C(CH_3)_3$ and $-NHC(O)CH_2C(CH_3)_3$.

"Alkylcarboxyl-" refers to an alkyl group, defined above that is attached to the parent structure through the oxygen atom of a carboxyl (C(O)—O—) functionality. Examples of $(C_1$-$C_6$alkyl)carboxyl- include acetoxy, propionoxy, propylcarboxyl, and isopentylcarboxyl.

"-Alkylene-", "-alkenylene-", and "-alkynylene-" refer to alkyl-, alkenyl-, and alkynyl- groups, as defined above, having two points of attachment within a chemical structure. Examples of $-C_1$-$C_6$alkylene- include methylene ($-CH_2-$), ethylene ($-CH_2CH_2-$), propylene ($-CH_2CH_2CH_2-$), and dimethylpropylene ($-CH_2C(CH_3)_2CH_2-$). Likewise, examples of $-C_2$-$C_6$alkenylene- include ethenylene ($-CH=CH-$ and propenylene ($-CH=CH-CH_2-$). Examples of $-C_2$-$C_6$alkynylene- include ethynylene ($-C\equiv C-$) and propynylene ($-C\equiv C-CH_2-$).

"Alkynyl-" refers to a straight or branched chain unsaturated hydrocarbon containing at least one triple bond. Examples of a $C_2$-$C_{10}$alkynyl- group include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne, isohexyne, 1-heptyne, 2-heptyne, 3-heptyne, 1-octyne, 2-octyne, 3-octyne, 4-octyne, 1-nonyne, 2-nonyne, 3-nonyne, 4-nonyne, 1-decyne, 2-decyne, 3-decyne, 4-decyne and 5-decyne. An alkynyl group can be unsubstituted or substituted with one or more of the following groups: halogen, $H_2N-$, $(C_1$-$C_6$alkyl)amino-, di($C_1$-$C_6$alkyl)amino-, $(C_1$-$C_6$alkyl)C(O)N($C_1$-$C_3$alkyl)-, $(C_1$-$C_6$alkyl)carboxyamido-, $HC(O)NH-$, $H_2NC(O)-$, $(C_1$-$C_6$alkyl)NHC(O)-, di($C_1$-$C_6$alkyl)NC(O)-, $NC-$, hydroxyl, $C_1$-$C_6$alkoxy-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, and $C_3$-$C_8$cycloalkyl-.

"Amine-protecting group" refers to a radical when attached to a nitrogen atom in a target molecule is capable of surviving subsequent chemical reactions applied to the target molecule i.e. hydrogenation, reaction with acylating agents, alkylation etc. The amine-protecting group can later be removed. Amine protecting groups include, but are not limited to, fluorenylmethoxycarbonyl (FMOC), tert-butoxycarbonyl (t-BOC), benzyloxycarbonyl (Z), those of the acyl type (e.g., formyl, benzoyl, trifluoroacetyl, p-tosyl, aryl- and alkylphosphoryl, phenyl- and benzylsulfonyl, o-nitrophenylsulfenyl, o-nitrophenoxyacetyl), and of the urethane type (e.g. tosyloxyalkyloxy-, cyclopentyloxy-, cyclohexyloxy-, 1,1-dimethylpropyloxy, 2-(p-biphenyl)-2-propyloxy- and benzylthiocarbonyl). Amine-protecting groups are made using a reactive agent capable of transferring an amine-protecting group to a nitrogen atom in the target molecule. Examples of an amine-protecting agent include, but are not limited to, $C_1$-$C_6$ aliphatic acid chlorides or anhydrides, $C_6$-$C_{14}$arylcarboxylic acid chlorides or anhydrides, t-butylchloroformate, di-tert-butyl dicarbonate, butoxycarbonyloxyimino-2-phenylacetonitrile, t-butoxycarbonyl azide, t-butylfluoroformate, fluorenylmethoxycarbonyl chloride, fluorenylmethoxycarbonyl azide, fluorenylmethoxycarbonyl benzotriazol-1-yl, (9-fluorenylmethoxycarbonyl)succinimidyl carbonate, fluorenylmethoxycarbonyl pentafluorophexoxide, trichloroacetyl chloride, methyl-, ethyl-, trichloromethyl- chloroformate, and other amine protecting agents known in the art. Examples of such known amine-protecting agents are found in pages 385-397 of T. W. Green, P. G. M. Wuts, "Protective Groups in Organic Synthesis, Second Edition", Wiley-Interscience, New York, 1991.

"Amino(alkyl)-" refers to an alkyl group, as defined above, wherein one or more of the alkyl group's hydrogen atoms have been replaced with —$NH_2$. Representative examples of an amino($C_1$-$C_6$alkyl) group include, but are not limited to —$CH_2NH_2$, —$CH_2CH_2NH_2$, —$CH_2CH_2CH_2$ $NH_2$, —$CH_2CH_2CH_2CH_2NH_2$, —$CH_2CH(NH_2)CH_3$, —$CH_2CH(NH_2)CH_2CH_3$, —$CH(NH_2)CH_2CH_3$ and —$C(CH_3)_2(CH_2NH_2)$, —$CH_2CH_2CH_2CH_2CH_2NH_2$, and —$CH_2CH_2CH(NH_2)CH_2CH_3$. An amino(alkyl) group can be unsubstituted or substituted with one or two of the following groups $C_1$-$C_6$alkoxy, $C_6$-$C_{14}$aryl, $C_1$-$C_9$heteroaryl, $C_3$-$C_8$cycloalkyl, and $C_1$-$C_6$alkyl.

"Aryl-" refers to an aromatic hydrocarbon group. Examples of an $C_6$-$C_{14}$aryl- group include, but are not limited to, phenyl, 1-naphthyl, 2-naphthyl, 3-biphen-1-yl, anthryl, tetrahydronaphthyl, fluorenyl, indanyl, biphenylenyl, and acenaphthenyl. An aryl group can be unsubstituted or substituted with one or more of the following groups: $C_1$-$C_6$alkyl-, halogen, haloalkyl-, hydroxyl, hydroxyl($C_1$-$C_6$alkyl)-, $H_2N$—, amino($C_1$-$C_6$alkyl)-, di($C_1$-$C_6$alkyl)amino-, $HO_2C$—, ($C_1$-$C_6$alkoxy)carbonyl-, ($C_1$-$C_6$alkyl)carboxyl-, di($C_1$-$C_6$alkyl)amido-, $H_2NC(O)$—, ($C_1$-$C_6$alkyl)amido-, or $O_2N$—.

"(Aryl)alkyl-" refers to an alkyl group, as defined above, wherein one or more of the alkyl group's hydrogen atoms have been replaced with an aryl group as defined above. ($C_6$-$C_{14}$Aryl)alkyl- moieties include benzyl, benzhydryl, 1-phenylethyl, 2-phenylethyl, 3-phenylpropyl, 2-phenylpropyl, 1-naphthylmethyl, 2-naphthylmethyl and the like. An (aryl)alkyl group can be unsubstituted or substituted with one or more of the following groups: halogen, $H_2N$—, hydroxyl, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O) NH—, $H_2NC(O)$—, ($C_1$-$C_6$alkyl)NHC(O)—, di($C_1$-$C_6$alkyl) NC(O)—, NC—, hydroxyl, $C_1$-$C_6$alkoxy-, $C_1$-$C_6$alkyl-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, ($C_1$-$C_6$alkyl)carboxyl-, $C_1$-$C_6$-carboxyamidoalkyl-, or $O_2N$—.

"Carboxyamidoalkyl-" refers to a primary carboxamide ($CONH_2$), a secondary carboxyamide (CONHR') or a tertiary carboxyamide (CONR'R"), where R' and R" are the same or different substituent groups selected from $C_1$-$C_6$alkyl-, $C_2$-$C_6$alkenyl, $C_2$-$C_6$alkynyl, $C_6$-$C_{14}$aryl-, $C_1$-$C_9$heteroaryl-, or $C_3$-$C_8$cycloalkyl-, attached to the parent compound by an —$C_1$-$C_6$alkylene- group as defined above. Exemplary $C_1$-$C_6$carboxyamidoalkyl- groups include but are not limited to $NH_2C(O)$—$CH_2$—, $CH_3NHC(O)$—$CH_2CH_2$—, $(CH_3)_2NC(O)$—$CH_2CH_2CH_2$—, $CH_2$=$CHCH_2NHC(O)$—$CH_2CH_2CH_2CH_2$—, $HCCCH_2NHC(O)$—$CH_2CH_2CH_2CH_2CH_2$—, $C_6H_5NHC(O)$—$CH_2CH_2CH_2CH_2CH_2CH_2$—, 3-pyridylNHC(O)—$CH_2CH(CH_3)CH_2CH_2$—, and cyclopropyl-$CH_2NHC(O)$—$CH_2CH_2C(CH_3)_2CH_2$—.

"Cycloalkyl-" refers to a monocyclic, non-aromatic, saturated hydrocarbon ring. Representative examples of a $C_3$-$C_8$cycloalkyl- include, but are not limited to, cyclopropyl, cyclobutyl, cyclopentyl, cyclohexyl, cycloheptyl, and cyclooctyl. A cycloalkyl can be unsubstituted or independently substituted with one or more of the following groups: halogen, $H_2N$—, ($C_1$-$C_6$alkyl)amino-, di($C_1$-$C_6$alkyl) amino-, ($C_1$-$C_6$alkyl)C(O)N($C_1$-$C_3$alkyl)-, ($C_1$-$C_6$alkyl)carboxyamido-, HC(O)NH—, $H_2NC(O)$—, ($C_1$-$C_6$alkyl)NHC (O)—, di($C_1$-$C_6$alkyl)NC(O)—, NC—, hydroxyl, $C_1$-$C_6$alkoxy-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, or $C_3$-$C_8$cycloalkyl-, $C_1$-$C_6$haloalkyl-, amino($C_1$-$C_6$alkyl)-, ($C_1$-$C_6$alkyl)carboxyl-, $C_1$-$C_6$carboxyamidoalkyl-, or $O_2N$—. Additionally, each of any two hydrogen atoms on the same carbon atom of the carbocyclic ring can be replaced by an oxygen atom to form an oxo (=O) substituent or the two hydrogen atoms can be replaced by an alkylenedioxy group so that the alkylenedioxy group, when taken together with the carbon atom to which it is attached, form a 5- to 7-membered heterocycle containing two oxygen atoms.

"Di(alkyl)amino-" refers to a nitrogen atom attached to two alkyl groups, as defined above. Each alkyl group can be independently selected. Representative examples of an di($C_1$-$C_6$alkyl)amino- group include, but are not limited to, —$N(CH_3)_2$, —$N(CH_2CH_3)(CH_3)$, —$N(CH_2CH_3)_2$, —$N(CH_2CH_2CH_3)_2$, —$N(CH_2CH_2CH_2CH_3)_2$, —$N(CH(CH_3)_2)_2$, —$N(CH(CH_3)_2)(CH_3)$, —$N(CH_2CH(CH_3)_2)_2$, —$NH(CH(CH_3)CH_2CH_3)_2$, —$N(C(CH_3)_3)_2$, —$N(C(CH_3)_3)(CH_3)$, and —$N(CH_3)(CH_2CH_3)$. The two alkyl groups on the nitrogen atom, when taken together with the nitrogen to which they are attached, can form a 3- to 7-membered nitrogen containing heterocycle wherein up to two of the carbon atoms of the heterocycle can be replaced with —N(H)—, —N($C_3$-$C_8$cycloalkyl)-, —N($C_6$-$C_{14}$aryl)-, —N($C_1$-$C_9$heteroaryl)-, —N(amino($C_1$-$C_6$alkyl))-, —N($C_6$-$C_{14}$arylamino)-, —O—, —S—, —S(O)—, or —S(O)$_2$—.

"Halo" or "halogen" refers to fluorine, chlorine, bromine, or iodine.

"$C_1$-$C_6$Haloalkyl-" refers to a $C_1$-$C_6$alkyl group, as defined above, wherein one or more of the $C_1$-$C_6$alkyl group's hydrogen atoms has been replaced with —F, —Cl, —Br, or —I. Each substitution can be independently selected from —F, —Cl, —Br, or —I. Representative examples of an $C_1$-$C_6$haloalkyl- group include, but are not limited to, —CHF, —$CF_3$, —$CH_2CF_3$, —$CH_2CH_2Br$, —$CH_2CH_2I$, —CH$_2$CH$_2$CH$_2$F, —CH$_2$CH$_2$CH$_2$Cl, —CH$_2$CH$_2$CH$_2$CH$_2$Br, —CH$_2$CH$_2$CH$_2$CH$_2$I, —CH$_2$CH$_2$CH$_2$CH$_2$CH$_2$Br, —CH$_2$CH$_2$CH$_2$CH$_2$CH$_2$I, —CH$_2$CH(Br)CH$_3$, —CH$_2$CH(Cl)CH$_2$CH$_3$, —CH(F)CH$_2$CH$_3$ and —C(CH$_3$)$_2$(CH$_2$Cl).

"Heteroaryl-" refers to 5-10-membered mono and bicyclic aromatic groups containing at least one heteroatom selected from oxygen, sulfur and nitrogen. Examples of monocyclic C$_9$heteroaryl- radicals include, but are not limited to, oxazinyl, thiazinyl, diazinyl, triazinyl, thiadiazoyl, tetrazinyl, imidazolyl, tetrazolyl, isoxazolyl, furanyl, furazanyl, oxazolyl, thiazolyl, thiophenyl, pyrazolyl, triazolyl, pyrimidinyl, N-pyridyl, 2-pyridyl, 3-pyridyl and 4-pyridyl. Examples of bicyclic C$_1$-C$_9$heteroaryl- radicals include but are not limited to, benzimidazolyl, indolyl, isoquinolinyl, benzofuranyl, benzothiophenyl, indazolyl, quinolinyl, quinazolinyl, purinyl, benzisoxazolyl, benzoxazolyl, benzthiazolyl, benzodiazolyl, benzotriazolyl, isoindolyl, and indazolyl. The contemplated heteroaryl- rings or ring systems have a minimum of 5 members. Therefore, for example, C$_1$heteroaryl- radicals would include but are not limited to tetrazolyl, C$_2$heteroaryl- radicals include but are not limited to triazolyl, thiadiazoyl, and tetrazinyl, C$_9$heteroaryl- radicals include but are not limited to quinolinyl and isoquinolinyl. A heteroaryl group can be unsubstituted or substituted with one or more of the following groups: C$_1$-C$_6$alkyl-, halogen, C$_1$-C$_6$haloalkyl-, hydroxyl, C$_1$-C$_6$hydroxylalkyl-, H$_2$N—, amino(C$_1$-C$_6$alkyl), di(C$_1$-C$_6$alkyl)amino-, —COOH, (C$_1$-C$_6$alkoxy)carbonyl-, (C$_1$-C$_6$alkyl)carboxyl-, di(C$_1$-C$_6$alkyl)amido-, H$_2$NC(O)—, (C$_1$-C$_6$alkyl)amido-, or O$_2$N—.

"(Heteroaryl)alkyl-" refers to an alkyl group, as defined above, wherein one or more of the alkyl group's hydrogen atoms have been replaced with a heteroaryl- group as defined above. Examples of (C$_1$-C$_9$heteroaryl)alkyl- moieties include 2-pyridylmethyl, 2-thiophenylethyl, 3-pyridylpropyl, 2-quinolinylmethyl, 2-indolylmethyl, and the like. A (heteroaryl)alkyl group can be unsubstituted or substituted with one or more of the following groups: halogen, H$_2$N—, hydroxyl, (C$_1$-C$_6$alkyl)amino-, di(C$_1$-C$_6$alkyl)amino-, (C$_1$-C$_6$alkyl)C(O)N(C$_1$-C$_3$alkyl)-, (C$_1$-C$_6$alkyl)carboxyamido-, HC(O)NH—, H$_2$NC(O)—, (C$_1$-C$_6$alkyl)NHC(O)—, di(C$_1$-C$_6$alkyl)NC(O)—, NC—, hydroxyl, C$_1$-C$_6$alkoxy-, HO$_2$C—, (C$_1$-C$_6$alkoxy)carbonyl-, (C$_1$-C$_6$alkyl)C(O)—, C$_6$-C$_{14}$aryl-, C$_1$-C$_9$heteroaryl-, C$_3$-C$_6$cycloalkyl-, C$_1$-C$_6$haloalkyl-, amino (C$_1$-C$_6$alkyl)-, (C$_1$-C$_6$alkyl)carboxyl-, C$_1$-C$_6$carboxyamidoalkyl-, or O$_2$N—.

"Heteroatom" refers to a sulfur, nitrogen, or oxygen atom.

"Heterocycle" or "heterocyclyl-" refers to 3-10-membered monocyclic, fused bicyclic, and bridged bicyclic groups containing at least one heteroatom selected from oxygen, sulfur and nitrogen. A heterocycle may be saturated or partially saturated. Exemplary C$_1$-C$_9$heterocyclyl- groups include but are not limited to aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, oxazine, 5,6-dihydro-4H-1,3-oxazin-2-yl, 2,5-diazabicyclo[2.2.1]heptane, 2,5-diazabicyclo[2.2.2]octane, diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl-, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, thiazine, dithiane, and dioxane. The contemplated heterocycle rings or ring systems have a minimum of 3 members. Therefore, for example, C$_1$heterocyclyl- radicals would include but are not limited to oxaziranyl, diaziridinyl, and diazirinyl, C$_2$heterocyclyl- radicals include but are not limited to aziridinyl, oxiranyl, and diazetidinyl, C$_9$heterocyclyl- radicals include but are not limited to azecanyl, tetrahydroquinolinyl, and perhydroisoquinolinyl.

"Heterocyclyl(alkyl)-" refers to an alkyl group, as defined above, wherein one or more of the alkyl group's hydrogen atoms have been replaced with a heterocycle group as defined above. Heterocyclyl(C$_1$-C$_6$alkyl)- moieties include 2-pyridylmethyl, 1-piperazinylethyl, 4-morpholinylpropyl, 6-piperazinylhexyl, and the like. A heterocyclyl(alkyl) group can be unsubstituted or substituted with one or more of the following groups: halogen, H$_2$N—, (C$_1$-C$_6$alkyl)amino-, di(C$_1$-C$_6$alkyl)amino-, (C$_1$-C$_6$alkyl)C(O)N(C$_1$-C$_3$alkyl)-, (C$_1$-C$_6$alkyl)carboxyamido-, HC(O)NH—, H$_2$NC(O)—, (C$_1$-C$_6$alkyl)NHC(O)—, di(C$_1$-C$_6$alkyl)NC(O)—, NC—, hydroxyl, C$_1$-C$_6$alkoxy-, C$_1$-C$_6$alkyl-, HO$_2$C—, (C$_1$-C$_6$alkoxy)carbonyl-, (C$_1$-C$_6$alkyl)C(O)—, 4- to 7-membered monocyclic heterocycle, C$_6$-C$_{14}$aryl-, C$_1$-C$_9$heteroaryl-, or C$_3$-C$_8$cycloalkyl-.

"Bridged heterobicyclyl- group containing at least one oxygen atom, at least one nitrogen atom, and optionally additional heteroatoms selected from oxygen, sulfur and nitrogen, and is connected to the pyrimidinyl group through one of the nitrogen atoms;" refers to 5-10-membered bridged bicyclic groups containing at least one nitrogen atom, one oxygen atom, and optionally additional heteroatom selected from oxygen, sulfur and nitrogen. A bridged heterobicyclyl- group containing at least one oxygen atom, at least one nitrogen atom, and optionally additional heteroatoms selected from oxygen, sulfur and nitrogen, and is connected to the pyrimidinyl group through one of the nitrogen atoms; may be saturated or partially saturated. Exemplary bridged C$_5$-C$_9$heterobicyclic rings containing at least one oxygen atom, at least one nitrogen atom, and connected through one of the nitrogen atom include but are not limited to 2-oxa-5-azabicyclo[2.2.1]heptane, 2-oxa-5-azabicyclo[2.2.2]octane, 7-oxa-2,5-diazabicyclo[2.2.2]octane, 2,7-dioxa-5-azabicyclo[2.2.2]octane, 5,7-dioxa-2-azabicyclo[2.2.2]octane, 3-oxa-6-azabicyclo[3.1.1]heptane, 6-oxa-3-azabicyclo[3.1.1]heptane, 6-oxa-3,8-diazabicyclo[3.2.1]octane, 3,6-dioxa-8-azabicyclo[3.2.1]octane, 3-oxa-8-azabicyclo[3.2.1]octane, 6,8-dioxa-3-azabicyclo[3.2.1]octane, 6,8-dioxa-3-azabicyclo[3.2.1]octane, 8-oxa-3-azabicyclo[3.2.1]octane, 3-oxa-7,9-diazabicyclo[3.3.1]nonane, 7-methyl-3-oxa-7,9-diazabicyclo[3.3.1]nonane, 9-oxa-3,7-diazabicyclo[3.3.1]none, 9-oxa-3-azabicyclo[3.3.1]nonane, 3-oxa-9-azabicyclo[3.3.1]nonane, and 3,7-dioxa-9-azabicyclo[3.3.1]nonane. The contemplated heterocycle rings or ring systems have a minimum of 3 members. Therefore, for example, C$_5$heterobicyclyl- radicals include but are not limited to 2-oxa-5-azabicyclo[2.2.1]heptan-5-yl, (1R,4R)-2-oxa-5-azabicyclo[2.2.1]heptan-5-yl, (1S,4S)-2-oxa-5-azabicyclo[2.2.1]heptan-5-yl, and 6,8-dioxa-3-azabicyclo[3.2.1]octan-3-yl. C$_6$heterobicyclyl- radicals include but are not limited to 2-oxa-5-azabicyclo[2.2.2]octan-5-yl, 3-oxa-8-azabicyclo[3.2.1]octan-8-yl, 8-oxa-3-azabicyclo[3.2.1]octan-3-yl, 9-oxa-3,7-diazabicyclo[3.3.1]non-3-yl, 7-methyl-3-oxa-7,9-diazabicyclo[3.3.1]nonan-9-yl, 3-oxa-7,9-diazabicyclo[3.3.1]nonan-7-yl, 3-oxa-7,9-diazabicyclo[3.3.1]nonan-9-yl, and 3,7-dioxa-9-azabicyclo[3.3.1]nonan-9-yl. $C_7$heterobicyclyl- radicals include but are not limited to 9-oxa-3-azabicyclo[3.3.1]nonan-3-yl and 3-oxa-9-azabicyclo[3.3.1]nonan-9-yl.

"Hydroxylalkyl-" refers to an alkyl group, as defined above, wherein one or more of the alkyl group's hydrogen atoms have been replaced with hydroxyl groups. Examples of $C_1$-$C_6$hydroxylalkyl- moieties include, for example, —$CH_2OH$, —$CH_2CH_2OH$, —$CH_2CH_2CH_2OH$, —$CH_2CH(OH)CH_2OH$, —$CH_2CH(OH)CH_3$, —$CH(CH_3)CH_2OH$ and higher homologs.

"Leaving group" refers an atom or group (charged or uncharged) that becomes detached from an atom in what is considered to be the residual or main part of the substrate in a specified reaction. For example, in the heterolytic solvolysis of benzyl bromide in acetic acid: the leaving group is bromide. In the reaction of N,N,N-trimethyl-1-phenylmethanaminium ion with methanethiolate, the leaving group is trimethylamine. In the electrophilic nitration of benzene, it is $H^+$. The term has meaning only in relation to a specified reaction. Examples of leaving groups include, for example, carboxylates (i.e. $CH_3COO^-$, $CF_3CO_2^-$), F, water, $Cl^-$, $Br^-$, $I^-$, $N_3^-$, $SCN^-$, trichloroacetimidate, thiopyridyl, tertiary amines (i.e. trimethylamine), phenoxides nitrophenoxide), and sulfonates (i.e. tosylate, mesylate, triflate).

"Perfluoroalkyl-" refers to alkyl group, defined above, having two or more fluorine atoms. Examples of a $C_1$-$C_6$perfluoroalkyl- group include $CF_3$, $CH_2CF_3$, $CF_2CF_3$ and $CH(CF_3)_2$.

The term "optionally substituted", unless otherwise specified, as used herein means that at least one hydrogen atom of the optionally substituted group has been substituted with halogen, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_8$alkyl)carboxyamido-, HC(O)NH—, $H_2NC(O)$—, ($C_1$-$C_6$alkyl)NHC(O)—, di($C_1$-$C_6$alkyl)NC(O)—, NC—, hydroxyl, $C_1$-$C_6$alkoxy-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, or $C_3$-$C_8$cycloalkyl-.

A "subject" is a mammal, e.g., a human, mouse, rat, guinea pig, dog, cat, horse, cow, pig, or non-human primate, such as a monkey, chimpanzee, baboon or gorilla.

The compounds of the present invention exhibit an mTOR inhibitory activity and, therefore, can be utilized to inhibit abnormal cell growth in which mTOR plays a role. Thus, the compounds of the present invention are effective in the treatment of disorders with which abnormal cell growth actions of mTOR are associated, such as restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, cancer, etc. In particular, the compounds of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, advanced renal cell carcinoma, acute lymphoblastic leukemia, malignant melanoma, soft-tissue or bone sarcoma, etc.

The compounds of the present invention exhibit a PI3 kinase inhibitory activity and, therefore, can be utilized in order to inhibit abnormal cell growth in which PI3 kinases play a role. Thus, the compounds of the present invention are effective in the treatment of disorders with which abnormal cell growth actions of PI3 kinases are associated, such as restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, cancer, etc. In particular, the compounds of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, advanced renal cell carcinoma, acute lymphoblastic leukemia, malignant melanoma, soft-tissue or bone sarcoma, etc.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions of this invention include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington: The Science and Practice of Pharmacy*, 20th Edition. Baltimore, Md.: Lippincott Williams & Wilkins, 2000.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that one skilled in the art would adjust the unit dosage form accordingly to reflect the relative level of activity. The decision as to the particular dosage to be employed (and the number of times to be administered per day is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 mg/kg to 10 mg/kg body weight. For parenteral administration, the dose may be in the range of 0.1 mg/kg to 1 mg/kg body weight for intravenous administration. For oral administration, the dose may be in the range about 0.1 mg/kg to 5 mg/kg body weight. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The amount of the compound of the present invention or a pharmaceutically acceptable salt thereof that is effective for inhibiting mTOR or PI3K in a subject. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one compound of the present invention or a pharmaceutically acceptable salt thereof is administered, the effective dosage amounts correspond to the total amount administered.

In one embodiment, the compound of the present invention or a pharmaceutically acceptable salt thereof is administered concurrently with another therapeutic agent.

In one embodiment, a composition comprising an effective amount of a compound of the present invention or a pharmaceutically acceptable salt thereof and an effective amount of another therapeutic agent within the same composition can be administered.

Effective amounts of the other therapeutic agents are well known to those skilled in the art. However, it is well within the skilled artisan's purview to determine the other therapeutic agent's optimal effective amount range. The compound of the present invention or a pharmaceutically acceptable salt thereof and the other therapeutic agent can act additively or, in one embodiment, synergistically. In one embodiment, of the invention, where another therapeutic agent is administered to an animal, the effective amount of the compound of the present invention or a pharmaceutically acceptable salt thereof is less than its effective amount would be where the other therapeutic agent is not administered. In this case, without being bound by theory, it is believed that the compound of the present invention or a pharmaceutically acceptable salt thereof and the other therapeutic agent act synergistically.

Procedures used to synthesize the compounds of the present invention are described in Schemes 1-36 and are illustrated in the examples. Reasonable variations of the described procedures are intended to be within the scope of the present invention:

Scheme 1

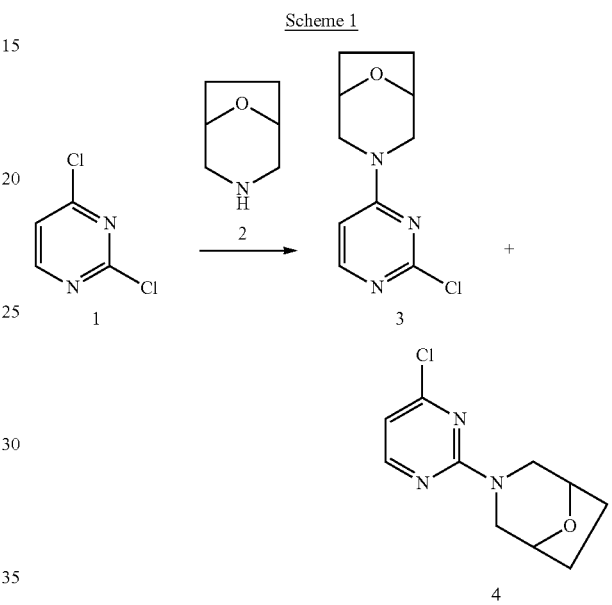

Reaction of 2,4-dichloropyrimidine (1) with bridged $C_5$-$C_9$ heterobicycle compound 2 gave a mixture of regioisomers in an 89:4 ratio, which were separated by silica gel chromatography as shown in Scheme 1.

Scheme 2

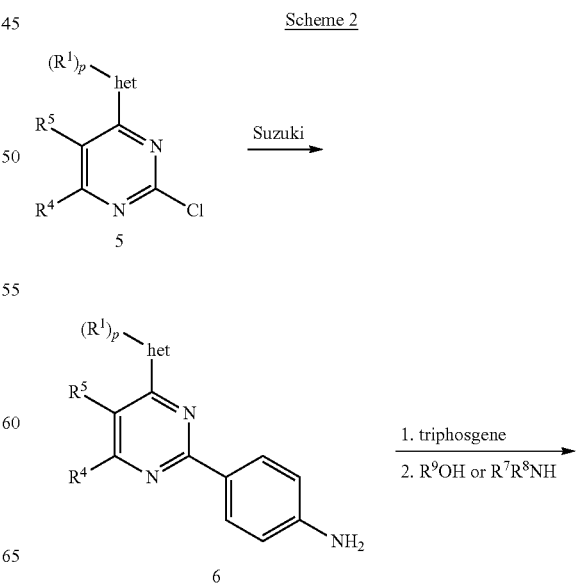

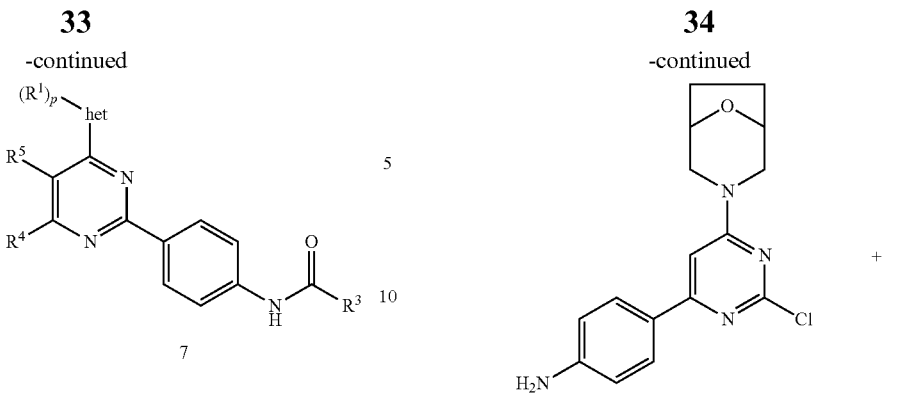

As shown in Scheme 2, Suzuki coupling with 4-aminophenylboronic acid, pinacol ester gave the aniline intermediate 6.

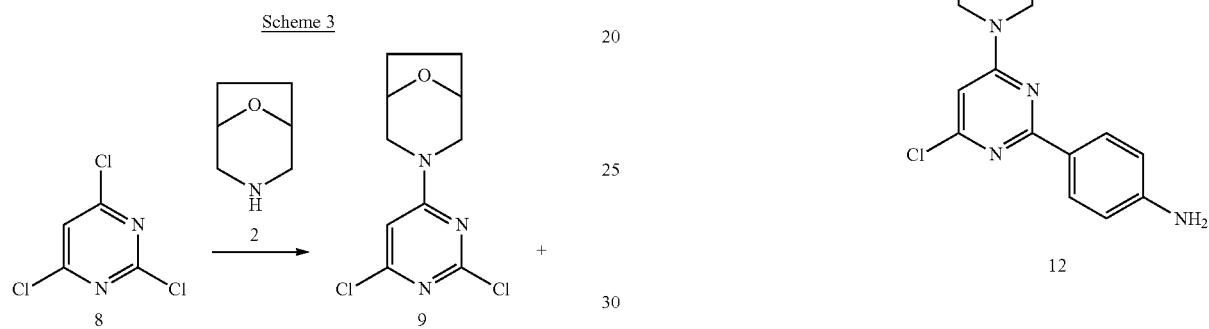

As shown in Scheme 3, reaction of 2,4,6-trichloropyrimidine (8) with bridged $C_5$-$C_9$ heterobicycle compound 2 gave a mixture of regioisomers in an 83:11 ratio, which were separated by silica gel chromatography.

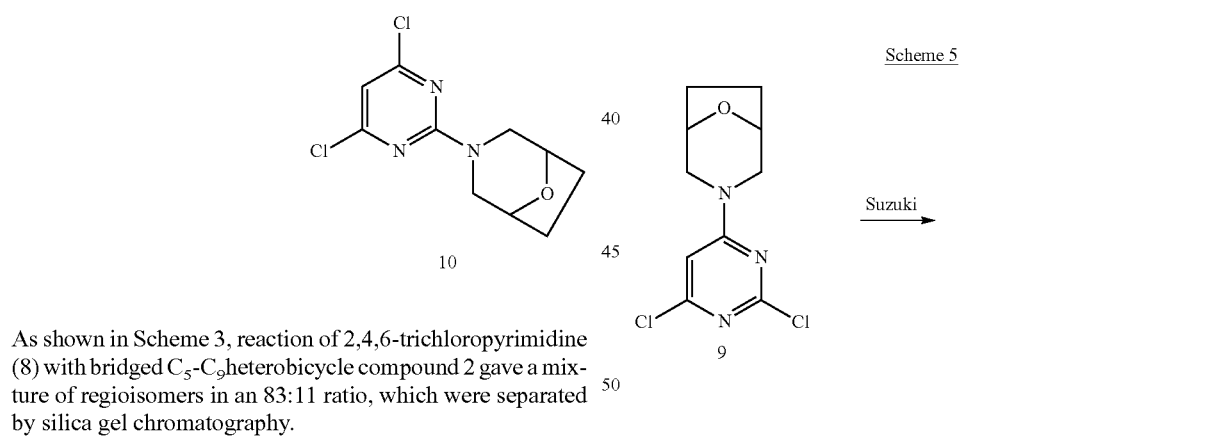

As shown in Scheme 4, reaction of 3-(2,6-dichloropyrimidin-4-yl)-8-oxa-3-azabicyclo[3.2.1]octane (9) with 4-aminophenylboronic acid, pinacol ester gave the aniline intermediates 11 and 12 in a 16:15 ratio.

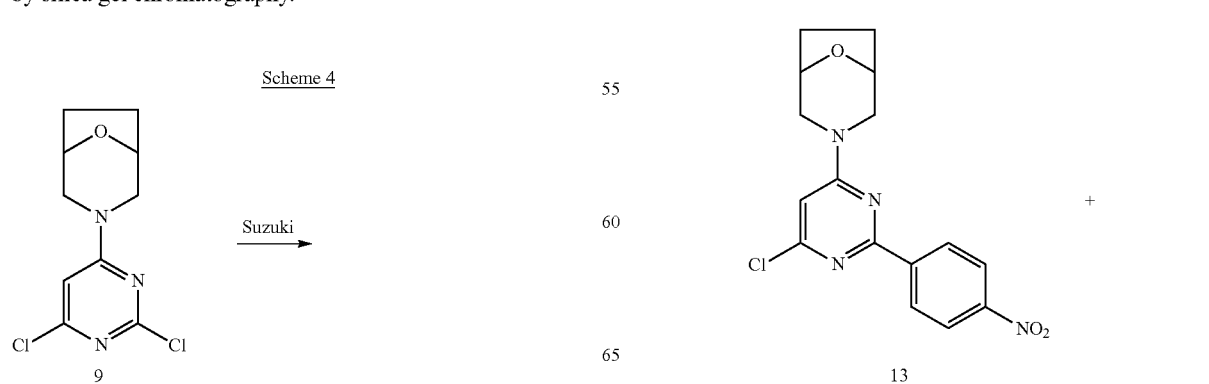

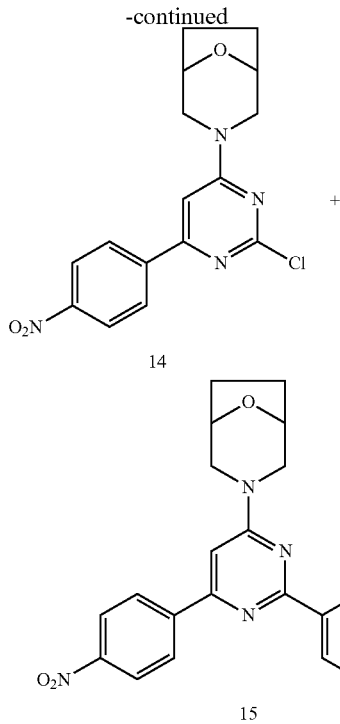

As shown in Scheme 5, reaction of 3-(2,6-dichloropyrimidin-4-yl)-8-oxa-3-azabicyclo[3.2.1]octane (9) with 4-nitrophenylboronic acid, pinacol ester gave the dicoupled material 15 as an insoluble material. The mono-coupled intermediates 13 and 14 were obtained after silica gel chromatography in a 10:8 ratio.

Scheme 6

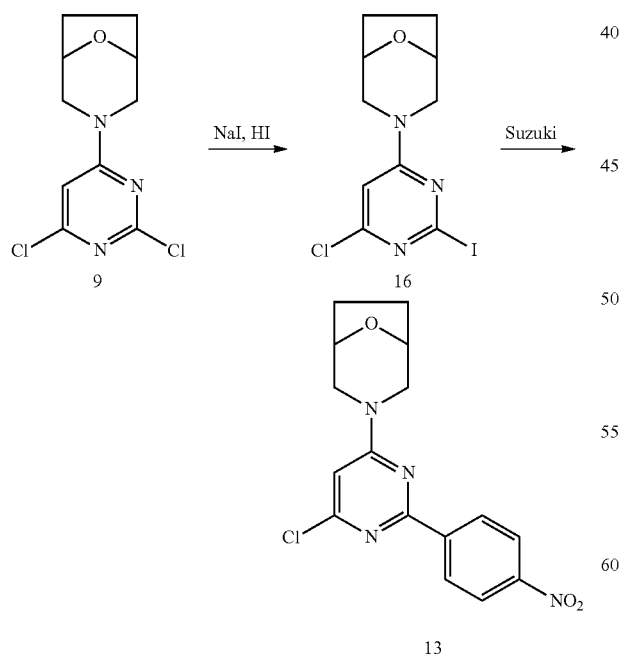

As shown in Scheme 6, reaction of 3-(2,6-dichloropyrimidin-4-yl)-8-oxa-3-azabicyclo[3.2.1]octane (9) with NaI/HI gave desired product (16) as the main peak along with a dehalogenated impurity and starting material (9). None of the 2-chloro-6-iodopyrimidine isomer was detected.

Scheme 7

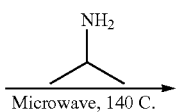

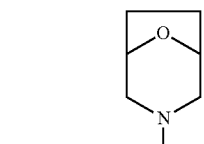

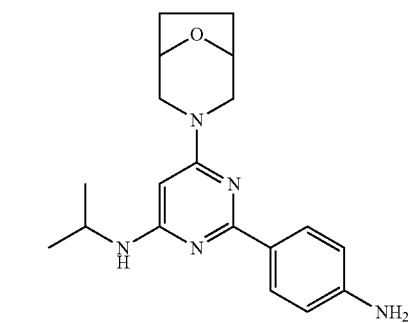

As shown in Scheme 7, reaction of 3-(6-chloro-2-(4-nitrophenyl)pyrimidin-4-yl)-8-oxa-3-azabicyclo[3.2.1]octane (13) was uneventful.

Scheme 8

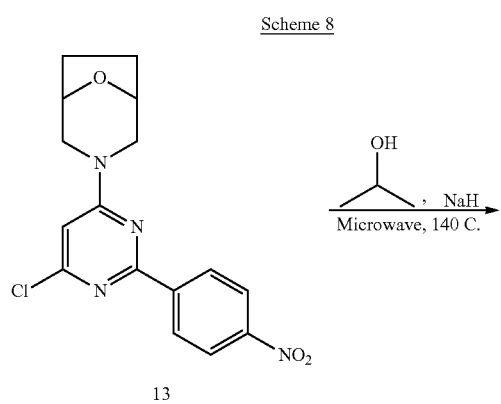

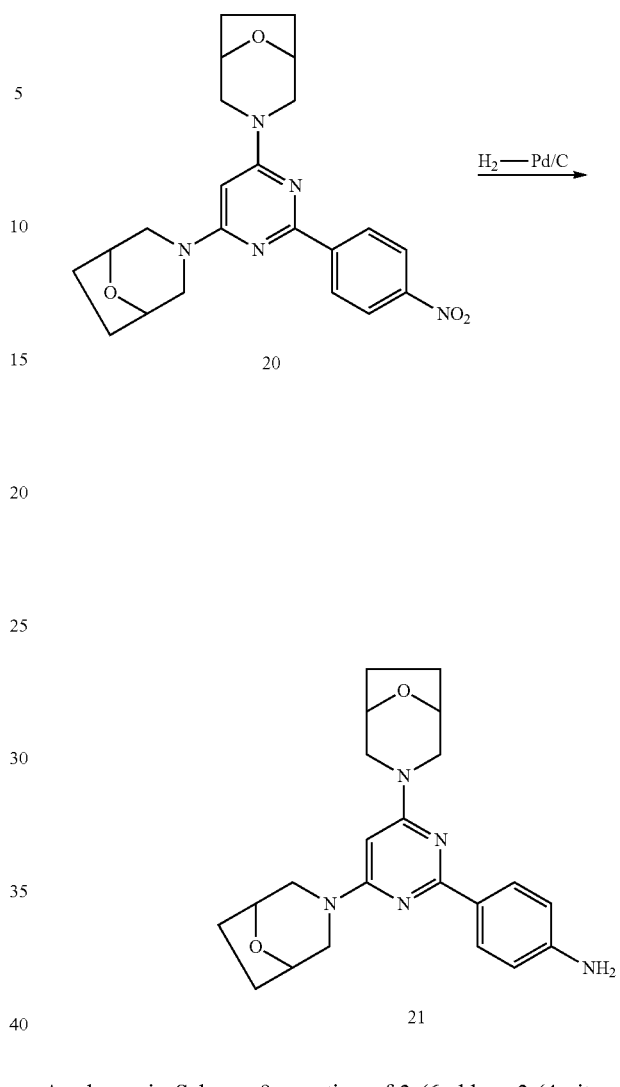

As shown in Scheme 7, reaction of 3-(6-chloro-2-(4-nitrophenyl)pyrimidin-4-yl)-8-oxa-3-azabicyclo[3.2.1]octane (13) with 2-propanol also went smoothly. The nitro group was reduced under the high temperature reaction conditions.

As shown in Scheme 9, reaction of 3-(6-chloro-2-(4-nitrophenyl)pyrimidin-4-yl)-8-oxa-3-azabicyclo[3.2.1]octane (13) with bridged $C_5$-$C_9$ heterobicycle compound 2 gave intermediate 20 containing two bridged $C_5$-$C_9$ heterobicyclic rings.

Scheme 9

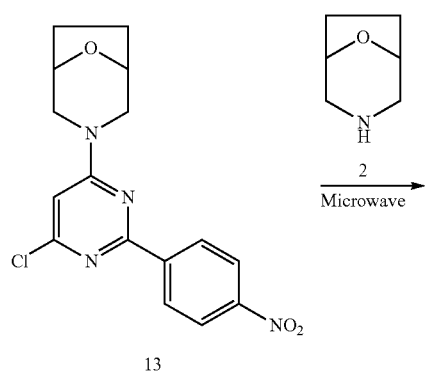

Scheme 10

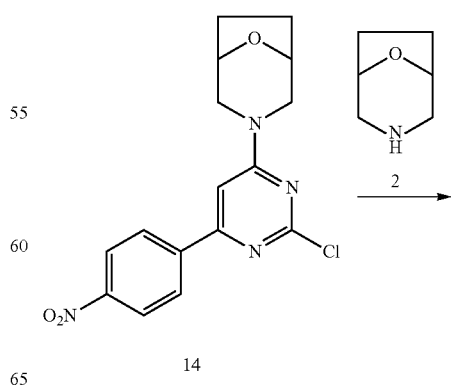

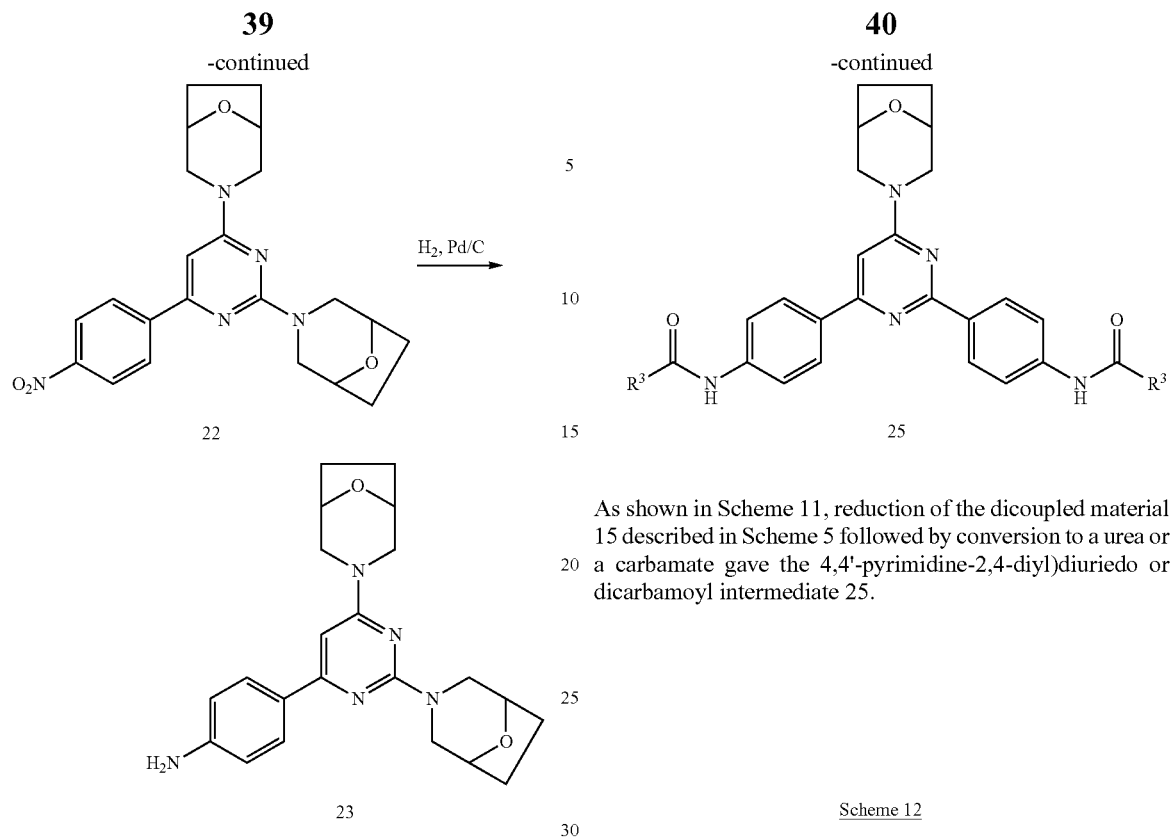

As shown in Scheme 10, the mono-coupled intermediate 14 described in Scheme 5 also reacted with bridged $C_5$-$C_9$ heterobicycle compound 2 to give isomeric intermediate 22 containing two bridged $C_5$-$C_9$ heterobicyclic rings.

Scheme 11

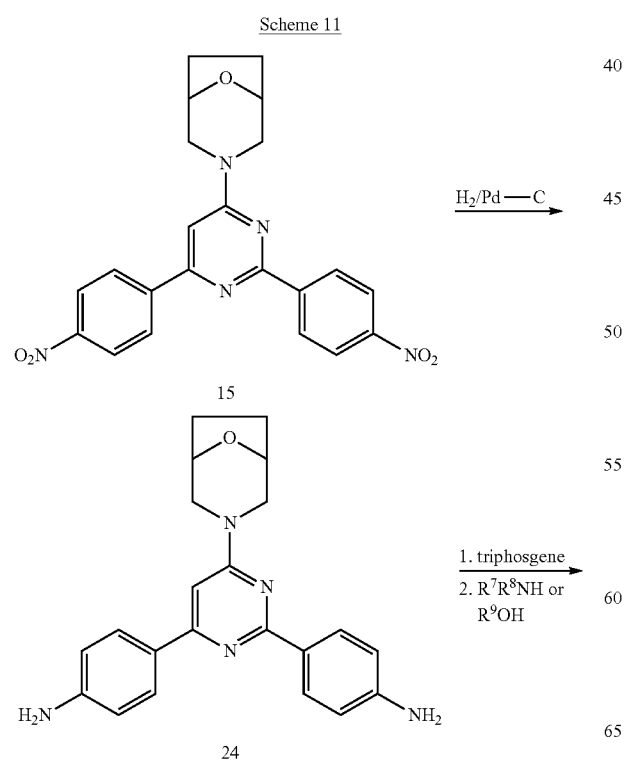

As shown in Scheme 11, reduction of the dicoupled material 15 described in Scheme 5 followed by conversion to a urea or a carbamate gave the 4,4'-pyrimidine-2,4-diyl)diuriedo or dicarbamoyl intermediate 25.

Scheme 12

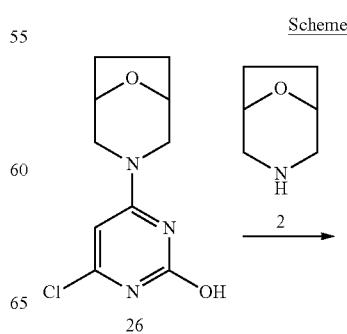

As shown in Scheme 12, reaction of 3-(2,6-dichloropyrimidin-4-yl)-8-oxa-3-azabicyclo[3.2.1]octane (9) with sodium hydroxide occurred selectively at position 2 of pyrimidine ring.

Scheme 13

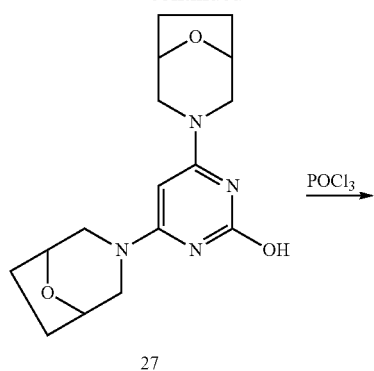

27

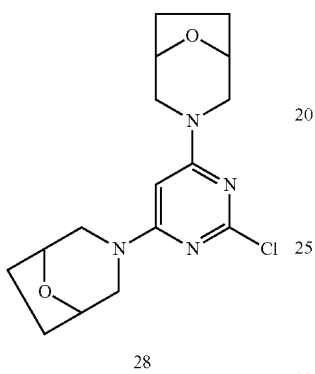

28

As shown in Scheme 13, reaction of the 6-chloropyrimidine produced in the previous scheme with bridged C$_5$-C$_9$ heterobicycle compound 2 gave a 2-hydroxypyridine intermediate (27), the hydroxyl group of which could be reconverted to 3,3'-(2-chloropyrimidine-4,6-diyl)bis(8-oxa-3-azabicyclo[3.2.1]octane) (28).

Scheme 14

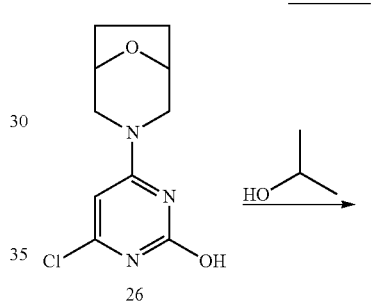

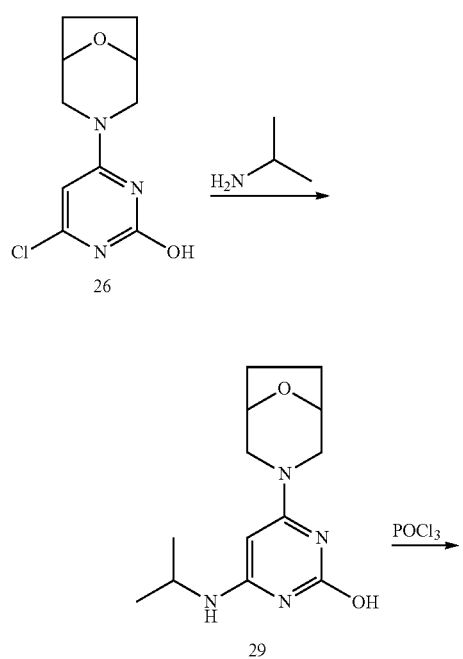

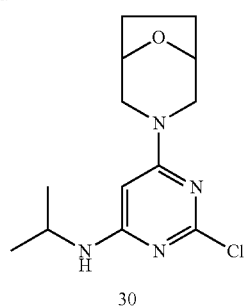

30

As shown in Scheme 14, reaction of the 6-chloropyrimidine (26) produced in Scheme 12 with a simple primary amine gave a 2-hydroxypyridine intermediate (29), the hydroxyl group of which could be reconverted to 6-(8-oxa-3-azabicyclo[3.2.1]octan-3-yl)-2-chloro-N-isopropylpyrimidin-4-amine (30).

Scheme 15

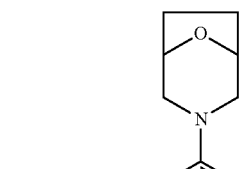

26

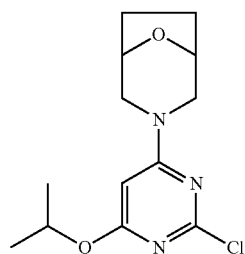

31

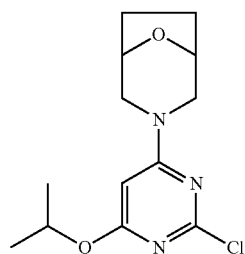

32

As shown in Scheme 15, reaction of the 6-chloropyrimidine (26) produced in Scheme 12 with a simple secondary alcohol gave a 2-hydroxypyridine intermediate (31), the hydroxyl group of which could be reconverted to 3-(2-chloro-6-isopropoxypyrimidin-4-yl)-8-oxa-3-azabicyclo[3.2.1]octane (32).

Scheme 16

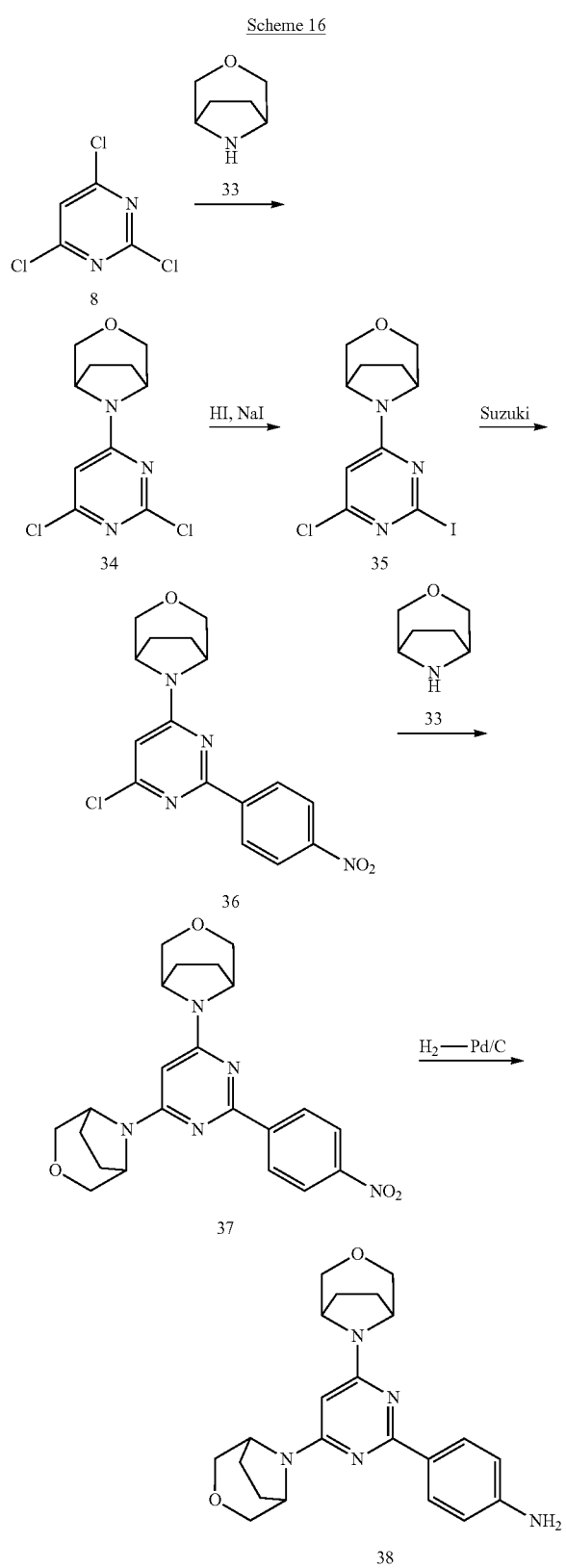

Scheme 17

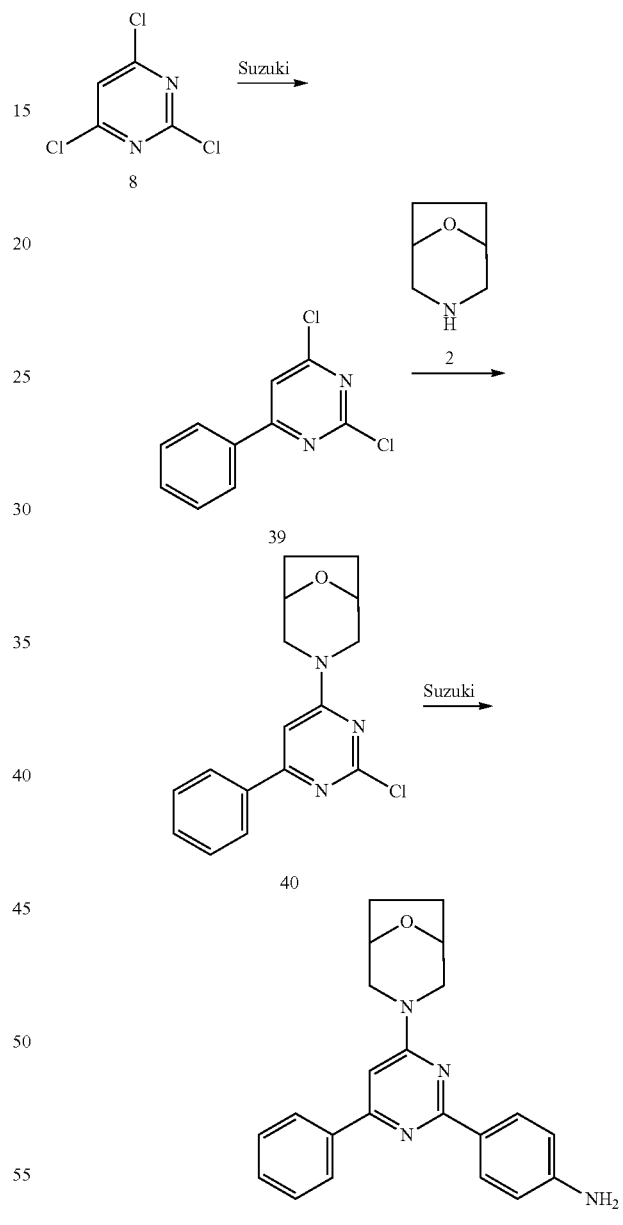

with the mixture of regioisomers obtained in Scheme 3 using a less hindered bridged $C_5$-$C_9$ heterobicycle amine. Selective reaction at position 2 of the pyrimidine ring with iodide gave the intermediate 8-(6-chloro-2-iodopyrimidin-4-yl)-3-oxa-8-azabicyclo[3.2.1]octane (35), which served to differentiate the 2 and 6 positions of the pyrimidine ring for subsequent Suzuki coupling.

As shown in Scheme 16, reaction of 2,4,6-trichloropyrimidine (8) with bridged $C_5$-$C_9$ heterobicycle compound 33 gave regioisomer 34 as the only isolated product. This is in contrast As shown in Scheme 17, reaction of 2,4,6-trichloropyrimidine (8) with phenylboronic acid occurred at position 6 of the pyrimidine ring to give 2,4-dichloro-6-phenylpyrimidine (39) as the only isolated product. This is in contrast to the amine displacement reactions of Schemes 3 and 16, which occurred largely at the 4 position. Subsequent reaction with bridged $C_5$-$C_9$ heterobicycle compound 2 occurred as expected at position 4.

Scheme 18

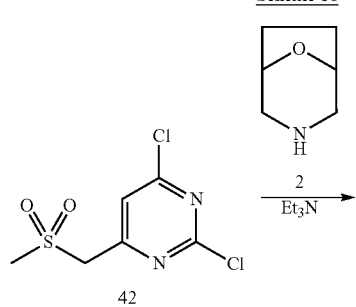

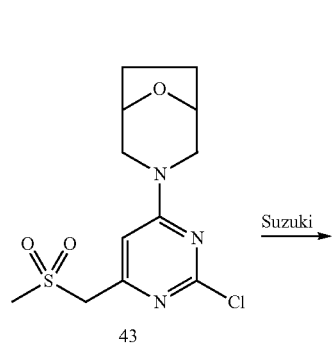

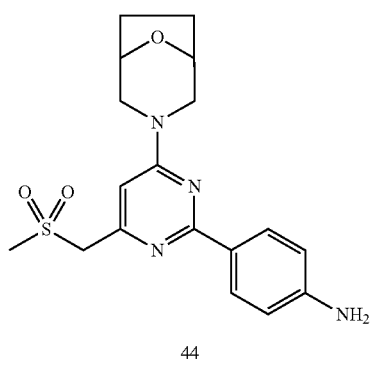

As shown in Scheme 18, reaction of 2,4-dichloro-6-(methylsulfonylmethyl)pyrimidine (42) with bridged $C_5$-$C_9$ heterobicycle compound 2 gave the monochloro compound 43 as the only isolated product.

Scheme 19

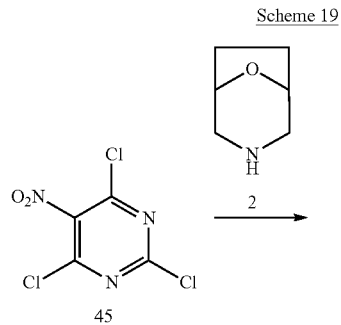

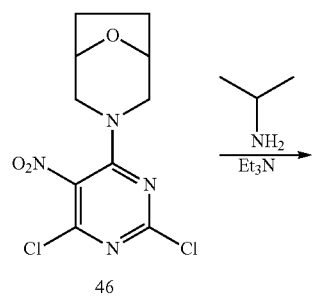

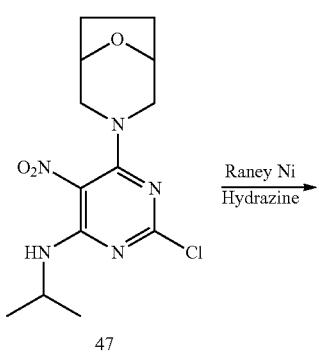

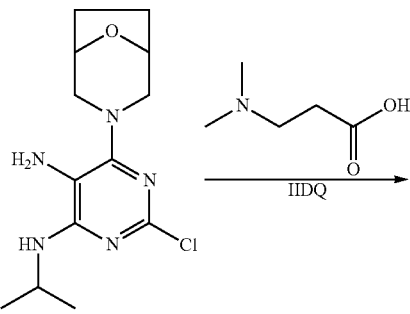

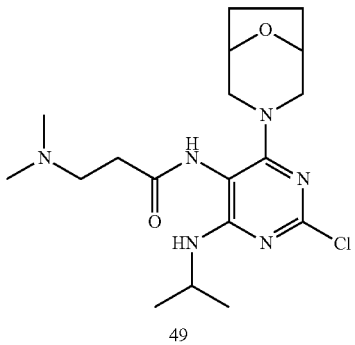

As shown in Scheme 19, the nitro group of 2,4,6-trichloro-5-nitropyrimidine (45) served to activate the 4 position of the pyrimidine ring in preference to the 2 position. Reaction with the bridged $C_5$-$C_9$ heterobicycle compound 2 gave 3-(2,6-dichloro-5-nitropyrimidin-4-yl)-8-oxa-3-azabicyclo[3.2.1]octane (46) as the only isolated product.

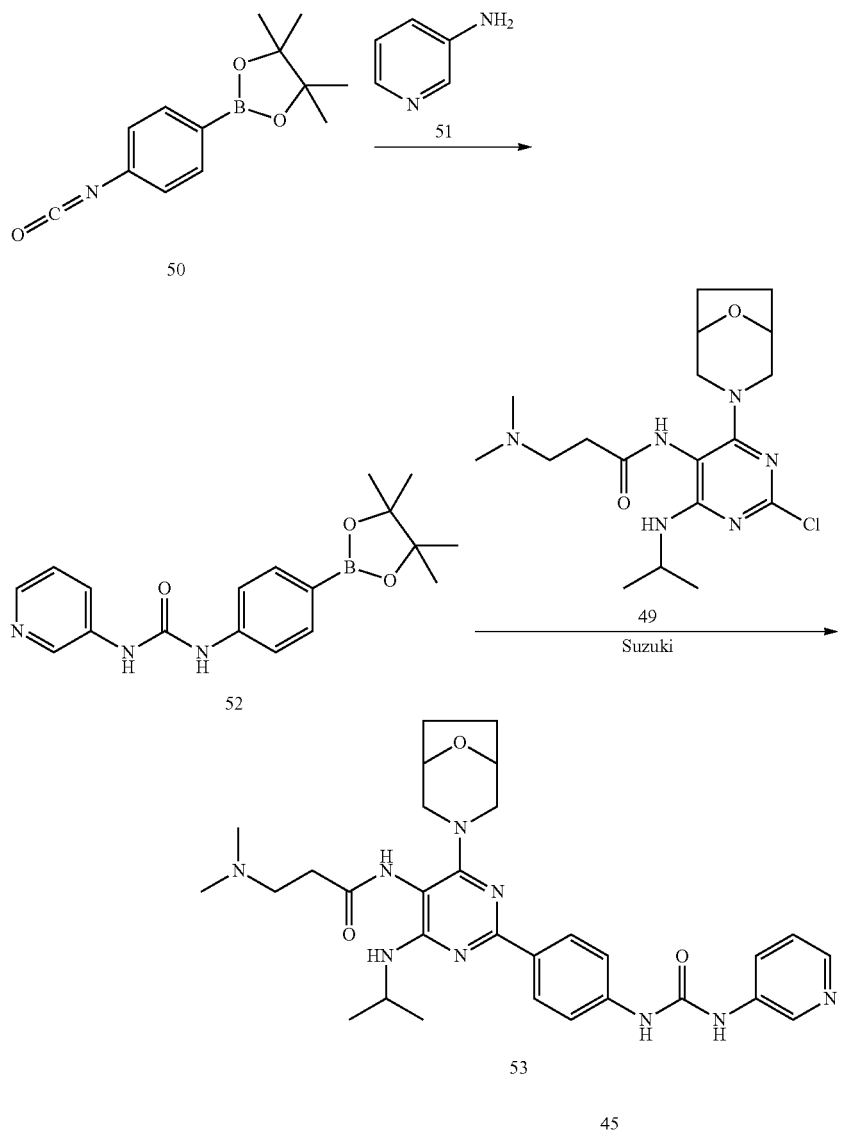
In Scheme 20 is shown the synthesis of the 1-(pyridin-3-yl)-3-(4-(4,4,5,5-tetramethyl-1,3,2-dioxaborolan-2-yl)phenyl)urea (52) reagent for the Suzuki coupling reaction.
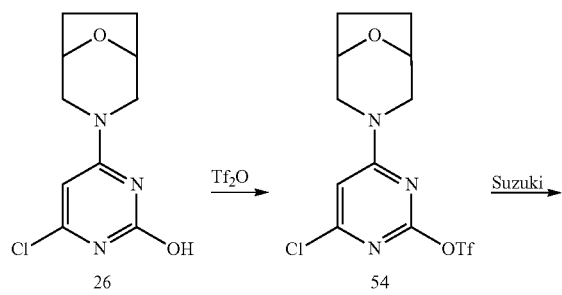
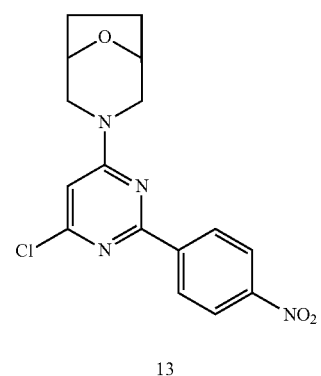
As shown in Scheme 12, 4-(8-oxa-3-azabicyclo[3.2.1]octan-3-yl)-6-chloropyrimidin-2-ol (26) produced in Scheme 12 was activated in the 2 position of the pyrimidine ring towards Suzuki coupling by formation of the triflate (54).

Scheme 22
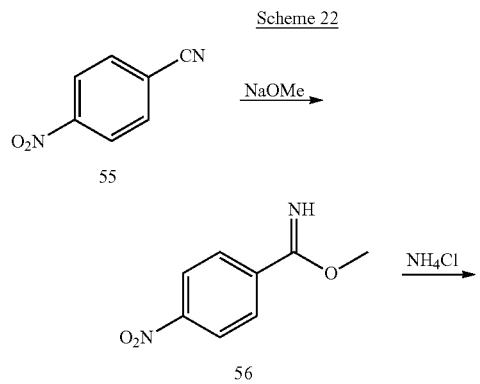
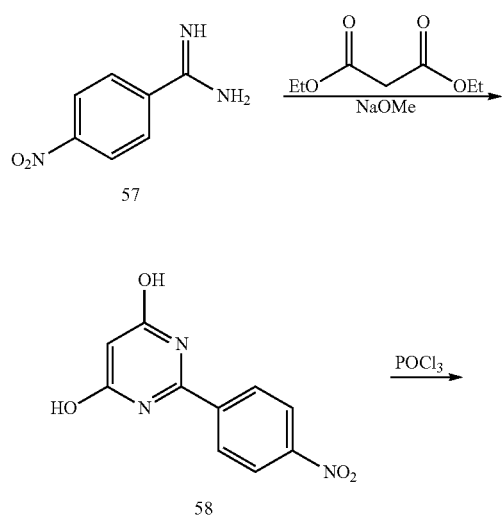
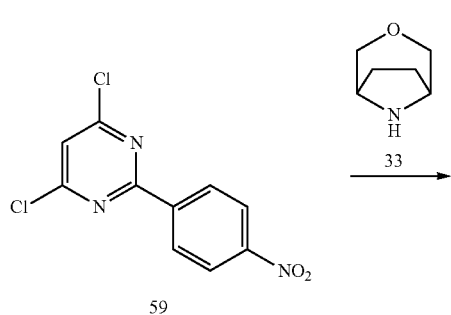
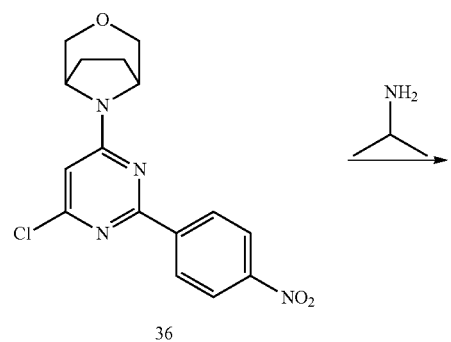
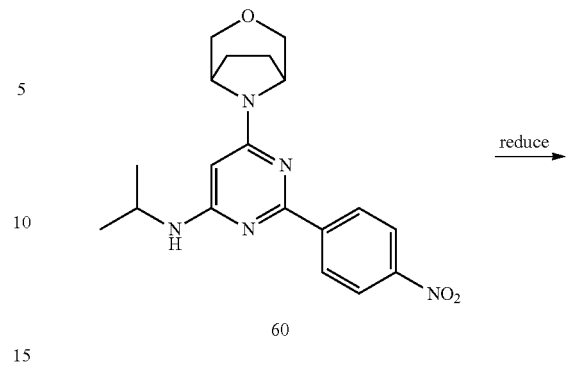
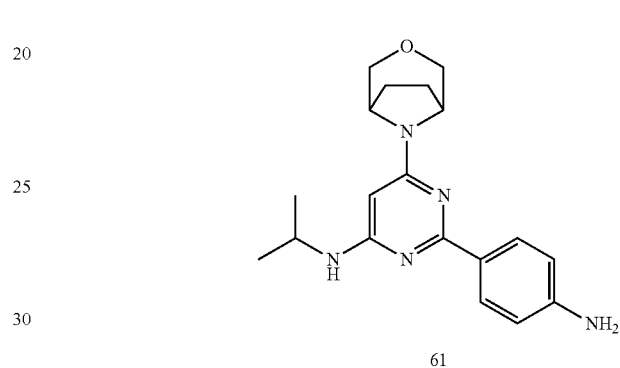
An alternative synthesis of 8-(6-chloro-2-(4-nitrophenyl)pyrimidin-4-yl)-3-oxa-8-azabicyclo[3.2.1]octane (36) is shown in Scheme 22.
Scheme 23
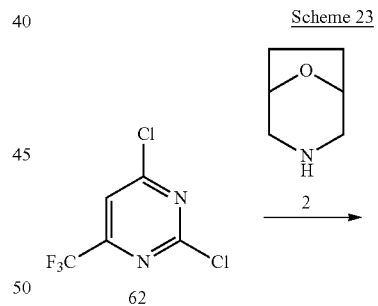
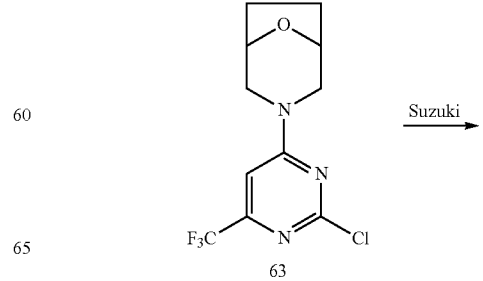

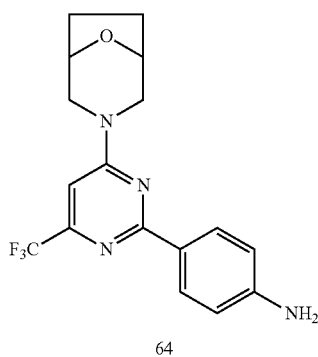

64

As shown in Scheme 23, the trifluoromethyl group of 2,4-dichloro-6-(trifluoromethyl)pyrimidine (62) served to activate the 4 position of the pyrimidine ring in preference to the 2 position. Reaction with the bridged $C_5$-$C_9$heterobicycle compound 2 gave 3-(2,6-dichloro-5-nitropyrimidin-4-yl)-8-oxa-3-azabicyclo[3.2.1]octane (46) as the only isolated product.

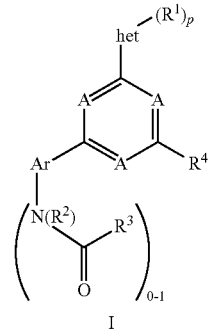

I

The preparation of the pyrimidine compounds I are shown in scheme 24. Starting with bis activated pyrimidine 65 where X is a leaving group, coupling with the appropriate bridged $C_5$-$C_9$heterobicycleyl amine $(R^1)_p$-het-H reagent gave pyrimidine 66. Suzuki coupling of 66 with the appropriate amino boronic acid pinacol ester 67, boronic ester, or boronic acid leads to amino heterobicyclyl pyrimidine 68. Transformation to the amido, ureido, or carbamoyl heterobicycle compounds I is as described previously in scheme 2.

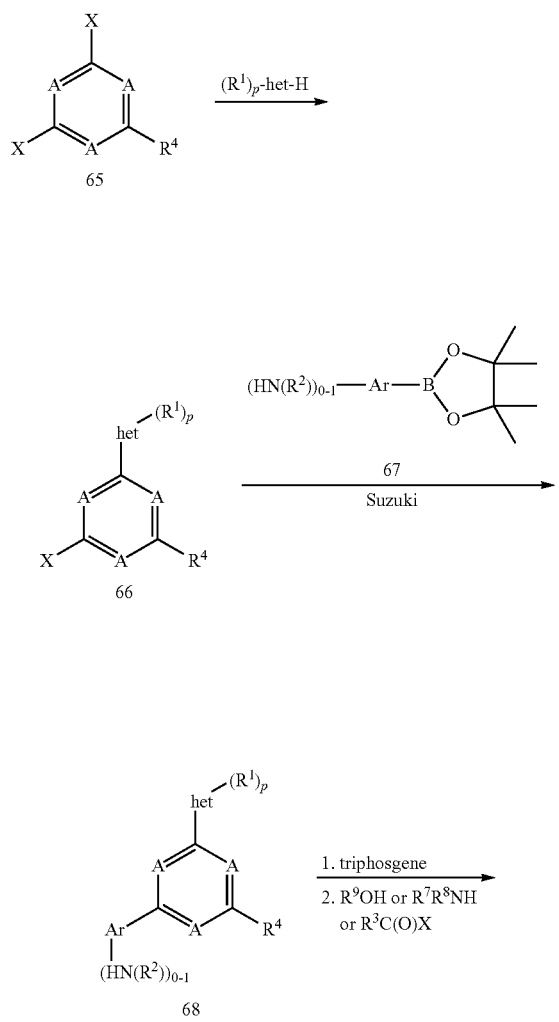

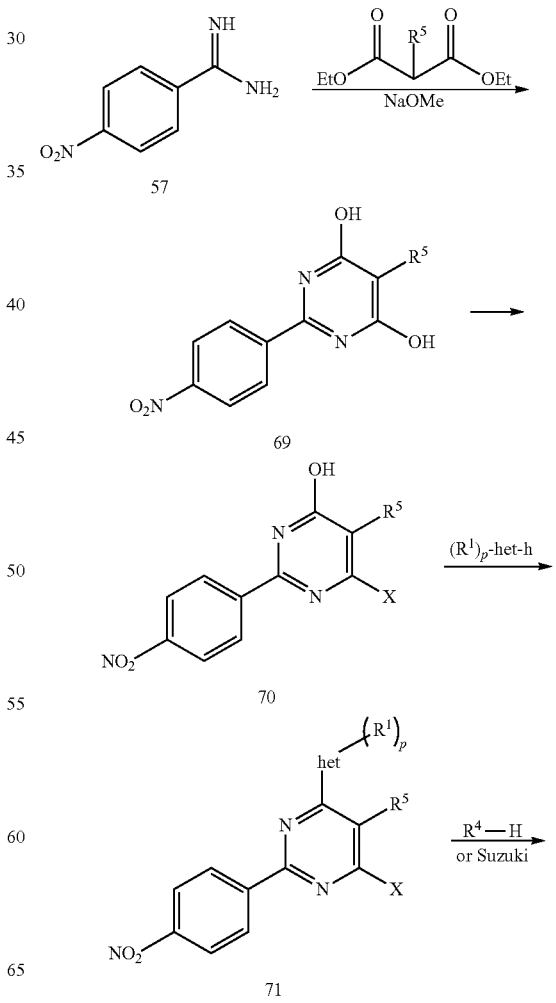

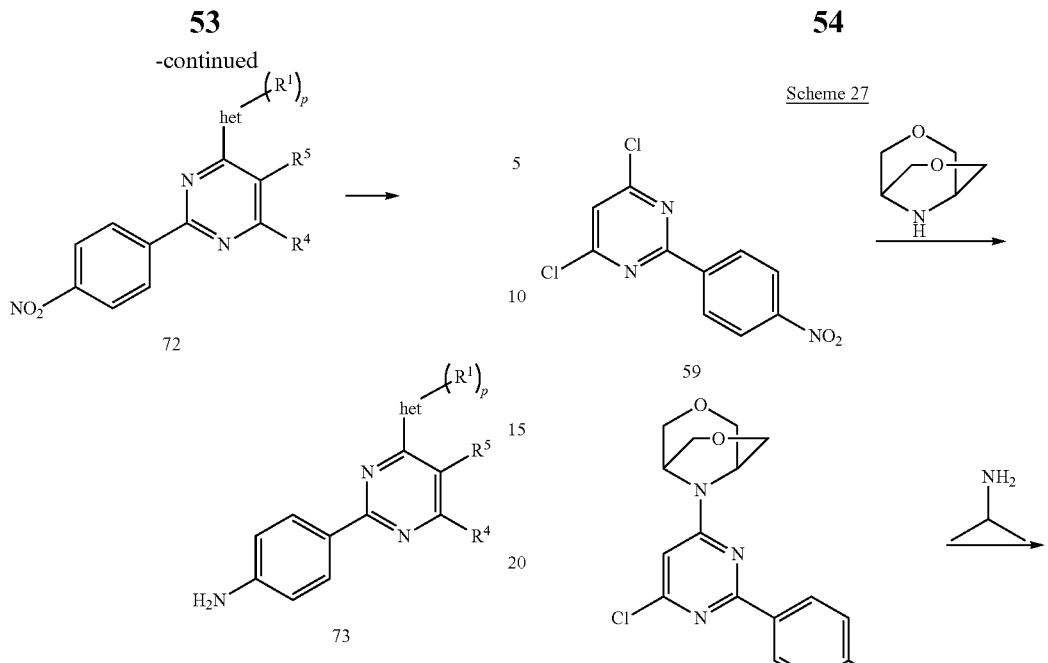
An alternative synthesis of 2-(4-aminophenyl)pyrimidine (73) is shown in Scheme 25.
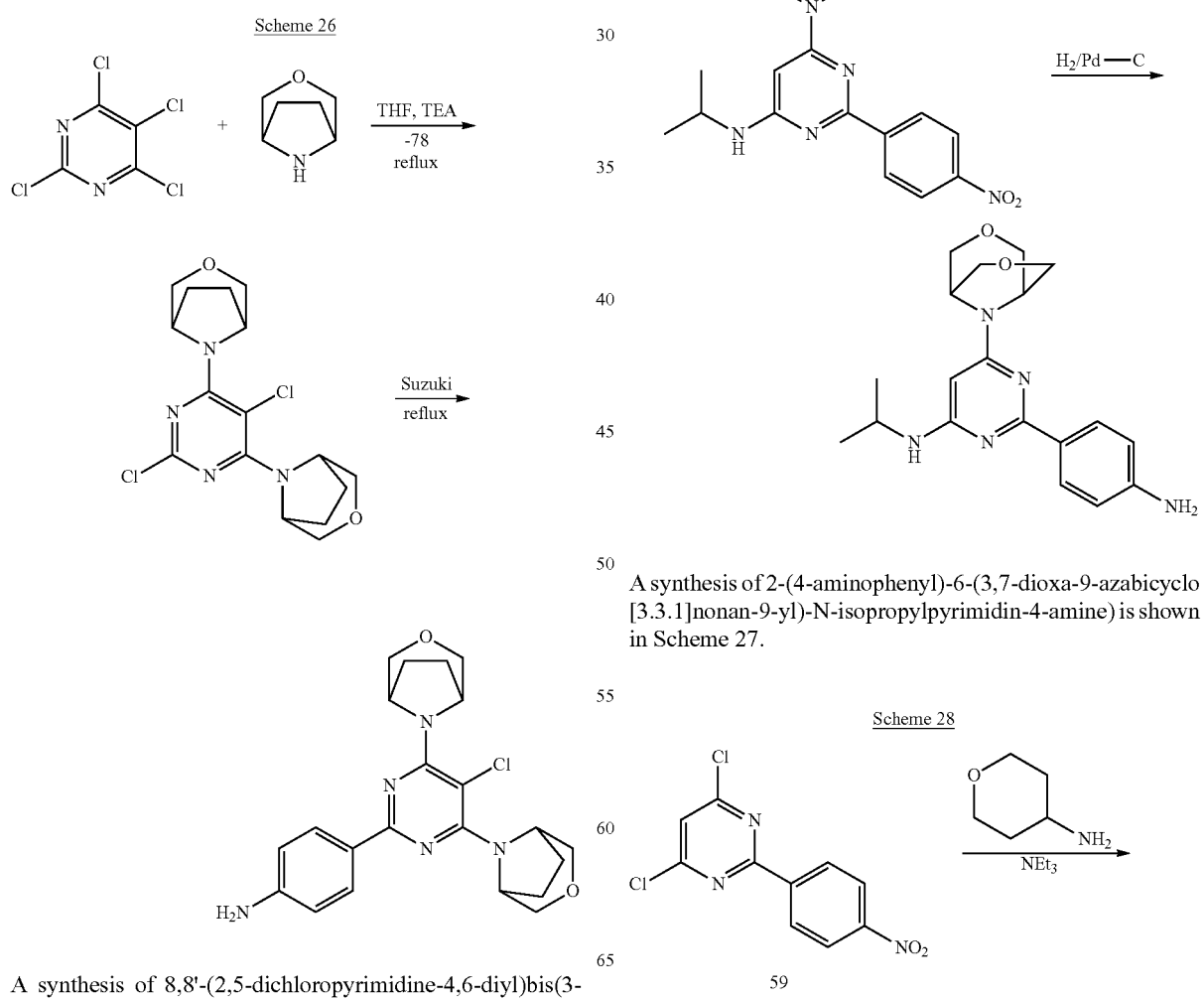
A synthesis of 8,8'-(2,5-dichloropyrimidine-4,6-diyl)bis(3-oxa-8-azabicyclo[3.2.1]octane) is shown in Scheme 26.
A synthesis of 2-(4-aminophenyl)-6-(3,7-dioxa-9-azabicyclo[3.3.1]nonan-9-yl)-N-isopropylpyrimidin-4-amine) is shown in Scheme 27.

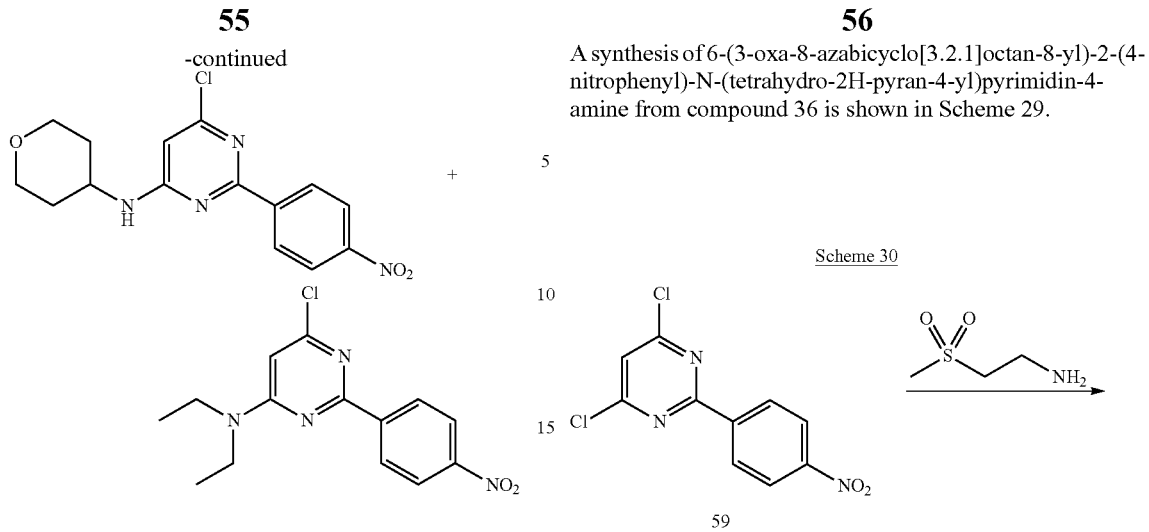
A synthesis of 6-chloro-2-(4-nitrophenyl)-N-(tetrahydro-2H-pyran-4-yl)pyrimidin-4-amine from compound 59 is shown in Scheme 28.
A synthesis of 6-(3-oxa-8-azabicyclo[3.2.1]octan-8-yl)-2-(4-nitrophenyl)-N-(tetrahydro-2H-pyran-4-yl)pyrimidin-4-amine from compound 36 is shown in Scheme 29.
Scheme 30
Scheme 29
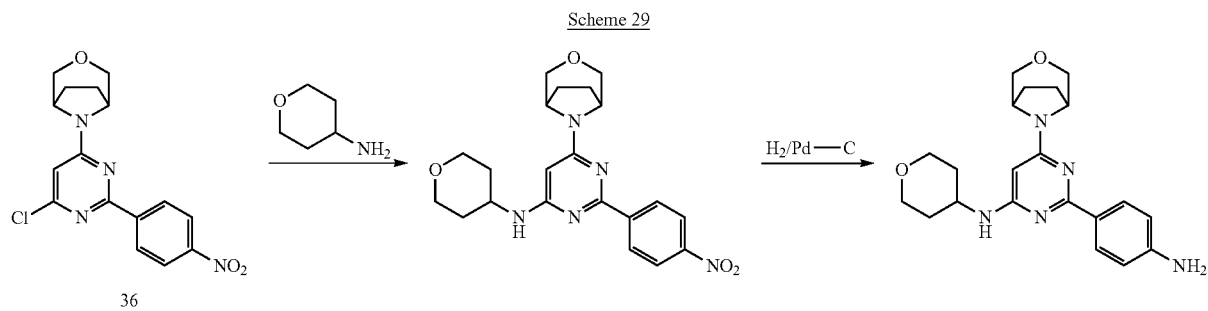
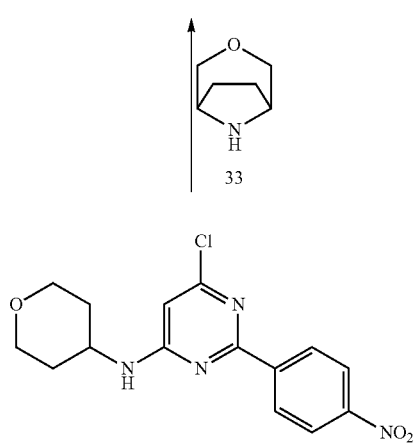

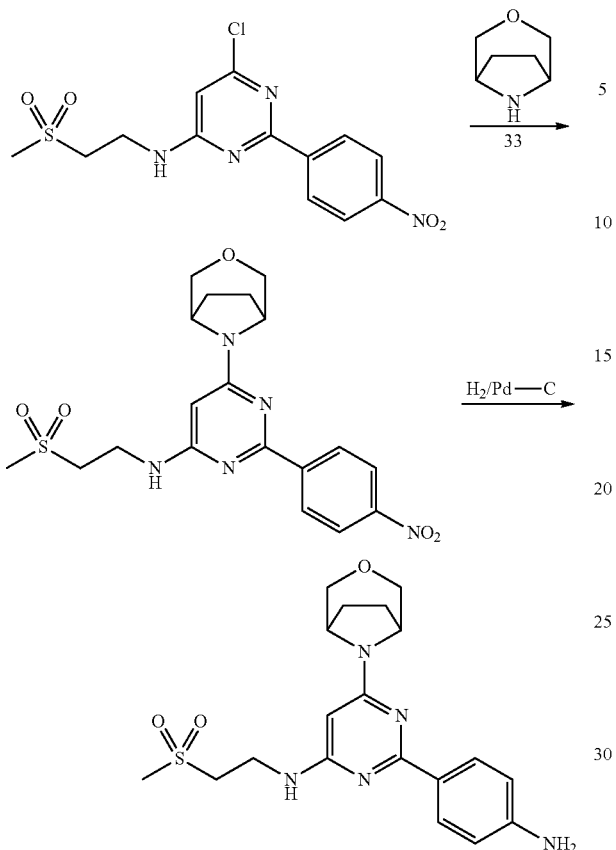

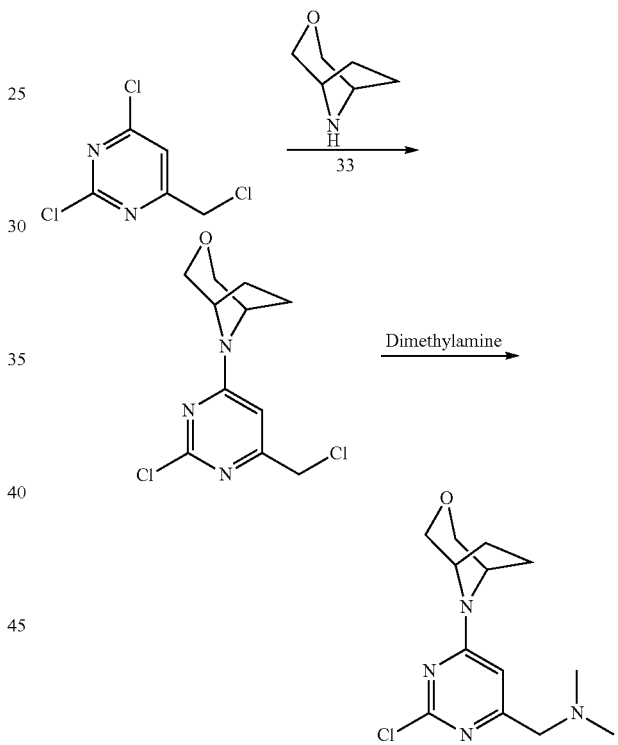

A synthesis of 2-(4-aminophenyl)-6-(3-oxa-8-azabicyclo[3.2.1]octan-8-yl)-N,N-diethylpyrimidin-4-amine from compound 33 is shown in Scheme 31.

Scheme 32

A synthesis of 2-(4-aminophenyl)-6-(3-oxa-8-azabicyclo[3.2.1]octan-8-yl)-N-(2-(methylsulfonyl)ethyl)pyrimidin-4-amine from compound 59 is shown in Scheme 30.

Scheme 31

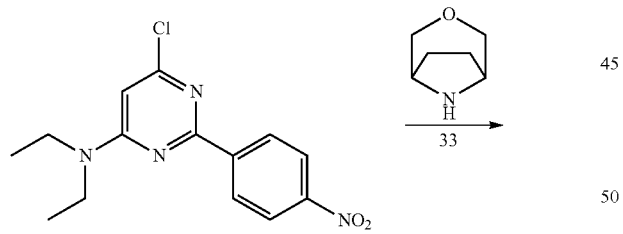

A synthesis of 1-(6-(3-oxa-8-azabicyclo[3.2.1]octan-8-yl)-2-chloropyrimidin-4-yl)-N,N-dimethylmethanamine from compound 33 is shown in Scheme 32.

Scheme 33

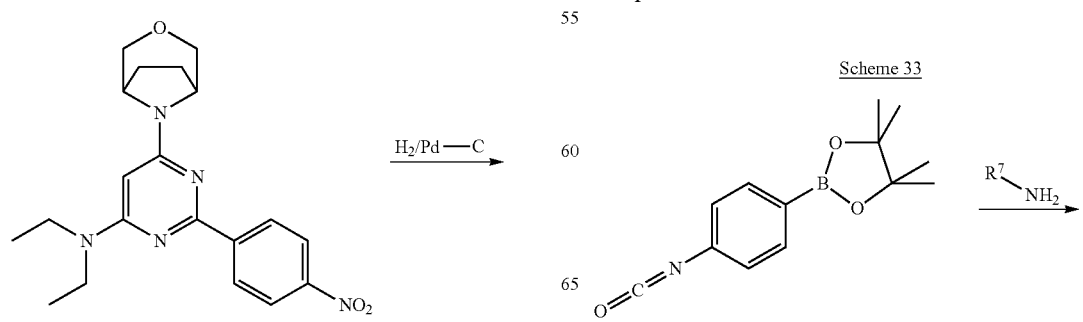

-continued

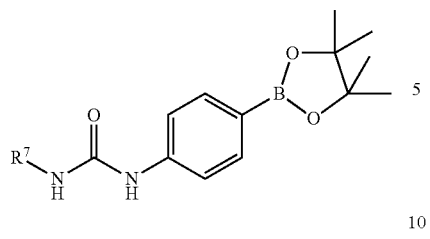

A synthesis of the urea boronic esters from the isocyanate boronates is shown in Scheme 33.

Scheme 34

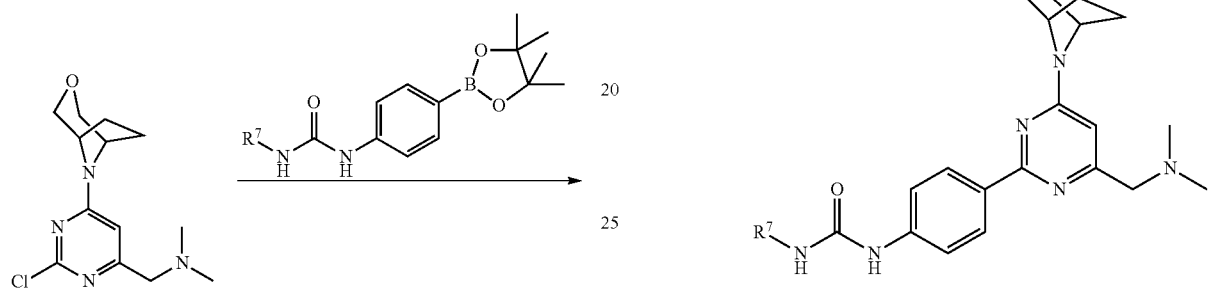

A synthesis of the 1-(4-(4-(3-oxa-8-azabicyclo[3.2.1]octan-8-yl)-6-((dimethylamino)methyl)pyrimidin-2-yl)phenyl)-3-ureas from the urea boronic esters is shown in Scheme 34.

Scheme 35

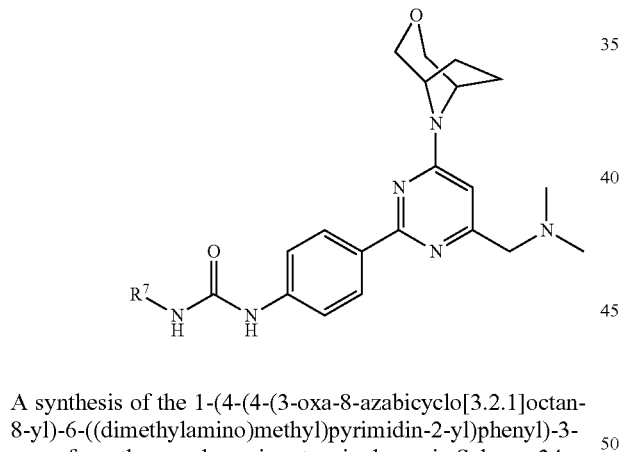

-continued

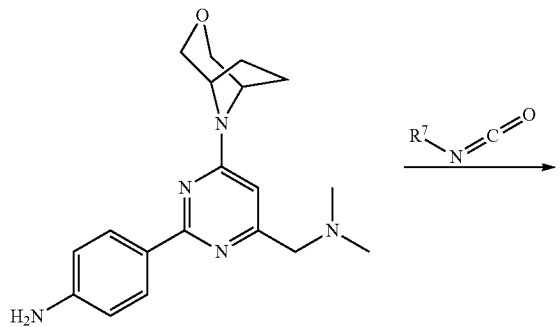

A synthesis of the 1-(4-(4-(3-oxa-8-azabicyclo[3.2.1]octan-8-yl)-6-((dimethylamino)methyl)pyrimidin-2-yl)phenyl)-3-ureas from 4-(4,4,5,5-tetramethyl-1,3,2-dioxaborolan-2-yl)aniline is shown in Scheme 35.

Scheme 36

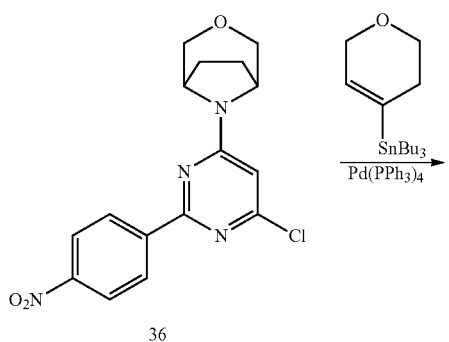

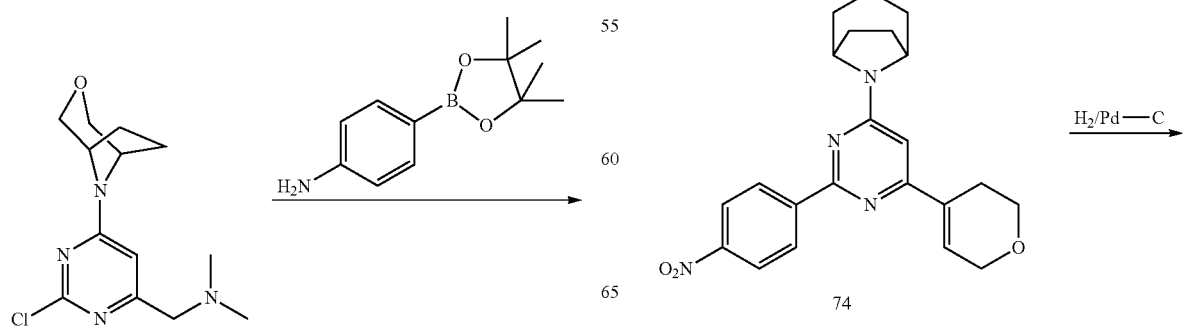

-continued

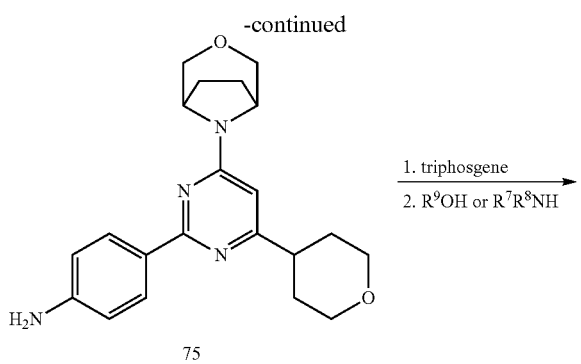

75

1. triphosgene
2. R⁹OH or R⁷R⁸NH

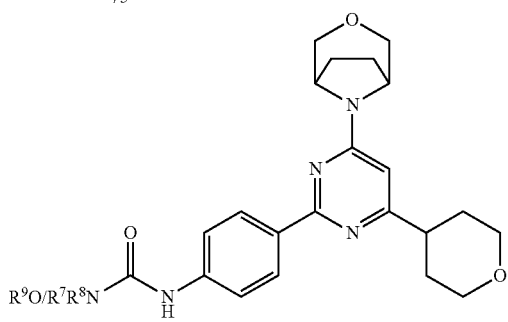

Stille coupling on compound 36 as prepared in Scheme 16 followed by hydrogenation gave 75. Transformation of the aniline in 75 into urea or carbamate compounds was effected as before as shown in Scheme 36.

One of skill in the art will recognize that Schemes 1-36 can be adapted to produce the other compounds of Formula I and pharmaceutically acceptable salts of compounds of Formula I according to the present invention.

EXAMPLES

The following abbreviations are used herein and have the indicated definitions: ATP is adenosine triphosphate, βME is 2-mercaptoethanol, BOC is tertiary-butyloxycarbonyl, and BSA is Bovine Serum Albumin. Celite™ is flux-calcined diatomaceous earth. Celite™ is a registered trademark of World Minerals Inc. CHAPS is (3-[(3-cholamidopropyl)dimethylammonio]-1-propanesulfonic acid, DELFIA is Dissociation-Enhanced Lanthanide Fluorescent Immunoassay. DIPEA or Hunig's Base is diisopropylethylamine, DME is 1,2-dimethoxyethane, DMF is N,N-dimethylformamide, DMSO is dimethylsulfoxide, DPBS is Dulbecco's Phosphate Buffered Saline Formulation. DTT is (2S,3S)-1,4-bis-sulfanylbutane-2,3-diol or dithiothreitol, EDTA is ethylenediaminetetraacetic acid, EGTA is ethylene glycol tetraacetic acid, EtOAc is ethyl acetate, FLAG-TOR is a FLAG-tagged TOR protein, HEPES is 4-(2-hydroxyethyl)-1-piperazineethanesulfonic acid, HPLC is high-pressure liquid chromatography. LC/MS is Liquid Chromatography/Mass Spectrometry, microcrystin LR is the cyclic heptapeptide hepatotoxin produced *Microcystis aeruginosa* containing the amino acids leucine (L) and arginine (R) in the variable positions, MS is mass spectrometry, mTOR is Mammalian Target of Rapamycin (a protein), MTS is 3-(4,5-dimethylthiazol-2-yl)-5-(3 carboxymethoxyphenyl)-2-(4-sulfophenyl)-2H-tetrazolium, inner salt, PBS is phosphate-buffered saline (pH 7.4), PI3K is phosphoinositide 3-kinase (an enzyme). Ni(Ra) is Raney™ nickel, a sponge-metal catalyst produced when a block of nickel-aluminum alloy is treated with concentrated sodium hydroxide. Raney™ is a registered trademark of W. R. Grace and Company. RPMI 1640 is a buffer (Sigma-Aldrich Corp., St. Louis, Mo., USA), RT is retention time, SDS is dodecyl sulfate (sodium salt), SRB is Sulforhodamine B, TAMRA is tetramethyl-6-carboxyrhodamine, TFA is trifluoroacetic acid, THF is tetrahydrofuran, and TRIS is tris (hydroxymethyl)aminomethane.

Synthetic Methods

The following methods outline the synthesis of the Examples of the present invention.

Scheme 1

3-(2-Chloro-pyrimidin-4-yl)-8-oxa-3-aza-bicyclo [3.2.1]octane (3)

A 745 mg (5 mmol) portion 2,4-dichloropyrimidine (1) was dissolved in 20 mL EtOH at 0 C. 8-oxa-3-aza-bicyclo [3.2.1]octane hydrochloride (2, 748 mg, 5 mmol) was added followed by the addition of NEt₃ (2.1 mL, 15 mmol). The mixture was stirred for 1 hour at ambient temperature. The mixture was concentrated, dissolved in EtOAc and washed with saturated NaHCO₃. The aqueous phase was extracted with EtOAc and the combined organic phases were dried (MgSO₄), filtered and concentrated. The mixture was purified by silica gel chromatography (20-70% EtOAc in hexanes) to give 1,003 mg (4.4 mmol, 89%) of 3-(2-chloro-pyrimidin-4-yl)-8-oxa-3-aza-bicyclo[3.2.1]octane (3) along with 50 mg (0.22 mmol, 4%) of 3-(4-chloro-pyrimidin-2-yl)-8-oxa-3-aza-bicyclo[3.2.1]octane (4).

Scheme 2

General Conditions for Suzuki Coupling (Formation of 6)

Aryl chloride 5 (1 eq) and 4-aminophenylboronic acid, pinacol ester (1.1 eq) are dissolved in toluene (10 mL/mmol) and EtOH (6 mL/mmol). A 2M solution of Na₂CO₃ is added (2 mL/mmol, 4 eq) and the mixture is degassed by leading a stream of nitrogen through the solution. Tetrakis(triphenylphosphine) palladium is added (5-10 mol %) and the mixture is heated under reflux until the reaction is complete (4-48 hours). The reaction mixture is diluted with EtOAc, washed with saturated NaHCO₃ and the organic phase is dried (MgSO₄), filtered and concentrated. The mixture is purified by silica gel chromatography using a gradient of ethyl acetate in hexanes.

Illustrative Example for Suzuki Coupling

4-[4-(8-Oxa-3-azabicyclo[3.2.1]oct-3-yl)pyrimidin-2-yl]aniline 3-(2-Chloro-pyrimidin-4-yl)-8-oxa-3-aza-bicyclo[3.2.1] octane (3, 564 mg, 2.5 mmol) and 4-aminophenylboronic acid, pinacol ester (602 mg, 2.75 mmol) are dissolved in toluene (25 mL) and EtOH (15 mL). A 2M solution of Na₂CO₃ is added (5 mL) and the mixture is degassed by leading a stream of nitrogen through the solution. Tetrakis (triphenylphosphine) palladium is added (144 mg, 5 mol %) and the mixture is heated under reflux for 48 hours. The mixture is diluted with EtOAc, washed with saturated NaHCO₃, the organic phase is dried (MgSO₄), filtered, and concentrated. The mixture is purified by silica gel chromatography using a gradient of ethyl acetate in hexanes (40-

100%) to give 576 mg (2.04 mmol, 82%) of 4-[4-(8-oxa-3-azabicyclo[3.2.1]oct-3-yl)pyrimidin-2-yl]aniline. RT 1.51, M+H=283.1

General Conditions for Urea or Carbamate Formation (Conversion of 6 into 7)

Aniline 6 (1 eq) is dissolved in dichloromethane (10 mL/mmol) and NEt₃ is added (0.65 mL per mmol of 6). This solution is added in drops to a solution of triphosgene (0.5 eq) in dichloromethane (10 mL per mmol of 6). The mixture is stirred for 5-30 min at room temperature and is then added to excess (3-10 eq) alcohol or amine in dichloromethane or THF. The mixture is stirred at room temperature (4-24 hours), concentrated, and purified by HPLC.

Illustrative Example for Urea or Carbamate Formation (Conversion of 6 into 7)

A 0.36 mmol portion of 4-[4-(8-oxa-3-aza-bicyclo[3.2.1]oct-3-yl)-pyrimidin-2-yl]-phenylamine (101 mg) was dissolved in dichloromethane (3 mL) and NEt₃ was added (0.195 mL). This solution was added in drops to a solution of 53 mg (0.18 mmol) triphosgene in dichloromethane (3 mL). After 5 min, the solution was divided over 3 vials containing excess amine or alcohol in dichloromethane or THF. After stirring for 4 hours at room temperature the solvents were evaporated and the mixtures were purified by HPLC (Waters, TFA buffers) to give the following products:

2-Hydroxyethyl {4-[4-(8-oxa-3-azabicyclo[3.2.1]oct-3-yl)pyrimidin-2-yl]phenyl}carbamate Using a solution of 56 µL ethylene glycol in 1 mL dichloromethane, the title compound was obtained (41 mg, 92%). RT 1.54, M+H=371.2.

1-Methyl-3-{4-[4-(8-oxa-3-azabicyclo[3.2.1]oct-3-yl)pyrimidin-2-yl]phenyl}urea

Using a 2N solution of methylamine in THF, the title compound was obtained (35 mg, 87%). RT 1.52, M+H=340.2.

1-{4-[4-(8-Oxa-3-azabicyclo[3.2.1]oct-3-yl)pyrimidin-2-yl]phenyl}-3-pyridin-4-ylurea Using a suspension of 4-aminopyridine (47 mg) in 1 mL dichloromethane, the title compound was obtained (44 mg, 71%). RT 1.44, M+H=403.2.

Scheme 3

3-(2,6-Dichloro-pyrimidin-4-yl)-8-oxa-3-aza-bicyclo [3.2.1]octane (9)

2,4,6-Trichloropyrimidine (8, 6.325 mL, 55 mmol) was dissolved in 220 mL EtOH at 0° C. 8-Oxa-3-aza-bicyclo [3.2.1]octane hydrochloride (2, 8.23 g, 55 mmol) was added followed by the addition of NEt₃ (23.1 mL, 165 mmol). The mixture was allowed to warm to room temperature and stirred for 1 hour at ambient temperature. The mixture was concentrated, dissolved in EtOAc and washed with saturated NaHCO₃. The aqueous phase was extracted with EtOAc the combined organic phases were dried (MgSO₄), filtered, and concentrated. The mixture was purified by silica gel chromatography (10-80% EtOAc in hexanes) to give 11.807 g (45 mmol, 83%) of 3-(2,6-dichloro-pyrimidin-4-yl)-8-oxa-3-aza-bicyclo[3.2.1]octane (9) along with 1.631 g (6.2 mmol, 11%) of 3-(4,6-dichloro-pyrimidin-2-yl)-8-oxa-3-aza-bicyclo[3.2.1]octane (10).

Scheme 4

4-[2-Chloro-6-(8-oxa-3-aza-bicyclo[3.2.1]oct-3-yl)-pyrimidin-4-yl]-phenylamine (11) and 4-[4-chloro-6-(8-oxa-3-aza-bicyclo[3.2.1]oct-3-yl)-pyrimidin-2-yl]-phenylamine (12)

In a 2-5 mL microwave vial was placed 3-(2,6-dichloropyrimidin-4-yl)-8-oxa-3-azabicyclo[3.2.1]octane (9, 100 mg, 0.384 mmol) and 4-(4,4,5,5-tetramethyl-1,3,2-dioxaborolan-2-yl)aniline (84 mg, 0.384 mmol) in toluene (1.500 mL) and ethanol (1 mL) to give a light yellow solution. Na₂CO₃ (2M solution in water) (0.769 mL, 1.538 mmol) was added. The mixture was degassed by bubbling nitrogen through the solution. Pd(PPh₃)₄ (22.21 mg, 0.019 mmol) was added. The reaction was heated under microwave irradiation at 120° C. for 30 min. The reaction mixture was diluted with ethyl acetate and washed with sat NaHCO₃ (2×). The organic layer was dried over MgSO₄, filtered and concentrated. The crude product was added to a silica gel column and was eluted with 20-80% ethyl acetate in hexanes. Collected fractions were concentrated to give 4-[2-chloro-6-(8-oxa-3-aza-bicyclo [3.2.1]oct-3-yl)-pyrimidin-4-yl]-phenylamine (11, 19 mg, 16%) and 4-[4-chloro-6-(8-oxa-3-aza-bicyclo[3.2.1]oct-3-yl)-pyrimidin-2-yl]-phenylamine (12, 18 mg, 15%).

Scheme 5

3-[6-Chloro-2-(4-nitro-phenyl)-pyrimidin-4-yl]-8-oxa-3-aza-bicyclo[3.2.1]octane (13), 3-[2-chloro-6-(4-nitro-phenyl)-pyrimidin-4-yl]-8-oxa-3-aza-bicyclo[3.2.1]octane (14) and 3-[2,6-bis-(4-nitro-phenyl)-pyrimidin-4-yl]-8-oxa-3-aza-bicyclo[3.2.1]octane (15):

3-(2,6-Dichloropyrimidin-4-yl)-8-oxa-3-aza-bicyclo [3.2.1]octane (9) was dissolved in toluene (24 mL) and EtOH (16 mL). To this solution was added 4-nitrophenylboronic acid pinacol ester (1.25 g, 5 mmol) and 8 mL of a 2M solution of Na₂CO₃. The mixture was degassed by bubbling nitrogen through the solution. Pd(PPh₃)₄ (231 mg, 0.2 mmol) was added and the mixture was heated under reflux overnight. The mixture was filtered. The solids, consisting of 3-[2,6-bis-(4-nitro-phenyl)-pyrimidin-4-yl]-8-oxa-3-aza-bicyclo[3.2.1] octane (15), were collected and washed with water and dichloromethane. The combined filtrates were concentrated, dissolved in dichloromethane and washed with saturated NaHCO₃. The organic phase was dried (MgSO₄), filtered and concentrated. The crude product was added to a silica gel column and was eluted with 10-50% ethyl acetate in hexanes. Collected fractions were concentrated to give 3-[6-chloro-2-(4-nitro-phenyl)-pyrimidin-4-yl]-8-oxa-3-aza-bicyclo [3.2.1]octane (13, 135 mg, 10%) along with 3-[2-chloro-6-(4-nitro-phenyl)-pyrimidin-4-yl]-8-oxa-3-aza-bicyclo [3.2.1]octane (14, 110 mg, 8%).

Scheme 6

3-(6-Chloro-2-iodo-pyrimidin-4-yl)-8-oxa-3-aza-bicyclo[3.2.1]octane (16):

In a 20 mL scintillation vial was placed 3-(2,6-dichloropyrimidin-4-yl)-8-oxa-3-azabicyclo[3.2.1]octane (9, 780 mg, 3 mmol) in chloroform (2 ml) to give a very light yellow solution. Sodium iodide (749 mg, 5 mmol) was added to give a suspension. The mixture was cooled to 0° C. and an aqueous solution (57% w/w) of hydrogen iodide (0.356 ml, 2.70 mmol) was added, resulting in a thick yellow precipitate. The mixture was stirred at room temperature for 16 hours. LCMS indicated only a trace of product being formed. Additional aqueous. HI (356 μL) was added and the mixture was stirred at room temperature for 64 hours. Additional aqueous HI was added (712 μL) and the suspension was stirred for an additional 7 hours. LCMS showed the presence of the desired product as the main peak along with a dehalogenated impurity and starting material. The mixture was diluted with water and solid $K_2CO_3$ was added to pH~8. The aqueous phase was extracted with dichloromethane. The organic phase was washed with aqueous sodium thiosulfate to decolorize, dried over $MgSO_4$, filtered and concentrated. The crude product was added to a silica gel column and was eluted with ethyl acetate in hexanes (15-40%). Collected fractions were concentrated to give 588 mg (1.7 mmol, 56%) of a white solid, which was a mixture of the desired product containing approximately 20% starting material. The mixture was carried on to the next step.

3-[6-Chloro-2-(4-nitro-phenyl)-pyrimidin-4-yl]-8-oxa-3-aza-bicyclo[3.2.1]octane (13)

In a 0.5-2 mL microwave vial was placed 3-(6-chloro-2-iodopyrimidin-4-yl)-8-oxa-3-azabicyclo[3.2.1]octane (16, 50 mg, 0.142 mmol) and 4,4,5,5-tetramethyl-2-(4-nitrophenyl)-1,3,2-dioxaborolane (35.4 mg, 0.142 mmol) in DME (1.5 ml) to give an orange solution. $Na_2CO_3$ (2M solution in water) (0.284 ml, 0.569 mmol) was added. The mixture was degassed by bubbling nitrogen through the solution. $Pd(PPh_3)_4$ (16.43 mg, 0.014 mmol) was added and the mixture was heated under microwave irradiation for 60 min at 100° C. The mixture was diluted with ethyl acetate and washed with a saturated solution of $NaHCO_3$. The organic phase was dried ($MgSO_4$) and concentrated. The crude product was added to a silica gel column and was eluted with ethyl acetate in hexanes (10-25%). Collected fractions were concentrated to give 39 mg (0.11 mmol, 79%) of the title compound as an off-white/yellow solid. The thus obtained compound was identical to the same compound prepared according to Scheme 5.

Scheme 7

Isopropyl-[2-(4-nitro-phenyl)-6-(8-oxa-3-aza-bicyclo[3.2.1]oct-3-yl)-pyrimidin-4-yl]-amine (17)

In a 2-5 mL microwave vial was placed 3-(6-chloro-2-(4-nitrophenyl)pyrimidin-4-yl)-8-oxa-3-azabicyclo[3.2.1]octane (13, 70 mg, 0.202 mmol) in $iPrNH_2$ (4 ml) to give a yellow suspension. The reaction was heated under microwave irradiation at 140° C. for 90 min. The mixture was concentrated, dissolved in dichloromethane and washed with sat $NaHCO_3$. The organic phase was dried over $MgSO_4$, filtered and concentrated to give 74 mg of the title compound as a yellow solid (99%).

[2-(4-Amino-phenyl)-6-(8-oxa-3-aza-bicyclo[3.2.1]oct-3-yl)-pyrimidin-4-yl]-isopropyl-amine (18)

In a 250 mL round-bottomed flask was placed 6-(8-oxa-3-azabicyclo[3.2.1]octan-3-yl)-N-isopropyl-2-(4-nitrophenyl)pyrimidin-4-amine (17, 74 mg, 0.200 mmol) in 2-propanol (7 mL) and dichloromethane (7 mL) to give a yellow solution. A catalytic amount of Pd on charcoal (wet) was added and the mixture was stirred under a hydrogen atmosphere for 1 hour. The mixture was filtered over Celite™, rinsed with dichloromethane and concentrated to give the title compound in quantitative yield.

The following products were prepared from [2-(4-aminophenyl)-6-(8-oxa-3-aza-bicyclo[3.2.1]oct-3-yl)-pyrimidin-4-yl]-isopropyl-amine (18), using the general procedure from scheme 2 for the preparation of 7:

1-Methyl-3-(4-{4-[(1-methylethyl)amino]-6-(8-oxa-3-azabicyclo[3.2.1]oct-3-yl)pyrimidin-2-yl}phenyl)urea Using a solution of 2N methylamine in THF, the title compound was obtained in a yield of 10 mg (35%). RT 1.72. M+H=397.2.

1-Cyclopropyl-3-(4-{4-[(1-methylethyl)amino]-6-(8-oxa-3-azabicyclo[3.2.1]oct-3-yl)pyrimidin-2-yl}phenyl)urea Using a solution of cyclopropylamine in dichloromethane, the title compound was obtained in a yield of 9 mg (29%). RT 1.76. M+H=423.2.

1-(4-{4-[(1-Methylethyl)amino]-6-(8-oxa-3-azabicyclo[3.2.1]oct-3-yl)pyrimidin-2-yl}phenyl)-3-pyridin-4-ylurea Using a suspension of 4-aminopyridine in dichloromethane, the title compound was obtained in a yield of 8 mg, 24%. RT 1.57. M+H=460.2.

1-(4-{4-[(1-Methylethyl)amino]-6-(8-oxa-3-azabicyclo[3.2.1]oct-3-yl)pyrimidin-2-yl}phenyl)-3-[4-(4-methylpiperazin-1-yl)phenyl]urea Using a solution of 4-(4-methylpiperazin-1-yl)aniline in dichloromethane, the title compound was obtained in a yield of 15 mg, 37%. RT 1.73. M+H=557.3.

Scheme 8

4-[4-Isopropoxy-6-(8-oxa-3-aza-bicyclo[3.2.1]oct-3-yl)-pyrimidin-2-yl]-phenylamine (19)

In a 2-5 mL microwave vial was placed 3-(6-chloro-2-(4-nitrophenyl)pyrimidin-4-yl)-8-oxa-3-azabicyclo[3.2.1]octane (13, 70 mg, 0.202 mmol) in 2-propanol (4 mL) to give a yellow suspension. Sodium hydride (60% in oil, 32.3 mg, 0.807 mmol) was added and the mixture was stirred until no further formation of hydrogen gas was observed. The reaction was heated under microwave irradiation at 140° C. for 30 min to give a bright orange suspension. Work-up: the solvents were evaporated. The residue was dissolved in dichloromethane and washed with sat $NaHCO_3$. The organic phase was dried over $MgSO_4$, filtered and concentrated to give the title compound in a quantitative yield.

The following products were prepared from 4-[4-isopropoxy-6-(8-oxa-3-aza-bicyclo[3.2.1]oct-3-yl)-pyrimidin-2- yl]-phenylamine (19), using the general procedure from scheme 2 for the preparation of 7:

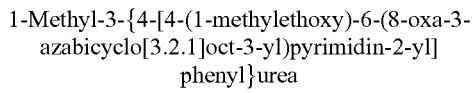
1-Methyl-3-{4-[4-(1-methylethoxy)-6-(8-oxa-3-azabicyclo[3.2.1]oct-3-yl)pyrimidin-2-yl]phenyl}urea Using a solution of 2N methylamine in THF, the title compound was obtained in a yield of 3 mg (9%).

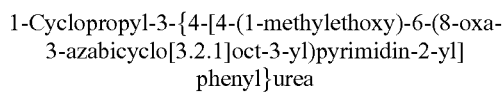
1-Cyclopropyl-3-{4-[4-(1-methylethoxy)-6-(8-oxa-3-azabicyclo[3.2.1]oct-3-yl)pyrimidin-2-yl]phenyl}urea Using a solution of cyclopropylamine in dichloromethane, the title compound was obtained in a yield of 3 mg (8%).

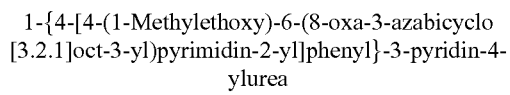
1-{4-[4-(1-Methylethoxy)-6-(8-oxa-3-azabicyclo[3.2.1]oct-3-yl)pyrimidin-2-yl]phenyl}-3-pyridin-4-ylurea Using a suspension of 4-aminopyridine in dichloromethane, the title compound was obtained in a yield of 6 mg, 16%. RT 1.92. M+H=461.2.

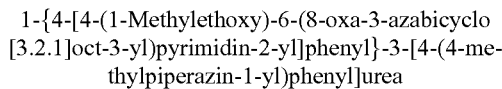
1-{4-[4-(1-Methylethoxy)-6-(8-oxa-3-azabicyclo[3.2.1]oct-3-yl)pyrimidin-2-yl]phenyl}-3-[4-(4-methylpiperazin-1-yl)phenyl]urea Using a solution of 4-(4-methylpiperazin-1-yl)aniline in dichloromethane, the title compound was obtained in a yield of 9 mg, 21%. RT 1.95. M+H=558.3.

Scheme 9

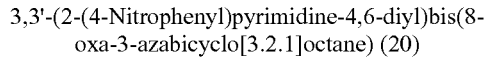
3,3'-(2-(4-Nitrophenyl)pyrimidine-4,6-diyl)bis(8-oxa-3-azabicyclo[3.2.1]octane) (20)

In a 100 mL round-bottomed flask was placed 3-(6-chloro-2-(4-nitrophenyl)pyrimidin-4-yl)-8-oxa-3-azabicyclo[3.2.1]octane (13, 135 mg, 0.39 mmol) in dioxane (5 ml). 8-Oxa-3-azabicyclo[3.2.1]octane, HCl (2, 0.15 g, 1 mmol) and triethylamine (0.28 ml, 2 mmol) were added. The mixture was stirred at 80° C. for 16 hours. DIPEA was added (0.3 mL) and stirring was continued at 80° C. for 64 hours. The reaction mixture was diluted with ethyl acetate and washed with sat NaHCO₃ followed by 0.1 N HCl. The organic phase was dried over MgSO₄, filtered and concentrated. The crude product was added to a silica gel column and eluted with ethyl acetate in hexanes (10-50%) to give 65 mg of the title compound (0.15 mmol, 39%).

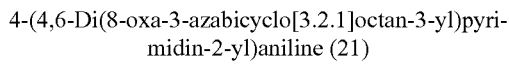
4-(4,6-Di(8-oxa-3-azabicyclo[3.2.1]octan-3-yl)pyrimidin-2-yl)aniline (21)

In a 250 mL round-bottomed flask was placed 3,3'-(2-(4-nitrophenyl)pyrimidine-4,6-diyl)bis(8-oxa-3-azabicyclo[3.2.1]octane) (20, 65 mg, 0.15 mmol) in ethanol (3 ml). A catalytic amount of Pd on charcoal (wet) was added and the mixture was stirred under a hydrogen atmosphere for 16 hours. The mixture was filtered over Celite™, rinsed with dichloromethane and concentrated to give a quantitative yield of the title compound along with an impurity (the N-ethyl aniline product). The crude mixture was reacted in the next step.

The following products were prepared from 4-(4,6-di(8-oxa-3-azabicyclo[3.2.1]octan-3-yl)pyrimidin-2-yl)aniline (21) using the general procedure from scheme 2 for the preparation of 7:

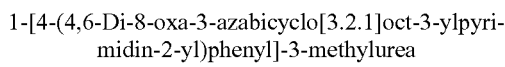
1-[4-(4,6-Di-8-oxa-3-azabicyclo[3.2.1]oct-3-ylpyrimidin-2-yl)phenyl]-3-methylurea Using a solution of 2N methylamine in THF, the title compound was obtained in a yield of 7 mg (31%). RT. 1.88. M+H=451.2.

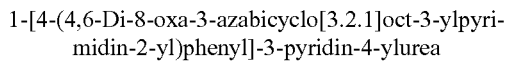
1-[4-(4,6-Di-8-oxa-3-azabicyclo[3.2.1]oct-3-ylpyrimidin-2-yl)phenyl]-3-pyridin-4-ylurea Using a suspension of 4-aminopyridine in dichloromethane, the title compound was obtained in a yield of 10 mg, 32%. RT 1.83. M+H=514.2.

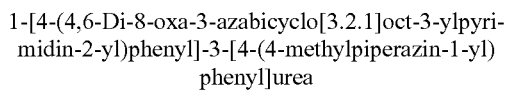
1-[4-(4,6-Di-8-oxa-3-azabicyclo[3.2.1]oct-3-ylpyrimidin-2-yl)phenyl]-3-[4-(4-methylpiperazin-1-yl)phenyl]urea Using a solution of 4-(4-methylpiperazin-1-yl)aniline in dichloromethane, the title compound was obtained in a yield of 16 mg, 43%. RT 1.74. M+H=611.3.

The following products were prepared from the N-ethyl impurity in 4-(4,6-di(8-oxa-3-azabicyclo[3.2.1]octan-3-yl)pyrimidin-2-yl)aniline (21) using the general procedure from scheme 2 for the preparation of 7:

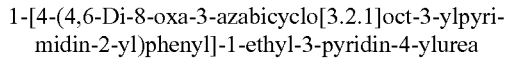
1-[4-(4,6-Di-8-oxa-3-azabicyclo[3.2.1]oct-3-ylpyrimidin-2-yl)phenyl]-1-ethyl-3-pyridin-4-ylurea Using a suspension of 4-aminopyridine in dichloromethane, the title compound was obtained in a yield of 5 mg, 16%. RT 2.04. M+H=542.3.

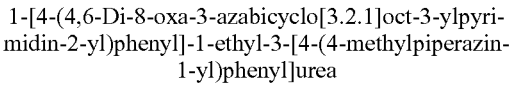
1-[4-(4,6-Di-8-oxa-3-azabicyclo[3.2.1]oct-3-ylpyrimidin-2-yl)phenyl]-1-ethyl-3-[4-(4-methylpiperazin-1-yl)phenyl]urea Using a solution of 4-(4-methylpiperazin-1-yl)aniline in dichloromethane, the title compound was obtained in a yield of 4 mg, 10%.

Scheme 10

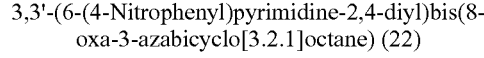
3,3'-(6-(4-Nitrophenyl)pyrimidine-2,4-diyl)bis(8-oxa-3-azabicyclo[3.2.1]octane) (22)

In a 100 mL round-bottomed flask was placed 3-[2-chloro-6-(4-nitro-phenyl)-pyrimidin-4-yl]-8-oxa-3-aza-bicyclo[3.2.1]octane (14, 110 mg, 0.32 mmol) in dioxane (5 ml). 8-Oxa-3-azabicyclo[3.2.1]octane, HCl (2, 0.15 g, 1 mmol) and triethylamine (0.28 ml, 2 mmol) were added. The mixture was stirred at 80° C. for 16 hours. DIPEA was added (0.3 mL) and stirring was continued at 80° C. for 64 hours. The reaction mixture was diluted with ethyl acetate and washed with sat NaHCO₃. The solids between the organic phase and aqueous phase were dissolved in dichloromethane and washed with saturated NaHCO₃. The combined organic phases were dried over MgSO₄, filtered and concentrated. The crude product was added to a silica gel column and eluted with ethyl acetate in hexanes (10-40%) to give 89 mg of the title compound (0.21 mmol, 65%).

4-(2,6-Di(8-oxa-3-azabicyclo[3.2.1]octan-3-yl)pyrimidin-4-yl)aniline (23)

In a 250 mL round-bottomed flask was placed 3,3'-(6-(4-nitrophenyl)pyrimidine-2,4-diyl)bis(8-oxa-3-azabicyclo[3.2.1]octane) (22, 89 mg, 0.21 mmol) in ethanol (3 ml). A catalytic amount of Pd on charcoal (wet) was added and the mixture was stirred under a hydrogen atmosphere for 16 hours. The mixture was filtered over Celite™, rinsed with dichloromethane and concentrated to give a quantitative yield of the title compound along with an impurity (the N-ethyl aniline product). The crude mixture was reacted in the next step.

The following products were prepared from 4-(2,6-di(8-oxa-3-azabicyclo[3.2.1]octan-3-yl)pyrimidin-4-yl)aniline (23) using the general procedure from scheme 2 for the preparation of 7:

1-[4-(2,6-Di-8-oxa-3-azabicyclo[3.2.1]oct-3-ylpyrimidin-4-yl)phenyl]-3-methylurea Using a solution of 2N methylamine in THF, the title compound was obtained in a yield of 11 mg (50%). RT. 1.64. M+H=451.2.

1-[4-(2,6-Di-8-oxa-3-azabicyclo[3.2.1]oct-3-ylpyrimidin-4-yl)phenyl]-3-pyridin-4-ylurea Using a suspension of 4-aminopyridine in dichloromethane, the title compound was obtained in a yield of 13 mg, 40%. RT 1.61. M+H=514.2.

1-[4-(2,6-Di-8-oxa-3-azabicyclo[3.2.1]oct-3-ylpyrimidin-4-yl)phenyl]-3-[4-(4-1-yl)phenyl]urea Using a solution of 4-(4-methylpiperazin-1-yl)aniline in dichloromethane, the title compound was obtained in a yield of 27 mg, 74%. RT 1.68. M+H=611.3.

1-Cyclopropyl-3-[4-(2,6-di-8-oxa-3-azabicyclo[3.2.1]oct-3-ylpyrimidin-4-yl)phenyl]urea Using a solution of cyclopropylamine in dichloromethane, the title compound was obtained in a yield of 16 mg (67%). RT. 1.81. M+H=477.3.

Scheme 11

3-[2,6-Bis-(4-aminophenyl)-pyrimidin-4-yl]-8-oxa-3-aza-bicyclo[3.2.1]octane (24)

In a 500 mL round-bottomed flask was placed 3-[2,6-bis-(4-nitro-phenyl)-pyrimidin-4-yl]-8-oxa-3-aza-bicyclo[3.2.1]octane (15) in ethanol (100 ml). A catalytic amount of Pd on charcoal (wet) was added and the mixture was stirred under a hydrogen atmosphere for 40 h. The mixture was filtered over Celite™, rinsed with MeOH, and concentrated. The crude product was added to a silica gel column and eluted with ethyl acetate in hexanes (40-100%) to give 295 mg of the title compound (0.79 mmol).

Formation of urea or carbamate (25) from 3-[2,6-Bis-(4-aminophenyl)-pyrimidin-4-yl]-8-oxa-3-aza-bicyclo[3.2.1]octane (24):

To 0.8 mmol (295 mg) of 3-[2,6-bis-(4-aminophenyl)-pyrimidin-4-yl]-8-oxa-3-aza-bicyclo[3.2.1]octane (24) was added dichloromethane (8 mL) and NEt$_3$ (0.52 mL). This suspension was added in drops to a solution of 237 mg (0.8 mmol) triphosgene in dichloromethane (8 mL). After 20 min, the solution was divided over 8 vials containing excess amine or alcohol in dichloromethane or THF. After stirring for 16 hours at room temperature the solvents were evaporated and the mixtures were purified by HPLC (Gilson, TFA buffers) to give the following products:

Bis(2-hydroxyethyl){[6-(8-oxa-3-azabicyclo[3.2.1]oct-3-yl)pyrimidine-2,4-diyl]di-4,1-phenylene}biscarbamate Using a solution of ethylene glycol in dichloromethane, the title compound was obtained (26 mg, 46%). RT. 1.72, M+H=550.2.

N',N'''-{[6-(8-oxa-3-azabicyclo[3.2.1]oct-3-yl)pyrimidine-2,4-diyl]di-4,1-phenylene}bis(1-methylurea)

Using a 2N solution of methylamine in THF, the title compound was obtained (29 mg, 59%). RT 1.68, M+H=488.2.

N',N'''-{[6-(8-oxa-3-azabicyclo[3.2.1]oct-3-yl)pyrimidine-2,4-diyl]di-4,1-phenylene}bis(1-ethylurea)

Using a 2N solution of ethylamine in THF, the title compound was obtained (29 mg, 56%). RT 1.79, M+H=516.3.

N',N'''-{[6-(8-oxa-3-azabicyclo[3.2.1]oct-3-yl)pyrimidine-2,4-diyl]di-4,1-phenylene}bis(1-cyclopropylurea)

Using a solution of cyclopropylamine in dichloromethane, the title compound was obtained (36 mg, 67%). RT. 1.82. M+H=540.3.

N,N''-{[6-(8-oxa-3-azabicyclo[3.2.1]oct-3-yl)pyrimidine-2,4-diyl]di-4,1-phenylene}bis(3-pyridin-3-ylurea)

Using a suspension of 3-aminopyridine in dichloromethane, the title compound was obtained (48 mg, 57%). RT 1.61, M+H=614.3.

N,N''-{[6-(8-oxa-3-azabicyclo[3.2.1]oct-3-yl)pyrimidine-2,4-diyl]di-4,1-phenylene}bis(3-pyridin-4-ylurea)

Using a suspension of 4-aminopyridine in dichloromethane, the title compound was obtained (42 mg, 59%). RT 1.58, M+H=614.3.

N',N'''-{[6-(8-oxa-3-azabicyclo[3.2.1]oct-3-yl)pyrimidine-2,4-diyl]di-4,1-phenylene}bis{1-[4-(4-methylpiperazin-1-yl)phenyl]urea}

Using a solution of 4-(4-methylpiperazin-1-yl)aniline in dichloromethane, the title compound was obtained (38 mg, 37%). RT 1.67. M+H=808.4.

4,4'-{[6-(8-Oxa-3-azabicyclo[3.2.1]oct-3-yl)pyrimidine-2,4-diyl]bis(4,1-phenylenecarbamoylimino)}dibenzamide Using a solution of p-aminobenzamide in dichloromethane, the title compound was obtained after heating for 2 hours at 50° C. (28 mg, 41%). RT. 1.87. M+H=698.3.

Scheme 12

4-(8-Oxa-3-azabicyclo[3.2.1]octan-3-yl)-6-chloropyrimidin-2-ol (26)

In three 2-5 mL microwave vials was each placed 3-(2,6-dichloropyrimidin-4-yl)-8-oxa-3-azabicyclo[3.2.1]octane (9, 100 mg, 0.384 mmol) in THF (2 ml). A 1N solution of sodium hydroxide (2 ml, 2.000 mmol) was added to each vial. The reaction was heated under microwave irradiation at 150° C. for 30 min. The contents of the three microwave vials were combined, 6 mL 2N HCl was added to acidify (pH~3). Silica gel was added and the mixture was concentrate purify by silica gel chromatography, using a gradient (0-15%) of MeOH in dichloromethane to give 205 mg (0.85 mmol, 74%) of the title compound as a white solid.

Scheme 13

4,6-Di(8-oxa-3-azabicyclo[3.2.1]octan-3-yl)pyrimidin-2-ol (27)

In a 2-5 mL microwave vial was placed 4-(8-oxa-3-azabicyclo[3.2.1]octan-3-yl)-6-chloropyrimidin-2-ol (26, 50 mg, 0.207 mmol) in MeOH (2.5 ml) to give a colorless solution. 8-Oxa-3-azabicyclo[3.2.1]octane, HCl (2, 61.9 mg, 0.414 mmol) and DIPEA (0.217 ml, 1.241 mmol) were added. The reaction was heated under microwave irradiation at 140° C. for 30 min. Silica gel was added and the solvents were removed under reduced pressure. The mixture was purified by HPLC, using $NH_4OH$ buffers (Waters semi-prep LCMS) to give the title compound (27.4 mg, 42%) as a white solid.

3,3'-(2-Chloropyrimidine-4,6-diyl)bis(8-oxa-3-azabicyclo[3.2.1]octane) (28)

In a 25 mL round-bottomed flask was placed 4,6-di(8-oxa-3-azabicyclo[3.2.1]octan-3-yl)pyrimidin-2-ol (27), 12 mg, 0.038 mmol) in $POCl_3$ (3 ml) to give a yellow solution. The mixture was stirred at 100° C. for 4 h. The mixture was cool to room temperature, poured on ice, and extracted with dichloromethane. The organic phase was dried over $MgSO_4$, filtered and concentrated to give the title compound as a white crystalline solid (12 mg, 93%).

Scheme 14

4-(8-Oxa-3-azabicyclo[3.2.1]octan-3-yl)-6-(isopropylamino)pyrimidin-2-ol (29)

In a 2-5 mL microwave vial was placed 4-(8-oxa-3-azabicyclo[3.2.1]octan-3-yl)-6-chloropyrimidin-2-ol (26, 30 mg, 0.124 mmol) in iPrNH2 (2.5 ml) to give a yellow solution. The reaction was heated under microwave irradiation at 140° C. for 30 min followed by 30 min of heating under microwave irradiation at 160° C. The solvents were removed under reduced pressure. The residue was dissolved in dichloromethane, and purified by silica gel chromatography, using gradient (0-10%) of MeOH in dichloromethane. The title compound was isolated as a yellow solid (20 mg, 61%)

6-(8-Oxa-3-azabicyclo[3.2.1]octan-3-yl)-2-chloro-N-isopropylpyrimidin-4-amine (30)

In a 250 mL round-bottomed flask was placed 4-(8-oxa-3-azabicyclo[3.2.1]octan-3-yl)-6-(isopropylamino)pyrimidin-2-ol (29, 124 mg, 0.469 mmol) in $POCl_3$ (20 ml) to give a yellow solution. The mixture was stirred at 100° C. for 16 h. The mixture was cooled to room temperature, concentrated, diluted with dichloromethane and washed with saturated $NaHCO_3$ followed by 0.2 N NaOH. The organic phase was dried over $MgSO_4$, filtered and concentrated to give the title compound (91 mg, 69%). Aryl chloride 30 could be transformed into aniline 18 as described in scheme 2 for the conversion of 5 into 6. Aniline 18 could be transformed into urea or carbamate compounds as described in scheme 2 (and illustrated in the experimental section for scheme 7).

Scheme 15

4-(8-Oxa-3-azabicyclo[3.2.1]octan-3-yl)-6-isopropoxypyrimidin-2-ol (31)

4-(8-Oxa-3-azabicyclo[3.2.1]octan-3-yl)-6-chloropyrimidin-2-ol (26, 460 mg, 1.903 mmol) was dissolved in 2-propanol (30 mL). The mixture was divided over two 20 mL microwave vials. Sodium hydride (305 mg, 7.61 mmol) was added (153 mg to each vial), resulting in a fine suspension. The vials were stirred at room temperature until no further formation of hydrogen gas was observed. The vials were flushed with nitrogen. The mixture was heated under microwave irradiation for 1 hour at 170° C. The 2 vials were combined and made acidic with 9 mL 1N HCl to pH~3. Silica gel was added and the solvents were evaporated. Silica gel chromatography, using a gradient (0-20%) of MeOH in dichloromethane, gave the title compound (215 mg, 0.81 mmol, 43%) as a yellow foam.

3-(2-Chloro-6-isopropoxypyrimidin-4-yl)-8-oxa-3-azabicyclo[3.2.1]octane (32)

In a 25 mL round-bottomed flask was placed 4-(8-oxa-3-azabicyclo[3.2.1]octan-3-yl)-6-isopropoxypyrimidin-2-ol (31, 215 mg, 0.810 mmol) in $POCl_3$ (20 ml) to give a fine off-white suspension. The mixture was stirred at 100° C. for 16 h. The mixture was cooled to room temperature, concentrated, diluted with dichloromethane, and washed with saturated $NaHCO_3$. The aqueous phase was made basic with NaOH (5N) to pH 10 and extracted with dichloromethane. The combined organic phases were dried over $MgSO_4$, filtered and concentrated to give the title compound (106 mg, 46%). Aryl chloride 32 could be transformed into aniline 19 as described in scheme 2 for the conversion of 5 into 6. Aniline 19 could be transformed into urea or carbamate compounds as described in scheme 2 (and illustrated in the experimental section for scheme 8).

Scheme 16

8-(2,6-Dichloropyrimidin-4-yl)-3-oxa-8-azabicyclo[3.2.1]octane (34)

In a 250 mL round-bottomed flask was placed 2,4,6-trichloropyrimidine (8, 0.575 mL, 5 mmol) in EtOH (20 mL) to give a colorless solution. 3-oxa-8-azabicyclo[3.2.1]octane hydrochloride (33, 748 mg, 5.00 mmol) was added and the solution was cooled to 0° C. Triethylamine (2.091 mL, 15 mmol) was added slowly and the mixture was allowed to slowly warm to room temperature. The mixture was stirred at room temperature for one hour and was then concentrated under reduced pressure. The residue was dissolved in ethyl acetate and washed with sat $NaHCO_3$. The organic phase was dried over $MgSO_4$, filtered and concentrated. The crude product was added to a silica gel column and was eluted with ethyl acetate in hexanes (5-20%) to give the title compound (980 mg, 75%) as a white solid.

8-(6-Chloro-2-iodopyrimidin-4-yl)-3-oxa-8-azabicyclo[3.2.1]octane (35)

In a 250 mL round-bottomed flask was placed 8-(2,6-dichloropyrimidin-4-yl)-3-oxa-8-azabicyclo[3.2.1]octane (34, 980 mg, 3.77 mmol) in chloroform (4 ml) to give a very light yellow solution. Sodium iodide (941 mg, 6.28 mmol) was added to give a suspension. The mixture was cooled to 0° C. and an aqueous solution (57% w/w) of hydrogen iodide (4.97 ml, 37.7 mmol) was added, resulting in a yellow precipitate. The mixture was slowly warmed to room temperature and stirred at room temperature for 4 h. The mixture was diluted with water and quenched with NaOH (5M) to pH~8. Aqueous sodium thiosulfate was added to decolorize. The mixture was extracted with dichloromethane, dried over $MgSO_4$ and concentrated. The crude product was added to a silica gel column and was eluted with ethyl acetate in hexanes (10-40%). Collected fractions were concentrated to give the title compound (516 mg) as a white solid. LCMS analysis revealed that the product contained ~20% starting material. The mixture was used without further purification in the next step.

8-(6-Chloro-2-(4-nitrophenyl)pyrimidin-4-yl)-3-oxa-8-azabicyclo[3.2.1]octane (36)

In a 250 mL round-bottomed flask was placed 8-(6-chloro-2-iodopyrimidin-4-yl)-3-oxa-8-azabicyclo[3.2.1]octane (35, 627 mg, 1.783 mmol) and 4,4,5,5-tetramethyl-2-(4-nitrophenyl)-1,3,2-dioxaborolane (444 mg, 1.783 mmol) in DME (20 ml) to give an orange solution. $Na_2CO_3$ (2M solution in water) (3.57 ml, 7.13 mmol) was added. The mixture was degassed by bubbling nitrogen through the solution. $Pd(PPh_3)_4$ (206 mg, 0.178 mmol) was added and the mixture was heated to reflux and stirred overnight. The mixture was diluted with ethyl acetate and washed with a saturated solution of $NaHCO_3$. The solids between the organic and aqueous phase were collected by filtration and washed with dichloromethane. The combined organic phases were dried ($MgSO_4$) and concentrated. The crude product was added to a silica gel column and was eluted with ethyl acetate in hexanes (5-20%). Collected fractions were concentrated to give the title compound (428 mg, 69%) as a yellow solid, containing some dichloride (34, ~20% by UV) and a trace of $OPPh_3$. The mixture was used without further purification in the next step.

8,8'-(2-(4-Nitrophenyl)pyrimidine-4,6-diyl)bis(3-oxa-8-azabicyclo[3.2.1]octane) (37)

In a 2-5 mL microwave vial was placed 8-(6-chloro-2-(4-nitrophenyl)pyrimidin-4-yl)-3-oxa-8-azabicyclo[3.2.1]octane (36, 214 mg, 0.617 mmol) in dioxane (4 ml) to give a yellow suspension. 3-Oxa-8-azabicyclo[3.2.1]octane hydrochloride (33, 277 mg, 1.851 mmol), potassium carbonate (341 mg, 2.469 mmol) and DIPEA (0.647 ml, 3.70 mmol) were added. The reaction was heated under microwave irradiation at 220° C. for 1 h. The reaction mixture was diluted with dichloromethane and washed with sat $NaHCO_3$. The organic phase was dried over $MgSO_4$, filtered and concentrated. The crude product was added to a silica gel column and was eluted with ethyl acetate in hexanes (10-40%) to give the title compound (120 mg) as a yellow solid. In addition, mixed fractions were concentrated, applied to a silica gel column and eluted with methanol in dichloromethane (2-5%) to give an additional 19 mg of title compound for a combined yield of 139 mg (0.33 mmol, 53%). HRMS: [M+H]+ mass error=0.6 mDa or 1.45 ppm.

4-(4,6-Di(3-oxa-8-azabicyclo[3.2.1]octan-8-yl)pyrimidin-2-yl)aniline (38)

In a 250 mL round-bottomed flask was placed 8,8'-(2-(4-nitrophenyl)pyrimidine-4,6-diyl)bis(3-oxa-8-azabicyclo[3.2.1]octane) (37, 246 mg, 0.581 mmol) in 2-propanol (3 mL) and dichloromethane (3 mL) to give a yellow solution. A catalytic amount of Pd on charcoal (wet) was added and the mixture was stirred under a hydrogen atmosphere for 4 hours. The mixture was filtered over Celite™, rinsed with dichloromethane and concentrated. The crude product was added to a silica gel column and was eluted with ethyl acetate in hexanes (40-60%). Collected fractions were concentrated to give the title compound (197 mg, 0.5 mmol, 86%) as a light yellow solid. For [M+H]+ mass error=0.2 mDa or 0.46 ppm.

The following products were prepared from 4-(4,6-di(3-oxa-8-azabicyclo[3.2.1]octan-8-yl)pyrimidin-2-yl)aniline (38) using the general procedure from scheme 2 for the preparation of 7:

1-[4-(4,6-Di-3-oxa-8-azabicyclo[3.2.1]oct-8-ylpyrimidin-2-yl)phenyl]-3-pyridin-4-ylurea Using a suspension of 4-aminopyridine in dichloromethane, the title compound was obtained (37 mg, 79%). RT 1.67, M+H=514.2.

1-{4-[2-(Dimethylamino)ethoxy]phenyl}-3-[4-(4,6-di-3-oxa-8-azabicyclo[3.2.1]oct-8-ylpyrimidin-2-yl)phenyl]urea Using a solution of 4-(2-(dimethylamino)ethoxy)aniline in dichloromethane, the title compound was obtained (48 mg, 72%). RT 1.71, M+H=600.3.

1-[4-(4,6-Di-3-oxa-8-azabicyclo[3.2.1]oct-8-ylpyrimidin-2-yl)phenyl]-3-[4-(4-methylpiperazin-1-yl)phenyl]urea Using a solution of 4-(4-methylpiperazin-1-yl)aniline in dichloromethane, the title compound was obtained (67 mg, 99%). RT 1.71, M+H=611.3.

1-[4-(4,6-Di-3-oxa-8-azabicyclo[3.2.1]oct-8-ylpyrimidin-2-yl)phenyl]-3-{4-[(4-methylpiperazin-1-yl)methyl]phenyl}urea Using a solution of 4-((4-methylpiperazin-1-yl)methyl)aniline in dichloromethane, the title compound was obtained (56 mg, 71%). RT 1.68, M+H=625.4.

1-[4-(4,6-Di-3-oxa-8-azabicyclo[3.2.1]oct-8-ylpyrimidin-2-yl)phenyl]-3-{4-[(4-methylpiperazin-1-yl)carbonyl]phenyl}urea Using a solution of (4-aminophenyl)(4-methylpiperazin-1-yl)methanone in dichloromethane, the title compound was obtained (62 mg, 88%). RT 1.69, M+H=639.3.

Scheme 17

2,4-Dichloro-6-phenylpyrimidine (39)

A mixture of 2,4,6-trichloropyrimidine 8 (1 g, 5.45 mmol), phenylboronic acid (665 mg, 5.45 mmol), Pd(PPh$_3$)$_4$ (100 mg) and 2N aqueous Na$_2$CO$_3$ (4.1 mL) in 1:1 toluene:EtOH (15 mL) was heated in a microwave at 120° C. for 20 min. The reaction mixture was diluted with EtOAc and washed with H$_2$O and brine. The organic layer was dried over MgSO$_4$ and concentrated in vacuo to give 2,4-dichloro-6-phenylpyrimidine as a solid (1.35 g), which was used without further purification in the next step.

3-(2-Chloro-6-phenylpyrimidin-4-yl)-8-oxa-3-azabicyclo[3.2.1]octane (40)

To 2,4-dichloro-6-phenylpyrimidine 39 (1 g) and 8-oxa-3-azabicyclo[3.2.1]octane hydrochloride 2 (600 mg) in ethanol (10 mL) at 25° C. was added Et$_3$N (1.25 mL). After 1 h the reaction mixture was concentrated in vacuo. Dichloromethane was added and washed with H$_2$O then brine. The organic layer was dried over MgSO$_4$ to give a foam (1.2 g). Silica gel chromatography (hexane/EtOAc) gave 3-(2-chloro-6-phenylpyrimidin-4-yl)-8-oxa-3-azabicyclo[3.2.1]octane (900 mg) as a yellow foam. M+H=302.

4-(4-(8-Oxa-3-azabicyclo[3.2.1]octan-3-yl)-6-phenylpyrimidin-2-yl)aniline (41)

A mixture of 3-(2-chloro-6-phenylpyrimidin-4-yl)-8-oxa-3-azabicyclo[3.2.1]octane (500 mg, 1.66 mmol), 4-(4,4,5,5-tetramethyl-1,3,2-dioxaborolan-2-yl)aniline (545 mg, 2.49 mmol), Pd(PPh$_3$)$_4$ (20 mg), and 2M aqueous Na$_2$CO$_3$ (1.25 mL) in 1:1 toluene:EtOH (8 mL) was heated in a microwave at 120° C. for 20 min. The reaction was repeated with 386 mg of 3-(2-chloro-6-phenylpyrimidin-4-yl)-8-oxa-3-azabicyclo[3.2.1]octane. The reaction mixtures were combined, diluted with EtOAc and washed with H$_2$O then brine. The organic layer was dried over MgSO$_4$ and concentrated in vacuo to give an orange oil. Silica gel chromatography (hexane/EtOAc) gave 4-(4-(8-oxa-3-azabicyclo[3.2.1]octan-3-yl)-6-phenylpyrimidin-2-yl)aniline as a white solid (450 mg).

Formation of urea or carbamate compounds from 4-(4-(8-oxa-3-azabicyclo[3.2.1]octan-3-yl)-6-phenylpyrimidin-2-yl)aniline (41)

Target compounds were prepared using the general method from scheme 2 for the preparation of 7. Thus, 4-(4-(8-oxa-3-azabicyclo[3.2.1]octan-3-yl)-6-phenylpyrimidin-2-yl)aniline (41) (450 mg) was treated with triphosgene (187 mg) in Dichloromethane in the presence of Et$_3$N (0.883 mL). The mixture was stirred for 30 min and was divided over 8 vials containing an excess of a primary amine or an alcohol to give the corresponding urea or carbamate:

1-Methyl-3-{4-[4-(8-oxa-3-azabicyclo[3.2.1]oct-3-yl)-6-phenylpyrimidin-2-yl]phenyl}urea Yield: 38.4 mg. M+H=416.2. RT 1.87.

2-Hydroxyethyl{4-[4-(8-oxa-3-azabicyclo[3.2.1]oct-3-yl)-6-phenylpyrimidin-2-yl]phenyl}carbamate Yield: 57.2 mg. M+H=447.2. RT 1.94.

1-[4-(4-Methylpiperazin-1-yl)phenyl]-3-{4-[4-(8-oxa-3-azabicyclo[3.2.1]oct-3-yl)-6-phenylpyrimidin-2-yl]phenyl}urea Yield: 37.1 mg. M+H=576.3. RT 1.87.

1-Ethyl-3-{4-[4-(8-oxa-3-azabicyclo[3.2.1]oct-3-yl)-6-phenylpyrimidin-2-yl]phenyl}urea Yield: 52.6 mg. M+H=430.2. RT 1.96.

1-Cyclopropyl-3-{4-[4-(8-oxa-3-azabicyclo[3.2.1]oct-3-yl)-6-phenylpyrimidin-2-yl]phenyl}urea Yield: 56.2 mg. M+H=442.2. RT 1.98.

1-{4-[4-(8-Oxa-3-azabicyclo[3.2.1]oct-3-yl)-6-phenylpyrimidin-2-yl]phenyl}-3-pyridin-4-ylurea Yield: 56.6 mg. M+H=479.2. RT 1.87.

1-[4-(Hydroxymethyl)phenyl]-3-{4-[4-(8-oxa-3-azabicyclo[3.2.1]oct-3-yl)-6-phenylpyrimidin-2-yl]phenyl}urea Yield: 39.8 mg. M+H=508.2. RT 2.05.

1-{4-[2-(Dimethylamino)ethoxy]phenyl}-3-{4-[4-(8-oxa-3-azabicyclo[3.2.1]oct-3-yl)-6-phenylpyrimidin-2-yl]phenyl}urea Yield: 47.8 mg. M+H=565.3. RT 1.86.

Scheme 18

3-(2-Chloro-6-(methylsulfonylmethyl)pyrimidin-4-yl)-8-oxa-3-azabicyclo[3.2.1]octane (43)

A 2,4-dichloro-6-(methylsulfonylmethyl)pyrimidine (42, prepared as reported in WO2008/023159, 1.60 g, 6.64 mmoles) was dissolved in dichloromethane and cooled to 0° C. A solution of 8-oxa-3-azabicyclo[3.2.1]octane (2, 0.990 g, 6.64 mmoles) in dichloromethane and triethylamine (1.94 mL, 13.94 mmoles) was slowly added over 15 minutes. The solution was allowed to warm to room temperature over 30 minutes then heated to reflux for 1.5 hours. The reaction mixture was stirred at room temperature for an additional 18 hours, then concentrated and purified by chromatography on silica gel (eluting with 2-3% methanol in dichloromethane) to provide 3-(2-chloro-6-(methylsulfonylmethyl)pyrimidin-4-yl)-8-oxa-3-azabicyclo[3.2.1]octane (43) as a white solid. Yield: 1.72 g (82%). HRMS; [M+H]+ Obs'd=318.0669, [M+H]+ Calc'd=318.0674.

4-(4-(8-Oxa-3-azabicyclo[3.2.1]octan-3-yl)-6-(methylsulfonylmethyl)pyrimidin-2-yl)aniline (44)

4-(4-(8-Oxa-3-azabicyclo[3.2.1]octan-3-yl)-6-(methylsulfonylmethyl)pyrimidin-2-yl)aniline was prepared by Suzuki coupling using the general method from scheme 2 for the preparation of 6 using 3-(2-chloro-6-(methylsulfonylmethyl)pyrimidin-4-yl)-8-oxa-3-azabicyclo[3.2.1]octane (43, 1.63 g, 5.13 mmoles) and 4-aminophenyl boronic acid pinacol ester (1.24 g, 5.64 mmoles) as starting materials. The crude product was purified by chromatography on silica gel (eluting with 0-3% methanol in dichloromethane) to provide the desired compound as a light yellow solid. Yield: 1.80 g (94%). HRMS; [M+H]+ Obs'd=375.1485, [M+H]+ Calc'd=375.1485

Formation of urea or carbamate compounds from 4-(4-(8-oxa-3-azabicyclo[3.2.1]octan-3-yl)-6-(methylsulfonylmethyl)pyrimidin-2-yl)aniline (44)

Target compounds were prepared using the general method from scheme 2 for the preparation of 7. Thus, 4-(4-(8-oxa-3-azabicyclo[3.2.1]octan-3-yl)-6-(methylsulfonylmethyl)pyrimidin-2-yl)aniline (44, 1.30 g, 3.47 mmoles) was treated with triphosgene (0.515 g, 1.74 mmoles) in Dichloromethane in the presence of Et$_3$N (1.45 mL, 10.41 mmoles). The mixture was stirred for 15 min. and was divided over 11 vials containing an excess of a primary amine or an alcohol to give the corresponding urea or carbamate:

1-(4-(4-(8-Oxa-3-azabicyclo[3.2.1]octan-3-yl)-6-(methylsulfonylmethyl)pyrimidin-2-yl)phenyl)-3-methylurea Yield: 6.0 mg (4%). RT 1.63, M+H=432.2.

1-(4-(4-(8-Oxa-3-azabicyclo[3.2.1]octan-3-yl)-6-(methylsulfonylmethyl)pyrimidin-2-yl)phenyl)-3-ethylurea Yield: 37.9 mg (27%). RT 1.70, M+H=446.2.

11-(4-(4-(8-Oxa-3-azabicyclo[3.2.1]octan-3-yl)-6-(methylsulfonylmethyl)pyrimidin-2-yl)phenyl)-3-cyclopropylurea Yield: 113.4 mg (78%). RT 1.73, M+H=458.2.

1-(4-(4-(8-Oxa-3-azabicyclo[3.2.1]octan-3-yl)-6-(methylsulfonylmethyl)pyrimidin-2-yl)phenyl)-3-phenylurea Yield: 88.3 mg (57%). RT 2.01, M+H=494.2.

1-(4-(4-(8-Oxa-3-azabicyclo[3.2.1]octan-3-yl)-6-(methylsulfonylmethyl)pyrimidin-2-yl)phenyl)-3-(pyridin-3-yl)urea Yield: 108.0 mg (69%). RT 1.61, M+H=495.2.

1-(4-(4-(8-Oxa-3-azabicyclo[3.2.1]octan-3-yl)-6-(methylsulfonylmethyl)pyrimidin-2-yl)phenyl)-3-(pyridin-4-yl)urea Yield: 80.4 mg (51%). RT 1.59, M+H=495.2.

1-(4-(4-(8-Oxa-3-azabicyclo[3.2.1]octan-3-yl)-6-(methylsulfonylmethyl)pyrimidin-2-yl)phenyl)-3-(4-(4-methylpiperazin-1-yl)phenyl)urea Yield: 112.8 mg (60%). RT 1.64, M+H=592.3.

1-(4-(4-(8-Oxa-3-azabicyclo[3.2.1]octan-3-yl)-6-(methylsulfonylmethyl)pyrimidin-2-yl)phenyl)-3-(4-(piperazin-1-yl)phenyl)urea tert-Butyl 4-(4-(3-(4-(4-(8-oxa-3-azabicyclo[3.2.1]octan-3-yl)-6-(methylsulfonylmethyl)pyrimidin-2-yl)phenyl)ureido)phenyl)piperazine-1-carboxylate was obtained according to the general procedure for formation of urea or carbamate compounds from 4-(4-(8-oxa-3-azabicyclo[3.2.1]octan-3-yl)-6-(methylsulfonylmethyl)pyrimidin-2-yl)aniline (44). Removal of the Boc group in tert-butyl 4-(4-(3-(4-(4-(8-oxa-3-azabicyclo[3.2.1]octan-3-yl)-6-(methylsulfonylmethyl)pyrimidin-2-yl)phenyl)ureido)phenyl)piperazine-1-carboxylate (85.2 mg, 0.126 mmoles) by treatment with trifluoroacetic acid in dichloromethane gave the title compound. Yield: 70.0 mg (38% over 2 steps). RT 1.64, M+H=578.2.

1-(4-(4-(8-Oxa-3-azabicyclo[3.2.1]octan-3-yl)-6-(methylsulfonylmethyl)pyrimidin-2-yl)phenyl)-3-(4-(2-(dimethylamino)ethoxy)phenyl)urea Yield: 96.0 mg (38%). RT 1.66, M+H=581.2.

1-(4-(4-(8-Oxa-3-azabicyclo[3.2.1]octan-3-yl)-6-(methylsulfonylmethyl)pyrimidin-2-yl)phenyl)-3-(4-((4-methylpiperazin-1-yl)methyl)phenyl)urea Yield: 112.8 mg (59%). RT 1.60, M+H=606.3.

Tert-butyl 4-(3-(4-(4-(8-oxa-3-azabicyclo[3.2.1]octan-3-yl)-6-(methylsulfonylmethyl)pyrimidin-2-yl)phenyl)ureido)benzyl(methyl)carbamate Yield: 129.4 mg (64%). HRMS: For [M+H]+ mass error=−0.3 mDa or −0.45 ppm. For [M+Na]+ mass error=−0.1 mDa or −0.22 ppm.

1-(4-(4-(8-Oxa-3-azabicyclo[3.2.1]octan-3-yl)-6-(methylsulfonylmethyl)pyrimidin-2-yl)phenyl)-3-(4-((methylamino)methyl)phenyl)urea tert-Butyl 4-(3-(4-(4-(8-oxa-3-azabicyclo[3.2.1]octan-3-yl)-6-(methylsulfonylmethyl)pyrimidin-2-yl)phenyl)ureido)benzyl(methyl)carbamate was prepared as described above. Removal of the Boc group in tert-butyl 4-(3-(4-(4-(8-oxa-3-azabicyclo[3.2.1]octan-3-yl)-6-(methylsulfonylmethyl)pyrimidin-2-yl)phenyl)ureido)benzyl(methyl)carbamate (98.3 mgs, 0.154 mmoles) by treatment with trifluoroacetic acid in dichloromethane gave the title compound. Yield: 70.8 mg (86%). RT 1.63, M+H=537.2.

Scheme 19

3-(2,6-Dichloro-5-nitropyrimidin-4-yl)-8-oxa-3-azabicyclo[3.2.1]octane (46)

2,4,6-Trichloro-5-nitropyrimidine (45, 1.43 g, 6.26 mmoles) was dissolved in dichloromethane and cooled to 0° C. A solution of 8-oxa-3-azabicyclo[3.2.1]octane (2, 0.934 g, 6.26 mmoles) in dichloromethane and triethylamine (0.873 mL, 6.26 mmoles) was slowly added over 1 hour. The solution was allowed to stir at 0° C. for 2 hours, then warmed to room temperature and stirred for an additional 16 hours. The reaction mixture was filtered, the filtrate was concentrated, dissolved in ethyl acetate, washed with 1N hydrochloric acid, saturated sodium bicarbonate, brine, dried, and concentrated to provide 3-(2,6-dichloro-5-nitropyrimidin-4-yl)-8-oxa-3-azabicyclo[3.2.1]octane (46). Yield: 1.53 g (80%). HRMS; [M+H]+ Obs'd=305.0200, [M+H]+ Calc'd=305.0203.

6-(8-Oxa-3-azabicyclo[3.2.1]octan-3-yl)-2-chloro-N-isopropyl-5-nitropyrimidin-4-amine (47)

3-(2,6-Dichloro-5-nitropyrimidin-4-yl)-8-oxa-3-azabicyclo[3.2.1]octane (46, 1.53 g, 5.01 mmoles) was dissolved in dichloromethane and added to a solution of isopropylamine (0.512 mL, 6.01 mmoles) in triethylamine (0.909 mL, 6.52 mmoles) and dichloromethane at 0° C. The reaction was allowed to warm to room temperature, stirred for an additional 16 hours, and then concentrated. Purification by chromatography on silica gel (eluting with 0-25% ethyl acetate in hexanes) provided 6-(8-oxa-3-azabicyclo[3.2.1]octan-3-yl)-2-chloro-N-isopropyl-5-nitropyrimidin-4-amine (47) as a yellow solid. Yield: 2.05 g (quantitative yield). LCMS (HP walk-on); 4.54 min., 328.2, M+H.

6-(8-Oxa-3-azabicyclo[3.2.1]octan-3-yl)-2-chloro-N4-isopropylpyrimidine-4,5-diamine-3-(dimethylamino)propanoate (48)

6-(8-Oxa-3-azabicyclo[3.2.1]octan-3-yl)-2-chloro-N-isopropyl-5-nitropyrimidin-4-amine (47, 1.45 g, 4.42 mmoles) was dissolved in methanol and Raney™ nickel (approx. 2:1 by weight with respect to starting material) was added under a nitrogen atmosphere. Hydrazine hydrate (0.833 mL, 26.54 mmoles) was added and the reaction mixture was stirred at room temperature for 18 hours, filtered over Celite™, and the filtrate was concentrated to provide 6-(8-oxa-3-azabicyclo[3.2.1]octan-3-yl)-2-chloro-N4-isopropylpyrimidine-4,5-diamine 3-(dimethylamino)propanoate (48) as a tan solid. Yield: 1.25 g (95%). LCMS (HP walk-on); 3.45 min., 298.5, M+H.

N-(4-(8-Oxa-3-azabicyclo[3.2.1]octan-3-yl)-2-chloro-6-(isopropylamino)pyrimidin-5-yl)-3-(dimethylamino)propanamide (49)

6-(8-Oxa-3-azabicyclo[3.2.1]octan-3-yl)-2-chloro-N4-isopropylpyrimidine-4,5-diamine 3-(dimethylamino)propanoate (48, 0.500 g, 1.68 mmoles) was dissolved in dimethylformamide and 3-dimethylaminopropionic acid (0.310 g, 2.02 mmoles) and isobutyl 2-isobutoxyquinoline-1(2H)-carboxylate (IIDQ, 0.699 mL, 2.35 mmoles) were added. The reaction mixture was allowed to stir at room temperature for 18 hours, concentrated, and purified by silica gel column chromatography (5-10% ethanol in dichloromethane) to provide N-(4-(8-oxa-3-azabicyclo[3.2.1]octan-3-yl)-2-chloro-6-(isopropylamino)pyrimidin-5-yl)-3-(dimethylamino)propanamide (49) as a tan solid. Yield: 0.350 g (53%). LCMS (Waters walk-on); 2.43 min., 397.2, M+H.

Scheme 20

1-(Pyridin-3-yl)-3-(4-(4,4,5,5-tetramethyl-1,3,2-dioxaborolan-2-yl)phenyl)urea (52)

1-(Pyridin-3-yl)-3-(4-(4,4,5,5-tetramethyl-1,3,2-dioxaborolan-2-yl)phenyl)urea was prepared by treatment of 2-(4-isocyanatophenyl)-4,4,5,5-tetramethyl-1,3,2-dioxaborolane (50, 2.50 g, 10.20 mmoles) in toluene/tetrahydrofuran (3:1) with pyridine-3-amine (51, 0.960 g, 10.20 mmoles). The reaction mixture was stirred at room temperature for 16 hours, then concentrated. Yield: 3.21 g (93%). LCMS (HP walk-on); 2.89 min., 340.6, M+H.

N-(4-(8-oxa-3-azabicyclo[3.2.1]octan-3-yl)-6-(isopropylamino)-2-(4-(3-pyridin-3-ylureido)phenyl)pyrimidin-5-yl)-3-(dimethylamino)propanamide (53)

N-(4-(8-oxa-3-azabicyclo[3.2.1]octan-3-yl)-6-(isopropylamino)-2-(4-(3-pyridin-3-ylureido)phenyl)pyrimidin-5-yl)-3-(dimethylamino)propanamide was prepared by Suzuki coupling using the general method from scheme 2 for the preparation of 6 using N-(4-(8-oxa-3-azabicyclo[3.2.1]octan-3-yl)-2-chloro-6-(isopropylamino)pyrimidin-5-yl)-3-(dimethylamino)propanamide (49, 0.050 g, 0.126 mmoles) and 1-(pyridin-3-yl)-3-(4-(4,4,5,5-tetramethyl-1,3,2-dioxaborolan-2-yl)phenyl)urea (52, 0.047 g, 0.139 mmoles). The crude product was purified by HPLC to provide the title compound as a yellow solid. Yield: 0.049 g (68%). HRMS; [M+H]+ Calc'd=574.3249, [M+H]+ Obs'd=574.3241.

Scheme 21

4-(8-Oxa-3-azabicyclo[3.2.1]octan-3-yl)-6-chloropyrimidin-2-yltrifluoromethanesulfonate (54)

Trifluoromethanesulfonic anhydride (0.084 mL, 0.499 mmol) was added slowly to dichloromethane (1 mL) and pyridine (1 mL) at 0° C. and stirred for 5 min at 0° C. This mixture was added to 4-(8-oxa-3-azabicyclo[3.2.1]octan-3-yl)-6-chloropyrimidin-2-ol (26, 93 mg, 0.384 mmol) in 1 mL dichloromethane at 0° C. The mixture was stirred at 0° C. for 5 minutes and was then slowly warmed to room temperature. More $Tf_2O$ was added: trifluoromethanesulfonic anhydride (0.25 ml, 1.5 mmol) was added slowly to dichloromethane (2 ml) and pyridine (2 ml) at 0° C. and stirred for 5 min at 0° C. This mixture was added slowly to the reaction mixture at 0° C. and stirred for 5 minutes at 0° C. The mixture was allowed to warm to room temperature, stirred for 30 min and diluted with dichloromethane. The mixture was washed with 0.5 N aqueous HCl (3×), water, and saturated $NaHCO_3$, dried over $MgSO_4$ and concentrated to give the title compound (101 mg, 70%) as an orange oil.

3-[6-Chloro-2-(4-nitro-phenyl)-pyrimidin-4-yl]-8-oxa-3-aza-bicyclo[3.2.1]octane (13)

In a 250 mL round-bottomed flask was placed 4-(8-oxa-3-azabicyclo[3.2.1]octan-3-yl)-6-chloropyrimidin-2-yltrifluoromethanesulfonate (54, 101 mg, 0.270 mmol) and 4,4,5,5-tetramethyl-2-(4-nitrophenyl)-1,3,2-dioxaborolane (67.3 mg, 0.270 mmol) in DME (5 mL) to give an orange solution. $Na_2CO_3$ (2M solution in water) (0.540 mL, 1.081 mmol) was added. The mixture was degassed by bubbling nitrogen through the solution. $Pd(PPh_3)_4$ (31.2 mg, 0.027 mmol) was added. The reaction was heated to reflux and stirred for 3 h. The mixture was diluted with ethyl acetate and washed with a saturated solution of $NaHCO_3$. The organic phase was dried ($MgSO_4$) and concentrated. The crude product was added to a silica gel column and was eluted with ethyl acetate in hexanes (5-30%). Collected fractions were concentrated to give the title compound (42 mg, 45%). The thus obtained compound was identical to the same compound prepared according to Scheme 5.

Scheme 22

4-Nitrobenzimidamide, HCl (57)

In a 50 mL round-bottomed flask was placed 4-nitrobenzonitrile (55, 1 g, 6.75 mmol) in MeOH (6.75 ml) to give a yellow suspension. Sodium methanolate (0.077 ml, 0.338 mmol) (25% by wt solution in MeOH) was added to give an orange suspension and the mixture was stirred at room temperature overnight at which point all solids had gone into solution. Ammonium chloride (0.379 g, 7.09 mmol) was added and stirring was continued overnight. A light yellow precipitate had formed. The solids were collected by filtration and dried to give the title compound (435 mg, 32%) as a light yellow solid.

2-(4-Nitrophenyl)pyrimidine-4,6-diol (58)

In a 50 mL round-bottomed flask was placed 4-nitrobenzimidamide (55, 0.435 g, 2.63 mmol) in MeOH (4 mL) to give a yellow suspension. Sodium methanolate (25% by wt in MeOH) (1.867 mL, 8.17 mmol) was added. The mixture was stirred at room temperature for 30 min. Diethyl malonate (0.480 mL, 3.16 mmol) was added in drops and stirring was continued at room temperature over 6 days, resulting in an orange suspension. The mixture was concentrated, dissolved in hot water and filtered. The filtrate was made acidic with AcOH to pH3. The resulting light yellow solids were collected by filtration and dried under vacuum to give the title compound (499 mg, 81%) as a light yellow solid. HRMS: For [M+H]+ mass error=−0.0 mDa or −0.17 ppm.

4,6-Dichloro-2-(4-nitrophenyl)pyrimidine (59)

In a 50 mL round-bottomed flask was placed 2-(4-nitrophenyl)pyrimidine-4,6-diol (58, 485 mg, 2.080 mmol) in $POCl_3$ (5 mL) to give a yellow suspension. The mixture was stirred at 100° C. for 13 hours. The mixture was concentrated, diluted with dichloromethane and washed with saturated $NaHCO_3$ and brine. The organic phase was dried over $MgSO_4$ and filtered. The filtrate was concentrated, dissolved in a small volume of dichloromethane and filtered over a silica gel plug (eluted with dichloromethane). The filtrate was concentrated to give the title compound (203 mg, 36%) as a white solid. HRMS: For [M+H]+ mass error=0.6 mDa or 2.31 ppm.

8-(6-Chloro-2-(4-nitrophenyl)pyrimidin-4-yl)-3-oxa-8-azabicyclo[3.2.1]octane (36)

In a 250 mL round-bottomed flask was placed 4,6-dichloro-2-(4-nitrophenyl)pyrimidine (59, 192 mg, 0.711 mmol) in dichloromethane (8 mL) to give a colorless solution. 3-oxa-8-azabicyclo[3.2.1]octane hydrochloride (33, 106 mg, 0.711 mmol) was added and the solution was cooled to 0° C. Triethylamine (0.297 mL, 2.133 mmol) was added slowly and the mixture was allowed to slowly warm to room temperature, and stirred for 16 hours at room temperature. The mixture was heated under reflux for 2 hours, diluted with dichloromethane and washed with saturated $NaHCO_3$. The organic phase was dried over $MgSO_4$, filtered and concentrated. the crude product was applied to a silica gel column and eluted with 5-40% EtOAc in hexanes to give the title compound (212 mg, 86%). The sample was identical to the same compound prepared according to Scheme 16. HRMS: For [M+H]+ mass error=0.1 mDa or 0.39 ppm.

6-(3-Oxa-8-azabicyclo[3.2.1]octan-8-yl)-N-isopropyl-2-(4-nitrophenyl)pyrimidin-4-amine (60)

In a 2-5 mL microwave vial was placed 8-(6-chloro-2-(4-nitrophenyl)pyrimidin-4-yl)-3-oxa-8-azabicyclo[3.2.1]octane (36, 200 mg, 0.577 mmol) in $iPrNH_2$ (5 mL) to give a yellow suspension. The reaction was heated under microwave irradiation at 140° C. for 3×45 min. The mixture was concentrated. The residue was dissolved in dichloromethane and washed with sat $NaHCO_3$. The organic phase was dried over $MgSO_4$, filtered and concentrated to give the title compound (208 mg, 98%) as a yellow foam. HRMS: For [M+H]+ mass error=0.1 mDa or 0.23 ppm.

2-(4-Aminophenyl)-6-(3-oxa-8-azabicyclo[3.2.1]octan-8-yl)-N-isopropylpyrimidin-4-amine (61)

In a 250 mL round-bottomed flask was placed 6-(3-oxa-8-azabicyclo[3.2.1]octan-8-yl)-N-isopropyl-2-(4-nitrophenyl)pyrimidin-4-amine (60, 196 mg, 0.53 mmol) in 2-propanol (5 mL) and dichloromethane (5 mL) to give a yellow solution. A catalytic amount of Pd on charcoal (wet) was added and the mixture was stirred under a hydrogen atmosphere for 16 hours. The mixture was filtered over Celite™, rinsed with dichloromethane and concentrated to give the title compound (176 mg, 0.52 mmol, 98%) as a yellow solid. HRMS: For [M+H]+ mass error=0.5 mDa or 1.46 ppm.

The following products were prepared from 2-(4-aminophenyl)-6-(3-oxa-8-azabicyclo[3.2.1]octan-8-yl)-N-isopropylpyrimidin-4-amine (61) using the general procedure from scheme 2 for the preparation of 7:

1-{4-[4-(Isopropylamino)-6-(3-oxa-8-azabicyclo[3.2.1]oct-8-yl)pyrimidin-2-yl]phenyl}-3-pyridin-4-ylurea Using a suspension of 4-aminopyridine in dichloromethane, the title compound was obtained (16 mg, 35%). RT 1.64, M+H=460.2.

1-{4-[2-(Dimethylamino)ethoxy]phenyl}-3-{4-[4-(isopropylamino)-6-(3-oxa-8-azabicyclo[3.2.1]oct-8-yl)pyrimidin-2-yl]phenyl}urea Using a solution of 4-(2-(dimethylamino)ethoxy)aniline in dichloromethane, the title compound was obtained (14 mg, 22%). RT 1.73, M+H=546.3.

1-{4-[4-(Isopropylamino)-6-(3-oxa-8-azabicyclo[3.2.1]oct-8-yl)pyrimidin-2-yl]phenyl}-3-[4-(4-methylpiperazin-1-yl)phenyl]urea Using a solution of 4-(4-methylpiperazin-1-yl)aniline in dichloromethane, the title compound was obtained (23 mg, 36%). RT 1.73, M+H=557.3.

1-{4-[4-(Isopropylamino)-6-(3-oxa-8-azabicyclo[3.2.1]oct-8-yl)pyrimidin-2-yl]phenyl}-3-{4-[(4-methylpiperazin-1-yl)methyl]phenyl}urea Using a solution of 4-((4-methylpiperazin-1-yl)methyl)aniline in dichloromethane, the title compound was obtained (26 mg, 33%). RT 1.66, M+H=571.3.

1-{4-[4-(Isopropylamino)-6-(3-oxa-8-azabicyclo[3.2.1]oct-8-yl)pyrimidin-2-yl]phenyl}-3-[6-(4-methylpiperazin-1-yl)pyridin-3-yl]urea Using a solution of 6-(4-methylpiperazin-1-yl)pyridine-3-amine in dichloromethane, the title compound was obtained (26 mg, 40%). RT 1.68, M+H=558.3.

Scheme 23

2,4-Dichloro-6-(trifluoromethyl)pyrimidine (62)

2,4-Dichloro-6-(trifluoromethyl)pyrimidine (62) was prepared from 6-trifluoromethluracil (6.7 mmol) according to literature precedent (Gershon, H.; Grefig, A. T.; Clarke, D. D. *J. Het. Chem.* 1987, 1243-1247).

3-(2-Chloro-6-trifluoromethyl-pyrimidin-4-yl)-8-oxa-3-aza-bicyclo[3.2.1]octane (63)

A solution of crude 2,4-dichloro-6-(trifluoromethyl)pyrimidine (62, 6.7 mmol) in diethyl ether (10 mL) was diluted with ethanol (25 mL) and cooled in an ice-water bath. 8-Oxa-3-azabicyclo[3.2.1]octane hydrochloride (2, 3.4 mmol) was added, followed by triethylamine (2 mL). Two additional portions of 8-oxa-3-azabicyclo[3.2.1]octane hydrochloride (2, 100 mg each) were added, the mixture was slowly warmed to room temperature and stirred overnight. Additional triethylamine (4 mL) was added to the mixture, which was then concentrated to dryness under reduced pressure. The residue was purified via flash silica gel chromatography (40% ethyl acetate/hexanes) to provide the title compound as a light colored solid (1.2 g, 61%). MS (ES$^+$): 294.2 (M+H)$^+$.

4-[4-(8-Oxa-3-aza-bicyclo[3.2.1]oct-3-yl)-6-trifluoromethyl-pyrimidin-2-yl]-phenylamine (64)

The title compound was prepared in 86% yield from 3-(2-chloro-6-trifluoromethyl-pyrimidin-4-yl)-8-oxa-3-aza-bicyclo[3.2.1]octane (63) and 4-(4,4,5,5-tetramethyl-1,3,2-dioxaborolan-2-yl)aniline, using the general procedure from scheme 2 for the preparation of 6. MS (ES$^+$): 351.2 (M+H)$^+$.

The following products were prepared from 4-[4-(8-oxa-3-aza-bicyclo[3.2.1]oct-3-yl)-6-trifluoromethyl-pyrimidin-2-yl]-phenylamine (64) using the general procedure from scheme 2 for the preparation of 7:

1-Methyl-3-{4-[4-(8-oxa-3-azabicyclo[3.2.1]oct-3-yl)-6-(trifluoromethyl)pyrimidin-2-yl]phenyl}urea Using a 2N solution of methylamine in THF, the title compound was obtained (27.3 mg, 60%). MS (ES$^+$): 408.2 (M+H)$^+$. RT.: 2.14 min.

1-Cyclopropyl-3-{4-[4-(8-oxa-3-azabicyclo[3.2.1]oct-3-yl)-6-(trifluoromethyl)pyrimidin-2-yl]phenyl}urea Using a solution of cyclopropylamine in dichloromethane, the title compound was obtained (29.4 mg, 60%). MS (ES$^+$): 434.2 (M+H)$^+$. RT.: 2.22 min.

2-Hydroxyethyl{4-[4-(8-oxa-3-azabicyclo[3.2.1]oct-3-yl)-6-(trifluoromethyl)pyrimidin-2-yl]phenyl}carbamate Using a solution of ethylene glycol in dichloromethane, the title compound was obtained (29.4 mg, 60%). MS (ES$^+$): 439.2 (M+H)$^+$. RT.: 2.16 min.

1-{4-[4-(8-Oxa-3-azabicyclo[3.2.1]oct-3-yl)-6-(trifluoromethyl)pyrimidin-2-yl]phenyl}-3-pyridin-4-ylurea, trifluoroacetate salt Using a suspension of 4-aminopyridine in dichloromethane, the title compound was obtained (39.5 mg, 63%). MS (ES$^+$): 471.2 (M+H)$^+$. RT.: 1.96 min.

1-[4-(4-Methylpiperazin-1-yl)phenyl]-3-{4-[4-(8-oxa-3-azabicyclo[3.2.1]oct-3-yl)-6-(trifluoromethyl)pyrimidin-2-yl]phenyl}urea trifluoroacetate salt Using a solution of 4-(4-methylpiperazin-1-yl)aniline in dichloromethane, the title compound was obtained (45.4 mg, 60%). MS (ES$^+$): 568.3 (M+H)$^+$. RT.: 2.04 min.

The following products were prepared from 4-(4,6-di(3-oxa-8-azabicyclo[3.2.1]octan-8-yl)pyrimidin-2-yl)aniline (38, Scheme 16) using the general procedure from scheme 2 for the preparation of 7:

1-[4-(4,6-di-3-oxa-8-azabicyclo[3.2.1]oct-8-ylpyrimidin-2-yl)phenyl]-3-pyridin-3-ylurea Using a solution of 3-aminopyridine in dichloromethane, the title compound was obtained (28.4 mg) MS m/z=514 (M+H).

Scheme 26

8,8'-(2,5-dichloropyrimidine-4,6-diyl)bis(3-oxa-8-azabicyclo[3.2.1]octane)

To a solution of 2,4,5,6-tetrachloro-pyrimidine (2.0 g, 9.2 mmol) in THF (20 mL) and triethylamine (excess) was added 3-oxa-8-aza-bicyclo[3.2.1]octane (2.7 g, 18 mmol) at −78° C. The reaction slowly warmed to room temperature and a white precipitate formed. To the reaction was added water (2.0 mL) and the mixture was refluxed for three days. The reaction was cooled and water was added to precipitate a white solid. The solids were collected by filtration and washed with diethyl ether to yield the title compound (2.0 g). MS m/z=372 (M+H).

4-(5-chloro-4,6-di-3-oxa-8-azabicyclo[3.2.1]oct-8-ylpyrimidin-2-yl)aniline

To a solution of 8,8'-(2,5-dichloropyrimidine-4,6-diyl)bis (3-oxa-8-azabicyclo[3.2.1]octane) (1.0 g, 2.7 mmol) in 1:1 ethanol:toluene (10 mL) was added 4-aminophenylboronic acid pinacol ester (0.7 g, 3.2 mmol), 2.0M solution of sodium carbonate (1.2 mL) and tetrakis(triphenylphosphine) palladium (0) (0.3 g, 10 mol %). The reaction was refluxed under nitrogen overnight. The reaction was cooled and water was added (75 mL) and the mixture was extracted 3 times with ethyl acetate. The organics were separated and dried over magnesium sulfate, then filtered through Magnesol™ and concentrated in vacuo to an oil. The crude product was purified via silica gel column with hexanes/ethyl acetate to yield the title compound as a white solid (0.708 g). MS m/z=428 (M+H).

The following products were prepared from 4-(5-chloro-4,6-di-3-oxa-8-azabicyclo[3.2.1]oct-8-ylpyrimidin-2-yl)aniline, using the general procedure from scheme 2 for the preparation of 7:

1-[4-(5-chloro-4,6-di-3-oxa-8-azabicyclo[3.2.1]oct-8-ylpyrimidin-2-yl)phenyl]-3-pyridin-3-ylurea Using a solution of 3-aminopyridine in dichloromethane, the title compound was obtained as a tan solid (32.8 mg) MS m/z=549 (M+H).

1-[4-(5-chloro-4,6-di-3-oxa-8-azabicyclo[3.2.1]oct-8-ylpyrimidin-2-yl)phenyl]-3-[4-(4-methylpiperazin-1-yl)phenyl]urea Using a solution of 4-(4-methyl-piperazin-1-yl)-phenylamine in dichloromethane, the title compound was obtained (43.6 mg) MS m/z=646 (M+H).

Scheme 27

9-(6-chloro-2-(4-nitrophenyl)pyrimidin-4-yl)-3,7-dioxa-9-azabicyclo[3.3.1]nonane In a round-bottom flask was placed 4,6-dichloror-2-(4-nitrophenyl)pyrimidine (59, 800 mg, 2.96 mmol) in dichloromethane (20 mL) to give a tan solution. 3,7-dioza-9-azabicyclo[3.3.1]nonane, HCl (540 mg, 3.26 mmol) was added followed by triethylamine (1.24 mL, 8.89 mmol). The mixture was stirred for 2 hours at room temperature followed by heating under reflux for 72 hours. LCMS showed a mixture of hydrolyzed starting material, starting material and product. Additional triethylamine was added (2 mL) and the mixture was heated for 1 hour under microwave irradiation at 100° C. The mixture was diluted with dichloromethane and washed with saturated $NaHCO_3$. The organic phase was dried ($MgSO_4$), filtered and concentrated. The crude product was purified by silica gel chromatography (20-60% ethyl acetate in hexanes) to give the title compound (142 mg, 13%). HRMS: 363.0847 $[M+H]^+$. For $[M+H]^+$ mass error=−0.7 mDa or −2.02 ppm.

6-(3,7-dioxa-9-azabicyclo[3.3.1]nonan-9-yl)-N-isopropyl-2-(4-nitrophenyl)pyrimidin-4-amine In a 2-5 mL microwave vial was placed 9-(6-chloro-2-(4-nitrophenyl)pyrimidin-4-yl)-3,7-dioxa-9-azabicyclo[3.3.1]nonane (130 mg, 0.358 mmol) in isopropylamine (5 mL) to give a yellow suspension. The reaction was heated under microwave irradiation at 145° C. for 60 min. The mixture was concentrated. The residue was dissolved in dichloromethane and washed with saturated $NaHCO_3$. The organic phase was dried ($MgSO_4$), filtered and concentrated to give 137 mg (99%) of a yellow foam. HRMS: 386.1824 $[M+H]^+$. For $[M+H]^+$ mass error=0.1 mDa or 0.21 ppm.

2-(4-aminophenyl)-6-(3,7-dioxa-9-azabicyclo[3.3.1]nonan-9-yl)-N-isopropylpyrimidin-4-amine In a 250 mL round bottom flask was placed 6-(3,7-dioxa-9-azabicyclo[3.3.1]nonan-9-yl)-N-isopropyl-2-(4-nitrophenyl)pyrimidin-4-amine (124 mg, 0.32 mmol) in 2-propanol (3 mL) and dichloromethane (3 mL) to give a yellow solution. A catalytic amount of palladium on charcoal (wet) was added and the mixture was stirred under a hydrogen atmosphere for 6 hours. The mixture was filtered over Celite™, rinsed with dichloromethane and concentrated to give 110 mg of a yellow solid (96%). HRMS: 356.2082 $[M+H]^+$. For $[M+H]^+$ mass error=0.1 mDa or 0.29 ppm.

The following products were prepared from 2-(4-aminophenyl)-6-(3,7-dioxa-9-azabicyclo[3.3.1]nonan-9-yl)-N-isopropylpyrimidin-4-amine, using the general procedure from scheme 2 for the preparation of 7:

1-{4-[4-(3,7-dioxa-9-azabicyclo[3.3.1]non-9-yl)-6-(isopropylamino)pyrimidin-2-yl]phenyl}-3-pyridin-4-ylurea Using a suspension of 4-aminopyridine in dichloromethane, the title compound was obtained. Yield: 18.8 mg, 57%. RT 1.57. M+H=587.3.

1-{4-[4-(3,7-dioxa-9-azabicyclo[3.3.1]non-9-yl)-6-(isopropylamino)pyrimidin-2-yl]phenyl}-3-{4-[(4-methylpiperazin-1-yl)methyl]phenyl}urea Using a solution of 4-((4-methylpiperazin-1-yl)methyl)aniline in dichloromethane, the title compound was obtained Yield 26.7 mg, 55%. RT 1.61. M+H=587.3.

1-{4-[4-(3,7-dioxa-9-azabicyclo[3.3.1]non-9-yl)-6-(isopropylamino)pyrimidin-2-yl]phenyl}-3-[4-(4-methylpiperazin-1-yl)phenyl]urea Using a solution of 4-(4-methylpiperazin-1-yl)aniline in dichloromethane, the title compound was obtained. Yield 27.2 mg, 57%. RT 1.67. M+H=573.3.

1-{4-[2-(dimethylamino)ethoxy]phenyl}-3-{4-[4-(3,7-dioxa-9-azabicyclo[3.3.1]non-9-yl)-6-(isopropylamino)pyrimidin-2-yl]phenyl}urea Using a solution of 4-[2-(dimethylamino)ethoxy]aniline.2HCl in 1N NaOH, the title compound was obtained. Yield: 17.3 mg, 37%. RT 1.68. M+H=562.3.

Scheme 28

6-chloro-2-(4-nitrophenyl)-N-(tetrahydro-2H-pyran-4-yl)pyrimidin-4-amine and 6-chloro-N,N-diethyl-2-(4-nitrophenyl)pyrimidin-4-amine In a 250 mL round-bottom flask was placed 4,6-dichloro-2-(4-nitrophenyl)pyrimidine (59, 500 mg, 1.85 mmol) in dichloromethane (25 mL) to give a white suspension. Tetrahydro-2H-pyan-4-amine, HCl (280 mg, 2.04 mmol) was added followed by addition of triethylamine (0.77 mL, 5.55 mmol). The mixture was stirred at room temperature for 19 hours and was then heated under reflux for 21 hour. Excess potassium carbonate was added and heating under reflux was continued for 6 hours. The mixture was cooled to room temperature and stirred at room temperature for 2 weeks. LCMS showed formation of the expected product 6-chloro-2-(4-nitrophenyl)-N-(tetrahydro-2H-pyran-4-yl)pyrimidin-4-amine along with the N,N-diethylamine product 6-chloro-N,N-diethyl-2-(4-nitrophenyl)pyrimidin-4-amine. The mixture was diluted with dichloromethane and washed with saturated $NaHCO_3$. The organic phase was dried ($MgSO_4$), filtered and concentrated. The crude product was purified by silica gel chromatography (20-60% ethyl acetate in hexanes) to give two products: 6-chloro-2-(4-nitrophenyl)-N-(tetrahydro-2H-pyran-4-yl)pyrimidin-4-amine: 152 mg (25%) of a yellow solid. HRMS: 335.0909 $[M+H]^+$. For $[M+H]^+$ mass error=0.4 mDa or 1.15 ppm. 6-chloro-N,N-diethyl-2-(4-nitrophenyl)pyrimidin-4-amine: 72 mg. HRMS: 307.0962 $[M+H]^+$. For $[M+H]^+$ mass error=0.5 mDa or 1.73 ppm.

Scheme 29

6-(3-oxa-8-azabicyclo[3.2.1]octan-8-yl)-2-(4-nitrophenyl)-N-(tetrahydro-2H-pyran-4-yl)pyrimidin-4-amine In a 2-5 mL microwave vial was placed 6-chloro-2-(4-nitrophenyl)-N-(tetrahydro-2H-pyran-4-yl)pyrimidin-4-amine (141 mg, 0.421 mmol) in dioxane (4 mL) to give a yellow suspension. 3-oxa-8-azabicyclo[3.2.1]octane.HCl (33, 189 mg, 1.264 mmol), potassium carbonate (233 mg, 1.685 mmol) and Hunig's base (0.44 mL, 2.52 mmol) were added. The mixture was heated under microwave irradiation at 220° C. for 2.5 hours. The mixture was diluted with dichloromethane and washed with saturated NaHCO$_3$. The organic phase was dried (MgSO$_4$), filtered and concentrated. The crude product was purified by silica gel chromatography (30-100% ethyl acetate in hexanes) to give the title compound as a bright yellow solid (78 mg, 45%). HRMS: 412.1985 [M+H]$^+$. For [M+H]$^+$ mass error=0.6 mDa or 1.39 ppm. Also isolated was a small amount of 2-(4-aminophenyl)-6-(3-oxa-8-azabicyclo[3.2.1]octan-8-yl)-N-(tetrahydro-2H-pyran-4-yl)pyrimidin-4-amine as a yellow oil (18 mg, 11%).

2-(4-aminophenyl)-6-(3-oxa-8-azabicyclo[3.2.1]
octan-8-yl)-N-(tetrahydro-2H-pyran-4-yl)pyrimidin-
4-amine In a 250 mL round bottom flask was placed 6-(3-oxa-8-azabicyclo[3.2.1]octan-8-yl)-2-(4-nitrophenyl)-N-(tetrahydro-2H-pyran-4-yl)pyrimidin-4-amine (82 mg, 0.199 mmol) in dichloromethane (7 mL) and 2-propanol (7 mL). A catalytic amount of palladium on charcoal (wet) was added and the mixture was stirred under a hydrogen atmosphere for 16 hours. The mixture was diluted with dichloromethane, filtered over Celite™ and concentrated to give 69 mg (0.18 mmol, 91%) of a tan solid. HRMS: 382.2236 [M+H]$^+$. For [M+H]$^+$ mass error=−0.1 mDa or −0.35 ppm.

Alternative procedure for the preparation of 2-(4-
aminophenyl)-6-(3-oxa-8-azabicyclo[3.2.1]octan-8-
yl)-N-(tetrahydro-2H-pyran-4-yl)pyrimidin-4-amine:

Step 1:

In a 2-5 mL microwave vial was placed 8-(6-chloro-2-(4-nitrophenyl)pyrimidin-4-yl)-3-oxa-8-azabicyclo[3.2.1]octane (36, 143 mg, 0.412 mmol) and tetrahydro-2H-pyran-4-amine.HCl (113 mg, 0.825 mmol) in dioxane to give a yellow suspension. Triethylamine (0.23 mL, 1.65 mmol) was added and the mixture was heated under microwave irradiation at 180° C. for 30 min, followed by heating at 220° C. for 30 min. Additional tetrahydro-2H-pyran-4-amine.HCl (113 mg) was added along with Hunig's base (0.25 mL) and the mixture was heated for 2.5 hours at 250° C. resulting in complete conversion of starting material into a mixture of products. The mixture contained among others 6-(3-oxa-8-azabicyclo[3.2.1]octan-8-yl)-2-(4-nitrophenyl)-N-(tetrahydro-2H-pyran-4-yl)pyrimidin-4-amine as well as 2-(4-aminophenyl)-6-(3-oxa-8-azabicyclo[3.2.1]octan-8-yl)-N-(tetrahydro-2H-pyran-4-yl)pyrimidin-4-amine. The mixture was concentrated and used in step 2 without further purification.

Step 2:

The mixture from step 1 was dissolved in dichloromethane (7 mL) and 2-propanol (7 mL) to give a brown solution. A catalytic amount of palladium on charcoal (wet) was added and the mixture was stirred under a hydrogen atmosphere for 16 hours. The mixture was diluted with dichloromethane, filtered over Celite™ and concentrated. The crude product was purified by silica gel chromatography using a gradient of methanol and triethylamine (0-10% methanol, 0-1% NEt$_3$) in ethyl acetate to give 63 mg (40%) of a yellow oil.

The following products were prepared from 2-(4-aminophenyl)-6-(3-oxa-8-azabicyclo[3.2.1]octan-8-yl)-N-(tetrahydro-2H-pyran-4-yl)pyrimidin-4-amine, using the general procedure from scheme 2 for the preparation of 7:

1-{4-[4-(3-oxa-8-azabicyclo[3.2.1]oct-8-yl)-6-(tet-
rahydro-2H-pyran-4-ylamino)pyrimidin-2-yl]phe-
nyl}-3-pyridin-4-ylurea Using a suspension of 4-aminopyridine in dichloromethane, the title compound was obtained. Yield 17.4 mg, 39%. RT 1.68, M+H=502.2.

1-[4-(4-methylpiperazin-1-yl)phenyl]-3-{4-[4-(3-
oxa-8-azabicyclo[3.2.1]oct-8-yl)-6-(tetrahydro-2H-
pyran-4-ylamino)pyrimidin-2-yl]phenyl}urea Using a solution of 4-(4-methylpiperazin-1-yl)aniline in dichloromethane, the title compound was obtained. Yield 9.5 mg, 15%. RT 1.75, M+H=599.3.

1-{4-[4-(3-oxa-8-azabicyclo[3.2.1]oct-8-yl)-6-(tet-
rahydro-2H-pyran-4-ylamino)pyrimidin-2-yl]phe-
nyl}-3-pyridin-3-ylurea Using a solution of 3-aminopyridine in dichloromethane, the title compound was obtained. Yield 16.9 mg, 67%. RT 1.72, M+H=502.2.

1-{4-[2-(dimethylamino)ethoxy]phenyl}-3-{4-[4-(3-
oxa-8-azabicyclo[3.2.1]oct-8-yl)-6-(tetrahydro-2H-
pyran-4-ylamino)pyrimidin-2-yl]phenyl}urea Using a solution of 4-[2-(dimethylamino)ethoxy]aniline.2HCl in 1N NaOH, the title compound was obtained. Yield 15.2 mg, 43%. RT 1.76. M+H=588.3.

1-{4-[(4-methylpiperazin-1-yl)methyl]phenyl}-3-{4-
[4-(3-oxa-8-azabicyclo[3.2.1]oct-8-yl)-6-(tetrahydro-
2H-pyran-4-ylamino)pyrimidin-2-yl]phenyl}urea Using a solution of 4-[(4-methylpiperazin-1-yl)methyl]aniline in dichloromethane, the title compound was obtained. Yield 21 mg, 50%. RT 1.72, M+H=524.2.

Scheme 30

6-chloro-N-(2-(methylsulfonyl)ethyl)-2-(4-nitrophe-
nyl)pyrimidin-4-amine

In a 250 mL round-bottom flask was placed 4,6-dichloro-2-(4-nitrophenyl)pyrimidine (59, 500 mg, 1.85 mmol) in dichloromethane (20 mL) to give a colorless solution. 2-(methylsulfonyl)ethanamine.HCl (325 mg, 2.04 mmol) was added followed by addition of triethylamine (0.77 mL, 5.55 mmol). The mixture was stirred at room temperature for 19 hours and was then refluxed for 21 hour. Excess potassium carbonate was added and heating under reflux was continued for 6 hours. The mixture was cooled to room temperature and stirred at room temperature for 2 weeks. The mixture was diluted with dichloromethane and washed with saturated NaHCO$_3$. The organic phase was dried (MgSO$_4$), filtered and concentrated. The crude product was purified by column chromatography (20-100% ethyl acetate in hexanes) to give the title compound as a yellow solid (196 mg, 30%). HRMS: 357.0417 [M+H]$^+$. For [M+H]$^+$ mass error=−0.2 mDa or −0.60 ppm.

6-(3-oxa-8-azabicyclo[3.2.1]octan-8-yl)-N-(2-(meth-
ylsulfonyl)ethyl)-2-(4-nitrophenyl)pyrimidin-4-
amine In a 2-5 mL microwave vial was placed 6-chloro-N-(2-(methylsulfonyl)ethyl)-2-(4-nitrophenyl)pyrimidin-4-amine (185 mg, 0.52 mmol) in dioxane (4 mL) to give a yellow suspension. 3-oxa-8-azabicyclo[3.2.1]octane.HCl (33, 233 mg, 1.56 mmol), potassium carbonate (287 mg, 2.07 mmol) and Hunig's base (0.54 mL, 3.11 mmol) were added. The reaction was heated under microwave irradiation at 220° C. for 1.5 hours. The mixture was diluted with dichloromethane and washed with saturated NaHCO$_3$. The aqueous phase was extracted with dichloromethane. The combined organic phases were dried (MgSO$_4$), filtered and concentrated. The crude product was purified by silica gel column chromatography (50-100% ethyl acetate in hexanes) to give 137 mg (61%) of the title compound as a yellow foam. HRMS: 434.1497 [M+H]$^+$. For [M+H]$^+$ mass error=0.4 mDa or 1.03 ppm. Also isolated was a small amount (17 mg, 8%) of the reduced compound 2-(4-aminophenyl)-6-(3-oxa-8-azabicyclo[3.2.1]octan-8-yl)-N-(2-(methylsulfonyl)ethyl)pyrimidin-4-amine.

2-(4-aminophenyl)-6-(3-oxa-8-azabicyclo[3.2.1]octan-8-yl)-N-(2-(methylsulfonyl)ethyl)pyrimidin-4-amine In a 250 mL round bottom flask was placed 6-(3-oxa-8-azabicyclo[3.2.1]octan-8-yl)-N-(2-(methylsulfonyl)ethyl)-2-(4-nitrophenyl)pyrimidin-4-amine (143 mg, 0.33 mmol) in dichloromethane (7 mL) and 2-propanol (7 mL) to give a brown solution. A catalytic amount of palladium on charcoal (wet) was added and the mixture was stirred under a hydrogen atmosphere for 16 hours. The mixture was diluted with dichloromethane, filtered over Celite™ and concentrated to give 113 mg (85%) of a tan solid. HRMS: 404.1751 [M+H]$^+$. For [M+H]$^+$ mass error=−0.0 mDa or −0.07 ppm.

The following products were prepared from 2-(4-aminophenyl)-6-(3-oxa-8-azabicyclo[3.2.1]octan-8-yl)-N-(2-(methylsulfonyl)ethyl)pyrimidin-4-amine, using the general procedure from scheme 2 for the preparation of 7:

1-{4-[4-{[2-(methylsulfonyl)ethyl]amino}-6-(3-oxa-8-azabicyclo[3.2.1]oct-8-yl)pyrimidin-2-yl]phenyl}-3-pyridin-3-ylurea Using a solution of 3-aminopyridine in dichloromethane, the title compound was obtained. Yield: 19.1 mg (73%). RT 1.62, M+H=524.2

1-{4-[(4-methylpiperazin-1-yl)methyl]phenyl}-3-{4-[4-{[2-(methylsulfonyl)ethyl]amino}-6-(3-oxa-8-azabicyclo[3.2.1]oct-8-yl)pyrimidin-2-yl]phenyl}urea:

Using a solution of 4-[(4-methylpiperazin-1-yl)methyl]aniline in dichloromethane, the title compound was obtained. Yield: 22.6 mg (52%). RT 1.65, M+H=635.3.

1-{-4-[4-{[2-(methylsulfonyl)ethyl]amino}-6-(3-oxa-8-azabicyclo[3.2.1]oct-8-yl)pyrimidin-2-yl]phenyl}-3-pyridin-4-ylurea Using a suspension of 4-aminopyridine in dichloromethane, the title compound was obtained. Yield: 20.4 mg (78%). RT 1.60, M+H=524.2

1-{4-[2-(dimethylamino)ethoxy]phenyl}-3-{-4-[4-{[2-(methylsulfonyl)ethyl]amino}-6-(3-oxa-8-azabicyclo[3.2.1]oct-8-yl)pyrimidin-2-yl]phenyl}urea:

Using a solution of 4-[2-(dimethylamino)ethoxy]aniline.2HCl in 1N NaOH, the title compound was obtained. Yield: 21.9 mg (61%). RT 1.68, M+H=610.3

1-[4-(4-methylpiperazin-1-yl)phenyl]-3-{-4-[4-{[2-(methylsulfonyl)ethyl]amino}-6-(3-oxa-8-azabicyclo[3.2.1]oct-8-yl)pyrimidin-2-yl]phenyl}urea:

Using a solution of 4-(4-methylpiperazin-1-yl)aniline in dichloromethane, the title compound was obtained. Yield: 24.5 mg (67%). RT 1.68, M+H=621.3

The following products were prepared from 2-(4-aminophenyl)-6-(3-oxa-8-azabicyclo[3.2.1]octan-8-yl)-N-isopropylpyrimidin-4-amine (61, Scheme 22) using the general procedure from scheme 2 for the preparation of 7.

1-(4-{4-[(1-methylethyl)amino]-6-(3-oxa-8-azabicyclo[3.2.1]oct-8-yl)pyrimidin-2-yl}phenyl)-3-[4-(pyrrolidin-1-ylmethyl)phenyl]urea Using a solution of 4-pyrrolidin-1-ylmethyl-aniline in dichloromethane, the title compound was obtained. Yield: 45.3 mg (47%). RT 1.76, M+H=542.3.

1-(4-{4-[(1-methylethyl)amino]-6-(3-oxa-8-azabicyclo[3.2.1]oct-8-yl)pyrimidin-2-yl}phenyl)-3-pyridin-3-ylurea Using a solution of 3-aminopyridine in dichloromethane, the title compound was obtained. Yield: 44.5 mg (66%). RT 1.74, M+H=460.2.

1-{4-[(dimethylamino)methyl]phenyl}-3-(4-{4-[(1-methylethyl)amino]-6-(3-oxa-8-azabicyclo[3.2.1]oct-8-yl)pyrimidin-2-yl}phenyl)urea:

Using a solution of 4-[(dimethylamino)methyl]aniline in dichloromethane, the title compound was obtained. Yield: 39 mg (42%). RT 1.72, M+H=516.3.

1-(4-{4-[(1-methylethyl)amino]-6-(3-oxa-8-azabicyclo[3.2.1]oct-8-yl)pyrimidin-2-yl}phenyl)-3-[4-(2-pyrrolidin-1-ylethoxy)phenyl]urea Using a solution of 4-(2-pyrrolidin-1-yl-ethoxy)-phenylamine in dichloromethane, the title compound was obtained. Yield: 44.5 mg (44%). RT 1.77, M+H=572.3.

Scheme 31

6-(3-oxa-8-azabicyclo[3.2.1]octan-8-yl)-N,N-diethyl-2-(4-nitrophenyl)pyrimidin-4-amine In a 2-5 mL microwave vial was placed 6-chloro-N,N-diethyl-2-(4-nitrophenyl)pyrimidin-4-amine (59 mg, 0.192 mmol) in dioxane (2 mL) to give a yellow solution. 3-oxa-8-azabicyclo[3.2.1]octane.HCl (33, 86 mg, 0.577 mmol), potassium carbonate (106 mg, 0.769 mmol) and Hunig's base (0.20 mL, 1.15 mmol) were added. The mixture was heated under microwave irradiation at 220° C. for 3.5 hours. The mixture was diluted with dichloromethane and washed with saturated NaHCO$_3$. The organic phase was dried (MgSO$_4$), filtered and concentrated. The crude product was purified by column chromatography (10-40% ethyl acetate in hexanes) to give 22 mg (30%) of the title compound as a yellow solid. HRMS: 384.2027 [M+H]$^+$. For [M+H]$^+$ mass error=−0.3 mDa or −0.76 ppm. Also isolated was a small amount (10 mg) of the reduced product 2-(4-aminophenyl)-6-(3-oxa-8-azabicyclo[3.2.1]octan-8-yl)-N,N-diethylpyrimidin-4-amine.

2-(4-aminophenyl)-6-(3-oxa-8-azabicyclo[3.2.1] octan-8-yl)-N,N-diethylpyrimidin-4-amine In a 100 mL round bottom flask was placed 6-(3-oxa-8-azabicyclo[3.2.1]octan-8-yl)-N,N-diethyl-2-(4-nitrophenyl) pyrimidin-4-amine (22 mg, 0.057 mmol) in dichloromethane (2 mL) and 2-propanol (2 mL) to give a brown solution. A catalytic amount of palladium on charcoal (wet) was added and the mixture was stirred under a hydrogen atmosphere for 16 hours. The mixture was diluted with dichloromethane, filtered over Celite™ and concentrated to give 17 mg (84%) of the title compound as a tan solid. HRMS: 354.2288 [M+H]$^+$. For [M+H]$^+$ mass error=0.0 mDa or 0.01 ppm.

The following products were prepared from 2-(4-aminophenyl)-6-(3-oxa-8-azabicyclo[3.2.1]octan-8-yl)-N,N-diethylpyrimidin-4-amine, using the general procedure from scheme 2 for the preparation of 7:

1-{4-[4-(diethylamino)-6-(3-oxa-8-azabicyclo[3.2.1] oct-8-yl)pyrimidin-2-yl]phenyl}-3-pyridin-4-ylurea Using a suspension of 4-aminopyridine in dichloromethane, the title compound was obtained. Yield: 12.3 mg (68%). RT 1.77, M+H=474.3.

1-{4-[4-(diethylamino)-6-(3-oxa-8-azabicyclo[3.2.1] oct-8-yl)pyrimidin-2-yl]phenyl}-3-[4-(4-methylpiperazin-1-yl)phenyl]urea Using a solution of 4-(4-methylpiperazin-1-yl)aniline in dichloromethane, the title compound was obtained. Yield: 14.9 mg (57%). RT 1.83, M+H=571.3

Scheme 32

8-(2-chloro-6-(chloromethyl)pyrimidin-4-yl)-3-oxa-8-azabicyclo[3.2.1]octane

A flask was charged with 2,4-dichloro-6-(chloromethyl) pyrimidine (prepared as reported in *Bioorg. Med. Chem.*, 2002, 10, 525), 2.40 g, 12.15 mmol) in dichloromethane (30 mL) to give a yellow solution. 3-Oxa-8-azabicyclo[3.2.1] octane, HCl (33, 1.818 g, 12.15 mmol) and triethylamine (3.56 ml, 25.5 mmol) in dichloromethane (30 mL) were added slowly over 10 minutes, and the resulting solution was allowed to stir at room temperature for 16 hours, then concentrated. The crude product was added to a silica gel column and eluted with 0-40% ethyl acetate in hexanes to provide 8-(2-chloro-6-(chloromethyl)pyrimidin-4-yl)-3-oxa-8-azabicyclo[3.2.1]octane (2.30 g, 69%) as an off-white solid. HRMS; [M+H]$^+$ Obs'd=274.0510, [M+H]$^+$ Calc'd=274.0508

1-(6-(3-oxa-8-azabicyclo[3.2.1]octan-8-yl)-2-chloropyrimidin-4-yl)-N,N-dimethylmethanamine A flask was charged with 8-(2-chloro-6-(chloromethyl) pyrimidin-4-yl)-3-oxa-8-azabicyclo[3.2.1]octane (2.30 g, 8.39 mmol) and DMF (40 ml) was added to give a yellow solution. Potassium carbonate (2.90 g, 20.97 mmol) and dimethylamine (2.0M in THF, 4.6 ml, 9.23 mmol) were added and the reaction was allowed to stir at room temperature for 16 hours. The reaction mixture was filtered through a Buchner funnel and washed with methylene chloride and ethyl acetate. The filtrate was concentrated to provide crude product as a brown oil, which solidified upon standing (2.61 g). The crude product was added to a silica gel column and was eluted with 0-10% methanol in methylene chloride to provide 1-(6-(3-oxa-8-azabicyclo[3.2.1]octan-8-yl)-2-chloropyrimidin-4-yl)-N,N-dimethylmethanamine (2.01 g, 85%) as an off-white solid. HRMS; [M+H]$^+$ Obs'd=283.1320, [M+H]$^+$ Calc'd=283.1319.

Scheme 33

1-(pyridin-3-yl)-3-(4-(4,4,5,5-tetramethyl-1,3,2-dioxaborolan-2-yl)phenyl)urea A solution of 2-(4-isocyanatophenyl)-4,4,5,5-tetramethyl-1,3,2-dioxaborolane (1.30 g, 5.31 mmol) in toluene (50 ml) was prepared and 3-aminopyridine (0.499 g, 5.31 mmol) was added. A suspension was observed, and tetrahydrofuran (15 ml) was added. The solution was allowed to stir at room temperature for 2.5 hours, then concentrated to provide 1-(pyridin-3-yl)-3-(4-(4,4,5,5-tetramethyl-1,3,2-dioxaborolan-2-yl)phenyl)urea (1.82 g, quant. yield) as a tan solid, which was used without purification.

1-cyclopropyl-3-(4-(4,4,5,5-tetramethyl-1,3,2-dioxaborolan-2-yl)phenyl)urea

A solution of 2-(4-isocyanatophenyl)-4,4,5,5-tetramethyl-1,3,2-dioxaborolane (0.122 g, 0.496 mmol) in DME (3 ml) was prepared. Cyclopropylamine (0.028 g, 0.496 mmol) was added and the solution was allowed to stir at room temperature for 20 hours. The crude DME solution was used directly in the Suzuki reaction.

1-(4-(4-methylpiperazin-1-yl)phenyl)-3-(4-(4,4,5,5-tetramethyl-1,3,2-dioxaborolan-2-yl)phenyl)urea A procedure analogous to that used for the preparation of 1-cyclopropyl-3-(4-(4,4,5,5-tetramethyl-1,3,2-dioxaborolan-2-yl)phenyl)urea was used, using 4-(4-methylpiperazin-1-yl)aniline as the amine component.

1-(4-(2-(dimethylamino)ethoxy)phenyl)-3-(4-(4,4,5,5-tetramethyl-1,3,2-dioxaborolan-2-yl)phenyl)urea A procedure analogous to that used for the preparation of 1-cyclopropyl-3-(4-(4,4,5,5-tetramethyl-1,3,2-dioxaborolan-2-yl)phenyl)urea was used, using 4-(2-(dimethylamino) ethoxy)aniline as the amine component.

1-(4-((dimethylamino)methyl)phenyl)-3-(4-(4,4,5,5-tetramethyl-1,3,2-dioxaborolan-2-yl)phenyl)urea A procedure analogous to that used for the preparation of 1-cyclopropyl-3-(4-(4,4,5,5-tetramethyl-1,3,2-dioxaborolan-2-yl)phenyl)urea was used, using 4-((dimethylamino) methyl)aniline as the amine component.

1-phenyl-3-(4-(4,4,5,5-tetramethyl-1,3,2-dioxaborolan-2-yl)phenyl)urea

A procedure analogous to that used for the preparation of 1-cyclopropyl-3-(4-(4,4,5,5-tetramethyl-1,3,2-dioxaborolan-2-yl)phenyl)urea was used, using aniline as the amine component.

Scheme 34

1-(4-(4-(3-oxa-8-azabicyclo[3.2.1]octan-8-yl)-6-((dimethylamino)methyl)pyrimidin-2-yl)phenyl)-3-(pyridin-3-yl)urea A microwave vial was charged with 1-(6-(3-oxa-8-azabicyclo[3.2.1]octan-8-yl)-2-chloropyrimidin-4-yl)-N,N-dimethylmethanamine (0.080 g, 0.283 mmol) and sodium carbonate (2M in water, 0.425 mL, 0.849 mmol). DME (1.5 mL) was then added to give a yellow biphasic solution. The solution was sparged with nitrogen for 10 minutes, and tetrakis(triphenylphosphine)palladium(0) (0.020 g, 0.017 mmol) and 1-(pyridin-3-yl)-3-(4-(4,4,5,5-tetramethyl-1,3,2-dioxaborolan-2-yl)phenyl)urea (0.106 g, 0.311 mmol) were added. The vial was sealed and heated to 120° C. for 2 hours via microwave. The vessel was then cooled to room temperature and the reaction mixture was filtered through Celite™. The filter cake was washed with ethyl acetate and the filtrate was washed with saturated sodium chloride and concentrated under reduced pressure to provide a brown oil. The crude product was added to a HPLC column and was eluted with 5-90% acetonitrile in water (0.05% TFA buffer) to provide the mono-TFA salt of 1-(4-(4-(3-oxa-8-azabicyclo[3.2.1]octan-8-yl)-6-((dimethylamino)methyl)pyrimidin-2-yl)phenyl)-3-(pyridin-3-yl)urea (0.097 g, 75%) as a light yellow solid. HRMS; [M+H]$^+$ Obs'd=460.2454, [M+H]$^+$ Calc'd=460.2455.

1-(4-(4-(3-oxa-8-azabicyclo[3.2.1]octan-8-yl)-6-((dimethylamino)methyl)pyrimidin-2-yl)phenyl)-3-cyclopropylurea A microwave vial was charged with a solution of 1-cyclopropyl-3-(4-(4,4,5,5-tetramethyl-1,3,2-dioxaborolan-2-yl)phenyl)urea (0.496 mmol) in DME (3 ml). Sodium carbonate (2M in water, 0.530 ml, 1.061 mmol), tetrakis(triphenylphosphine)palladium(0) (0.025 g, 0.021 mmol), and 1-(6-(3-oxa-8-azabicyclo[3.2.1]octan-8-yl)-2-chloropyrimidin-4-yl)-N,N-dimethylmethanamine (0.100 g, 0.354 mmol) were added and the resulting solution was sparged with nitrogen for 5 minutes and then heated to 100° C. for 90 minutes via microwave. The vessel was then cooled to room temperature and the reaction mixture was filtered through Celite™. The filter cake was washed with ethyl acetate and the filtrate was washed with saturated sodium chloride and concentrated under reduced pressure to provide a brown oil. The crude product was added to a HPLC column and was eluted with 5-100% acetonitrile in water (0.05% TFA buffer) to provide the mono-TFA salt of 1-(4-(4-(3-oxa-8-azabicyclo[3.2.1]octan-8-yl)-6-((dimethylamino)methyl)pyrimidin-2-yl)phenyl)-3-cyclopropylurea (0.073 g, 49%) as a light yellow solid. MS; 423.2, M+H.

1-(4-(4-(3-oxa-8-azabicyclo[3.2.1]octan-8-yl)-6-((dimethylamino)methyl)pyrimidin-2-yl)phenyl)-3-(4-(4-methylpiperazin-1-yl)phenyl)urea A procedure analogous to that used for the preparation of 1-(4-(4-(3-oxa-8-azabicyclo[3.2.1]octan-8-yl)-6-((dimethylamino)methyl)pyrimidin-2-yl)phenyl)-3-cyclopropylurea was used, using 1-(4-(4-methylpiperazin-1-yl)phenyl)-3-(4-(4,4,5,5-tetramethyl-1,3,2-dioxaborolan-2-yl)phenyl)urea as the boronic ester component. Yield=0.128 g, 65%. MS; 557.5, M+H.

1-(4-(4-(3-oxa-8-azabicyclo[3.2.1]octan-8-yl)-6-((dimethylamino)methyl)pyrimidin-2-yl)phenyl)-3-(4-(2-(dimethylamino)ethoxy)phenyl)urea A procedure analogous to that used for the preparation of 1-(4-(4-(3-oxa-8-azabicyclo[3.2.1]octan-8-yl)-6-((dimethylamino)methyl)pyrimidin-2-yl)phenyl)-3-cyclopropylurea was used, using 1-(4-(2-(dimethylamino)ethoxy)phenyl)-3-(4-(4,4,5,5-tetramethyl-1,3,2-dioxaborolan-2-yl)phenyl)urea as the boronic ester component. Yield=0.034 g, 18%. MS; 546.5, M+H.

1-(4-(4-(3-oxa-8-azabicyclo[3.2.1]octan-8-yl)-6-((dimethylamino)methyl)pyrimidin-2-yl)phenyl)-3-(4-((dimethylamino)methyl)phenyl)urea A procedure analogous to that used for the preparation of 1-(4-(4-(3-oxa-8-azabicyclo[3.2.1]octan-8-yl)-6-((dimethylamino)methyl)pyrimidin-2-yl)phenyl)-3-cyclopropylurea was used, using 1-(4-((dimethylamino)methyl)phenyl)-3-(4-(4,4,5,5-tetramethyl-1,3,2-dioxaborolan-2-yl)phenyl)urea as the boronic ester component. Yield=0.070 g, 39%. MS; 516.5, M+H.

1-(4-(4-(3-oxa-8-azabicyclo[3.2.1]octan-8-yl)-6-((dimethylamino)methyl)pyrimidin-2-yl)phenyl)-3-phenylurea A procedure analogous to that used for the preparation of 1-(4-(4-(3-oxa-8-azabicyclo[3.2.1]octan-8-yl)-6-((dimethylamino)methyl)pyrimidin-2-yl)phenyl)-3-cyclopropylurea was used, using 1-phenyl-3-(4-(4,4,5,5-tetramethyl-1,3,2-dioxaborolan-2-yl)phenyl)urea as the boronic ester component. Yield=0.088 g, 55%. MS; 459.5, M+H.

Scheme 35

4-(4-(3-oxa-8-azabicyclo[3.2.1]octan-8-yl)-6-((dimethylamino)methyl)pyrimidin-2-yl)aniline A microwave vial was charged with 1-(6-(3-oxa-8-azabicyclo[3.2.1]octan-8-yl)-2-chloropyrimidin-4-yl)-N,N-dimethylmethanamine (0.400 g, 1.42 mmol) and sodium carbonate (2M in water, 2.12 mL, 4.24 mmol). DME (7 mL) was then added to give a yellow biphasic solution. The solution was degassed with nitrogen for 10 minutes, and tetrakis(triphenylphosphine)palladium(0) (0.098 g, 0.085 mmol) and 4-(4,4,5,5-tetramethyl-1,3,2-dioxaborolan-2-yl)aniline (0.372 g, 1.697 mmol) were added. The vial was sealed and heated to 120° C. for 40 minutes under microwave irradiation. LCMS indicated that the reaction had not gone to completion. Additional tetrakis(triphenylphosphine)palladium(0) (0.049 g, 0.043 mmol) was added and the reaction was heated to 120° C. for an additional 80 minutes under microwave irradiation. The vessel was then cooled to room temperature and the reaction mixture was filtered through Celite™. The filter cake was washed with ethyl acetate and the filtrate was then concentrated under reduced pressure to provide a brown oil. The crude product was added to a silica gel column and was eluted with 0-10% methanol in methylene chloride to provide 4-(4-(3-oxa-8-azabicyclo[3.2.1]octan-8-yl)-6-((dimethylamino)methyl)pyrimidin-2-yl)aniline (0.365 g, 76%) as a light orange solid. HRMS; [M+H]$^+$ Obs'd=340.2133, [M+H]$^+$ Calc'd=340.2131

1-(4-(4-(3-oxa-8-azabicyclo[3.2.1]octan-8-yl)-6-((dimethylamino)methyl)pyrimidin-2-yl)phenyl)-3-methylurea A solution of 4-(4-(3-oxa-8-azabicyclo[3.2.1]octan-8-yl)-6-((dimethylamino)methyl)pyrimidin-2-yl)aniline (0.058 g, 0.171 mmol) in dichloromethane (2 mL) was prepared and methylisocyanate (2M in toluene, 0.214 mL, 0.427 mmol) was added. The solution was allowed to stir at room temperature for 140 hours, then concentrated. The crude product was added to a HPLC column and was eluted with 5-90% acetonitrile in water (0.05% TFA buffer) to provide the mono-TFA salt of 1-(4-(4-(3-oxa-8-azabicyclo[3.2.1]octan-8-yl)-6-((dimethylamino)methyl)pyrimidin-2-yl)phenyl)-3-methylurea (0.061 g, 90%) as a white solid. MS: 397.4, M+H.

1-(4-(4-(3-oxa-8-azabicyclo[3.2.1]octan-8-yl)-6-((dimethylamino)methyl)pyrimidin-2-yl)phenyl)-3-ethylurea A procedure similar to that used for the preparation of 1-(4-(4-(3-oxa-8-azabicyclo[3.2.1]octan-8-yl)-6-((dimethylamino)methyl)pyrimidin-2-yl)phenyl)-3-methylurea was used, substituting ethylisocyanate for methylisocyanate, to provide the mono-TFA salt of 1-(4-(4-(3-oxa-8-azabicyclo[3.2.1]octan-8-yl)-6-((dimethylamino)methyl)pyrimidin-2-yl)phenyl)-3-ethylurea (0.014 g, 21%) as a white solid. MS: 411.4, M+H.

Scheme 36

8-[6-(3,6-dihydro-2H-pyran-4-yl)-2-(4-nitrophenyl)pyrimidin-4-yl]-3-oxa-8-azabicyclo[3.2.1]octane (74):

In a 20 mL microwave vial was placed 8-(6-chloro-2-(4-nitrophenyl)pyrimidin-4-yl)-3-oxa-8-azabicyclo[3.2.1]octane (36, 500 mg, 1.442 mmol) in toluene (15 ml) to give a yellow suspension. The mixture was degassed with a stream of nitrogen and tributyl(3,6-dihydro-2H-pyran-4-yl)stannane (646 mg, 1.730 mmol) and Pd(PPH$_3$)$_4$ (167 mg, 0.144 mmol) were added. The reaction mixture was heated under microwave irradiation at 150° C. for 1 hour. The mixture was concentrated and the crude product was added to a silica gel column and was eluted with ethyl acetate in hexanes (25-70%). Collected fractions were concentrated to give 373 mg of a yellow solid. HRMS: 395.1707 [M+H]+. For [M+H]+ mass error=−0.6 mDa or −1.51 ppm.

4-[4-(3-oxa-8-azabicyclo[3.2.1]oct-8-yl)-6-(tetrahydro-2H-pyran-4-yl)pyrimidin-2-yl]aniline (75)

In a 250 mL round-bottomed flask was placed 8-(6-(3,6-dihydro-2H-pyran-4-yl)-2-(4-nitrophenyl)pyrimidin-4-yl)-3-oxa-8-azabicyclo[3.2.1]octane (74, 353 mg, 0.895 mmol) in dichloromethane (10 mL) and 2-propanol (10 mL) to give a yellow solution. Pd—C (95 mg, 0.089 mmol) was added. The reaction mixture was stirred for 72 hours under an atmosphere of hydrogen. The reaction mixture was diluted with dichloromethane, filtered through Celite™ and washed with dichloromethane. The mixture was concentrated under reduced pressure to give 324 mg of a yellow solid. HRMS: 367.2130 [M+H+. For [M+H]+ mass error=0.3 mDa or 0.7 ppm.

General procedure for formation of carbamoyl or urea compounds from 4-[4-(3-oxa-8-azabicyclo[3.2.1]oct-8-yl)-6-(tetrahydro-2H-pyran-4-yl)pyrimidin-2-yl]aniline (75):

In a 250 mL round-bottomed flask was placed 4-(4-(3-oxa-8-azabicyclo[3.2.1]octan-8-yl)-6-(tetrahydro-2H-pyran-4-yl)pyrimidin-2-yl)aniline (75, 305 mg, 0.832 mmol) and triethylamine (0.464 ml, 3.33 mmol) in dichloromethane (7 ml) to give a yellow solution. This mixture was added dropwise to a solution of triphosgene (123 mg, 0.416 mmol) in dichloromethane (7 ml). The mixture was stirred for 30 min and was then divided over seven solutions (0.119 mmol to each) of amine (0.3 mmol) in 1 mL of dichloromethane. The mixture was stirred for 3 hours, concentrated and purified by HPLC (Gilson, TFA buffers) to give the target compounds.

The following compounds were prepared according to the general procedure:

1-{4-[4-(3-oxa-8-azabicyclo[3.2.1]oct-8-yl)-6-(tetrahydro-2H-pyran-4-yl)pyrimidin-2-yl]phenyl}-3-pyridin-3-ylurea Yield: 36 mg, 63%. LCMS: purity 100%, 487.2 [M+H]+, RT 1.63

1-{4-[4-(3-oxa-8-azabicyclo[3.2.1]oct-8-yl)-6-(tetrahydro-2H-pyran-4-yl)pyrimidin-2-yl]phenyl}-3-pyridin-4-ylurea Yield: 36 mg, 63%. LCMS: purity 100%, 487.2 [M+H]+, RT 1.59

1-[4-(4-methylpiperazin-1-yl)phenyl]-3-{4-[4-(3-oxa-8-azabicyclo[3.2.1]oct-8-yl)-6-(tetrahydro-2H-pyran-4-yl)pyrimidin-2-yl]phenyl}urea Yield: 60 mg, 72% (TFA salt). LCMS: purity 96%, 584.3 [M+H]+, RT 1.67

1-[6-(4-methylpiperazin-1-yl)pyridin-3-yl]-3-{4-[4-(3-oxa-8-azabicyclo[3.2.1]oct-8-yl)-6-(tetrahydro-2H-pyran-4-yl)pyrimidin-2-yl]phenyl}urea Yield: 60 mg, 72% (TFA salt). LCMS: purity 99%, 585.3 [M+H]+, RT 1.63

1-{4-[(4-methylpiperazin-1-yl)carbonyl]phenyl}-3-{4-[4-(3-oxa-8-azabicyclo[3.2.1]oct-8-yl)-6-(tetrahydro-2H-pyran-4-yl)pyrimidin-2-yl]phenyl}urea Yield: 46 mg, 53% (TFA salt). LCMS: purity 100%, 612.3 [M+H]+, RT 1.64

1-(4-{[4-(1-methylethyl)piperazin-1-yl]carbonyl}phenyl)-3-{4-[4-(3-oxa-8-azabicyclo[3.2.1]oct-8-yl)-6-(tetrahydro-2H-pyran-4-yl)pyrimidin-2-yl]phenyl}urea:

Yield: 38 mg, 52% (TFA salt). LCMS: purity 94%, 640.4 [M+H]+, RT 1.69

1-{4-[2-(dimethylamino)ethoxy]phenyl}-3-{4-[4-(3-oxa-8-azabicyclo[3.2.1]oct-8-yl)-6-(tetrahydro-2H-pyran-4-yl)pyrimidin-2-yl]phenyl}urea Yield: 50 mg, 61% (TFA salt). LCMS: purity 100%, 573.3 [M+H]+, RT 1.67

The following compounds were prepared according to existing schemes (mostly Scheme 25, and step 2 from Scheme 2).

1-(4-{4-[(3R)-3-methylmorpholin-4-yl]-6-(3-oxa-8-azabicyclo[3.2.1]oct-8-yl)pyrimidin-2-yl}phenyl)-3-pyridin-4-ylurea

LCMS: 502.200 [M+H]+, RT 1.780

1-(4-{4-[(3R)-3-methylmorpholin-4-yl]-6-(3-oxa-8-azabicyclo[3.2.1]oct-8-yl)pyrimidin-2-yl}phenyl)-3-[4-(4-methylpiperazin-1-yl)phenyl]urea

LCMS: 599.300 [M+H]+, RT 1.810

1-(4-{4-[(3R)-3-methylmorpholin-4-yl]-6-(3-oxa-8-azabicyclo[3.2.1]oct-8-yl)pyrimidin-2-yl}phenyl)-3-[6-(4-methylpiperazin-1-yl)pyridin-3-yl]urea

LCMS: 600.300 [M+H]+, RT 1.770

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-pyridin-4-ylurea

LCMS: 516.300 [M+H]+, RT 1.870

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-[4-(4-methylpiperazin-1-yl)phenyl]urea

LCMS: 613.400 [M+H]+, RT 1.890

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-[6-(4-methylpiperazin-1-yl)pyridin-3-yl]urea

LCMS: 614.300 [M+H]+, RT 1.860

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-{4-[(4-methylpiperazin-1-yl)carbonyl]phenyl}urea

LCMS: 641.300 [M+H]+, RT 1.860

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-(4-{[4-(1-methylethyl)piperazin-1-yl]carbonyl}phenyl)urea

LCMS: 669.400 [M+H]+, RT 1.910

1-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)-3-pyridin-4-ylurea

LCMS: 500.200 [M+H]+, RT 1.650

1-[4-(4-methylpiperazin-1-yl)phenyl]-3-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)urea

LCMS: 597.300 [M+H]+, RT 1.710

1-{4-[(dimethylamino)methyl]phenyl}-3-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)urea

LCMS: 556.300 [M+H]+, RT 1.700

1-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)-3-pyridin-4-ylurea

LCMS: 500.200 [M+H]+, RT 1.650

1-[4-(4-methylpiperazin-1-yl)phenyl]-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea

LCMS: 597.300 [M+H]+, RT 1.710

1-{4-[(4-methylpiperazin-1-yl)methyl]phenyl}-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea

LCMS: 611.300 [M+H]+, RT 1.670

1-{4-[2-(dimethylamino)ethoxy]phenyl}-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea

LCMS: 586.300 [M+H]+, RT 1.700

1-(4-{4-[(3R)-3-methylmorpholin-4-yl]-6-(3-oxa-8-azabicyclo[3.2.1]oct-8-yl)pyrimidin-2-yl}phenyl)-3-pyridin-3-ylurea

LCMS: 502.200 [M+H]+, RT 1.780

1-(4-{4-[(3R)-3-methylmorpholin-4-yl]-6-(3-oxa-8-azabicyclo[3.2.1]oct-8-yl)pyrimidin-2-yl}phenyl)-3-{4-[(4-methylpiperazin-1-yl)methyl]phenyl}urea

LCMS: 613.400 [M+H]+, RT 1.770

1-{4-[2-(dimethylamino)ethoxy]phenyl}-3-(4-{4-[(3R)-3-methylmorpholin-4-yl]-6-(3-oxa-8-azabicyclo[3.2.1]oct-8-yl)pyrimidin-2-yl}phenyl)urea

LCMS: 588.300 [M+H]+, RT 1.800

N,N-dimethyl-4-{[(4-{4-[(3R)-3-methylmorpholin-4-yl]-6-(3-oxa-8-azabicyclo[3.2.1]oct-8-yl)pyrimidin-2-yl}phenyl)carbamoyl]amino}benzamide

LCMS: 572.300 [M+H]+, RT 2.020

1-(4-{4-[(3R)-3-methylmorpholin-4-yl]-6-(3-oxa-8-azabicyclo[3.2.1]oct-8-yl)pyrimidin-2-yl}phenyl)-3-{4-[(4-methylpiperazin-1-yl)carbonyl]phenyl}urea

LCMS: 627.300 [M+H]+, RT 1.780

1-(4-{[4-(1-methylethyl)piperazin-1-yl]
carbonyl}phenyl)-3-(4-{4-[(3R)-3-methylmorpholin-
4-yl]-6-(3-oxa-8-azabicyclo[3.2.1]oct-8-yl)pyrimi-
din-2-yl}phenyl)urea

LCMS: 655.400 [M+H]+, RT 1.810

1-(4-{4-[(dimethylamino)methyl]-6-(3-oxa-8-azabi-
cyclo[3.2.1]oct-8-yl)pyrimidin-2-yl}phenyl)-3-me-
thylurea Biological Evaluation PI3K-Alpha and PI3K-Gamma Fluorescence
Polarization Assay Protocols The reaction buffer was 20 mM HEPES, pH 7.5, 2 mM $MgCl_2$, 0.05% CHAPS; and 0.01% βME (added fresh). The stop/detection buffer was 100 mM HEPES, pH 7.5, 4 mM EDTA, 0.05% CHAPS; ATP 20 mM in water; PIP2 (diC8, Echelon, Salt Lake City Utah cat #P-4508) 1 mM in water (MW=856.5). The GST-GRP was 1.75 mg/mL or 1.4 mg/mL in 10% glycerol. The red detector (TAMRA) was 2.5 µM. Nunc 384-well black polypropylene fluorescent plates were used for PI3K assays.

The assay is run by placing 5 µL of diluted enzyme per well, then 5 µL of diluted compound (or 9.5 µL enzyme then 0.5 µL compound in DMSO) is added and mixed. Then, 10 µL substrate is added to start the reaction. The samples are incubated 30-60 minutes, then the reaction is stopped by adding 20 µL stop/detector mix. PI3K is diluted with reaction buffer (e.g., 5 µL or 7.5 µL PI3K into 620 µL reaction buffer), and 5 µL of diluted enzyme is used per well. A 5 µL portion of reaction buffer or of drug diluted in buffer (e.g., 4 µL/100 so final DMSO is 1% in reaction) is added to each. Pipetting up and down mixes the samples. Alternatively, the enzyme can be diluted to 1215 µL. In this case 9.8 µL is added per well and 0.2 µL compound is added in DMSO.

To prepare 1 mL of substrate solution, 955 µL reaction buffer, 40 µL PIP2, and 2.5 µL ATP are mixed. 10 µL of substrate is added to each well to start the reaction. This results in 20 µM PIP2, and 25 µM ATP per reaction. The stop/detector mix is prepared by mixing 4 µL red detector and 1.6 µL or 2.0 µL GST-GRP with 1 mL stop buffer, which results in 10 nM probe and 70 nM GST-GRP. 20 µL of the stop/detector mix is added to each well to stop the reaction. The plates are read after 30-90 minutes keeping the red probe solutions dark. For the zero time point, stop/detector mix is added to the enzyme just before adding substrate. For an extra control, stop/detector mix is added to buffer (no enzyme) and substrate or to just buffer (no substrate). Pooled PI3K preparations had a protein concentration of 0.25 mg/mL. The recommended reaction has 0.06 µL per 20 µL (0.015 µg/20 µL) or 0.01125 µg/15 µL or 0.75 µg/mL.

Plates are read on machines with filters for TAMRA. The units are mP with no enzyme controls reading app 190-220 mP units. Fully active enzyme reduces fluorescence polarization down to 70-100 mP after 30 minutes. An active compound raises the mP values halfway to control or to 120-150 mP units. Compounds of the invention had $IC_{50}$s against PI3K-alpha ranging from 7 nM to 2,858 nM.

mTOR Enzyme Assay (See Toral-Barza, et al. *Biochem Biophys. Res. Commun.* 2005 Jun. 24; 332(1):304-10) The routine human TOR assays with purified enzyme were performed in 96-well plates by DELFIA format as follows. Enzymes were first diluted in kinase assay buffer (10 mM HEPES (pH 7.4), 50 mM NaCl, 50 mM 3-glycerophosphate, 10 mM $MnCl_2$, 0.5 mM DTT, 0.25 µM microcystin LR, and 100 µg/mL BSA). To each well, 12 µL of the diluted enzyme were mixed briefly with 0.5 µL test inhibitor or the control vehicle dimethylsulfoxide (DMSO). The kinase reaction was initiated by adding 12.5 µL kinase assay buffer containing ATP and His6-S6K to give a final reaction volume of 25 µL containing 800 ng/mL FLAG-TOR, 100 µM ATP and 1.25 µM His6-S6K. The reaction plate was incubated for 2 hours (linear at 1-6 hours) at room temperature with gentle shaking and then terminated by adding 25 µL Stop buffer (20 mM HEPES (pH 7.4), 20 mM EDTA, 20 mM EGTA). The DELFIA detection of the phosphorylated (Thr-389) His6-S6K was performed at room temperature using a monoclonal anti-P(T389)-p70S6K antibody (1A5, Cell Signaling) labeled with Europium-N1-ITC (Eu) (10.4 Eu per antibody, PerkinElmer). The DELFIA assay buffer and enhancement solution were purchased from PerkinElmer. 45 µL of the terminated kinase reaction mixture was transferred to a MaxiSorp plate (Nunc) containing 55 µL PBS. The His6-S6K was allowed to attach for 2 hours after which the wells were aspirated and washed once with PBS. 100 µL of DELFIA assay buffer with 40 ng/mL Eu-P(T389)-S6K antibody was added. The antibody binding was continued for 1 hour with gentle agitation. The wells were then aspirated and washed 4 times with PBS containing 0.05% Tween-20 (PBST). 100 µL of DELFIA enhancement solution was added to each well and the plates were read in a PerkinElmer Victor model plate reader. Data obtained were used to calculate enzymatic activity and enzyme inhibition by potential inhibitors. Compounds of the invention had $IC_{50}$ activities ranging from <1 nM to 580 nM.

In Vitro Cell Growth Assay

The cell lines used were human prostate lines LNCap and PC3MM2, human breast lines MDA468 and MCF7, human renal line HTB44 (A498), human colon line HCT116, and human ovarian line OVCAR3. Cells were plated in 96-well culture plates. One day following plating, the inhibitors were added to cells. Three days after drug treatment, viable cell densities were determined by metabolic conversion (by viable cells) of the dye MTS, a well-established cell proliferation assay. The assays were performed using an assay kit purchased from Promega Corp. (Madison, Wis.) following the protocol supplied with the kit. The MTS assay results were read in a 96-well plate reader by measuring absorbance at 490 nm. The effect of each treatment was calculated as percent of control growth relative to the vehicle-treated cells grown in the same culture plate. The drug concentration that conferred 50% inhibition of growth was determined as $IC_{50}$. Compounds of the invention had $IC_{50}$ activities against LNCAP cells ranging from 6 nM to >60 uM.

Table 1 shows the results of the described biological assays.

TABLE 1

| Name | mTOR IC$_{50}$ (nM) | PI3Kα IC$_{50}$ (nM) | PI3Kγ IC$_{50}$ (nM) | LNCAP IC$_{50}$ (μM) | MDA IC$_{50}$ (μM) |
|---|---|---|---|---|---|
| 1-methyl-3-{4-[4-(8-oxa-3-azabicyclo[3.2.1]oct-3-yl)-6-phenylpyrimidin-2-yl]phenyl}urea | 22 | 953 | | 0.51 | 2 |
| 2-hydroxyethyl {4-[4-(8-oxa-3-azabicyclo[3.2.1]oct-3-yl)-6-phenylpyrimidin-2-yl]phenyl}carbamate | 21.5 | 452 | | 0.6 | 5.5 |
| 1-[4-(4-methylpiperazin-1-yl)phenyl]-3-{4-[4-(8-oxa-3-azabicyclo[3.2.1]oct-3-yl)-6-phenylpyrimidin-2-yl]phenyl}urea | 17.5 | 2430 | | 0.078 | 0.27 |
| 1-ethyl-3-{4-[4-(8-oxa-3-azabicyclo[3.2.1]oct-3-yl)-6-phenylpyrimidin-2-yl]phenyl}urea | 11 | 2048 | | 0.45 | 1.9 |
| 1-cyclopropyl-3-{4-[4-(8-oxa-3-azabicyclo[3.2.1]oct-3-yl)-6-phenylpyrimidin-2-yl]phenyl}urea | 19.5 | 3678 | | 1 | 5 |
| 1-{4-[4-(8-oxa-3-azabicyclo[3.2.1]oct-3-yl)-6-phenylpyrimidin-2-yl]phenyl}-3-pyridin-4-ylurea | 5.6 | 229 | | 0.29 | 0.39 |
| 1-[4-(hydroxymethyl)phenyl]-3-{4-[4-(8-oxa-3-azabicyclo[3.2.1]oct-3-yl)-6-phenylpyrimidin-2-yl]phenyl}urea | 2.9 | 102 | | 0.056 | 0.13 |
| 1-{4-[2-(dimethylamino)ethoxy]phenyl}-3-{4-[4-(8-oxa-3-azabicyclo[3.2.1]oct-3-yl)-6-phenylpyrimidin-2-yl]phenyl}urea | 19 | 141 | | 0.12 | 0.3 |
| 2-hydroxyethyl {4-[4-(8-oxa-3-azabicyclo[3.2.1]oct-3-yl)pyrimidin-2-yl]phenyl}carbamate | 165 | 5070 | | 4 | 24 |
| 1-methyl-3-{4-[4-(8-oxa-3-azabicyclo[3.2.1]oct-3-yl)pyrimidin-2-yl]phenyl}urea | 132.5 | 1843 | | 2.5 | 10.5 |
| 1-{4-[4-(8-oxa-3-azabicyclo[3.2.1]oct-3-yl)pyrimidin-2-yl]phenyl}-3-pyridin-4-ylurea | 14.5 | 224 | | 0.18 | 0.65 |
| 1-[4-(4,6-di-8-oxa-3-azabicyclo[3.2.1]oct-3-ylpyrimidin-2-yl)phenyl]-3-methylurea | 7.05 | 1085 | | 0.25 | 1 |
| 1-[4-(4,6-di-8-oxa-3-azabicyclo[3.2.1]oct-3-ylpyrimidin-2-yl)phenyl]-3-pyridin-4-ylurea | 0.56 | 125 | | 0.028 | 0.05 |
| 1-[4-(4,6-di-8-oxa-3-azabicyclo[3.2.1]oct-3-ylpyrimidin-2-yl)phenyl]-3-[4-(4-methylpiperazin-1-yl)phenyl]urea | 2.55 | 328.5 | | 0.0024 | 0.019 |
| 1-[4-(4,6-di-8-oxa-3-azabicyclo[3.2.1]oct-3-ylpyrimidin-2-yl)phenyl]-1-ethyl-3-pyridin-4-ylurea | 200 | 2256 | | 5.8 | 20 |
| 1-[4-(4,6-di-8-oxa-3-azabicyclo[3.2.1]oct-3-ylpyrimidin-2-yl)phenyl]-1-ethyl-3-[4-(4-methylpiperazin-1-yl)phenyl]urea | 195 | 2438 | | 2.8 | 7 |
| bis(2-hydroxyethyl) {[6-(8-oxa-3-azabicyclo[3.2.1]oct-3-yl)pyrimidine-2,4-diyl]di-4,1-phenylene}biscarbamate | 9.4 | 5004 | | 0.24 | 1.6 |
| N',N'''-{[6-(8-oxa-3-azabicyclo[3.2.1]oct-3-yl)pyrimidine-2,4-diyl]di-4,1-phenylene}bis(1-methylurea) | 2.8 | 990 | | 1.2 | 1.1 |
| N',N'''-{[6-(8-oxa-3-azabicyclo[3.2.1]oct-3-yl)pyrimidine-2,4-diyl]di-4,1-phenylene}bis(1-ethylurea) | 1.85 | 1663 | | 0.31 | 0.79 |
| N',N'''-{[6-(8-oxa-3-azabicyclo[3.2.1]oct-3-yl)pyrimidine-2,4-diyl]di-4,1-phenylene}bis(1-cyclopropylurea) | 4 | 2925 | | 0.31 | 1.5 |
| N,N''-{[6-(8-oxa-3-azabicyclo[3.2.1]oct-3-yl)pyrimidine-2,4-diyl]di-4,1-phenylene}bis(3-pyridin-3-ylurea) | 2.8 | 101 | | 0.18 | 0.38 |
| N,N''-{[6-(8-oxa-3-azabicyclo[3.2.1]oct-3-yl)pyrimidine-2,4-diyl]di-4,1-phenylene}bis(3-pyridin-4-ylurea) | 3.2 | 69.5 | | 0.22 | 0.78 |
| N',N'''-{[6-(8-oxa-3-azabicyclo[3.2.1]oct-3-yl)pyrimidine-2,4-diyl]di-4,1-phenylene}bis{1-[4-(4-methylpiperazin-1-yl)phenyl]urea} | 2.15 | 1018 | | 0.3 | 0.76 |
| 4,4'-{[6-(8-oxa-3-azabicyclo[3.2.1]oct-3-yl)pyrimidine-2,4-diyl]bis(4,1-phenylenecarbamoylimino)}dibenzamide | 0.58 | 44.5 | | 0.041 | 0.045 |
| 1-methyl-3-{4-[4-(1-methylethoxy)-6-(8-oxa-3-azabicyclo[3.2.1]oct-3-yl)pyrimidin-2-yl]phenyl}urea | 3 | 700 | | 0.19 | 0.89 |
| 1-cyclopropyl-3-{4-[4-(1-methylethoxy)-6-(8-oxa-3-azabicyclo[3.2.1]oct-3-yl)pyrimidin-2-yl]phenyl}urea | 4.45 | 7200 | | 0.29 | 1.8 |
| 1-{4-[4-(1-methylethoxy)-6-(8-oxa-3-azabicyclo[3.2.1]oct-3-yl)pyrimidin-2-yl]phenyl}-3-pyridin-4-ylurea | 1.35 | 264 | | 0.023 | 0.18 |

TABLE 1-continued

| Name | mTOR IC$_{50}$ (nM) | PI3Kα IC$_{50}$ (nM) | PI3Kγ IC$_{50}$ (nM) | LNCAP IC$_{50}$ (μM) | MDA IC$_{50}$ (μM) |
| --- | --- | --- | --- | --- | --- |
| 1-{4-[4-(1-methylethoxy)-6-(8-oxa-3-azabicyclo[3.2.1]oct-3-yl)pyrimidin-2-yl]phenyl}-3-[4-(4-methylpiperazin-1-yl)phenyl]urea | 3.325 | 518.5 | | 0.03 | 0.105 |
| 1-methyl-3-(4-{4-[(1-methylethyl)amino]-6-(8-oxa-3-azabicyclo[3.2.1]oct-3-yl)pyrimidin-2-yl}phenyl)urea | 12 | 810 | | 0.5 | 2.1 |
| 1-cyclopropyl-3-(4-{4-[(1-methylethyl)amino]-6-(8-oxa-3-azabicyclo[3.2.1]oct-3-yl)pyrimidin-2-yl}phenyl)urea | 8.2 | 3623 | | 0.7 | 4.2 |
| 1-(4-{4-[(1-methylethyl)amino]-6-(8-oxa-3-azabicyclo[3.2.1]oct-3-yl)pyrimidin-2-yl}phenyl)-3-pyridin-4-ylurea | 0.785 | 140 | | 0.051 | 0.31 |
| 1-(4-{4-[(1-methylethyl)amino]-6-(8-oxa-3-azabicyclo[3.2.1]oct-3-yl)pyrimidin-2-yl}phenyl)-3-[4-(4-methylpiperazin-1-yl)phenyl]urea | 4.175 | 211.5 | | 0.0134 | 0.05 |
| N~3~,N~3~-dimethyl-N-(4-[(1-methylethyl)amino]-6-(8-oxa-3-azabicyclo[3.2.1]oct-3-yl)-2-{4-[(pyridin-3-ylcarbamoyl)amino]phenyl}pyrimidin-5-yl)-beta-alaninamide | 13500 | 5979 | | 30 | 60 |
| 1-methyl-3-{4-[4-(8-oxa-3-azabicyclo[3.2.1]oct-3-yl)-6-(trifluoromethyl)pyrimidin-2-yl]phenyl}urea | 11.5 | 1553 | | 0.67 | 2.1 |
| 1-cyclopropyl-3-{4-[4-(8-oxa-3-azabicyclo[3.2.1]oct-3-yl)-6-(trifluoromethyl)pyrimidin-2-yl]phenyl}urea | 10.4 | 8159 | | 0.45 | 3 |
| 2-hydroxyethyl {4-[4-(8-oxa-3-azabicyclo[3.2.1]oct-3-yl)-6-(trifluoromethyl)pyrimidin-2-yl]phenyl}carbamate | 15.5 | 5158 | | 0.95 | 4 |
| 1-{4-[4-(8-oxa-3-azabicyclo[3.2.1]oct-3-yl)-6-(trifluoromethyl)pyrimidin-2-yl]phenyl}-3-pyridin-4-ylurea | 2.45 | 280 | | 0.05 | 0.25 |
| 1-[4-(4-methylpiperazin-1-yl)phenyl]-3-{4-[4-(8-oxa-3-azabicyclo[3.2.1]oct-3-yl)-6-(trifluoromethyl)pyrimidin-2-yl]phenyl}urea | 11 | 440 | | 0.05 | 0.19 |
| 1-[4-(4,6-di-3-oxa-8-azabicyclo[3.2.1]oct-8-ylpyrimidin-2-yl)phenyl]-3-pyridin-4-ylurea | 0.655 | 954 | | 0.003 | 0.019 |
| 1-{4-[2-(dimethylamino)ethoxy]phenyl}-3-[4-(4,6-di-3-oxa-8-azabicyclo[3.2.1]oct-8-ylpyrimidin-2-yl)phenyl]urea | 2.5 | 1542 | | 0.004 | 0.009 |
| 1-[4-(4,6-di-3-oxa-8-azabicyclo[3.2.1]oct-8-ylpyrimidin-2-yl)phenyl]-3-[4-(4-methylpiperazin-1-yl)phenyl]urea | 1.7 | 1136 | | 0.0008 | 0.0008 |
| 1-[4-(4,6-di-3-oxa-8-azabicyclo[3.2.1]oct-8-ylpyrimidin-2-yl)phenyl]-3-{4-[(4-methylpiperazin-1-yl)methyl]phenyl}urea | 2.25 | 1952 | | 0.0008 | 0.004 |
| 1-[4-(4,6-di-3-oxa-8-azabicyclo[3.2.1]oct-8-ylpyrimidin-2-yl)phenyl]-3-{4-[(4-methylpiperazin-1-yl)carbonyl]phenyl}urea | 0.94 | 129 | | 0.0008 | 0.0008 |
| tert-butyl methyl(4-{[(4-{4-[(methylsulfonyl)methyl]-6-(8-oxa-3-azabicyclo[3.2.1]oct-3-yl)pyrimidin-2-yl}phenyl)carbamoyl]amino}benzyl)carbamate | 30 | 1933 | | 0.21 | 0.47 |
| 1-methyl-3-(4-{4-[(methylsulfonyl)methyl]-6-(8-oxa-3-azabicyclo[3.2.1]oct-3-yl)pyrimidin-2-yl}phenyl)urea | 13.5 | 1727 | | 2.05 | 3.3 |
| 1-ethyl-3-(4-{4-[(methylsulfonyl)methyl]-6-(8-oxa-3-azabicyclo[3.2.1]oct-3-yl)pyrimidin-2-yl}phenyl)urea | 5.75 | 1807 | | 1 | 1.9 |
| 1-cyclopropyl-3-(4-{4-[(methylsulfonyl)methyl]-6-(8-oxa-3-azabicyclo[3.2.1]oct-3-yl)pyrimidin-2-yl}phenyl)urea | 5.7 | 4640 | | 1 | 2.5 |
| 1-(4-{4-[(methylsulfonyl)methyl]-6-(8-oxa-3-azabicyclo[3.2.1]oct-3-yl)pyrimidin-2-yl}phenyl)-3-phenylurea | 3 | 172 | | 0.0009 | 0.009 |
| 1-(4-{4-[(methylsulfonyl)methyl]-6-(8-oxa-3-azabicyclo[3.2.1]oct-3-yl)pyrimidin-2-yl}phenyl)-3-pyridin-3-ylurea | 1.02 | 341 | | 0.195 | 0.17 |
| 1-(4-{4-[(methylsulfonyl)methyl]-6-(8-oxa-3-azabicyclo[3.2.1]oct-3-yl)pyrimidin-2-yl}phenyl)-3-pyridin-4-ylurea | 0.825 | 236 | | 0.15 | 0.075 |
| 1-[4-(4-methylpiperazin-1-yl)phenyl]-3-(4-{4-[(methylsulfonyl)methyl]-6-(8-oxa-3- | 2.95 | 343 | | 0.015 | 0.03 |

TABLE 1-continued

| Name | mTOR IC$_{50}$ (nM) | PI3Kα IC$_{50}$ (nM) | PI3Kγ IC$_{50}$ (nM) | LNCAP IC$_{50}$ (μM) | MDA IC$_{50}$ (μM) |
|---|---|---|---|---|---|
| azabicyclo[3.2.1]oct-3-yl)pyrimidin-2-yl}phenyl)urea | | | | | |
| 1-(4-{4-[(methylsulfonyl)methyl]-6-(8-oxa-3-azabicyclo[3.2.1]oct-3-yl)pyrimidin-2-yl}phenyl)-3-(4-piperazin-1-ylphenyl)urea | 3 | 242 | | 0.09 | 0.11 |
| 1-{4-[2-(dimethylamino)ethoxy]phenyl}-3-(4-{4-[(methylsulfonyl)methyl]-6-(8-oxa-3-azabicyclo[3.2.1]oct-3-yl)pyrimidin-2-yl}phenyl)urea | 5 | 405 | | 0.09 | 0.165 |
| 1-{4-[(4-methylpiperazin-1-yl)methyl]phenyl}-3-(4-{4-[(methylsulfonyl)methyl]-6-(8-oxa-3-azabicyclo[3.2.1]oct-3-yl)pyrimidin-2-yl}phenyl)urea | 4.05 | 520 | | 0.08 | 0.14 |
| 1-{4-[(methylamino)methyl]phenyl}-3-(4-{4-[(methylsulfonyl)methyl]-6-(8-oxa-3-azabicyclo[3.2.1]oct-3-yl)pyrimidin-2-yl}phenyl)urea | 4.15 | 63.5 | | 1.1 | 1.56 |
| 1-{4-[4-(isopropylamino)-6-(3-oxa-8-azabicyclo[3.2.1]oct-8-yl)pyrimidin-2-yl]phenyl}-3-pyridin-4-ylurea | 1.4 | 2498 | | 0.013 | 0.029 |
| 1-{4-[2-(dimethylamino)ethoxy]phenyl}-3-{4-[4-(isopropylamino)-6-(3-oxa-8-azabicyclo[3.2.1]oct-8-yl)pyrimidin-2-yl]phenyl}urea | 3.6 | 2380 | | 0.05 | 0.71 |
| 1-{4-[4-(isopropylamino)-6-(3-oxa-8-azabicyclo[3.2.1]oct-8-yl)pyrimidin-2-yl]phenyl}-3-[4-(4-methylpiperazin-1-yl)phenyl]urea | 2.7 | 1996 | | 0.019 | 0.034 |
| 1-{4-[4-(isopropylamino)-6-(3-oxa-8-azabicyclo[3.2.1]oct-8-yl)pyrimidin-2-yl]phenyl}-3-{4-[(4-methylpiperazin-1-yl)methyl]phenyl}urea | 3.2 | 3410 | | 0.07 | 0.11 |
| 1-{4-[4-(isopropylamino)-6-(3-oxa-8-azabicyclo[3.2.1]oct-8-yl)pyrimidin-2-yl]phenyl}-3-[6-(4-methylpiperazin-1-yl)pyridin-3-yl]urea | 4.2 | 3870 | | 0.09 | 0.1 |
| 1-[4-(2,6-di-8-oxa-3-azabicyclo[3.2.1]oct-3-ylpyrimidin-4-yl)phenyl]-3-methylurea | 20.5 | 2488 | | 1.6 | 4.2 |
| 1-[4-(2,6-di-8-oxa-3-azabicyclo[3.2.1]oct-3-ylpyrimidin-4-yl)phenyl]-3-pyridin-4-ylurea | 2.45 | 137 | | 0.13 | 0.38 |
| 1-[4-(2,6-di-8-oxa-3-azabicyclo[3.2.1]oct-3-ylpyrimidin-4-yl)phenyl]-3-[4-(4-methylpiperazin-1-yl)phenyl]urea | 9.55 | 588 | | 0.04 | 0.16 |
| 1-cyclopropyl-3-[4-(2,6-di-8-oxa-3-azabicyclo[3.2.1]oct-3-ylpyrimidin-4-yl)phenyl]urea | 38.5 | 3931 | | 0.8 | 6 |
| 4-[4-(8-oxa-3-azabicyclo[3.2.1]oct-3-yl)pyrimidin-2-yl]aniline | 4000 | 6846 | | 41 | 60 |
| 4-[4-chloro-6-(8-oxa-3-azabicyclo[3.2.1]oct-3-yl)pyrimidin-2-yl]aniline | | | | | |
| 4-[2-chloro-6-(8-oxa-3-azabicyclo[3.2.1]oct-3-yl)pyrimidin-4-yl]aniline | | | | | |
| 8,8'-[2-(4-nitrophenyl)pyrimidine-4,6-diyl]bis(3-oxa-8-azabicyclo[3.2.1]octane) | | | | | |
| 4-(4,6-di-3-oxa-8-azabicyclo[3.2.1]oct-8-ylpyrimidin-2-yl)aniline | | | | | |
| 4-{4-[(methylsulfonyl)methyl]-6-(8-oxa-3-azabicyclo[3.2.1]oct-3-yl)pyrimidin-2-yl}aniline | | | | | |
| 1-[4-(4,6-di-3-oxa-8-azabicyclo[3.2.1]oct-8-ylpyrimidin-2-yl)phenyl]-3-pyridin-3-ylurea | 0.58 | 1128 | 4487 | 0.8 | 5 |
| 1-[4-(5-chloro-4,6-di-3-oxa-8-azabicyclo[3.2.1]oct-8-ylpyrimidin-2-yl)phenyl]-3-pyridin-3-ylurea | 0.655 | 922 | 932 | 48 | 220 |
| 1-[4-(5-chloro-4,6-di-3-oxa-8-azabicyclo[3.2.1]oct-8-ylpyrimidin-2-yl)phenyl]-3-[4-(4-methylpiperazin-1-yl)phenyl]urea | 0.505 | 998 | 1016 | 65 | 210 |
| 1-{4-[4-(3,7-dioxa-9-azabicyclo[3.3.1]non-9-yl)-6-(isopropylamino)pyrimidin-2-yl]phenyl}-3-pyridin-4-ylurea | 5 | 1521 | 9238 | 280 | 400 |
| 1-{4-[4-(3,7-dioxa-9-azabicyclo[3.3.1]non-9-yl)-6-(isopropylamino)pyrimidin-2-yl]phenyl}-3-{4-[(4-methylpiperazin-1-yl)methyl]phenyl}urea | 17.5 | 3164 | 6872 | 600 | 1000 |
| 1-{4-[4-(3,7-dioxa-9-azabicyclo[3.3.1]non-9-yl)-6-(isopropylamino)pyrimidin-2-yl]phenyl}-3-[4-(4-methylpiperazin-1-yl)phenyl]urea | 14.5 | 1509 | 7889 | 280 | 320 |

TABLE 1-continued

| Name | mTOR IC$_{50}$ (nM) | PI3Kα IC$_{50}$ (nM) | PI3Kγ IC$_{50}$ (nM) | LNCAP IC$_{50}$ (μM) | MDA IC$_{50}$ (μM) |
|---|---|---|---|---|---|
| 1-{4-[2-(dimethylamino)ethoxy]phenyl}-3-{4-[4-(3,7-dioxa-9-azabicyclo[3.3.1]non-9-yl)-6-(isopropylamino)pyrimidin-2-yl]phenyl}urea | 16.5 | 1758 | 8629 | 420 | 600 |
| 1-{4-[4-(3-oxa-8-azabicyclo[3.2.1]oct-8-yl)-6-(tetrahydro-2H-pyran-4-ylamino)pyrimidin-2-yl]phenyl}-3-pyridin-4-ylurea | 3.8 | 2012 | 11985 | 40 | 40 |
| 1-[4-(4-methylpiperazin-1-yl)phenyl]-3-{4-[4-(3-oxa-8-azabicyclo[3.2.1]oct-8-yl)-6-(tetrahydro-2H-pyran-4-ylamino)pyrimidin-2-yl]phenyl}urea | 7.5 | 2262 | 9231 | 7 | 10 |
| 1-{4-[4-{[2-(methylsulfonyl)ethyl]amino}-6-(3-oxa-8-azabicyclo[3.2.1]oct-8-yl)pyrimidin-2-yl]phenyl}-3-pyridin-3-ylurea | 5 | 1639 | 10000 | 2000 | 800 |
| 1-{4-[(4-methylpiperazin-1-yl)methyl]phenyl}-3-{4-[4-{[2-(methylsulfonyl)ethyl]amino}-6-(3-oxa-8-azabicyclo[3.2.1]oct-8-yl)pyrimidin-2-yl]phenyl}urea | 17.5 | 3982 | 10765 | 400 | 500 |
| 1-{4-[4-(3-oxa-8-azabicyclo[3.2.1]oct-8-yl)-6-(tetrahydro-2H-pyran-4-ylamino)pyrimidin-2-yl]phenyl}-3-pyridin-3-ylurea | 3.3 | 2675 | 10000 | 50 | 160 |
| 1-{4-[2-(dimethylamino)ethoxy]phenyl}-3-{4-[4-(3-oxa-8-azabicyclo[3.2.1]oct-8-yl)-6-(tetrahydro-2H-pyran-4-ylamino)pyrimidin-2-yl]phenyl}urea | 7.6 | 1112 | 4537 | 30 | 48 |
| 1-{4-[4-{[2-(methylsulfonyl)ethyl]amino}-6-(3-oxa-8-azabicyclo[3.2.1]oct-8-yl)pyrimidin-2-yl]phenyl}-3-pyridin-4-ylurea | 4.05 | 1301 | 10781 | 1000 | 400 |
| 1-{4-[2-(dimethylamino)ethoxy]phenyl}-3-{4-[4-{[2-(methylsulfonyl)ethyl]amino}-6-(3-oxa-8-azabicyclo[3.2.1]oct-8-yl)pyrimidin-2-yl]phenyl}urea | 26 | 1859 | 10000 | 480 | 420 |
| 1-[4-(4-methylpiperazin-1-yl)phenyl]-3-{4-[4-{[2-(methylsulfonyl)ethyl]amino}-6-(3-oxa-8-azabicyclo[3.2.1]oct-8-yl)pyrimidin-2-yl]phenyl}urea | 14.5 | 1840 | 10000 | 17 | 19 |
| 1-{4-[(4-methylpiperazin-1-yl)methyl]phenyl}-3-{4-[4-(3-oxa-8-azabicyclo[3.2.1]oct-8-yl)-6-(tetrahydro-2H-pyran-4-ylamino)pyrimidin-2-yl]phenyl}urea | 6.3 | 931 | 2181 | 40 | 65 |
| 1-{4-[4-(diethylamino)-6-(3-oxa-8-azabicyclo[3.2.1]oct-8-yl)pyrimidin-2-yl]phenyl}-3-pyridin-4-ylurea | 4.55 | 2411 | 1987 | | |
| 1-{4-[4-(diethylamino)-6-(3-oxa-8-azabicyclo[3.2.1]oct-8-yl)pyrimidin-2-yl]phenyl}-3-[4-(4-methylpiperazin-1-yl)phenyl]urea | 5.85 | 2914 | 3390 | 132 | 560 |
| 1-(4-{4-[(1-methylethyl)amino]-6-(3-oxa-8-azabicyclo[3.2.1]oct-8-yl)pyrimidin-2-yl}phenyl)-3-[4-(pyrrolidin-1-ylmethyl)phenyl]urea | 2.95 | 1093 | 3576 | 110 | 80 |
| 1-(4-{4-[(1-methylethyl)amino]-6-(3-oxa-8-azabicyclo[3.2.1]oct-8-yl)pyrimidin-2-yl}phenyl)-3-pyridin-3-ylurea | 1.1 | 4354 | 10000 | 45 | 100 |
| 1-{4-[(dimethylamino)methyl]phenyl}-3-(4-{4-[(1-methylethyl)amino]-6-(3-oxa-8-azabicyclo[3.2.1]oct-8-yl)pyrimidin-2-yl}phenyl)urea | 2.65 | 1186 | 3880 | 120 | 120 |
| 1-(4-{4-[(1-methylethyl)amino]-6-(3-oxa-8-azabicyclo[3.2.1]oct-8-yl)pyrimidin-2-yl}phenyl)-3-[4-(2-pyrrolidin-1-ylethoxy)phenyl]urea | 3.05 | 1324 | 4733 | 50 | 55 |
| 1-(4-{4-[(dimethylamino)methyl]-6-(3-oxa-8-azabicyclo[3.2.1]oct-8-yl)pyrimidin-2-yl}phenyl)-3-pyridin-3-ylurea | 10.85 | 3163 | >10000 | 600 | 1000 |
| 1-(4-{4-[(dimethylamino)methyl]-6-(3-oxa-8-azabicyclo[3.2.1]oct-8-yl)pyrimidin-2-yl}phenyl)-3-methylurea | 77 | 7996 | >10000 | 3600 | 7000 |
| 1-(4-{4-[(dimethylamino)methyl]-6-(3-oxa-8-azabicyclo[3.2.1]oct-8-yl)pyrimidin-2-yl}phenyl)-3-ethylurea | 40 | 6243 | 12584 | 1100 | 3000 |
| 1-{4-[4-(3-oxa-8-azabicyclo[3.2.1]oct-8-yl)-6-(tetrahydro-2H-pyran-4-yl)pyrimidin-2-yl]phenyl}-3-pyridin-3-ylurea | 0.320 | 2686 | 10000 | 0.004 | 0.2 |
| 1-{4-[4-(3-oxa-8-azabicyclo[3.2.1]oct-8-yl)-6-(tetrahydro-2H-pyran-4-yl)pyrimidin-2-yl]phenyl}-3-pyridin-4-ylurea | 0.365 | 1784 | 7975 | 0.0008 | 0.004 |

TABLE 1-continued

| Name | mTOR IC$_{50}$ (nM) | PI3Kα IC$_{50}$ (nM) | PI3Kγ IC$_{50}$ (nM) | LNCAP IC$_{50}$ (μM) | MDA IC$_{50}$ (μM) |
|---|---|---|---|---|---|
| 1-[4-(4-methylpiperazin-1-yl)phenyl]-3-{4-[4-(3-oxa-8-azabicyclo[3.2.1]oct-8-yl)-6-(tetrahydro-2H-pyran-4-yl)pyrimidin-2-yl]phenyl}urea | 0.855 | 1060 | 4728 | 0.0008 | 0.004 |
| 1-[6-(4-methylpiperazin-1-yl)pyridin-3-yl]-3-{4-[4-(3-oxa-8-azabicyclo[3.2.1]oct-8-yl)-6-(tetrahydro-2H-pyran-4-yl)pyrimidin-2-yl]phenyl}urea | 1.215 | 2589 | 10000 | 0.0008 | 0.004 |
| 1-{4-[(4-methylpiperazin-1-yl)carbonyl]phenyl}-3-{4-[4-(3-oxa-8-azabicyclo[3.2.1]oct-8-yl)-6-(tetrahydro-2H-pyran-4-yl)pyrimidin-2-yl]phenyl}urea | 0.440 | 230 | 3053 | 0.0008 | 0.0008 |
| 1-(4-{[4-(1-methylethyl)piperazin-1-yl]carbonyl}phenyl)-3-{4-[4-(3-oxa-8-azabicyclo[3.2.1]oct-8-yl)-6-(tetrahydro-2H-pyran-4-yl)pyrimidin-2-yl]phenyl}urea | 0.295 | 353 | 3209 | 0.0008 | 0.0008 |
| 1-{4-[2-(dimethylamino)ethoxy]phenyl}-3-{4-[4-(3-oxa-8-azabicyclo[3.2.1]oct-8-yl)-6-(tetrahydro-2H-pyran-4-yl)pyrimidin-2-yl]phenyl}urea | 1.150 | 1462 | 7296 | 0.004 | 0.011 |
| 1-(4-{4-[(3R)-3-methylmorpholin-4-yl]-6-(3-oxa-8-azabicyclo[3.2.1]oct-8-yl)pyrimidin-2-yl}phenyl)-3-pyridin-4-ylurea | 0.645 | 314 | 778 | 0.001 | 0.005 |
| 1-(4-{4-[(3R)-3-methylmorpholin-4-yl]-6-(3-oxa-8-azabicyclo[3.2.1]oct-8-yl)pyrimidin-2-yl}phenyl)-3-[4-(4-methylpiperazin-1-yl)phenyl]urea | 1.250 | 864 | 3502 | 0.0008 | 0.001 |
| 1-(4-{4-[(3R)-3-methylmorpholin-4-yl]-6-(3-oxa-8-azabicyclo[3.2.1]oct-8-yl)pyrimidin-2-yl}phenyl)-3-[6-(4-methylpiperazin-1-yl)pyridin-3-yl]urea | 2.500 | 1096 | 2985 | 0.0035 | 0.008 |
| 1-(4-{4-[(2R,6S)-2,6-dimethylmorpholin-4-yl]-6-(3-oxa-8-azabicyclo[3.2.1]oct-8-yl)pyrimidin-2-yl}phenyl)-3-pyridin-4-ylurea | 2.600 | 1344 | 5371 | 0.05 | 0.28 |
| 1-(4-{4-[(2R,6S)-2,6-dimethylmorpholin-4-yl]-6-(3-oxa-8-azabicyclo[3.2.1]oct-8-yl)pyrimidin-2-yl}phenyl)-3-[4-(4-methylpiperazin-1-yl)phenyl]urea | 4.400 | 1547 | 6437 | 0.03 | 0.13 |
| 1-(4-{4-[(2R,6S)-2,6-dimethylmorpholin-4-yl]-6-(3-oxa-8-azabicyclo[3.2.1]oct-8-yl)pyrimidin-2-yl}phenyl)-3-[6-(4-methylpiperazin-1-yl)pyridin-3-yl]urea | 15.250 | 1694 | 15308 | 0.1 | 0.2 |
| 1-(4-{4-[(2R,6S)-2,6-dimethylmorpholin-4-yl]-6-(3-oxa-8-azabicyclo[3.2.1]oct-8-yl)pyrimidin-2-yl}phenyl)-3-{4-[(4-methylpiperazin-1-yl)carbonyl]phenyl}urea | 3.550 | 180 | 1028 | 0.0008 | 0.0008 |
| 1-(4-{4-[(2R,6S)-2,6-dimethylmorpholin-4-yl]-6-(3-oxa-8-azabicyclo[3.2.1]oct-8-yl)pyrimidin-2-yl}phenyl)-3-(4-{[4-(1-methylethyl)piperazin-1-yl]carbonyl}phenyl)urea | 2.700 | 293 | 915 | 0.0008 | 0.0008 |
| 1-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)-3-pyridin-4-ylurea | 3.050 | 2809 | 10000 | 0.03 | 0.075 |
| 1-[4-(4-methylpiperazin-1-yl)phenyl]-3-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)urea | 9.750 | 1784 | 10000 | 0.01 | 0.018 |
| 1-{4-[(dimethylamino)methyl]phenyl}-3-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)urea | 16.000 | 1244 | 10000 | 0.06 | 0.15 |
| 1-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)-3-pyridin-4-ylurea | 2.250 | 1889 | 7428 | 0.09 | 0.11 |
| 1-[4-(4-methylpiperazin-1-yl)phenyl]-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea | 7.550 | 2094 | 8714 | 0.04 | 0.048 |
| 1-{4-[(4-methylpiperazin-1-yl)methyl]phenyl}-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea | 9.900 | 1187 | 7592 | 0.18 | 0.19 |
| 1-{4-[2-(dimethylamino)ethoxy]phenyl}-3-(4-{4-[(1R,4R)-2-oxa-5-azabicyclo[2.2.1]hept-5-yl]- | 12.000 | 2745 | 9468 | 0.12 | 0.13 |

TABLE 1-continued

| Name | mTOR IC$_{50}$ (nM) | PI3Kα IC$_{50}$ (nM) | PI3Kγ IC$_{50}$ (nM) | LNCAP IC$_{50}$ (μM) | MDA IC$_{50}$ (μM) |
|---|---|---|---|---|---|
| 6-(3-oxa-8-azabicyclo[3.2.1]oct-8-yl)pyrimidin-2-yl}phenyl)urea | | | | | |
| 1-(4-{4-[(3R)-3-methylmorpholin-4-yl]-6-(3-oxa-8-azabicyclo[3.2.1]oct-8-yl)pyrimidin-2-yl}phenyl)-3-pyridin-3-ylurea | 0.770 | 1062 | 7474 | 0.02 | 0.08 |
| 1-(4-{4-[(3R)-3-methylmorpholin-4-yl]-6-(3-oxa-8-azabicyclo[3.2.1]oct-8-yl)pyrimidin-2-yl}phenyl)-3-{4-[(4-methylpiperazin-1-yl)methyl]phenyl}urea | 1.200 | 1298 | 8480 | 0.006 | 0.012 |
| 1-{4-[2-(dimethylamino)ethoxy]phenyl}-3-(4-{4-[(3R)-3-methylmorpholin-4-yl]-6-(3-oxa-8-azabicyclo[3.2.1]oct-8-yl)pyrimidin-2-yl}phenyl)urea | 1.550 | 853 | 6473 | 0.004 | 0.013 |
| N,N-dimethyl-4-{[(4-{4-[(3R)-3-methylmorpholin-4-yl]-6-(3-oxa-8-azabicyclo[3.2.1]oct-8-yl)pyrimidin-2-yl}phenyl)carbamoyl]amino}benzamide | 0.440 | 108 | 1637 | 0.0008 | 0.0008 |
| 1-(4-{4-[(3R)-3-methylmorpholin-4-yl]-6-(3-oxa-8-azabicyclo[3.2.1]oct-8-yl)pyrimidin-2-yl}phenyl)-3-{4-[(4-methylpiperazin-1-yl)carbonyl]phenyl}urea | 0.750 | 78 | 1130 | 0.0008 | 0.0008 |
| 1-(4-{[4-(1-methylethyl)piperazin-1-yl]carbonyl}phenyl)-3-(4-{4-[(3R)-3-methylmorpholin-4-yl]-6-(3-oxa-8-azabicyclo[3.2.1]oct-8-yl)pyrimidin-2-yl}phenyl)urea | 0.600 | 123 | 1203 | 0.0008 | 0.0008 |
| 1-(4-{4-[(dimethylamino)methyl]-6-(3-oxa-8-azabicyclo[3.2.1]oct-8-yl)pyrimidin-2-yl}phenyl)-3-methylurea | 77.000 | 7996 | 10000 | 3.6 | 7 |

Throughout this application, various publications are referenced. The disclosures of these publications in their entireties are hereby incorporated by reference into this application in order to more fully describe the state of the art as known to those skilled therein as of the date of the invention described and claimed herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A compound of Formula I:

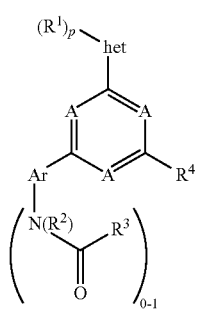

I or a pharmaceutically acceptable salt thereof wherein;
$R^1$ is independently $C_1$-$C_6$alkyl-, $C_6$-$C_{14}$aryl-, $C_1$-$C_9$heteroaryl-, halogen, or hydroxyl;
p is 0, 1, 2, 3, or 4;

het is a bridged $C_5$-$C_9$heterobicyclyl- group containing at least one oxygen atom, at least one nitrogen atom, and optionally additional heteroatoms selected from oxygen, sulfur and nitrogen, and is connected to the pyrimidinyl group through one of the nitrogen atoms;
one of A is C—$R^5$ and the other two are N;
Ar is $C_6$-$C_{14}$aryl- or $C_1$-$C_9$heteroaryl- wherein the $C_6$-$C_{14}$aryl- or $C_1$-$C_9$heteroaryl- is optionally substituted with from 1 to 4 substituents independently selected from $C_1$-$C_6$alkyl-, halogen, haloalkyl-, hydroxyl, hydroxyl($C_1$-$C_6$alkyl)-, $H_2N$—, aminoalkyl-, di($C_1$-$C_6$alkyl)amino-, $HO_2C$—, ($C_1$-$C_6$alkoxy)carbonyl-, ($C_1$-$C_6$alkyl)carboxyl-, di($C_1$-$C_6$alkyl)amido-, $H_2NC(O)$—, ($C_1$-$C_6$alkyl)amido-, and $O_2N$—;
and wherein the $C_6$-$C_{14}$aryl- or $C_1$-$C_9$heteroaryl- is bonded to the pyrimidine core through a carbon atom of the $C_6$-$C_{14}$aryl- or $C_1$-$C_9$heteroaryl-;
$R^2$ is H or $C_1$-$C_6$alkyl-;
$R^3$ is $R^6$, $R^7R^8N$—, $R^9S$—, or $R^9O$—;
$R^6$ is:
  (a) H;
  (b) $C_1$-$C_6$alkyl- optionally substituted with from 1 to 3 substituents independently selected from:
    (i) $C_1$-$C_6$alkoxy-,
    (ii) $H_2N$—,
    (iii) ($C_1$-$C_6$alkyl)amino-,
    (iv) di($C_1$-$C_6$alkyl)amino-,
    (v) $C_6$-$C_{14}$aryl-,
    (vi) $C_1$-$C_9$heterocyclyl- optionally substituted by $C_1$-$C_6$alkyl-,
    (vii) and $C_1$-$C_9$heteroaryl-;
  (c) $C_1$-$C_6$alkoxy-;
  (d) $C_1$-$C_9$heteroaryl- optionally substituted with from 1 to 3 substituents independently selected from:
    (i) $C_1$-$C_6$alkyl- optionally substituted with $H_2N$—,
    (ii) heterocyclyl($C_1$-$C_6$alkyl)-, (iii) halogen,
(iv) hydroxyl,
(v) $H_2N$—,
(vi) $O_2N$—,
(vii) $H_2NSO_2$—,
(viii) $HO_2C$—,
(ix) ($C_1$-$C_6$alkoxy)carbonyl-,
(x) ($C_1$-$C_6$alkoxy)C(O)NH—,
(xi) ($C_1$-$C_6$alkyl)amino-,
(xii) di($C_1$-$C_6$alkyl)amino-,
(xiii) $R^{10}R^{11}NC(O)$—,
(xiv) $R^{10}O$—,
(xv) $R^{10}R^{11}N$—,
(xvi) $R^{10}R^{11}NS(O)_2$—,
(xvii) $R^{10}S(O)_2NR^{11}$—,
(xviii) $R^{10}R^{11}NC(O)NH$—,
(xix) $R^{10}S$—,
(xx) $R^{10}S(O)$—,
(xxi) $R^{10}S(O)_2$—,
(xxii) $R^{10}C(O)$—,
(xxiii) $C_1$-$C_9$heterocyclyl- optionally substituted by $C_1$-$C_6$alkyl- or $C_1$-$C_6$hydroxylalkyl-,
(xxiv) $C_1$-$C_6$hydroxylalkyl-,
(xxv) and perfluoro($C_1$-$C_6$)alkyl-;
(e) $C_1$-$C_6$hydroxylalkyl-;
(f) $C_1$-$C_9$heterocyclyl-;
(g) $C_6$-$C_{14}$aryl- optionally substituted with from 1 to 3 substituents independently selected from:
(i) $C_1$-$C_6$alkyl- optionally substituted with $H_2N$—,
(ii) heterocyclyl($C_1$-$C_6$alkyl)-,
(iii) halogen,
(iv) hydroxyl,
(v) $H_2N$—,
(vi) $O_2N$—,
(vii) $H_2NSO_2$—,
(viii) $HO_2C$—,
(ix) ($C_1$-$C_6$alkoxy)carbonyl-,
(x) ($C_1$-$C_6$alkoxy)C(O)NH—,
(xi) ($C_1$-$C_6$alkyl)amino-,
(xii) di($C_1$-$C_6$alkyl)amino-,
(xiii) $R^{10}R^{11}NC(O)$—,
(xiv) $R^{10}O$—,
(xv) $R^{10}R^{11}N$—,
(xvi) $R^{10}R^{11}NS(O)_2$—,
(xvii) $R^{10}S(O)_2NR^{11}$—,
(xviii) $R^{10}R^{11}NC(O)NH$—,
(xix) $R^{10}S$—,
(xx) $R^{10}S(O)$—,
(xxi) $R^{10}S(O)_2$—,
(xxii) $R^{10}C(O)$—,
(xxiii) $C_1$-$C_9$heterocyclyl- optionally substituted by $C_1$-$C_6$alkyl- or $C_1$-$C_6$hydroxylalkyl-,
(xxiv) $C_1$-$C_6$hydroxylalkyl-,
(xxv) and perfluoro($C_1$-$C_6$)alkyl-;
(h) or $C_3$-$C_8$cycloalkyl-;
$R^{10}$ and $R^{11}$ are each independently H, $C_1$-$C_6$alkoxy-, $C_1$-$C_6$alkyl-, $C_1$-$C_6$alkoxy($C_2$-$C_6$alkylene)-, ($C_1$-$C_6$alkyl)amino-$C_2$-$C_6$alkylene-, di($C_1$-$C_6$alkyl)amino-$C_2$-$C_6$alkylene-, $C_2$-$C_6$alkenyl, $C_2$-$C_6$alkynyl, $C_6$-$C_{14}$aryl-, ($C_6$-$C_{14}$aryl)alkyl-, $C_3$-$C_8$cycloalkyl-, $C_1$-$C_9$heteroaryl-, ($C_1$-$C_9$heteroaryl)alkyl-, $C_1$-$C_9$heterocyclyl- optionally substituted by $C_1$-$C_6$alkyl-, or heterocyclyl($C_1$-$C_6$alkyl-);
or $R^{10}$ and $R^{11}$, when taken together with the nitrogen to which they are attached, form a 3- to 7- membered heterocycle wherein up to two of the carbon atoms of the heterocycle are optionally replaced with —N(H)—, —N($C_1$-$C_6$alkyl)-, —N($C_3$-$C_8$cycloalkyl)-, —N($C_6$-$C_{14}$aryl)-, —N($C_1$-$C_9$heteroaryl)-, —S—, —SO—, —S(O)$_2$—, or —O— and wherein any carbon atom of the heterocycle is optionally substituted with from 1 or 2 substituents independently selected from $C_1$-$C_6$alkyl-, $H_2N$—, ($C_1$-$C_6$alkyl)amino-, di($C_1$-$C_6$alkyl)amino-, and $C_1$-$C_9$heterocyclyl-;
$R^7$ and $R^8$ are each independently selected from:
(a) H;
(b) $C_1$-$C_6$alkyl- optionally substituted with from 1 to 3 substituents independently selected from:
(i) $C_1$-$C_8$acyl-
(ii) $C_1$-$C_6$alkoxy- optionally substituted with —$NH_2$,
(iii) ($C_1$-$C_6$alkoxy)carbonyl-,
(iv) $H_2N$—,
(v) ($C_1$-$C_6$alkyl)amino-,
(vi) di($C_1$-$C_6$alkyl)amino-,
(vii) ($C_1$-$C_6$alkyl)carboxyamido-, optionally substituted with
A) $H_2N$—,
B) ($C_1$-$C_6$alkyl)amino-,
C) or di($C_1$-$C_6$alkyl)amino-,
(viii) $C_6$-$C_{14}$aryl-,
(ix) $C_3$-$C_8$cycloalkyl-
(x) halogen,
(xi) $C_1$-$C_9$heterocyclyl- optionally substituted by $C_1$-$C_6$alkyl-,
(xii) $HO_2C$—,
(xiii) NC—,
(xiv) $R^{10}C(O)NR^{11}$—,
(xv) $R^{10}R^{11}NC(O)$—,
(xvi) and $C_1$-$C_9$heteroaryl-;
(c) $C_1$-$C_6$alkoxy-;
(d) $C_1$-$C_9$heteroaryl- optionally substituted with from 1 to 3 substituents independently selected from:
(i) $C_1$-$C_6$alkoxy- optionally substituted with
A) $H_2N$—,
B) ($C_1$-$C_6$alkyl)amino-,
C) di($C_1$-$C_6$alkyl)amino-,
D) $C_1$-$C_9$heterocyclyl- optionally substituted by $C_1$-$C_6$alkyl-,
E) and hydroxyl,
(ii) ($C_1$-$C_6$alkoxy)carbonyl-,
(iii) ($C_1$-$C_6$alkoxy)C(O)NH—,
(iv) $C_1$-$C_6$alkyl- optionally substituted with
A) $H_2N$—,
B) ($C_1$-$C_6$alkyl)amino-,
C) or di($C_1$-$C_6$alkyl)amino-,
(v) ($C_1$-$C_6$alkyl)amino-,
(vi) di($C_1$-$C_6$alkyl)amino-,
(vii) ($C_1$-$C_6$alkyl)amido- optionally substituted with
A) $H_2N$—,
B) ($C_1$-$C_6$alkyl)amino-,
C) or di($C_1$-$C_6$alkyl)amino-,
(viii) ($C_1$-$C_6$alkyl)carboxyamido-,
(ix) $C_1$-$C_9$heterocyclyl- optionally substituted by $C_1$-$C_6$alkyl- or $C_1$-$C_6$hydroxylalkyl-,
(x) heterocyclyl($C_1$-$C_6$alkyl)- optionally substituted by $C_1$-$C_6$alkyl-,
(xi) halogen,
(xii) hydroxyl,
(xiii) $C_1$-$C_6$hydroxylalkyl-,
(xiv) perfluoro($C_1$-$C_6$)alkyl-,
(xv) $H_2N$—,
(xvi) $O_2N$—,
(xvii) $H_2NSO_2$—,
(xviii) $HO_2C$—, (xix) NC—,
(xx) $R^{10}R^{11}NC(O)$—,
(xxi) $R^{10}R^{11}NNHC(O)$—,
(xxii) $R^{10}O$—,
(xxiii) $R^{10}R^{11}N$—,
(xxiv) $R^{10}R^{11}NS(O)_2$—,
(xxv) $R^{10}S(O)_2NR^{11}$—,
(xxvi) $R^{10}R^{11}NC(O)NH$—,
(xxvii) $R^{10}S$—,
(xxviii) $R^{10}S(O)$—,
(xxix) $R^{10}S(O)_2$—,
(xxx) and $R^{10}C(O)$—;
(e) $C_1$-$C_6$hydroxylalkyl-;
(f) $C_1$-$C_9$heterocyclyl- optionally substituted with from 1 to 3 substituents independently selected from:
(i) $C_1$-$C_6$alkyl-,
(ii) heterocyclyl($C_1$-$C_6$alkyl)-,
(iii) ($C_6$-$C_{14}$aryl)alkyl-,
(iv) $C_1$-$C_6$acyl-,
(v) ($C_1$-$C_6$alkoxy)carbonyl-,
(vi) ($C_1$-$C_6$alkyl)carboxyl-,
(vii) halogen,
(viii) $C_1$-$C_6$haloalkyl-,
(ix) hydroxyl,
(x) $C_1$-$C_6$hydroxyalkyl-,
(xi) $H_2N$—,
(xii) ($C_1$-$C_6$alkyl)amino-,
(xiii) di($C_1$-$C_6$alkyl)amino-,
(xiv) $HO_2C$—,
(xv) ($C_1$-$C_6$alkoxy)carbonyl-,
(xvi) ($C_1$-$C_6$alkyl)carboxyl-,
(xvii) ($C_1$-$C_6$alkyl)amido-,
(xviii) $H_2NC(O)$—,
(xix) ($C_1$-$C_6$alkyl)carboxyamido-,
(xx) and —$NO_2$;
(g) $C_6$-$C_{14}$aryl- optionally substituted with from 1 to 3 substituents independently selected from:
(i) $C_1$-$C_6$alkoxy- optionally substituted with
 A) $H_2N$—,
 B) ($C_1$-$C_6$alkyl)amino-,
 C) di($C_1$-$C_6$alkyl)amino-,
 D) $C_1$-$C_9$heterocyclyl- optionally substituted by $C_1$-$C_6$alkyl-,
 E) and hydroxyl,
(ii) ($C_1$-$C_6$alkoxy)carbonyl-,
(iii) ($C_1$-$C_6$alkoxy)C(O)NH—,
(iv) $C_1$-$C_6$alkyl- optionally substituted with
 A) $H_2N$—,
 B) ($C_1$-$C_6$alkyl)amino-,
 C) or di($C_1$-$C_6$alkyl)amino-,
(v) ($C_1$-$C_6$alkyl)amino-,
(vi) di($C_1$-$C_6$alkyl)amino-,
(vii) ($C_1$-$C_6$alkyl)amido- optionally substituted with
 A) $H_2N$—,
 B) ($C_1$-$C_6$alkyl)amino-,
 C) or di($C_1$-$C_6$alkyl)amino-,
(viii) ($C_1$-$C_6$alkyl)carboxyamido-,
(ix) $C_1$-$C_9$heterocyclyl- optionally substituted by $C_1$-$C_6$alkyl- or $C_1$-$C_6$hydroxylalkyl-,
(x) heterocyclyl($C_1$-$C_6$alkyl)- optionally substituted by $C_1$-$C_6$alkyl-,
(xi) halogen,
(xii) hydroxyl,
(xiii) $C_1$-$C_6$hydroxylalkyl-,
(xiv) perfluoro($C_1$-$C_6$)alkyl-,
(xv) $H_2N$—,
(xvi) $O_2N$—,
(xvii) $H_2NSO_2$—,
(xviii) $HO_2C$—,
(xix) NC—,
(xx) $R^{10}R^{11}NC(O)$—,
(xxi) $R^{10}R^{11}NNHC(O)$—,
(xxii) $R^{10}O$—,
(xxiii) $R^{10}R^{11}N$—,
(xxiv) $R^{10}R^{11}NS(O)_2$—,
(xxv) $R^{10}S(O)_2NR^{11}$—,
(xxvi) $R^{10}R^{11}NC(O)NH$—,
(xxvii) $R^{10}S$—,
(xxviii) $R^{10}S(O)$—,
(xxix) $R^{10}S(O)_2$—,
(xxx) and $R^{10}C(O)$—;
(h) and $C_3$-$C_8$cycloalkyl- optionally substituted with from 1 to 3 substituents independently selected from:
(i) $C_1$-$C_6$alkyl- optionally substituted with halogen,
(ii) ($C_1$-$C_6$alkoxy)carbonyl-,
(iii) ($C_1$-$C_6$alkyl)amido-,
(iv) ($C_1$-$C_6$alkyl)carboxyamido-,
(v) ($C_1$-$C_6$alkyl)carboxyl-,
(vi) $C_1$-$C_6$alkoxy-,
(vii) $H_2N$—,
(viii) ($C_1$-$C_6$alkyl)amino-,
(ix) di($C_1$-$C_6$alkyl)amino-,
(x) hydroxyl,
(xi) $H_2NC(O)$—,
(xii) $HO_2C$—,
(xiii) and —$NO_2$;
wherein any two hydrogen atoms on the same carbon atom of the $C_3$-$C_8$cycloalkyl- ring can be replaced by an oxygen atom to form an oxo (═O) substituent,
and wherein any two hydrogen atoms on the same carbon atom of the $C_3$-$C_8$cycloalkyl- ring can be replaced by an alkylenedioxy group so that the alkylenedioxy group, when taken together with the carbon atom to which it is attached, forms a 5- to 7-membered heterocycle containing two oxygen atoms;
or $R^7$ and $R^8$, when taken together with the nitrogen to which they are attached, form a 3- to 7- membered heterocycle wherein up to two of the carbon atoms of the heterocycle are optionally replaced with —N(H)—, —N($C_1$-$C_6$alkyl)-, —N($C_6$-$C_{14}$aryl)-, —S—, —SO—, —S(O)$_2$—, or —O—;
$R^9$ is $C_1$-$C_6$alkyl-, $C_6$-$C_{14}$aryl-, ($C_6$-$C_{14}$aryl)alkyl- optionally substituted by $H_2N$—, $C_1$-$C_9$heterocyclyl- optionally substituted by $C_1$-$C_6$alkyl-, $C_3$-$C_8$cycloalkyl-, $C_1$-$C_6$hydroxylalkyl-, or $C_1$-$C_6$perfluoroalkyl-;
$R^4$ is:
a) hydrogen;
b) $C_1$-$C_6$acyl-;
c) $C_1$-$C_6$alkyl-;
d) $H_2N$— optionally substituted with $C_1$-$C_9$heterocycle,
e) ($C_1$-$C_6$alkyl)amino- optionally substituted with ($C_1$-$C_6$alkyl)SO$_2$—,
f) di($C_1$-$C_6$alkyl)amino- optionally substituted with ($C_1$-$C_6$alkyl)SO$_2$—,
g) ($C_1$-$C_6$alkyl)amino-$C_1$-$C_6$alkylene-,
h) di($C_1$-$C_6$alkyl)amino-$C_1$-$C_6$alkylene-,
i) amino($C_1$-$C_6$alkyl)-;
j) $C_3$-$C_8$cycloalkyl-;
k) $C_6$-$C_{14}$aryl- optionally substituted with a substituent selected from:
 i) $HO_2C$—,
 ii) $C_1$-$C_6$hydroxylalkyl-,
 iii) $R^{12}R^{13}NC(O)$—,
 iv) and ($C_1$-$C_6$alkoxy)carbonyl-;

l) $C_1$-$C_9$heterocycle optionally substituted with $C_1$-$C_6$alkyl-;
m) ($C_1$-$C_6$heteroaryl)alkyl-;
n) heterocyclyl($C_1$-$C_6$alkyl)-;
o) ($C_6$-$C_{14}$aryl)alkyl-;
p) heterocyclyl($C_1$-$C_6$alkyl);
q) ($C_1$-$C_6$heteroaryl)alkyl-;
r) ($C_6$-$C_{14}$aryl)alkyl-;
s) $C_1$-$C_6$hydroxylalkyl-;
t) $C_1$-$C_6$perfluoroalkyl-;
u) $C_1$-$C_9$heteroaryl- optionally substituted with a substituent selected from:
  i) $HO_2C$—,
  ii) $C_1$-$C_6$hydroxylalkyl-,
  iii) $R^{12}R^{13}NC(O)$—,
  iv) and ($C_1$-$C_6$alkoxy)carbonyl-;
v) $R^3C(O)$—$N(R^2)$—Ar—;
w) $R^{12}R^{13}NC(O)$—;
x) $R^{14}OC(O)$—;
y) or $R^{14}S(O)_2$—;
$R^5$ is:
a) hydrogen;
b) $C_1$-$C_6$acyl-;
c) $C_1$-$C_6$alkyl-;
d) amino($C_1$-$C_6$alkyl)-;
e) $C_3$-$C_8$cycloalkyl-;
f) $C_6$-$C_{14}$aryl- optionally substituted with a substituent selected from:
  i) $HO_2C$—,
  ii) $C_1$-$C_6$hydroxylalkyl-,
  iii) $R^{12}R^{13}NC(O)$—,
  iv) and ($C_1$-$C_6$alkoxy)carbonyl-;
g) halogen;
h) $C_1$-$C_9$heterocycle optionally substituted with $C_1$-$C_6$alkyl-;
i) ($C_1$-$C_9$heteroaryl)alkyl-;
j) heterocyclyl($C_1$-$C_6$alkyl)-;
k) ($C_6$-$C_{14}$aryl)alkyl-;
l) heterocyclyl($C_1$-$C_6$alkyl);
m) ($C_1$-$C_9$heteroaryl)alkyl-;
n) ($C_6$-$C_{14}$aryl)alkyl-;
o) $C_1$-$C_6$hydroxylalkyl-;
p) $C_1$-$C_6$perfluoroalkyl-;
q) $C_1$-$C_9$heteroaryl- optionally substituted with a substituent selected from:
  i) $HO_2C$—,
  ii) $C_1$-$C_6$hydroxylalkyl-,
  iii) $R^{12}R^{13}NC(O)$—,
  iv) and ($C_1$-$C_6$alkoxy)carbonyl-;
r) $R^{12}R^{13}NC(O)$—;
s) $R^{14}OC(O)$—;
t) or $R^{14}S(O)_2$—;
$R^{12}$ and $R^{13}$ are each independently H, $C_1$-$C_6$alkyl-, $C_3$-$C_8$cycloalkyl-, $C_6$-$C_{14}$aryl-, $C_1$-$C_9$heteroaryl-, ($C_1$-$C_9$heteroaryl)alkyl-, heterocyclyl($C_1$-$C_6$alkyl)-, ($C_6$-$C_{14}$aryl)alkyl-, or $C_1$-$C_9$heterocyclyl- optionally substituted by $C_1$-$C_6$alkyl-;
or $R^{12}$ and $R^{13}$, when taken together with the nitrogen to which they are attached, form a 3- to 7- membered heterocycle wherein up to two of the carbon atoms of the heterocycle are optionally replaced with —N(H)—, —N($C_1$-$C_6$alkyl)-, —N($C_6$-$C_{14}$aryl)-, —S—, —SO—, —S(O)$_2$—, or —O—;
$R^{14}$ is $C_1$-$C_6$alkyl-, $C_6$-$C_{14}$aryl-, ($C_6$-$C_{14}$aryl)alkyl-, $C_1$-$C_9$heterocyclyl- optionally substituted by $C_1$-$C_6$alkyl-, $C_3$-$C_8$cycloalkyl-, $C_1$-$C_6$hydroxylalkyl-, or $C_1$-$C_6$perfluoroalkyl-.

2. A compound of claim 1 of the Formula II:

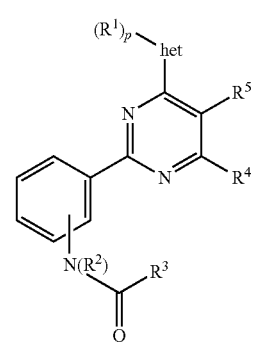

II or a pharmaceutically acceptable salt thereof.

3. A compound of claim 2 of the Formula III:

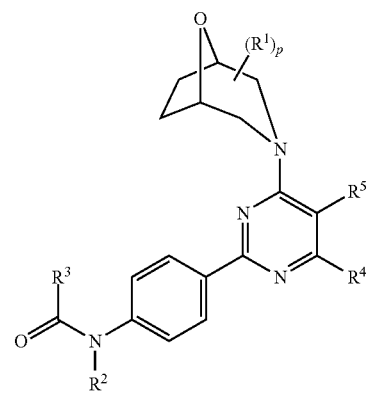

III or a pharmaceutically acceptable salt thereof.

4. A compound of claim 2 of the Formula IV:

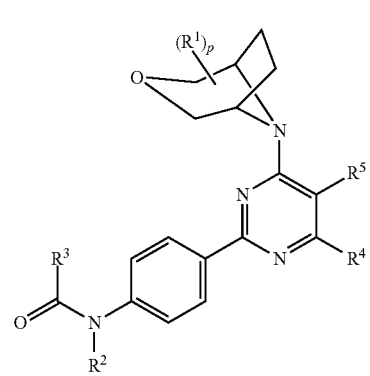

IV or a pharmaceutically acceptable salt thereof.

5. A compound of claim 1 of the Formula V:

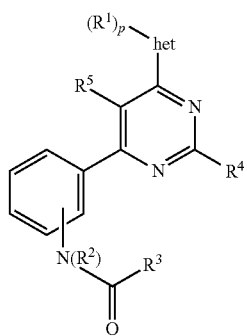

or a pharmaceutically acceptable salt thereof.

6. A compound of claim 5 of the Formula VI:

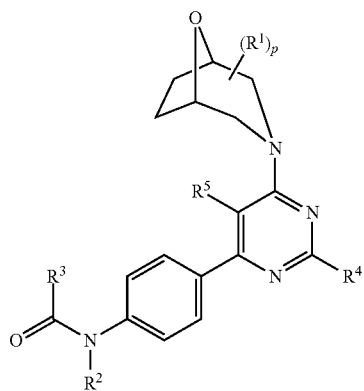

or a pharmaceutically acceptable salt thereof.

7. A compound of claim 1 wherein p is 0.
8. A compound of claim 1 wherein $R^2$ is H.
9. A compound of claim 1 wherein $R^3$ is $R^7R^8N-$.
10. A compound of claim 9 wherein $R^7$ is 4-pyridyl-.
11. A compound of claim 1 wherein $R^8$ is H.
12. A compound of claim 1 wherein $R^4$ is $C_1$-$C_9$heterocyclyl-.
13. A compound of claim 1 wherein $R^5$ is H.
14. A compound of claim 1 selected from the group consisting of:

1-{4-[4-(3,7-dioxa-9-azabicyclo[3.3.1]non-9-yl)-6-(isopropylamino)pyrimidin-2-yl]phenyl}-3-pyridin-4-ylurea;
1-{4-[4-(3,7-dioxa-9-azabicyclo[3.3.1]non-9-yl)-6-(isopropylamino)pyrimidin-2-yl]phenyl}-3-{4-[(4-methylpiperazin-1-yl)methyl]phenyl}urea;
1-{4-[4-(3,7-dioxa-9-azabicyclo[3.3.1]non-9-yl)-6-(isopropylamino)pyrimidin-2-yl]phenyl}-3-[4-(4-methylpiperazin-1-yl)phenyl]urea;
1-{4-[2-(dimethylamino)ethoxy]phenyl}-3-{4-[4-(3,7-dioxa-9-azabicyclo[3.3.1]non-9-yl)-6-(isopropylamino)pyrimidin-2-yl]phenyl}urea;
1-methyl-3-{4-[4-(8-oxa-3-azabicyclo[3.2.1]oct-3-yl)-6-phenylpyrimidin-2-yl]phenyl}urea;
2-hydroxyethyl {4-[4-(8-oxa-3-azabicyclo[3.2.1]oct-3-yl)-6-phenylpyrimidin-2-yl]phenyl}carbamate;
1-[4-(4-methylpiperazin-1-yl)phenyl]-3-{4-[4-(8-oxa-3-azabicyclo[3.2.1]oct-3-yl)-6-phenylpyrimidin-2-yl]phenyl}urea;
1-ethyl-3-{4-[4-(8-oxa-3-azabicyclo[3.2.1]oct-3-yl)-6-phenylpyrimidin-2-yl]phenyl}urea;
1-cyclopropyl-3-{4-[4-(8-oxa-3-azabicyclo[3.2.1]oct-3-yl)-6-phenylpyrimidin-2-yl]phenyl}urea;
1-{4-[4-(8-oxa-3-azabicyclo[3.2.1]oct-3-yl)-6-phenylpyrimidin-2-yl]phenyl}-3-pyridin-4-ylurea;
1-[4-(hydroxymethyl)phenyl]-3-{4-[4-(8-oxa-3-azabicyclo[3.2.1]oct-3-yl)-6-phenylpyrimidin-2-yl]phenyl}urea;
1-{4-[2-(dimethylamino)ethoxy]phenyl}-3-{4-[4-(8-oxa-3-azabicyclo[3.2.1]oct-3-yl)-6-phenylpyrimidin-2-yl]phenyl}urea;
2-hydroxyethyl {4-[4-(8-oxa-3-azabicyclo[3.2.1]oct-3-yl)pyrimidin-2-yl]phenyl}carbamate;
1-methyl-3-{4-[4-(8-oxa-3-azabicyclo[3.2.1]oct-3-yl)pyrimidin-2-yl]phenyl}urea;
1-{4-[4-(8-oxa-3-azabicyclo[3.2.1]oct-3-yl)pyrimidin-2-yl]phenyl}-3-pyridin-4-ylurea;
1-[4-(4,6-di-8-oxa-3-azabicyclo[3.2.1]oct-3-ylpyrimidin-2-yl)phenyl]-3-methylurea;
1-[4-(4,6-di-8-oxa-3-azabicyclo[3.2.1]oct-3-ylpyrimidin-2-yl)phenyl]-3-pyridin-4-ylurea;
1-[4-(4,6-di-8-oxa-3-azabicyclo[3.2.1]oct-3-ylpyrimidin-2-yl)phenyl]-3-[4-(4-methylpiperazin-1-yl)phenyl]urea;
1-[4-(4,6-di-8-oxa-3-azabicyclo[3.2.1]oct-3-ylpyrimidin-2-yl)phenyl]-1-ethyl-3-pyridin-4-ylurea;
1-[4-(4,6-di-8-oxa-3-azabicyclo[3.2.1]oct-3-ylpyrimidin-2-yl)phenyl]-1-ethyl-3-[4-(4-methylpiperazin-1-yl)phenyl]urea;
bis(2-hydroxyethyl) {[6-(8-oxa-3-azabicyclo[3.2.1]oct-3-yl)pyrimidine-2,4-diyl]di-4,1-phenylene}biscarbamate;
N',N'''-{[6-(8-oxa-3-azabicyclo[3.2.1]oct-3-yl)pyrimidine-2,4-diyl]di-4,1-phenylene}bis(1-methylurea);
N',N'''-{[6-(8-oxa-3-azabicyclo[3.2.1]oct-3-yl)pyrimidine-2,4-diyl]di-4,1-phenylene}bis(1-ethylurea);
N',N'''-{[6-(8-oxa-3-azabicyclo[3.2.1]oct-3-yl)pyrimidine-2,4-diyl]di-4,1-phenylene}bis(1-cyclopropylurea);
N,N''-{[6-(8-oxa-3-azabicyclo[3.2.1]oct-3-yl)pyrimidine-2,4-diyl]di-4,1-phenylene}bis(3-pyridin-3-ylurea);
N,N''-{[6-(8-oxa-3-azabicyclo[3.2.1]oct-3-yl)pyrimidine-2,4-diyl]di-4,1-phenylene}bis(3-pyridin-4-ylurea);
N',N'''-{[6-(8-oxa-3-azabicyclo[3.2.1]oct-3-yl)pyrimidine-2,4-diyl]di-4,1-phenylene}bis{1-[4-(4-methylpiperazin-1-yl)phenyl]urea};
4,4'-{[6-(8-oxa-3-azabicyclo[3.2.1]oct-3-yl)pyrimidine-2,4-diyl]bis(4,1-phenylenecarbamoylimino)}dibenzamide;
1-methyl-3-{4-[4-(1-methylethoxy)-6-(8-oxa-3-azabicyclo[3.2.1]oct-3-yl)pyrimidin-2-yl]phenyl}urea;
1-cyclopropyl-3-{4-[4-(1-methylethoxy)-6-(8-oxa-3-azabicyclo[3.2.1]oct-3-yl)pyrimidin-2-yl]phenyl}urea;
1-{4-[4-(1-methylethoxy)-6-(8-oxa-3-azabicyclo[3.2.1]oct-3-yl)pyrimidin-2-yl]phenyl}-3-pyridin-4-ylurea;
1-{4-[4-(1-methylethoxy)-6-(8-oxa-3-azabicyclo[3.2.1]oct-3-yl)pyrimidin-2-yl]phenyl}-3-[4-(4-methylpiperazin-1-yl)phenyl]urea;
1-methyl-3-(4-{4-[(1-methylethyl)amino]-6-(8-oxa-3-azabicyclo[3.2.1]oct-3-yl)pyrimidin-2-yl}phenyl)urea;
1-cyclopropyl-3-(4-{4-[(1-methylethyl)amino]-6-(8-oxa-3-azabicyclo[3.2.1]oct-3-yl)pyrimidin-2-yl}phenyl)urea;
1-(4-{4-[(1-methylethyl)amino]-6-(8-oxa-3-azabicyclo[3.2.1]oct-3-yl)pyrimidin-2-yl}phenyl)-3-pyridin-4-ylurea;

1-(4-{4-[(1-methylethyl)amino]-6-(8-oxa-3-azabicyclo [3.2.1]oct-3-yl)pyrimidin-2-yl}phenyl)-3-[4-(4-methylpiperazin-1-yl)phenyl]urea;
N~3~,N~3~-dimethyl-N-(4-[(1-methylethyl)amino]-6-(8-oxa-3-azabicyclo[3.2.1]oct-3-yl)-2-{4-[(pyridin-3-ylcarbamoyl)amino]phenyl}pyrimidin-5-yl)-beta-alaninamide;
1-methyl-3-{4-[4-(8-oxa-3-azabicyclo[3.2.1]oct-3-yl)-6-(trifluoromethyl)pyrimidin-2-yl]phenyl}urea;
1-cyclopropyl-3-{4-[4-(8-oxa-3-azabicyclo[3.2.1]oct-3-yl)-6-(trifluoromethyl)pyrimidin-2-yl]phenyl}urea;
2-hydroxyethyl {4-[4-(8-oxa-3-azabicyclo[3.2.1]oct-3-yl)-6-(trifluoromethyl)pyrimidin-2-yl] phenyl}carbamate;
1-{4-[4-(8-oxa-3-azabicyclo[3.2.1]oct-3-yl)-6-(trifluoromethyl)pyrimidin-2-yl]phenyl}-3-pyridin-4-ylurea;
1-[4-(4-methylpiperazin-1-yl)phenyl]-3-{4-[4-(8-oxa-3-azabicyclo[3.2.1]oct-3-yl)-6-(trifluoromethyl)pyrimidin-2-yl]phenyl}urea;
tert-butyl methyl(4-{[(4-{4-[(methylsulfonyl)methyl]-6-(8-oxa-3-azabicyclo[3.2.1]oct-3-yl)pyrimidin-2-yl}phenyl)carbamoyl]amino}benzyl)carbamate;
1-methyl-3-(4-{4-[(methylsulfonyl)methyl]-6-(8-oxa-3-azabicyclo[3.2.1]oct-3-yl)pyrimidin-2-yl}phenyl)urea;
1-ethyl-3-(4-{4-[(methylsulfonyl)methyl]-6-(8-oxa-3-azabicyclo[3.2.1]oct-3-yl)pyrimidin-2-yl}phenyl)urea;
1-cyclopropyl-3-(4-{4-[(methylsulfonyl)methyl]-6-(8-oxa-3-azabicyclo[3.2.1]oct-3-yl)pyrimidin-2-yl}phenyl)urea;
1-(4-{4-[(methylsulfonyl)methyl]-6-(8-oxa-3-azabicyclo [3.2.1]oct-3-yl)pyrimidin-2-yl}phenyl)-3-phenylurea;
1-(4-{4-[(methylsulfonyl)methyl]-6-(8-oxa-3-azabicyclo [3.2.1]oct-3-yl)pyrimidin-2-yl}phenyl)-3-pyridin-3-ylurea;
1-(4-{4-[(methylsulfonyl)methyl]-6-(8-oxa-3-azabicyclo [3.2.1]oct-3-yl)pyrimidin-2-yl}phenyl)-3-pyridin-4-ylurea;
1-[4-(4-methylpiperazin-1-yl)phenyl]-3-(4-{4-[(methylsulfonyl)methyl]-6-(8-oxa-3-azabicyclo[3.2.1]oct-3-yl)pyrimidin-2-yl}phenyl)urea;
1-(4-{4-[(methylsulfonyl)methyl]-6-(8-oxa-3-azabicyclo [3.2.1]oct-3-yl)pyrimidin-2-yl}phenyl)-3-(4-piperazin-1-ylphenyl)urea;
1-{4-[2-(dimethylamino)ethoxy]phenyl}-3-(4-{4-[(methylsulfonyl)methyl]-6-(8-oxa-3-azabicyclo[3.2.1]oct-3-yl)pyrimidin-2-yl}phenyl)urea;
1-{4-[(4-methylpiperazin-1-yl)methyl]phenyl}-3-(4-{4-[(methylsulfonyl)methyl]-6-(8-oxa-3-azabicyclo [3.2.1]oct-3-yl)pyrimidin-2-yl}phenyl)urea;
1-{4-[(methylamino)methyl]phenyl}-3-(4-{4-[(methylsulfonyl)methyl]-6-(8-oxa-3-azabicyclo[3.2.1]oct-3-yl)pyrimidin-2-yl}phenyl)urea;
1-[4-(4,6-di-3-oxa-8-azabicyclo[3.2.1]oct-8-ylpyrimidin-2-yl)phenyl]-3-pyridin-4-ylurea;
1-{4-[2-(dimethylamino)ethoxy]phenyl}-3-[4-(4,6-di-3-oxa-8-azabicyclo[3.2.1]oct-8-ylpyrimidin-2-yl)phenyl] urea;
1-[4-(4,6-di-3-oxa-8-azabicyclo[3.2.1]oct-8-ylpyrimidin-2-yl)phenyl]-3-[4-(4-methylpiperazin-1-yl)phenyl] urea;
1-[4-(4,6-di-3-oxa-8-azabicyclo[3.2.1]oct-8-ylpyrimidin-2-yl)phenyl]-3-{4-[(4-methylpiperazin-1-yl)methyl] phenyl}urea;
1-[4-(4,6-di-3-oxa-8-azabicyclo[3.2.1]oct-8-ylpyrimidin-2-yl)phenyl]-3-{4-[(4-methylpiperazin-1-yl)carbonyl] phenyl}urea;
1-{4-[4-(isopropylamino)-6-(3-oxa-8-azabicyclo[3.2.1] oct-8-yl)pyrimidin-2-yl]phenyl}-3-pyridin-4-ylurea;
1-{4-[2-(dimethylamino)ethoxy]phenyl}-3-{4-[4-(isopropylamino)-6-(3-oxa-8-azabicyclo[3.2.1]oct-8-yl) pyrimidin-2-yl]phenyl}urea;
1-{4-[4-(isopropylamino)-6-(3-oxa-8-azabicyclo[3.2.1] oct-8-yl)pyrimidin-2-yl]phenyl}-3-[4-(4-methylpiperazin-1-yl)phenyl]urea;
1-{4-[4-(isopropylamino)-6-(3-oxa-8-azabicyclo[3.2.1] oct-8-yl)pyrimidin-2-yl]phenyl}-3-{4-[(4-methylpiperazin-1-yl)methyl]phenyl}urea;
1-{4-[4-(isopropylamino)-6-(3-oxa-8-azabicyclo[3.2.1] oct-8-yl)pyrimidin-2-yl]phenyl}-3-[6-(4-methylpiperazin-1-yl)pyridin-3-yl]urea;
1-[4-(4,6-di-3-oxa-8-azabicyclo[3.2.1]oct-8-ylpyrimidin-2-yl)phenyl]-3-pyridin-3-ylurea;
1-[4-(5-chloro-4,6-di-3-oxa-8-azabicyclo[3.2.1]oct-8-ylpyrimidin-2-yl)phenyl]-3-pyridin-3-ylurea;
1-[4-(5-chloro-4,6-di-3-oxa-8-azabicyclo[3.2.1]oct-8-ylpyrimidin-2-yl)phenyl]-3-[4-(4-methylpiperazin-1-yl)phenyl]urea;
1-{4-[4-(3-oxa-8-azabicyclo[3.2.1]oct-8-yl)-6-(tetrahydro-2H-pyran-4-ylamino)pyrimidin-2-yl]phenyl}-3-pyridin-4-ylurea;
1-[4-(4-methylpiperazin-1-yl)phenyl]-3-{4-[4-(3-oxa-8-azabicyclo[3.2.1]oct-8-yl)-6-(tetrahydro-2H-pyran-4-ylamino)pyrimidin-2-yl]phenyl}urea;
1-{4-[4-{[2-(methylsulfonyl)ethyl]amino}-6-(3-oxa-8-azabicyclo[3.2.1]oct-8-yl)pyrimidin-2-yl]phenyl}-3-pyridin-3-ylurea;
1-{4-[(4-methylpiperazin-1-yl)methyl]phenyl}-3-{4-[4-{[2-(methylsulfonyl)ethyl]amino}-6-(3-oxa-8-azabicyclo[3.2.1]oct-8-yl)pyrimidin-2-yl]phenyl}urea;
1-{4-[4-(3-oxa-8-azabicyclo[3.2.1]oct-8-yl)-6-(tetrahydro-2H-pyran-4-ylamino)pyrimidin-2-yl]phenyl}-3-pyridin-3-ylurea;
1-{4-[2-(dimethylamino)ethoxy]phenyl}-3-{4-[4-(3-oxa-8-azabicyclo[3.2.1]oct-8-yl)-6-(tetrahydro-2H-pyran-4-ylamino)pyrimidin-2-yl]phenyl}urea;
1-{4-[4-{[2-(methylsulfonyl)ethyl]amino}-6-(3-oxa-8-azabicyclo[3.2.1]oct-8-yl)pyrimidin-2-yl]phenyl}-3-pyridin-4-ylurea;
1-{4-[2-(dimethylamino)ethoxy]phenyl}-3-{4-[4-{[2-(methylsulfonyl)ethyl]amino}-6-(3-oxa-8-azabicyclo [3.2.1]oct-8-yl)pyrimidin-2-yl]phenyl}urea;
1-[4-(4-methylpiperazin-1-yl)phenyl]-3-{4-[4-{[2-(methylsulfonyl)ethyl]amino}-6-(3-oxa-8-azabicyclo[3.2.1] oct-8-yl)pyrimidin-2-yl]phenyl}urea;
1-{4[(4-methylpiperazin-1-yl)methyl]phenyl}-3-{4-[4-(3-oxa-8-azabicyclo[3.2.1]oct-8-yl)-6-(tetrahydro-2H-pyran-4-ylamino)pyrimidin-2-yl]phenyl}urea;
1-{4-[4-(diethylamino)-6-(3-oxa-8-azabicyclo[3.2.1]oct-8-yl)pyrimidin-2-yl]phenyl}-3-pyridin-4-ylurea;
1-{4-[4-(diethylamino)-6-(3-oxa-8-azabicyclo[3.2.1]oct-8-yl)pyrimidin-2-yl]phenyl}-3-[4-(4-methylpiperazin-1-yl)phenyl]urea;
1-(4-{4-[(1-methylethyl)amino]-6-(3-oxa-8-azabicyclo [3.2.1]oct-8-yl)pyrimidin-2-yl}phenyl)-3-[4-(pyrrolidin-1-ylmethyl)phenyl]urea;
1-(4-{4-[(1-methylethyl)amino]-6-(3-oxa-8-azabicyclo [3.2.1]oct-8-yl)pyrimidin-2-yl}phenyl)-3-pyridin-3-ylurea;
1-{4-[(dimethylamino)methyl]phenyl}-3-(4-{4-[(1-methylethyl)amino]-6-(3-oxa-8-azabicyclo[3.2.1]oct-8-yl) pyrimidin-2-yl}phenyl)urea;

1-(4-{4-[(1-methylethyl)amino]-6-(3-oxa-8-azabicyclo[3.2.1]oct-8-yl)pyrimidin-2-yl}phenyl)-3-[4-(2-pyrrolidin-1-ylethoxy)phenyl]urea;

1-(4-{4-[(dimethylamino)methyl]-6-(3-oxa-8-azabicyclo[3.2.1]oct-8-yl)pyrimidin-2-yl}phenyl)-3-pyridin-3-ylurea;

1-(4-{4-[(dimethylamino)methyl]-6-(3-oxa-8-azabicyclo[3.2.1]oct-8-yl)pyrimidin-2-yl}phenyl)-3-methylurea;

1-(4-{4-[(dimethylamino)methyl]-6-(3-oxa-8-azabicyclo[3.2.1]oct-8-yl)pyrimidin-2-yl}phenyl)-3-ethylurea;

1-(4-(4-(3-oxa-8-azabicyclo[3.2.1]octan-8-yl)-6-((dimethylamino)methyl)pyrimidin-2-yl)phenyl)-3-cyclopropylurea;

1-(4-(4-(3-oxa-8-azabicyclo[3.2.1]octan-8-yl)-6-((dimethylamino)methyl)pyrimidin-2-yl)phenyl)-3-(4-(4-methyl piperazin-1-yl)phenyl)urea;

1-(4-(4-(3-oxa-8-azabicyclo[3.2.1]octan-8-yl)-6-((dimethylamino)methyl)pyrimidin-2-yl)phenyl)-3-(4-(2-(dimethylamino)ethoxy)phenyl)urea;

1-(4-(4-(3-oxa-8-azabicyclo[3.2.1]octan-8-yl)-6-((dimethylamino)methyl)pyrimidin-2-yl)phenyl)-3-(4-((dimethylamino)methyl)phenyl)urea;

1-(4-(4-(3-oxa-8-azabicyclo[3.2.1]octan-8-yl)-6-((dimethylamino)methyl)pyrimidin-2-yl)phenyl)-3-phenylurea;

1-{4-[4-(3-oxa-8-azabicyclo[3.2.1]oct-8-yl)-6-(tetrahydro-2H-pyran-4-yl)pyrimidin-2-yl]phenyl}-3-pyridin-3-ylurea;

1-{4-[4-(3-oxa-8-azabicyclo[3.2.1]oct-8-yl)-6-(tetrahydro-2H-pyran-4-yl)pyrimidin-2-yl]phenyl}-3-pyridin-4-ylurea;

1-[4-(4-methylpiperazin-1-yl)phenyl]-3-{4-[4-(3-oxa-8-azabicyclo[3.2.1]oct-8-yl)-6-(tetrahydro-2H-pyran-4-yl)pyrimidin-2-yl]phenyl}urea;

1-[6-(4-methylpiperazin-1-yl)pyridin-3-yl]-3-{4-[4-(3-oxa-8-azabicyclo[3.2.1]oct-8-yl)-6-(tetrahydro-2H-pyran-4-yl)pyrimidin-2-yl]phenyl}urea;

1-{4-[(4-methylpiperazin-1-yl)carbonyl]phenyl}-3-{4-[4-(3-oxa-8-azabicyclo[3.2.1]oct-8-yl)-6-(tetrahydro-2H-pyran-4-yl)pyrimidin-2-yl]phenyl}urea;

1-(4-{[4-(1-methylethyl)piperazin-1-yl]carbonyl}phenyl)-3-{4-[4-(3-oxa-8-azabicyclo[3.2.1]oct-8-yl)-6-(tetrahydro-2H-pyran-4-yl)pyrimidin-2-yl]phenyl}urea;

1-{4-[2-(dimethylamino)ethoxy]phenyl}-3-{4-[4-(3-oxa-8-azabicyclo[3.2.1]oct-8-yl)-6-(tetrahydro-2H-pyran-4-yl)pyrimidin-2-yl]phenyl}urea;

1-(4-{4-[(3R)-3-methylmorpholin-4-yl]-6-(3-oxa-8-azabicyclo[3.2.1]oct-8-yl)pyrimidin-2-yl}phenyl)-3-pyridin-4-ylurea;

1-(4-{4-[(3R)-3-methylmorpholin-4-yl]-6-(3-oxa-8-azabicyclo[3.2.1]oct-8-yl)pyrimidin-2-yl}phenyl)-3-[4-(4-methylpiperazin-1-yl)phenyl]urea;

1-(4-{4-[(3R)-3-methylmorpholin-4-yl]-6-(3-oxa-8-azabicyclo[3.2.1]oct-8-yl)pyrimidin-2-yl}phenyl)-3-[6-(4-methylpiperazin-1-yl)pyridin-3-yl]urea;

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-pyridin-4-ylurea;

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-[4-(4-methylpiperazin-1-yl)phenyl]urea;

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-[6-(4-methylpiperazin-1-yl)pyridin-3-yl]urea;

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-{4-[(4-methylpiperazin-1-yl)carbonyl]phenyl}urea;

1-(4-{4-[(2R,6S)-2,6-dimethylmorpholin-4-yl]-6-(3-oxa-8-azabicyclo[3.2.1]oct-8-yl)pyrimidin-2-yl}phenyl)-3-(4-{[4-(1-methylethyl)piperazin-1-yl]carbonyl}phenyl)urea;

1-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)-3-pyridin-4-ylurea;

1-[4-(4-methylpiperazin-1-yl)phenyl]-3-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)urea;

1-{4-[(dimethylamino)methyl]phenyl}-3-(4-{4-[(1S,4S)-2-oxa-5-azabicyclo[2.2.1]hept-5-yl]-6-(3-oxa-8-azabicyclo[3.2.1]oct-8-yl)pyrimidin-2-yl}phenyl)urea;

1-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)-3-pyridin-4-ylurea;

1-[4-(4-methylpiperazin-1-yl)phenyl]-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea;

1-{4-[(4-methylpiperazin-1-yl)methyl]phenyl}-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea;

1-{4-[2-(dimethylamino)ethoxy]phenyl}-3-(4-{4-[(1R,4R)-2-oxa-5-azabicyclo[2.2.1]hept-5-yl]-6-(3-oxa-8-azabicyclo[3.2.1]oct-8-yl)pyrimidin-2-yl}phenyl)urea;

1-(4-{4-[(3R)-3-methylmorpholin-4-yl]-6-(3-oxa-8-azabicyclo[3.2.1]oct-8-yl)pyrimidin-2-yl}phenyl)-3-pyridin-3-ylurea;

1-(4-{4-[(3R)-3-methylmorpholin-4-yl]-6-(3-oxa-8-azabicyclo[3.2.1]oct-8-yl)pyrimidin-2-yl}phenyl)-3-{4-[(4-methylpiperazin-1-yl)methyl]phenyl}urea;

1-{4-[2-(dimethylamino)ethoxy]phenyl}-3-(4-{4-[(3R)-3-methylmorpholin-4-yl]-6-(3-oxa-8-azabicyclo[3.2.1]oct-8-yl)pyrimidin-2-yl}phenyl)urea;

N,N-dimethyl-4-{[(4-{4-[(3R)-3-methylmorpholin-4-yl]-6-(3-oxa-8-azabicyclo[3.2.1]oct-8-yl)pyrimidin-2-yl}phenyl)carbamoyl]amino}benzamide;

1-(4-{4-[(3R)-3-methylmorpholin-4-yl]-6-(3-oxa-8-azabicyclo[3.2.1]oct-8-yl)pyrimidin-2-yl}phenyl)-3-{4-[(4-methylpiperazin-1-yl)carbonyl]phenyl}urea;

1-(4-{[4-(1-methylethyl)piperazin-1-yl]carbonyl}phenyl)-3-(4-{4-[(3R)-3-methylmorpholin-4-yl]-6-(3-oxa-8-azabicyclo[3.2.1]oct-8-yl)pyrimidin-2-yl}phenyl)urea;

1-(4-{4-[(dimethylamino)methyl]-6-(3-oxa-8-azabicyclo[3.2.1]oct-8-yl)pyrimidin-2-yl}phenyl)-3-methylurea;

1-[4-(2,6-di-8-oxa-3-azabicyclo[3.2.1]oct-3-ylpyrimidin-4-yl)phenyl]-3-methylurea;

1-[4-(2,6-di-8-oxa-3-azabicyclo[3.2.1]oct-3-ylpyrimidin-4-yl)phenyl]-3-pyridin-4-ylurea;

1-[4-(2,6-di-8-oxa-3-azabicyclo[3.2.1]oct-3-ylpyrimidin-4-yl)phenyl]-3-[4-(4-methylpiperazin-1-yl)phenyl]urea;

1-cyclopropyl-3-[4-(2,6-di-8-oxa-3-azabicyclo[3.2.1]oct-3-ylpyrimidin-4-yl)phenyl]urea;

4-[4-(8-oxa-3-azabicyclo[3.2.1]oct-3-yl)pyrimidin-2-yl]aniline;

4-[4-chloro-6-(8-oxa-3-azabicyclo[3.2.1]oct-3-yl)pyrimidin-2-yl]aniline;

4-[2-chloro-6-(8-oxa-3-azabicyclo[3.2.1]oct-3-yl)pyrimidin-4-yl]aniline;

8,8'-[2-(4-nitrophenyl)pyrimidine-4,6-diyl]bis(3-oxa-8-azabicyclo[3.2.1]octane);

4-(4,6-di-3-oxa-8-azabicyclo[3.2.1]oct-8-ylpyrimidin-2-yl)aniline;
4-{4-[(methylsulfonyl)methyl]-6-(8-oxa-3-azabicyclo[3.2.1]oct-3-yl)pyrimidin-2-yl}aniline;
4-(5-chloro-4,6-di-3-oxa-8-azabicyclo[3.2.1]oct-8-ylpyrimidin-2-yl)aniline;
9-(6-chloro-2-(4-nitrophenyl)pyrimidin-4-yl)-3,7-dioxa-9-azabicyclo[3.3.1]nonane;
6-(3,7-dioxa-9-azabicyclo[3.3.1]nonan-9-yl)-N-isopropyl-2-(4-nitrophenyl)pyrimidin-4-amine;
2-(4-aminophenyl)-6-(3,7-dioxa-9-azabicyclo[3.3.1]nonan-9-yl)-N-isopropylpyrimidin-4-amine;
6-(3-oxa-8-azabicyclo[3.2.1]octan-8-yl)-2-(4-nitrophenyl)-N-(tetrahydro-2H-pyran-4-yl)pyrimidin-4-amine;
2-(4-aminophenyl)-6-(3-oxa-8-azabicyclo[3.2.1]octan-8-yl)-N-(tetrahydro-2H-pyran-4-yl)pyrimidin-4-amine;
6-(3-oxa-8-azabicyclo[3.2.1]octan-8-yl)-N-(2-(methylsulfonyl)ethyl)-2-(4-nitrophenyl)pyrimidin-4-amine;
2-(4-aminophenyl)-6-(3-oxa-8-azabicyclo[3.2.1]octan-8-yl)-N-(2-(methylsulfonyl)ethyl)pyrimidin-4-amine;
6-(3-oxa-8-azabicyclo[3.2.1]octan-8-yl)-N,N-diethyl-2-(4-nitrophenyl)pyrimidin-4-amine;
2-(4-aminophenyl)-6-(3-oxa-8-azabicyclo[3.2.1]octan-8-yl)-N,N-diethylpyrimidin-4-amine;
4-(4-(3-oxa-8-azabicyclo[3.2.1]octan-8-yl)-6-((dimethylamino)methyl)pyrimidin-2-yl)aniline;
8-[6-(3,6-dihydro-2H-pyran-4-yl)-2-(4-nitrophenyl)pyrimidin-4-yl]-3-oxa-8-azabicyclo[3.2.1]octane; and
4-[4-(3-oxa-8-azabicyclo[3.2.1]oct-8-yl)-6-(tetrahydro-2H-pyran-4-yl)pyrimidin- 2-yl]aniline.

15. A composition comprising a compound of claim 1 and a pharmaceutically acceptable carrier.

16. A composition comprising a compound of claim 1; a second compound selected from the group consisting of a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, docetaxel, paclitaxel, leucovorin, levamisole, irinotecan, estramustine, etoposide, nitrogen mustards, BCNU, carmustine, lomustine, vinblastine, vincristine, vinorelbine, cisplatin, carboplatin, oxaliplatin, imatinib mesylate, Avastin (bevacizumab), hexamethylmelamine, topotecan, tyrosine kinase inhibitors, tyrphostins, herbimycin A, genistein, erbstatin, lavendustin A, hydroxyzine, glatiramer acetate, interferon beta-1a, interferon beta-1b, and natalizumab and lavendustin A; and a pharmaceutically acceptable carrier.

17. The composition of claim 16, wherein the second compound is Avastin.

18. The compound of claim 1 used for treating breast cancer.

* * * * *